United States Patent
Slusher et al.

(10) Patent No.: US 11,926,640 B2
(45) Date of Patent: Mar. 12, 2024

(54) PRODRUGS OF GLUTAMINE ANALOGS

(71) Applicants: THE JOHNS HOPKINS UNIVERSITY, Baltimore, MD (US); Ústav organické chemie a biochemie AV ČR, v.v.i., Prague (CZ)

(72) Inventors: Barbara Slusher, Kingsville, MD (US); Rana Rais, West Friendship, MD (US); Lukas Tenora, Prague (CZ); Pavel Majer, Sykesville, MD (US); Andrej Jancarik, Koprivnice (CZ)

(73) Assignees: The Johns Hopkins University, Baltimore, MD (US); Ústav organické chemie a biochemie AV ČR, v.v.i., Prague (CZ)

( * ) Notice: Subject to any disclaimer, the term of this patent is extended or adjusted under 35 U.S.C. 154(b) by 264 days.

(21) Appl. No.: 17/207,388

(22) Filed: Mar. 19, 2021

(65) Prior Publication Data
US 2021/0206787 A1    Jul. 8, 2021

Related U.S. Application Data

(60) Division of application No. 16/454,853, filed on Jun. 27, 2019, now Pat. No. 10,954,257, which is a
(Continued)

(51) Int. Cl.
| | | |
|---|---|---|
| A61K 31/404 | (2006.01) | |
| A61P 35/00 | (2006.01) | |
| C07C 227/14 | (2006.01) | |
| C07C 245/18 | (2006.01) | |
| C07C 271/22 | (2006.01) | |
| C07D 209/18 | (2006.01) | |
| C07D 209/20 | (2006.01) | |
| C07D 211/90 | (2006.01) | |
| C07D 263/04 | (2006.01) | |
| C07D 263/18 | (2006.01) | |
| C07D 309/10 | (2006.01) | |
| C07D 317/38 | (2006.01) | |
| C07D 317/40 | (2006.01) | |
| C07D 473/34 | (2006.01) | |
| C07F 9/24 | (2006.01) | |
| C07F 9/6561 | (2006.01) | |
| C07H 15/203 | (2006.01) | |
| C07H 19/207 | (2006.01) | |
| C07K 5/062 | (2006.01) | |
| C07K 5/078 | (2006.01) | |
(Continued)

(52) U.S. Cl.
CPC .......... *C07F 9/2458* (2013.01); *A61K 31/404* (2013.01); *A61P 35/00* (2018.01); *C07C 227/14* (2013.01); *C07C 245/18* (2013.01); *C07C 271/22* (2013.01); *C07D 209/18* (2013.01); *C07D 209/20* (2013.01); *C07D 211/90* (2013.01); *C07D 263/04* (2013.01); *C07D 263/18* (2013.01); *C07D 309/10* (2013.01); *C07D 317/38* (2013.01); *C07D 317/40* (2013.01); *C07D 473/34* (2013.01); *C07F 9/65616* (2013.01); *C07H 15/203* (2013.01); *C07H 19/207* (2013.01); *C07K 5/06026* (2013.01); *C07K 5/06156* (2013.01); *C07K 5/0808* (2013.01); *A61K 38/00* (2013.01)

(58) Field of Classification Search
CPC .................................................. A61K 31/404
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| (Continued) | | |

FOREIGN PATENT DOCUMENTS

| | | |
|---|---|---|
| EP | 0058481 A1 | 8/1982 |
| EP | 0102324 A2 | 3/1984 |
| (Continued) | | |

OTHER PUBLICATIONS

Abdelmalek, M.F., et.al., "Sirolimus Conversion Regimen Versus Continued Calcineurin Inhibitors in Liver Allograft Recipients: a Randomized Trial.," American Journal of Transplantation : Official Journal of the American Society of Transplantation and the American Society of Transplant Surgeons 12(3):694-705, Wiley-blackwell on Behalf of the American Society of Transplant Surgeons and the American Society of Transplantation, United States (Jan. 2012).
(Continued)

*Primary Examiner* — Brian E McDowell
(74) *Attorney, Agent, or Firm* — Sterne, Kessler, Goldstein & Fox P.L.L.C.

(57) ABSTRACT

The disclosure provides compounds having formula (I):

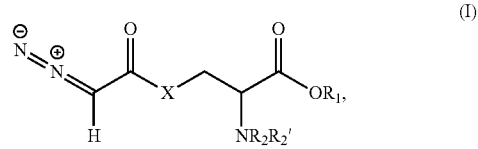

and the pharmaceutically acceptable salts thereof, wherein $R_1$, $R_2$, $R_2'$, and X are as defined as set forth in the specification. Compounds having formula (I) are prodrugs that release glutamine analogs, e.g., 6-diazo-5-oxo-L-norleucine (DON). The disclosure also provides compounds having formula (I) for use in treating cancer.

16 Claims, 80 Drawing Sheets

Related U.S. Application Data division of application No. 15/885,258, filed on Jan. 31, 2018, now Pat. No. 10,336,778, which is a continuation-in-part of application No. PCT/US2016/044767, filed on Jul. 29, 2016.

(60) Provisional application No. 62/199,566, filed on Jul. 31, 2015.

(51) Int. Cl.
  *C07K 5/083* (2006.01)
  *A61K 38/00* (2006.01)

(56) References Cited

U.S. PATENT DOCUMENTS

| | | | |
|---|---|---|---|
| 4,544,545 | A | 10/1985 | Ryan et al. |
| 4,568,646 | A | 2/1986 | Lee et al. |
| 5,328,470 | A | 7/1994 | Nabel et al. |
| 6,362,226 | B2 | 3/2002 | Phillips, III et al. |
| 7,723,330 | B2 | 5/2010 | Blake et al. |
| 10,568,868 | B2 | 2/2020 | Slusher et al. |
| 10,738,066 | B2 | 8/2020 | Slusher et al. |
| 10,954,257 | B2 | 3/2021 | Slusher et al. |
| 2004/0029801 | A1 | 2/2004 | Zhong et al. |
| 2006/0035838 | A1 | 2/2006 | Khosla et al. |
| 2006/0276438 | A1 | 12/2006 | Sethuraman et al. |
| 2008/0107624 | A1 | 5/2008 | D'Andrea et al. |
| 2008/0146526 | A1 | 6/2008 | Gallop et al. |
| 2008/0160024 | A1 | 7/2008 | Ware |
| 2009/0042806 | A1 | 2/2009 | Khosla et al. |
| 2009/0062223 | A1 | 3/2009 | Keicher et al. |
| 2009/0169537 | A1 | 7/2009 | Bausch et al. |
| 2014/0004081 | A1 | 1/2014 | Cobbold et al. |
| 2014/0065100 | A1 | 3/2014 | Rossignol et al. |
| 2015/0202291 | A1 | 7/2015 | Bosch et al. |
| 2015/0258082 | A1 | 9/2015 | Parlati et al. |
| 2016/0022674 | A1 | 1/2016 | Steggerda et al. |
| 2016/0193239 | A1 | 7/2016 | Baylin et al. |
| 2016/0310453 | A1 | 10/2016 | Mathios et al. |
| 2017/0190657 | A1 | 7/2017 | Gallop et al. |
| 2018/0193362 | A1 | 7/2018 | Slusher et al. |
| 2018/0221337 | A1 | 8/2018 | Slusher et al. |
| 2018/0221395 | A1 | 8/2018 | Slusher et al. |
| 2019/0216757 | A1 | 7/2019 | Slusher et al. |

FOREIGN PATENT DOCUMENTS

| | | |
|---|---|---|
| EP | 0123170 A2 | 10/1984 |
| EP | 0133988 A2 | 3/1985 |
| WO | WO-2004113363 A2 | 12/2004 |
| WO | WO-2005068455 A1 | 7/2005 |
| WO | WO-2005097108 A1 | 10/2005 |
| WO | WO-2013019058 A2 | 2/2013 |
| WO | WO-2014138391 A1 | 9/2014 |
| WO | WO-2014160071 A1 | 10/2014 |
| WO | WO-2015101957 A2 | 7/2015 |
| WO | WO-2017023774 A1 | 2/2017 |
| WO | WO-2017023787 A1 | 2/2017 |
| WO | WO-2017023791 A1 | 2/2017 |
| WO | WO-2017023793 A2 | 2/2017 |

OTHER PUBLICATIONS

Acevedo., et.al., "Synthesis and Analysis of the Sterically Constrained L-glutamine Analogues (3s,4r)-3,4-dimethyl-l-glutamine and (3s,4r)-3,4-dimethyl-l-pyroglutamic Acid," Tetrahedron 57 (30):6353-6359, Elsevier Science Ltd (Jul. 2001).

Ahluwalia.,G.S., et.al., "Metabolism and Action of Amino Acid Analog Anti-cancer Agents.," Pharmacology & Therapeutics 46(2):243-271, Pergamon Press, England (1990).

Alt,J., et.al., "Bioanalysis of 6-diazo-5-oxo-l-norleucine in Plasma and Brain by Ultra-performance Liquid Chromatography Mass Spectrometry.," Analytical Biochemistry 474:28-34, Elsevier, United States (Jan. 2010).

Altschul, S.F., et al., "Basic Local Alignment Search Tool," Journal of Molecular Biology 215(3):403-410, Elsevier, England (Oct. 1990).

Altschul, S.F., et al., "Gapped BLAST and PSI-BLAST: A New Generation of Protein Database Search Programs," Nucleic Acids Research 25(17):3389-3402, Oxford University Press, England (Sep. 1997).

Antinori, A., et.al., "Updated Research Nosology for HIV-associated Neurocognitive Disorders.," Neurology 69(18):1789-1799, Lippincott Williams & Wilkins, United States (Oct. 2007).

Arnold, R., et.al., "Association Between Calcineurin Inhibitor Treatment and Peripheral Nerve Dysfunction in Renal Transplant Recipients.," American Journal of Transplantation : Official Journal of the American Society of Transplantation and the American Society of Transplant Surgeons 13(9):2426-2432, Wiley-blackwell on Behalf of the American Society of Transplant Surgeons and the American Society of Transplantation, United States (Jul. 2010).

Barclay, R.K., et.al., "Effects of 6-diazo-5-oxol-norleucine and Other Tumor Inhibitors on the Biosynthesis of Nicotinamide Adenine Dinucleotide in Mice.," Cancer research 26(2):282-286, American Association for Cancer Research, United States (Feb. 1966).

Berge, S.M., et al., "Pharmaceutical Salts," Journal of Pharmaceutical Sciences 66(1):1-19, Wiley, United States (Jan. 1977).

Bestard, O., et.al., "Costimulatory Blockade With Mtor Inhibition Abrogates Effector T-cell Responses Allowing Regulatory T-cell Survival in Renal Transplantation.," Transplant International : Official Journal of the European Society for Organ Transplantation 24(5):451-460, Blackwell Pub, England (May 2011).

Borjabad, A., et.al., "Significant Effects of Antiretroviral Therapy on Global Gene Expression in Brain Tissues of Patients With HIV-1-associated Neurocognitive Disorders.," Plos Pathogens 7(9):e1002213, Public Library of Science, United States (Sep. 2011).

Buzzai, M., et.al., "Systemic Treatment With the Antidiabetic Drug Metformin Selectively Impairs P53-deficient Tumor Cell Growth.," Cancer Research 67(14):6745-6752, American Association for Cancer Research, United States (Jul. 2007).

Cao, X., et.al., "Astrocyte-derived Atp Modulates Depressive-like Behaviors.," Nature Medicine 19(6):773-777, Nature Publishing Company, United States (Jun. 2013).

Carr, E.L., et.al., "Glutamine Uptake and Metabolism Are Coordinately Regulated by Erk/mapk During T Lymphocyte Activation.," Journal of Immunology (Baltimore, Md. : 1950) 185(2):1037-1044, American Association of Immunologists, United States (Jul. 2010).

Cervantes-Madrid, D., et al., "Reviving Lonidamine and 6-Diazo-5-oxo-L-norleucine to be used in Combination for Metabolic Cancer Therapy," BioMed Research International 2015:690492, Hindawi Pub. Co, United States (2015).

Cham, C.M and Gajewski, T.F, "Glucose Availability Regulates IFN-gamma Production and p70S6 Kinase Activation in CD8+ Effector T Cells," Journal of Immunology (Baltimore, Md. : 1950) 174(8):4670-4677, American Association of Immunologists, United States (Apr. 2005).

Cham, C.M., et.al., "Glucose Deprivation Inhibits Multiple Key Gene Expression Events and Effector Functions in Cd8+ T Cells.," European Journal of Immunology 38(9):2438-2450, Wiley-vch, Germany (Sep. 2008).

Chambers, J.W., et al., "Glutamine Metabolism is Essential for Human Cytomegalovirus Infection," Journal of Virology 84(4):1867-1873, American Society For Microbiology, United States (Feb. 2010).

Chang, L., et al., "Persistent Brain Abnormalities in Antiretroviral-naive HIV Patients 3 Months after HAART," Antiviral Therapy 8(1):17-26, International Medical Press, England (Feb. 2003).

Chapman, A.P., "PEGylated Antibodies and Antibody Fragments for Improved Therapy: a Review," Advanced Drug Delivery Reviews 54(4):531-545, Elsevier Science Publishers, Netherlands (Jun. 2002).

Chen, S.H., et al., "Gene Therapy for Brain Tumors: Regression of Experimental Gliomas by Adenovirus-mediated Gene Transfer in Vivo," Proceedings of the National Academy of Sciences 91(8):3054-3057, National Academy of Sciences, United States (Apr. 1994 ).

(56) References Cited

OTHER PUBLICATIONS

Cheng, G., et al., "Mitochondria-targeted Drugs Synergize with 2-deoxyglucose to Trigger Breast Cancer Cell Death," Cancer Research 72(10):2634-2644, American Association for Cancer Research, United States (May 2012).

Cheng, G., et al., "Profiling and Targeting of Cellular Bioenergetics: Inhibition of Pancreatic Cancer Cell Proliferation," British Journal of Cancer 111(1):85-93, Nature Publishing Group on behalf of Cancer Research UK, England (Jul. 2014).

Cheong, J.H., et al., "Dual inhibition of tumor energy pathway by 2-Deoxyglucose and Metformin is Effective against a Broad Spectrum of Preclinical Cancer Models," Molecular Cancer Therapeutics 10(12):2350-2362, American Association for Cancer Research, United States (Dec. 2011).

Cinatl, J., et al., "Antiviral Effects of 6-diazo-5-oxo-L-norleucin on Replication of Herpes Simplex Virus Type 1," Antiviral Research 33(3):165-175, Elsevier, Netherlands (Feb. 1997).

Coffey, G.L., et al., "6-diazo-5-oxo-L-norleucine, a New Tumor-inhibitory Substance. I. Biologic Studies," Antibiotics & Chemotherapy 6(8):487-497, Washington Institute of Medicine, United States (Aug. 1956).

Coggin, Jr., J.H. and Martin, W. R., "6-Diazo-5-Oxo-l-Norleucine Inhibition of *Escherichia coli*," Journal of Bacteriology 89(5):1348-1353, American Society For Microbiology, United States (May 1965).

Corry, R.J., et al., "Primarily Vascularized Allografts of Hearts in Mice. The Role of H-2D, H-2K, and Non-H-2 Antigens in Rejection," Transplantation 16(4):343-350, Lippincott Williams & Wilkins, United States (Oct. 1973).

Csibi, A., et al., "The mTORC1 Pathway Stimulates Glutamine Metabolism and Cell Proliferation by Repressing SIRT4," Cell 153(4):840-854, Cell Press, United States (May 2013).

Cui, F., et al., "Overexpression of Cathepsin L is Associated with Gefitinib Resistance in Non-small Cell Lung Cancer," Clinical & Translational Oncology 18(7):722-727, Springer Italia, Italy (Jul. 2016).

Cunningham-Rundles, C., et al., "Biological Activities of Polyethyleneglycol Immunoglobulin Conjugates. Resistance to Enzymatic Degradation," Journal of Immunological Methods 152(2):177-190, Elsevier, Netherlands (Aug. 1992).

Crutchlow, M.F. and Bloom, R.D., "Transplant-Associated Hyperglycemia: A New Look at an Old Problem," Clinical Journal of the American Society of Nephrology 2(2):343-355, American Society of Nephrology, United States (Mar. 2007).

Dickens, A.M., et al., "Cerebrospinal Fluid Metabolomics Implicate Bioenergetic Adaptation as a Neural Mechanism Regulating Shifts in Cognitive States of HIV-infected Patients," AIDS 29(5):559-569, Lippincott Williams & Wilkins, England (Mar. 2015).

Darmaun, D., et al., "Phenylbutyrate-induced Glutamine Depletion in Humans: Effect on Leucine Metabolism," The American Journal of Physiology 274(5pt1):E801-E807, American Physiological Society, United States (May 1998).

Deberardinis, R.J. and Cheng, T., "Q's Next: the Diverse Functions of Glutamine in Metabolism, Cell Biology and Cancer," Oncogene 29(3):313-324, Nature Publishing Group, England (Jan. 2010).

Delgoffe, G.M., et al., "The Kinase mTOR Regulates the Differentiation of Helper T Cells Through the Selective Activation of Signaling by mTORCI and mTORC2," Nature Immunology 12(4):295-303, Nature America Inc, United States (Apr. 2011).

Delgoffe, G.M., et al., "The mTOR Kinase Differentially Regulates Effector and Regulatory T Cell Lineage Commitment," Immunity 30(6):832-844, Cell Press, United States (Jun. 2009).

Dewald, H.A.and Alexander M.M., "6-diazo-5-oxo-L-norleucine, a New Tumor-inhibitory Substance. Preparation of L-, D- and Dl-forms," Journal of the American Chemical Society 80(15):3941-3945, (Aug. 1958).

Dion, H.W., et al., "6-Diazo-5-oxo-L-norleucine, A New Tumor-inhibitory Substance. II. Isolation and Characterization," Journal of the American Chemical Society 78(13):3075-3077, (Jul. 1956).

Dolan, D.E. and Gupta, S., "PD-1 Pathway Inhibitors: Changing the Landscape of Cancer Immunotherapy," Cancer Control 21(3):231-237, Sage Publishing, United States (Jul. 2014).

Dranoff, G., et al., "Combination Chemotherapy in Vitro Exploiting Glutamine Metabolism of Human Glioma and Medulloblastoma," Cancer Research 45(9):4082-4086, American Association for Cancer Research, United States (Sep. 1985).

Dranoff, G., et al., "Influence of Glutamine on the Growth of Human Glioma and Medulloblastoma in Culture," Cancer Research 45(9):4077-4081, American Association for Cancer Research, United States (Sep. 1985).

Eagan, R.T., et al., "Phase II Study on DON in Patients with Previously Treated Advanced Lung Cancer," Cancer Treatment Reports 66(8):1665-1666, National Cancer Institute, United States (Aug. 1982).

Earhart, R.H., et al., "Phase I Trial of 6-diazo-5-oxo-L-norleucine (DON) Administered by 5-day Courses," Cancer Treatment Reports 66(5):1215-1217, National Cancer Institute, United States (May 1982).

Earhart, R.H., et al., "Phase II Trial of 6-diazo-5-oxo-L-norleucine Versus Aclacinomycin-a in Advanced Sarcomas and Mesotheliomas," Investigational New Drugs 8(1):113-119, Springer, United States (Feb. 1990).

Ellis, R., et al., "HIV and Antiretroviral Therapy in the Brain: Neuronal Injury and Repair," Nature Reviews. Neuroscience 8(1):33-44, Nature Pub. Group, England (Jan. 2007).

El-Mir, M.Y., et al., "Dimethylbiguanide Inhibits Cell Respiration via an Indirect Effect Targeted on the Respiratory Chain Complex I," The Journal of Biological Chemistry 275(1):223-228, American Society for Biochemistry and Molecular Biology, United States (Jan. 2000).

Engels, E.A., et al., "Spectrum of Cancer Risk among U.S. Solid Organ Transplant Recipients: the Transplant Cancer Match Study," JAMA 306(17):1891-1901, American Medical Association, United States (Nov. 2011).

Eppstein, D.A., et al., "Biological activity of liposome-encapsulated murine interferon gamma is mediated by a cell membrane receptor," Proceedings of the National Academy of Sciences 82(11):3688-3692, National Academy of Sciences, United States (1985).

Erickson, J.W. and Cerione R.A., "Glutaminase: A Hot Spot for Regulation of Cancer Cell Metabolism?," Oncotarget 1(8):734-740, Impact Journals, United States (Dec. 2010).

Eshleman, J.S., et al., "Inhibition of the Mammalian Target of Rapamycin Sensitizes U87 Xenografts to Fractionated Radiation Therapy," Cancer Research 62(24):7291-7297, American Association for Cancer Research, United States (Dec. 2002).

Everall, I., et al., "Cliniconeuropathologic Correlates of Human Immunodeficiency Virus in the Era of Antiretroviral Therapy," Journal of Neurovirology 15(5-6):360-370, Springer, United States (Sep. 2009).

Franciosi, M., et al., "Metformin Therapy and Risk of Cancer in Patients with Type 2 Diabetes: Systematic Review," PloS one 8(8):e71583, Public Library of Science, United States (Aug. 2013).

Kull, F.C., et al., "Mixtures of Quaternary Ammonium Compounds and Long-chain Fatty Acids as Antifungal Agents," Applied Microbiology 9(6):538-541, American Society For Microbiology, United States (Nov. 1961).

Fogal, V., et al., "Mitochondrial p32 is Upregulated in Myc Expressing Brain Cancers and Mediates Glutamine Addiction," Oncotarget 6(2):1157-1170, Impact Journals, United States (Jan. 2015).

Gelman, B.B., et al., "The National NeuroAIDS Tissue Consortium Brain Gene Array: Two Types of HIV-associated Neurocognitive Impairment," PLoS One 7(9):e46178, Public Library of Science, United States (2012).

Grayzel, A.I., et al., "Suppression of Uric Acid Synthesis in the Gouty Human by the Use of 6-diazo-5-oxo-L-norleucine.," The Journal of Clinical Investigation 39:447-454, American Society for Clinical Investigation, United States (Mar. 1960).

Gross, M.I., et al., "Antitumor Activity of the Glutaminase Inhibitor CB-839 in Triple-Negative Breast Cancer," Molecular Cancer Therapeutics 13(4):890-901, American Association for Cancer Research, United States (Apr. 2014).

(56) References Cited

OTHER PUBLICATIONS

Grupp, S.A., et al., "Chimeric Antigen Receptor-Modified T Cells for Acute Lymphoid Leukemia," The New England Journal of Medicine 368(16):1509-1518, Massachusetts Medical Society, United States (Apr. 2013).

Guba, M., et al., "Pro- and Anti-cancer Effects of Immunosuppressive Agents used in Organ Transplantation," Transplantation 77(12):1777-1782, Lippincott Williams & Wilkins, United States (Jun. 2004).

Harding, J.J., et al., "Safety and Tolerability of Increasing Doses of CB-839, a First-in-class, Orally Administered Small Molecule Inhibitor of Glutaminase, in Solid Tumors," Journal of Clinical Oncology 33(15_suppl ):2512, (May 2015).

Harezlak, J., et al., "Persistence of HIV-associated Cognitive Impairment, Inflammation, and Neuronal Injury in Era of Highly Active Antiretroviral Treatment," AIDS 25(5):625-633, Lippincott Williams & Wilkins, England (Mar. 2011).

Hart, R.G., et al., "Neuroprotection Trials in Parkinson's Disease: Systematic Review," Movement Disorders 24(5):647-654, Wiley-Liss, United States (Apr. 2009).

Hausch, F., et al., "Design, Synthesis, and Evaluation of Gluten Peptide Analogs as Selective Inhibitors of Human Tissue Transglutaminase," Chemistry & Biology 10(3):225-231, Elsevier, United States (Mar. 2003).

Heaton, R.K., et al., "HIV-associated Neurocognitive Disorders Before and During the Era of Combination Antiretroviral Therapy: Differences in Rates, Nature, and Predictors," Journal of Neurovirology 17(1):3-16, Springer, United States (Feb. 2011).

Heaton, R.K., et al., "HIV-associated Neurocognitive Disorders Persist in the Era of Potent Antiretroviral Therapy: Charter Study," Neurology 75(23):2087-2096, Lippincott Williams & Wilkins, United States (Dec. 2010).

Henderson, J.M., et al., "Hepatocellular Carcinoma: Mouse Models and the Potential Roles of Proteases," Cancer Letters 387:106-113, Elsevier Science Ireland, Ireland (Feb. 2017).

Hensley, C.T., et al., "Glutamine and Cancer: Cell Biology, Physiology, and Clinical Opportunities," The Journal of Clinical Investigation 123(9):3678-3684, American Society for Clinical Investigation, United States (Sep. 2013).

Hodes, G.E., et al., "Individual Differences in the Peripheral Immune System Promote Resilience Versus Susceptibility to Social Stress," Proceedings of the National Academy of Sciences of the United States of America 111(45):16136-16141, National Academy of Sciences, United States (Nov. 2014).

Hofer, A., et al., "Trypanosoma Brucei CTP Synthetase: a Target for the Treatment of African Sleeping Sickness," Proceedings of the National Academy of Sciences of the United States of America 98(11):6412-6416, National Academy of Sciences, United States (May 2001).

Hollinger, K.R., et al., "Dose-dependent Inhibition of GCPII to Prevent and Treat Cognitive Impairment in the EAE Model of Multiple Sclerosis," Brain Research 1635:105-112, North-Holland Biomedical Press, Netherlands (Mar. 2016).

Hoorn, E.J., et al., "Pathogenesis of Calcineurin Inhibitor-induced Hypertension," Journal of Nephrology 25(3):269-275, Springer, Italy (May-Jun. 2012).

Hu, X., et al., "Genetic Alterations and Oncogenic Pathways Associated with Breast Cancer Subtypes," Molecular Cancer Research 7(4):511-522, American Association for Cancer Research, United States (Apr. 2009).

Hutchinson, J.A., et al., "Peptide Hormones and Lipopeptides: from Self-assembly to Therapeutic Applications," Journal of Peptide Science 23(2):82-94, John Wiley & Sons, England (Feb. 2017).

Hwang, K.J., et al., "Hepatic uptake and degradation of unilamellar sphingomyelin/cholesterol liposomes: a kinetic study," Proceedings of the National Academy of Sciences 77(7):4030-4034, National Academy of Sciences, United States (1980).

International Search Report and Written Opinion for International Application No. PCT/US2016/044767, European Patent Office, Netherlands, dated Oct. 31, 2016, 9 pages.

International Search Report and Written Opinion for International Application No. PCT/US2016/044810, European Patent Office, Netherlands, dated Dec. 5, 2016, 10 pages.

International Search Report and Written Opinion for International Application No. PCT/US2016/044825, European Patent Office, Netherlands, dated Dec. 5, 2016, 10 pages.

Jacobs, S.R., et al., "Glucose Uptake is Limiting in T Cell Activation and Requires CD28-Mediated Akt-Dependent and Independent Pathways," Journal of Immunology 180(7):4476-4486, American Association of Immunologists, United States (Apr. 2008).

Jones, R.G. and Thompson, C.B., "Revving the Engine: Signal Transduction Fuels T Cell Activation," Immunity 27(2):173-178, Cell Press, United States (Aug. 2007).

Karlin, S. and Altschul, S.E., "Methods for Assessing the Statistical Significance of Molecular Sequence Features by using General Scoring Schemes," Proceedings of the National Academy of Sciences USA 87(6):2264-2268, National Academy of Sciences, United States (Mar. 1990).

Karlin, S, and Altschul, S.F., "Applications and Statistics for Multiple High-scoring Segments in Molecular Sequences," Proceedings of the National Academy of Sciences USA 90(12):5873-5877, National Academy of Sciences, United States (Jun. 1993).

Kaul, M., et al., "HIV-1 Infection and AIDS: Consequences for the Central Nervous System," Cell Death and Differentiation 12 Suppl 1:878-892, Nature Publishing Group, England (Aug. 2005).

Konopleva., et al., "Phase 1 study: Safety and tolerability of increasing doses of cb-839, an orally-administered small molecule inhibitor of glutaminase," In Acute Leukemia, Haematologica (2015).

Kovach, J.S., et al., "Phase I and Pharmacokinetic Studies of DON," Cancer Treatment Reports 65(11-12):1031-1036, National Cancer Institute, United States (Nov.-Dec. 1981).

Krishnan, V., et al., "Molecular Adaptations Underlying Susceptibility and Resistance to Social Defeat in Brain Reward Regions," Cell 131(2):391-404, Cell Press, United States (Oct. 2007).

Lagodzinski, Z., et al., "Effect of FK506 and Cyclosporine on Primary and Secondary Skin Allograft Survival in Mice," Immunology 71(1):148-150, Blackwell Scientific Publications, England (Sep. 1990).

Langer, R., et al., "Biocompatibility of Polymeric Delivery Systems for Macromolecules," Journal of Biomedical Materials Research 15(2):267-277, John Wiley & Sons, Inc., United States (1981).

Le, A., et al., "Glucose-independent Glutamine Metabolism via TCA Cycling for Proliferation and Survival in B Cells," Cell Metabolism 15(1):110-121, Cell Press, United States (Jan. 2012).

Le Maux, P., et al., "Chemical Reactivity of 6-diazo-5-oxo-L-norleucine (DON) Catalyzed by Metalloporphyrins (Fe,Ru)," Tetrahedron 66(25):4462-4468, Elsevier (Jun. 2010).

Lee, M.D., et al., "New Antitumor Antibiotic, LL-D05139 Beta. Fermentation, Isolation, Structure Determination and Biological Activities," The Journal of Antibiotics 40(12):1657-1663, Nature Publishing Group, Japan (Dec. 1987).

Lee, C.F., et al., "Preventing Allograft Rejection by Targeting Immune Metabolism," Cell Reports 13(4):760-770, Cell Press, United States (Oct. 2015).

Lee, Y.Z., et al., "Discovery of Selective Inhibitors of Glutaminase-2, which Inhibit mTORC1, Activate Autophagy and Inhibit Proliferation in Cancer Cells," Oncotarget 5(15):6087-6101, Impact Journals, United States (Aug. 2014).

Lentz, M.R., et al., "Changes in MRS Neuronal Markers and T Cell Phenotypes Observed During Early HIV Infection," Neurology 72(17):1465-1472, Lippincott Williams & Wilkins, United States (Apr. 2009).

Li, Q., et al., "A Central Role for mTOR Kinase in Homeostatic Proliferation Induced CD8+ T Cell Memory and Tumor Immunity," Immunity 34(4):541-553, Cell Press, United States (Apr. 2011).

Li, Y., et al., "Learning and Reconsolidation Implicate Different Synaptic Mechanisms," Proceedings of the National Academy of Sciences of the United States of America 110(12):4798-4803, National Academy of Sciences, United States (Mar. 2013).

Liddy, N., et al., "Monoclonal TCR-redirected Tumor Cell Killing," Nature Medicine 18(6):980-987, Nature Publishing Company, United States (Jun. 2012).

(56) References Cited

OTHER PUBLICATIONS

Lim, J.H., et al., "Targeting Mitochondrial Oxidative Metabolism in Melanoma Causes Metabolic Compensation through Glucose and Glutamine Utilization," Cancer Research 74(13):3535-3545, American Association for Cancer Research, United States (Jul. 2014).

Liu, W., et al., "Reprogramming of Proline and Glutamine Metabolism Contributes to the Proliferative and Metabolic Responses Regulated by Oncogenic Transcription Factor c-MYC," Proceedings of the National Academy of Sciences of the United States of America 109(23):8983-8988, National Academy of Sciences, United States (Jun. 2012).

Lo, Y.C., et al., "Insight into the Role of mTOR and Metabolism in T Cells Reveals New Potential Approaches to Preventing Graft Rejection," Current Opinion in Organ Transplantation 19(4):363-371, Lippincott Williams & Wilkins, United States (Aug. 2014).

Stupp, R., et al., "Effects of Radiotherapy with Concomitant and Adjuvant Temozolomide Versus Radiotherapy Alone on Survival in Glioblastoma in a Randomised Phase III Study: 5-year Analysis of the EORTC-NCIC Trial," The Lancet. Oncology 10(5):459-466, Lancet Pub. Group, England (May 2009).

Lynch, G., et al., "Phase II Evaluation of DON (6-diazo-5-oxo-L-norleucine) in Patients with Advanced Colorectal Carcinoma," American Journal of Clinical Oncology 5(5):541-543, Lippincott Williams & Wilkins, United States (Oct. 1982).

Macintyre, A.N., et al., "The Glucose Transporter Glut1 is Selectively Essential for CD4 T Cell Activation and Effector Function," Cell Metabolism 20(1):61-72, Cell Press, United States (Jul. 2014).

Maciver, N.J., et al., "Metabolic Regulation of T Lymphocytes," Annual Review of Immunology 31:259-283, Annual Reviews Inc, United States (2013).

Magill, G.B. and Myers, W.P., "Alterations in Calcium Metabolism in Cancer Patients Treated with 6-diazo-5-oxo-L-norleucine," Proceedings of the Society for Experimental Biology and Medicine 93(2):314-318, Blackwell Science, United States (Nov. 1956).

Magill, G.B., et al., "Pharmacological and Initial Therapeutic Observations on 6-diazo-5-oxo-l-norleucine (DON) in Human Neoplastic Disease," Cancer 10(6):1138-1150, Wiley, United States (Nov.-Dec. 1957).

Mcarthur, J.C., et al., "Human Immunodeficiency Virus-associated Neurocognitive Disorders: Mind the Gap," Annals of Neurology 67(6):699-714, Wiley-Liss, United States (Jun. 2010).

Mcdermott, L.A., et al., "Design and Evaluation of Novel Glutaminase Inhibitors," Bioorganic & Medicinal Chemistry 24(8):1819-1839, Elsevier Science, England (Apr. 2016).

Mcgaugh, J.L., "Memory—a Century of Consolidation," Science 287(5451):248-251, American Association for the Advancement of Science, United States (Jan. 2000).

Medina, M.A., et al., "Relevance of Glutamine Metabolism to Tumor Cell Growth," Molecular and Cellular Biochemistry 113(1):1-15, Springer, Netherlands (Jul. 1992).

Michalek, R.D., et al., "Cutting Edge: Distinct Glycolytic and Lipid Oxidative Metabolic Programs are Essential for Effector and Regulatory CD4+ T Cell Subsets," Journal of Immunology 186(6):3299-3303, American Association of Immunologists, United States (Mar. 2011).

Nakaya, M., et al., "Inflammatory T Cell Responses Rely on Amino Acid Transporter ASCT2 Facilitation of Glutamine Uptake and mTORC1 Kinase Activation," Immunity 40(5):692-705, Cell Press, United States (May 2014).

Nedelcovych, M.T., et al., "N-(Pivaloyloxy)alkoxy-carbonyl Prodrugs of the Glutamine Antagonist 6-Diazo-5-oxo-L-norleucine (DON) as a Potential Treatment for HIV Associated Neurocognitive Disorders," Journal of Medicinal Chemistry 60(16):7186-7198, American Chemical Society, United States (Aug. 2017).

Ngiow, S.F., et al., "Prospects for TIM3-Targeted Antitumor Immunotherapy," Cancer Research 71(21):6567-6571, American Association for Cancer Research, United States (Nov. 2011).

Nishio, M., et al., "Antiviral Effect of 6-diazo-5-oxo-L-norleucine, Antagonist of Gamma-glutamyl Transpeptidase, on Replication of Human Parainfluenza Virus Type 2," The Journal of General Virology 71( Pt 1):61-67, Microbiology Society, England (Jan. 1990).

Oberhuber, R., et al., "Murine Cervical Heart Transplantation Model using a Modified Cuff Technique," Journal of Visualized Experiments 92:e50753, MYJoVE Corporation, United States (Oct. 2014).

Oderup, C., et al., "Costimulation Blockade-Induced Cardiac Allograft Tolerance: Inhibition of T Cell Expansion and Accumulation of Intragraft cD4+Foxp3+ T Cells," Transplantation 82(11):1493-1500, Lippincott Williams & Wilkins, United States (Dec. 2006).

Online Mendelian Inheritance in Man, OMIM as of [retrieved on May 1, May 1, 2010]. World Wide Web Retrieved from the Internet: (URL: http://www.ncbi.nlm.nih.gov/omim/ and m OnlineMendelianInheritance in Animals (OMIA) at http://omia.angis.org.au/contact.shtml).

Ostrom, Q.T., et al., "CBTRUS Statistical Report: Primary Brain and Central Nervous System Tumors Diagnosed in the United States in 2008-2012," Neuro-oncology 17(Suppl 4):iv1-iv62, Oxford University Press, England (Oct. 2015).

Ovejera, A.A., et al., "Efficacy of 6-diazo-5-oxo-L-norleucine and N-[N-gamma-glutamyl-6-diazo-5-oxo-norleucinyl]-6-diazo-5-oxo-norleucine against Experimental Tumors in Conventional and Nude Mice," Cancer Research 39(8):3220-3224, American Association for Cancer Research, United States (Aug. 1979).

Pawlik, T.M., et al., "Hepatic Glutamine Transporter Activation in Burn Injury: Role of Amino Acids and Phosphatidylinositol-3-kinase," American Journal of Physiology. Gastrointestinal and Liver Physiology 278(4):G532-G541, American Physiological Society, United States (Apr. 2000).

Pearce, E.L., et al., "Fueling Immunity: Insights into Metabolism and Lymphocyte Function," Science 342(6155):1242454, American Association for the Advancement of Science, United States (Oct. 2013).

Pilon, C.B., et al., "Administration of Low Doses of IL-2 Combined to Rapamycin Promotes Allogeneic Skin Graft Survival in Mice," American Journal of Transplantation 14(12):2874-2882, Wiley-Blackwell, United States (Dec. 2014).

Pollizzi, K.N. and Powell, J.D., "Integrating Canonical and Metabolic Signalling Programmes in the Regulation of T Cell Responses," Nature Reviews. Immunology 14(7):435-446, Nature Pub. Group, England (Jul. 2014).

Potter, M.C., et al., "Neurological Sequelae Induced by Alphavirus Infection of the CNS are Attenuated by Treatment with the Glutamine Antagonist 6-diazo-5-oxo-l-norleucine," Journal of Neurovirology 21(2):159-173, Stockton Press, United States (Apr. 2015).

Potter, M.C., et al., "Targeting the Glutamatergic System for the Treatment of HIV-associated Neurocognitive Disorders," Journal of Neuroimmune Pharmacology 8(3):594-607, Springer Science, United States (Jun. 2013).

Powell, J.D. and Zheng, Y., "Dissecting the Mechanism of T-cell Anergy with Immunophilin Ligands," Current Opinion in Investigational Drugs 7(11):1002-1007, Thomson Reuters, England (Nov. 2006).

Powell, J.D., et al., "A Modified Model of T-Cell Differentiation Based on mTOR Activity and Metabolism," Cold Spring Harbor Symposia on Quantitative Biology 78(1):125-130, Cold Spring Harbor Laboratory Press, United States (2013).

Powell, J.D., et al., "A2ar Antagonists: Next Generation Checkpoint Blockade for Cancer Immunotherapy," Computational and Structural Biotechnology Journal 13:265-272, Elsevier B.V, Netherlands (Apr. 2015).

Pugh, C.R., et al., "Selective Effects of Peripheral Lipopolysaccharide Administration on Contextual and Auditory-cue Fear Conditioning," Brain, Behavior, and Immunity 12(3):212-229, Elsevier, Netherlands (Sep. 1998).

Raez, L.E., et al., "A Phase I Dose-escalation Trial of 2-deoxy-d-glucose Alone or Combined with Docetaxel in Patients with Advanced Solid Tumors," Cancer Chemotherapy and Pharmacology 71(2):523-530, Springer Verlag, Germany (Feb. 2013).

Rahman, A., et al., "Phase I Study and Clinical Pharmacology of 6-diazo-5-oxo-L-norleucine (DON)," Investigational New Drugs 3(4):369-374, Springer, United States (1985).

(56) References Cited

OTHER PUBLICATIONS

Rahn, K.A., et al., "Inhibition of Glutamate Carboxypeptidase II (GCPII) Activity as a Treatment for Cognitive Impairment in Multiple Sclerosis," Proceedings of the National Academy of Sciences of the United States of America 109(49):20101-20106, National Academy of Sciences, United States (Dec. 2012).

Rais, R., et al., "Discovery of 6-diazo-5-oxo-L-norleucine (DON) Prodrugs with Enhanced CSF Delivery in Monkeys: a Potential Treatment for Glioblastoma," Journal of Medicinal Chemistry 59(18):8621-8633, American Chemical Society, United States (Sep. 2016).

Rautio, J., et al., "Prodrugs: Design and Clinical Applications," Nature Reviews. Drug Discovery 7(3):255-270, Nature Publishing Group, England (Mar. 2008).

Reitzer, L.J., et al., "Evidence that Glutamine, not Sugar, is the Major Energy Source for Cultured HeLa Cells," The Journal of Biological Chemistry 254(8):2669-2676, American Society for Biochemistry and Molecular Biology, United States (Apr. 1979).

Robertson, K.R., et al., "The Prevalence and Incidence of Neurocognitive Impairment in the HAART Era," AIDS 21(14):1915-1921, Lippincott Williams & Wilkins, England (Sep. 2007).

Roodnat, J.I., et al., "15-year Follow-up of a Multicenter, Randomized, Calcineurin Inhibitor withdrawal Study in Kidney Transplantation," Transplantation 98(1):47-53, Lippincott Williams & Wilkins, United States (Jul. 2014).

Rowe, I., et al., "Defective Glucose Metabolism in Polycystic Kidney Disease Identifies a New Therapeutic Strategy," Nature Medicine 19(4):488-493, Nature Publishing Company, United States (Apr. 2013).

Roybal, K., et al., "Mania-like Behavior Induced by Disruption of CLOCK," Proceedings of the National Academy of Sciences of the United States of America 104(15):6406-6411, National Academy of Sciences, United States (Apr. 2007).

Ru, P., et al., "Tumor Metabolism of Malignant Gliomas," Cancers 5(4):1469-1484, MDPI, Switzerland (Dec. 2013).

Rubin, J., et al., "A Phase II Study of 6-diazo-5-oxo-L-norleucine (DON, NSC-7365) in Advanced Large Bowel Carcinoma," American Journal of Clinical Oncology 6(3):325-326, Lippincott Williams & Wilkins, United States (Jun. 1983).

Sailasuta, N., et al., "Change in Brain Magnetic Resonance Spectroscopy After Treatment During Acute HIV Infection," PLoS One 7(11):e49272, Public Library of Science, United States (2012).

Satake, A., et al., "Inhibition of Calcineurin Abrogates while Inhibition of mTOR Promotes Regulatory T Cell Expansion and Graft-versus-host Disease Protection by IL-2 in Allogeneic Bone Marrow Transplantation," PLoS One 9(3):e92888, Public Library of Science, United States (Mar. 2014).

Sayegh, M.H., and Carpente, C.B., "Transplantation 50 Years Later—progress, Challenges, and Promises," The New England Journal of Medicine 351(26):2761-2766, Massachusetts Medical Society, United States (Dec. 2004).

Sengupta, S., et al., "Regulation of the mTOR Complex 1 Pathway by Nutrients, Growth Factors, and Stress," Molecular Cell 40(2):310-322, Cell Press, United States (Oct. 2010).

Shah, U., and Hodgson, R., "Recent Progress in the Discovery of Adenosine A(2A) Receptor Antagonists for the Treatment of Parkinson's Disease," Current Opinion in Drug Discovery & Development 13(4):466-480, Thomson Reuters, England (Jul. 2010).

Shi, L.Z., et al., "HIF1alpha-dependent Glycolytic Pathway Orchestrates a Metabolic Checkpoint for the Differentiation of TH17 and Treg Cells," The Journal of Experimental Medicine 208(7):1367-1376, Rockefeller University Press, United States (Jul. 2011).

Shijie, J., et al., "Blockade of Glutamate Release from Microglia Attenuates Experimental Autoimmune Encephalomyelitis in Mice," The Tohoku Journal of Experimental Medicine 217(2):87-92, Tohoku University Medical Library, Japan (Feb. 2009).

Schulze, A. and Harris, A.L., "How Cancer Metabolism is Tuned for Proliferation and Vulnerable to Disruption," Nature 491(7424):364-373, Nature Publishing Group, England (Nov. 2012).

Shelton, L.M., et al., "Glutamine Targeting Inhibits Systemic Metastasis in the VM-M3 Murine Tumor Model," International Journal of Cancer 127(10):2478-2485, International Union Against Cancer, United States (Nov. 2010).

Shukla, K., et al., "Design, Synthesis, and Pharmacological Evaluation of Bis-2-(5-phenylacetamido-1,2,4-thiadiazol-2-yl)ethyl Sulfide 3 (BPTES) Analogs as Glutaminase Inhibitors," Journal of Medicinal Chemistry 55(23):10551-10563, American Chemical Society, United States (Dec. 2012).

Sidman, et al., "Controlled Release of Macromolecules and Pharmaceuticals from Synthetic Polypeptides Based on Glutamic Acid," Biopolymers 22:547-556, John Wiley & Sons, Inc., United States (Jan. 1983).

Simioni, S., et al., "Cognitive Dysfunction in HIV Patients Despite Long-standing Suppression of Viremia," AIDS 24(9):1243-1250, Lippincott Williams & Wilkins, England (Jun. 2010).

Sklaroff, R.B., et al., "Phase I Study of 6-diazo-5-oxo-L-norleucine (DON)," Cancer Treatment Reports 64(12):1247-1251, National Cancer Institute, United States (1980).

Srikanth, K., et al., "Synthesis, Screening and Quantitative Structure-activity Relationship (QSAR) Studies of Some Glutamine Analogues for Possible Anticancer Activity," Bioorganic & Medicinal Chemistry 10(7):2119-2131, Elsevier Science, England (Jul. 2002).

Stupp, R., et al., "Radiotherapy Plus Concomitant and Adjuvant Temozolomide for Glioblastoma," The New England Journal of Medicine 352(10):987-996, Massachusetts Medical Society, United States (Mar. 2005).

Sullivan, M.P., et al., "A Comparison of the Effectiveness of Standard Dose 6-mercaptopurine, Combination 6-mercaptopurine and DON, and High-loading 6-mercaptopurine Therapies in Treatment of the Acute Leukemias of Childhood: Results of a Coperative Study," Cancer Chemotherapy Reports 18:83-95, National Cancer Institute, United States (May 1962).

Sullivan, M.P., et al., "Pharmacokinetic and Phase I Study of Intravenous DON (6-diazo-5-oxo-L-norleucine) in Children," Cancer Chemotherapy Reports 21(1):78-84, Springer Verlag, Germany (1988).

Suzuki, A., et al., "Memory Reconsolidation and Extinction have Distinct Temporal and Biochemical Signatures," The Journal of Neuroscience 24(20):4787-4795, Society for Neuroscience, United States (May 2004).

Tanaka, K., et al., "Compensatory Glutamine Metabolism Promotes Glioblastoma Resistance to mTOR Inhibitor Treatment," The Journal of Clinical Investigation 125(4):1591-1602, American Society for Clinical Investigation, United States (Apr. 2015).

Tarnowski, G.S., and Stock, C.C., "Effects of Combinations of Azaserine and of 6-diazo-5-oxo-L-norleucine with Purine Analogs and Other Antimetabolites on the Growth of Two Mouse Mammary Carcinomas," Cancer Research 17(10):1033-1039, American Association for Cancer Research, United States (Nov. 1957).

Thangavelu, K., et al., "Structural Basis for the Active Site Inhibition Mechanism of Human Kidney-type Glutaminase (KGA)," Scientific Reports 4:3827, Nature Publishing Group, England (Jan. 2014).

Thomas, A.G., et al., "Kinetic Characterization of Ebselen, Chelerythrine and Apomorphine as Glutaminase Inhibitors," Biochemical and Biophysical Research Communications 438(2):243-248, Elsevier, United States (Aug. 2013).

Thomas, A.G., et al., "Small Molecule Glutaminase Inhibitors Block Glutamate Release from Stimulated Microglia," Biochemical and Biophysical Research Communications 443(1):32-36, Elsevier, United States (Jan. 2014).

Thomson, L.M., and Sutherland, R.J., "Systemic Administration of Lipopolysaccharide and Interleukin-1beta have Different Effects on Memory Consolidation," Brain Research Bulletin 67(1-2):24-29, Elsevier Science, United States (Sep. 2005).

Tran, T.Q., et al., "Glutamine Deficiency Induces DNA Alkylation Damage and Sensitizes Cancer Cells to Alkylating Agents through Inhibition of ALKBH Enzymes," PLoS Biology 15(11):e2002810, Public Library of Science, United States (Nov. 2017).

Tsilidis, K.K., et al., "Metformin does not Affect Cancer Risk: A Cohort Study in the U.K. Clinical Practice Research Datalink

(56) References Cited

OTHER PUBLICATIONS

Analyzed like an Intention-to-Treat Trial," Diabetes Care 37(9):2522-2532, American Diabetes Association, United States (Sep. 2014).
Ueki, N., et al., "Synthesis and Preclinical Evaluation of a Highly Improved Anticancer Prodrug Activated by Histone Deacetylases and Cathepsin L," Theranostics 6(6):808-816, Ivyspring International Publisher, Australia (Mar. 2016).
Upadhyay, R.K., "Drug Delivery Systems, CNS Protection, and the Blood Brain Barrier," BioMed Research International 2014:869269, Hindawi Pub. Co, United States (2014).
Vander Heiden, M.G., et al., "Understanding the Warburg Effect: The Metabolic Requirements of Cell Proliferation," Science 324(5930):1029-1033, American Association for the Advancement of Science, United States (May 2009).
Varoqui, H., et al., "Cloning and Functional Identification of a Neuronal Glutamine Transporter," The Journal of Biological Chemistry 275(6):4049-4054, American Society for Biochemistry and Molecular Biology, United States (Feb. 2000).
Waickman, A.T., and Powell, J.D., "mTOR, Metabolism, and the Regulation of T-cell Differentiation and Function," Immunological Reviews 249(1):43-58, Blackwell, England (Sep. 2012).
Wang, R., et al., "The Transcription Factor Myc Controls Metabolic Reprogramming upon T Lymphocyte Activation," Immunity 35(6):871-882, Cell Press, United States (Dec. 2011).
Warburg, O., "On Respiratory Impairment in Cancer Cells," Science 124(3215):269-270, American Association for the Advancement of Science, United States (Aug. 1956).
Weller, M., et al., "EANO Guideline for the Diagnosis and Treatment of Anaplastic Gliomas and Glioblastoma.," The Lancet. Oncology 15(9):e395-403, Lancet Pub. Group, England (Aug. 2014).
Willems, L., et al., "Inhibiting Glutamine Uptake Represents an Attractive New Strategy for Treating Acute Myeloid Leukemia," Blood 122(20):3521-3532, American Society of Hematology, United States (Nov. 2013).
Willis, R.C. and Seegmiller, J.E., "The Inhibition by 6-diazo-5-oxo-L-norleucine of Glutamine Catabolismof the Cultured Human Lymphoblast," Journal of Cellular Physiology 93(3):375-382, Wiley-Liss, United States (Dec. 1977).
Windmueller, H.G. and Spaeth, A.E., "Uptake and Metabolism of Plasma Glutamine by the Small Intestine," The Journal of Biological Chemistry 249(16):5070-5079, American Society for Biochemistry and Molecular Biology, United States (Aug. 1974).
Wise, D.R. and Thompson, C.B., "Glutamine Addiction: a New Therapeutic Target in Cancer," Trends in Biochemical Sciences 35(8):427-433, Elsevier Trends Journals, England (Aug. 2010).
Wise, D.R., et al., "Myc Regulates a Transcriptional Program that Stimulates Mitochondrial Glutaminolysis and Leads to Glutamine Addiction," Proceedings of the National Academy of Sciences of the United States of America 105(48):18782-18787, National Academy of Sciences, United States (Dec. 2008).
Wook Koo, J., et al., "Essential Role of Mesolimbic Brain-Derived Neurotrophic Factor in Chronic Social Stress-InducedDepressive Behaviors," Biological Psychiatry 80(6):469-478, Elsevier, United States (Sep. 2016).
Wu, T., et al., "Immunosuppressive Drugs on Inducing Ag-specific CD4(+)CD25(+)Foxp3(+) Treg Cells During Immune Response in Vivo," Transplant Immunology 27(1):30-38, Elsevier, Netherlands (Aug. 2012).
Yamasaki, T., et al., "Exploring a Glycolytic Inhibitor for the Treatment of an FH-deficient Type-2 Papillary RCC," Nature Reviews. Urology 8(3):165-171, Nature Pub. Group, England (Mar. 2011).
Yang, K. and Chi, H., "mTOR and Metabolic Pathways in T Cell Quiescence and Functional Activation," Seminars in Immunology 24(6):421-428, Academic Press, England (Dec. 2012).
Zgodka, D., et al., "A Diffusible Analogue of N3-(4-methoxyfumaroyl)-1-2,3-diaminopropanoic Acid With Antifungal Activity," Microbiology 147(Pt 7):1955-1959, (Jul. 2001).
Zhang, W., et al., "Overexpression of Cysteine Cathepsin L Is a Marker of Invasion and Metastasis in Ovarian Cancer," Oncology Reports 31(3):1334-1342, D.A. Spandidos, Greece (Mar. 2014).
Zheng, Y., et al., "Anergic T Cells Are Metabolically Anergic," Journal of Immunology 183(10):6095-6101, American Association of Immunologists, United States (Nov. 2009).
Zimmermann, S.C., et al., "N-substituted Prodrugs of Mebendazole Provide Improved Aqueous Solubility and Oral Bioavailability in Mice and Dogs," Journal of Medicinal Chemistry 61(9):3918-3929, American Chemical Society, United States (May 2018).
Zink, M.C, "Translational Research Models and Novel Adjunctive Therapies for NeuroAIDS," Journal of Neuroimmune Pharmacology 2(1):14-19, Springer Science + Business Media, United States (Mar. 2007).
Office Action dated Dec. 14, 2018, for co-pending U.S. Appl. No. 15/885,147, filed Jan. 31, 2018, U.S. Patent and Trademark Office, Alexandria, Virginia.
Daye, D., et al., "Metabolic reprogramming in cancer: Unraveling the role of glutamine in tumorigenesis," Seminars in Cell & Developmental Biology 23:362-369, Elsevier Ltd., (2012).
Ostroukhova, M., et al., "Switching of Glucose Metabolism from Oxidative Phosphorylation to Aerobic Glycolysis (the Warburg Effect) in T-Cells from Patients with Asthma," J Allergy Clin Immunol 125 (Issue 2, Supplement 1) p. AB39, abstract 155 (2010).
Extended European Search Report, European Appl. No. 16833623.8, dated Feb. 12, 2019.
Abo-Ghalia, M, et al., "Synthesis of inhibitors of the meso-diaminopimelate-adding enzyme from *Escherichia coli*", Int. J. Peptide Protein Res. 32:208-222, Munksgaard International Publishers, Copenhagen (1988).
Jancarik, A. "Novel lymphoid targeted prodrugs of the glutamine antagonist DON for the treatment of hematological malignancies", The FASEB Journal, Abstract No. lb472, Published Online: Apr. 1, 2016.
Englert, J. et al., "Abstract 1035: Targeting glutamine metabolism with the novel inhibitor JHU-083 inhibits tumor growth and alters the tumor immune microenvironment", Proceedings: AACR 107th Annual Meeting, New Orleans, LA, American Association for Cancer Research, Apr. 16-20, 2016.
Co-pending U.S. Appl. No. 16/454,853, inventors Slusher et al., filed Jun. 27, 2019 (Not Published).
Office Action dated Aug. 22, 2019, for co-pending U.S. Appl. No. 16/262,476, filed Jan. 30, 2019, U.S. Patent and Trademark Office, Alexandria, Virginia.
Office Action dated Jan. 3, 2020 for co-pending U.S. Appl. No. 16/262,476, filed Jan. 30, 2019, U.S. Patent and Trademark Office, Alexandria, Virginia.
Leone, R. D. et al., "A2aR antagonists: Next generation checkpoint blockade for cancer immunotherapy," Computational and Structural Biotechnology Journal 13:265-272, Elsevier B.V., Netherlands (2015).
Liwschitz, Y. et al., "Diazo-ketones with Potential Tumour-inhibitory Properties derived from L-Aspartic and L-Glutamic Acids," J. Chem. Soc. (C) 223-225, Royal Society of Chemistry, England (1971).
Noonan, K. et al., "Phase I/II Study of Marrow Infiltrating Lymphocytes (MILs) Generates Measurable Myeloma-Specific Immunity in the Autologous Stem Cell Transplant (SCT) Setting," Blood 118:997, The American Society of Hematology, United States (2011).
Simplicio, A. L. et al., "Prodrugs for Amines," Molecules 13:519-547, MDPI, Switzerland (2008).
Sznol M. and Chen, L., "Antagonist Antibodies to PD-1 and B7-H1 (PD-L1) in the Treatment of Advanced Human Cancer," Clin Cancer Res 19:1021-1034, American Association for Cancer Research, United States (2013).

|     | DON    | 25     | Normal Range    |
| --- | ------ | ------ | --------------- |
| WBC | 1.06   | 1.07   | 4.45-13.96 K/uL |
| Hgb | 11.80  | 13.87  | 10.8-19.2 g/dL  |
| Plt | 315.67 | 715.33 | 841-2159 K/uL   |

N = 3 mice per group

FIG. 15

|  | DON (n=2) | 25 (n=3) | Normal Range |
|---|---|---|---|
| AST | 158 | 94 | 46-392 U/L |
| ALT | 14 | 22 | 28-129 U/L |
| ALP | 70 | 143 | 111-275 U/L |
| GGT | 7 | 5 | 0-8 U/L |
| Tprot | 3.9 | 4.7 | 4.8-7.0 g/dL |
| Albumin | 2.3 | 3.4 | 2.8-3.8 g/dL |
| Creatinine | 0.30 | 0.30 | 0.2-0.5 mg/dL |
| Calcium | 8.6 | 8.5 | 9.7-12.5 mg/dL |
| BUN | 26 | 21 | 7-28 mg/dL |
| Tbili | 0.7 | 0.3 | 0.2-0.6 mg/dL |
| Glucose | 228 | 391 | 172-372 mg/dL |

FIG. 16

|  | Induction and Maintenance | BID Dosing | Reference |
|---|---|---|---|
| WBC | 11.25 | 11.19 | 4.45-13.96 K/uL |
| Hgb | 14.73 | 14.57 | 10.8-19.2 g/dL |
| Plt | 1567.00 | 1193.67 | 841-2159 K/uL |

N = 3 mice per group

Induction Maintenance dosing: 1.0 mg daily for 5 days followed by 0.3 mg daily for 9 days
BID Dosing: 0.1 mg PO BID for 14 days

FIG. 19A

|  | Induction then 0.1 mg/kg/day | Induction then 0.4 mg/kg/day | Reference |
|---|---|---|---|
| WBC | 10.16 | 8.36 | 4.45-13.96 K/uL |
| Hgb | 13.73 | 13.90 | 10.8-19.2 g/dL |
| Plt | 1040.67 | 1166.00 | 841-2159 K/uL |

N = 3 mice per group

Mice evaluated after 10 days of induction and 38 days of maintenance therapy on Compound 25

FIG. 19B

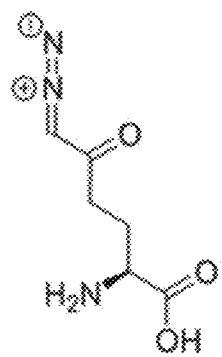
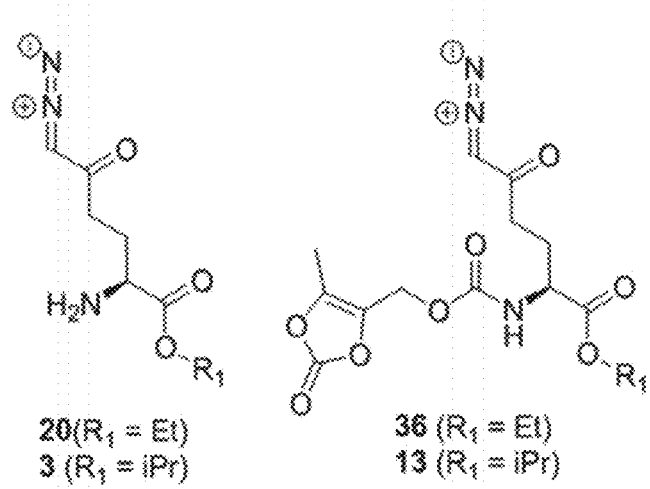
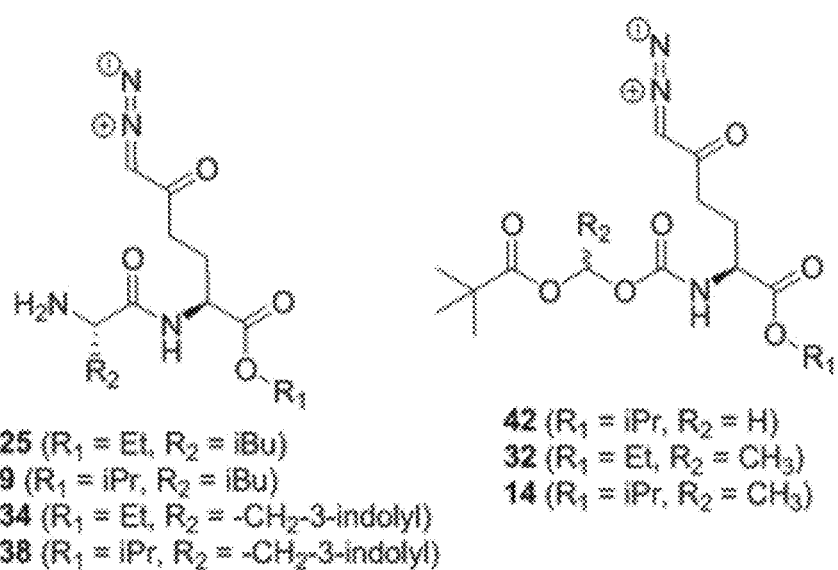
FIG. 20

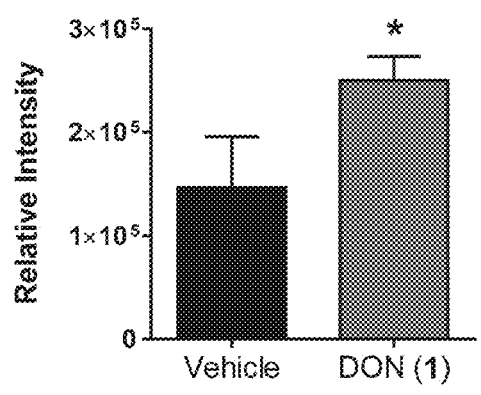
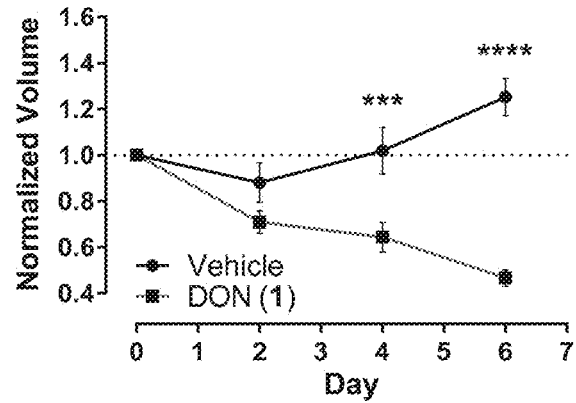
FIG. 21A  FIG. 21B

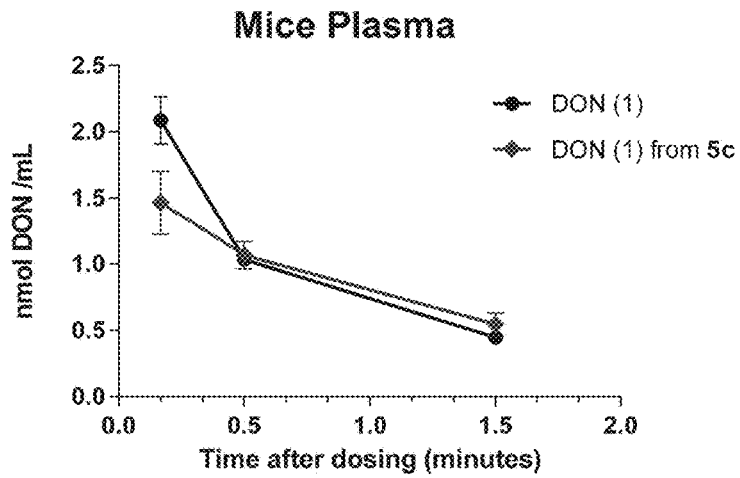
FIG. 22A
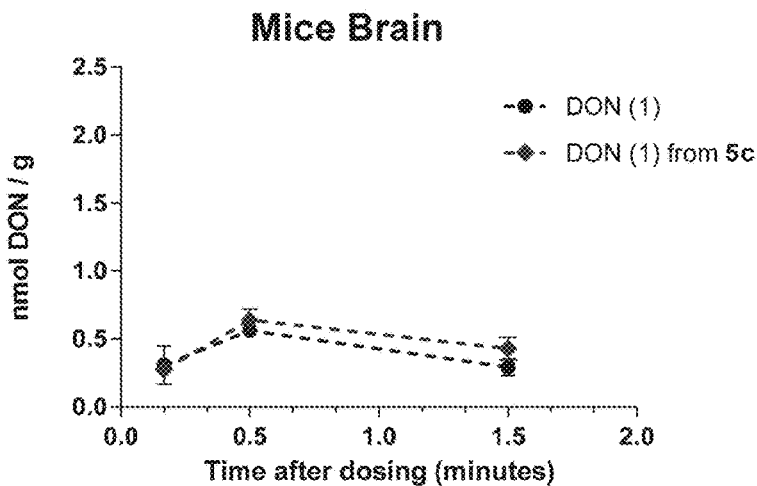
FIG. 22B
| Compound Dosed | Dose (mg/kg equiv) | Tissue | DON $C_{max}$ (nmol/mL or nmol/g) | DON $T_{max}$ (hr) | DON $AUC_{0-t}$ (hr*nmol/mL or hr*nmol/g) | Brain to plasma ratio |
|---|---|---|---|---|---|---|
| DON (1) | 0.8 | Plasma | 2.2 | 0.17 | 1.25 | 0.46 |
| | | Brain | 0.56 | 0.50 | 0.57 | |
| 5c | 0.8 | Plasma | 1.5 | 1.50 | 1.22 | 0.57 |
| | | Brain | 0.64 | 30 | 0.69 | |
FIG. 22C

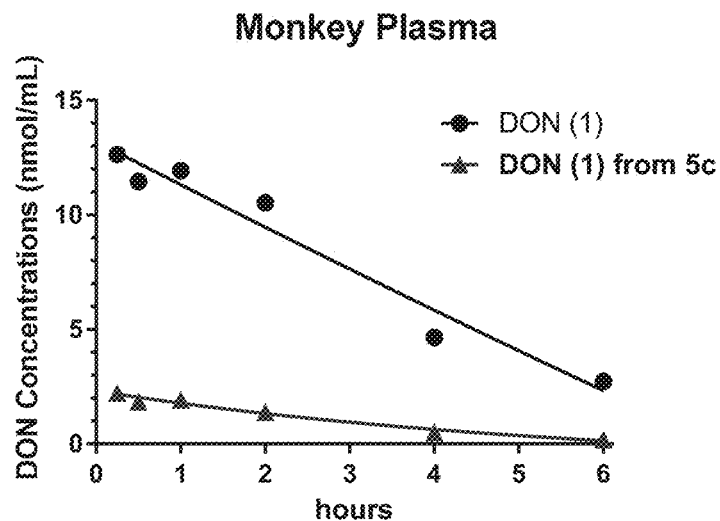
FIG. 23A
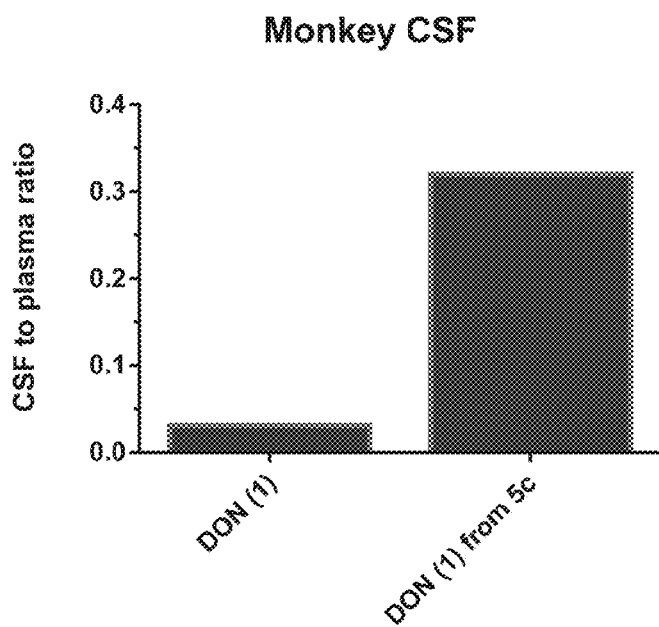
FIG. 23B
| Compound Dosed | Dose (mg/kg equiv) | DON $C_{max}$ (nmol/mL) | DON $T_{max}$ (hr) | DON $AUC_{0-t}$ (hr*nmol/mL) |
|---|---|---|---|---|
| 1 | 1.6 | 12.6 | 0.25 | 42.7 |
| 5c | 1.6 | 2.23 | 0.25 | 5.71 |
FIG. 23C Clinical findings over 5 day observation period

| | DON | | 38 | |
|---|---|---|---|---|
| | Pig 22987 | Pig 23302 | Pig 23172 | Pig 23199 |
| Day 1 | WNL | WNL | WNL | WNL |
| Day 2 | WNL | WNL | WNL | WNL |
| Day 3 | WNL | WNL | WNL | WNL |
| Day 4 | anorexia, lethargy | anorexia, lethargy, no bowel movement | reduced appetite | WNL |
| Day 5 | anorexia, lethargy, mild diarrhea | anorexia, no bowel movement | WNL | reduced appetite |

WNL (within normal limits)
Anorexia = no food consumption

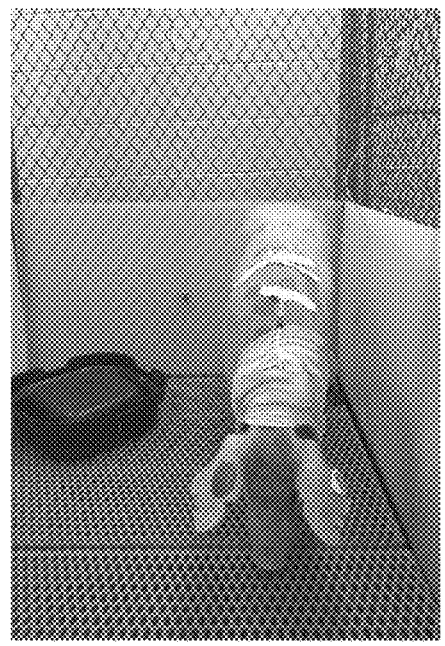

DON TREATED PIG #22987

FIG. 36

- blue ears and snout
- lowered head
- reduced activity in the cage
- reduced social interaction
- diarrhea

DON moderate localized

DON severe generalized

3 normal appearing gastric

3 normal appearing gastric

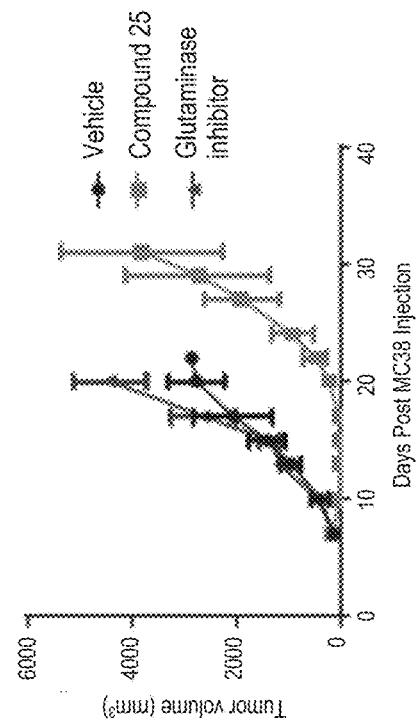
FIG. 41B
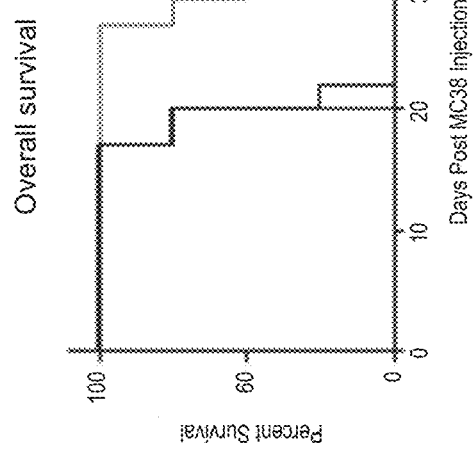
FIG. 41A
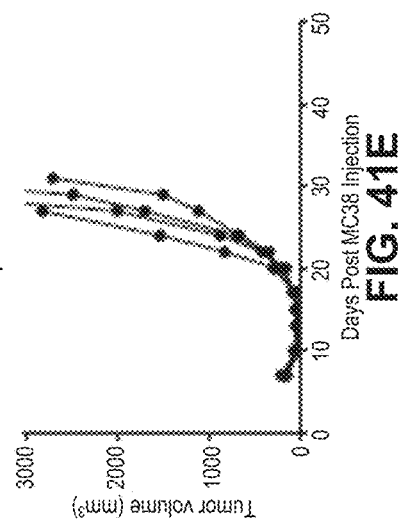
FIG. 41E
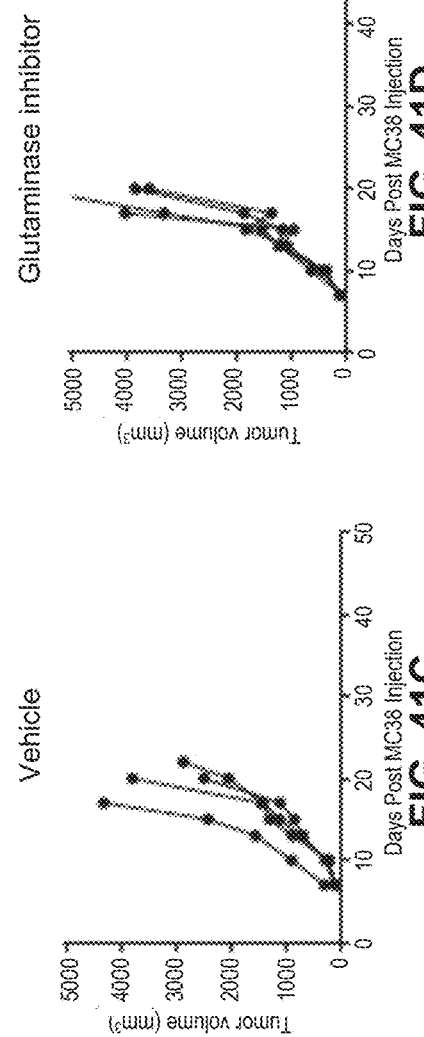
FIG. 41D
FIG. 41C

PRODRUGS OF GLUTAMINE ANALOGS

CROSS-REFERENCE TO RELATED APPLICATIONS

This application is a divisional application claiming priority to U.S. application Ser. No. 16/454,853, filed Jun. 27, 2019, which is a divisional application claiming priority to U.S. application Ser. No. 15/885,258, filed Jan. 31, 2018, which is a continuation-in-part of PCT/US2016/044767, filed Jul. 29, 2016, that claims the benefit of U.S. Provisional Application No. 62/199,566, filed Jul. 31, 2015, the contents of each of which are incorporated herein by reference in its entirety.

BACKGROUND

The prodrug approach is a well-established strategy to improve physicochemical, biopharmaceutic and pharmacokinetic properties of potential drug molecules. Approximately 5-7% of drugs approved worldwide are prodrugs with annual sales in 2013 of $11.2 billion. Most prodrugs are simple chemical derivatives of the original molecule. Ester prodrugs, the most common prodrugs, constitute 49% of all marketed prodrugs. Reasons for the popularity of ester prodrugs include their generally straight forward synthesis, their improved lipophilicity and membrane permeability, and the ubiquitousness of estereases. An example of an approach to make an ester prodrug is capping the acidic moiety (ies) with lipophilic alkyl or alkyloxymethyl esters (i.e., pivaloyloxymethyl (POM) or propyloxy-carbonyloxymethyl (POC); e.g., Enalapril, Adefovir). Another approach is to cap the acidic moiety(ies) with amino acids to make amides that are recognizable by amidases/peptidases in plasma for hydrolysis or to make them substrates for transporters, such as Peptide transporter 1 (PEPT1) (e.g., Pomaglumetad methionil, Valacyclovir).

Glutamine antagonists, such as 6-Diazo-5-oxo-L-norleucine (DON), and aza-serine, have been shown to exhibit broad anti-viral (Antiviral Res. 1997; 33(3):165-75; Antiviral Res. 1994; 25(3-4):269-79), anti-infective (J. Bacteriol. 1965; 89:1348-53), anti-cancer (see, e.g., Yoshioka et al., 1992; *Tokushima J. Exp. Med.* 39(1-2):69-76), anti-inflammatory, and immunosuppressive activities (Kulcsar et al., 2014; 111:16053-58; Maciolek et al., 2014; *Curr Opin Immunol.* 27:60-74; Carr et al., 2010; *J Immunol.* 185:1037-1044; Colombo et al., 2010; *Proc Natl Acad Sci USA.* 107:18868-73), as well as inhibition of convulsions (Proc R Soc Lond B Biol Sci. 1984 Apr. 24; 221(1223):145-68), multiple sclerosis (Tohoku, J. Exp. Med. 2009; 217(2):87-92), epilepsy, and viral encephalitis (J. Neurovirol. 2015 April; 21(2):159-73. doi: 10.1007/s13365-015-0314-6), in many published preclinical and several clinical studies. However, the occurrence of severe toxicity (e.g., dose limiting GI toxicities, such as oral mucosistis, gastric bleeding, nausea and vomiting, abdominal pain, leukopenia, thrombocytopenia, and the like) when administering such glutamine antagonists at therapeutic dose levels has hampered their clinical development.

Prior attempts to mitigate the severe toxicity associated with glutamine antagonists, such as DON, have been unsuccessful. For example, dividing daily dosing and administering of DON every four to six hours apparently doubled DON's toxicity potential (MgGill, et al., 1957). In another example, development of a treatment involving DON dosed with glutaminase to decrease plasma glutamine so that the DON dose could be reduced was halted after publication of a clinical trial.

SUMMARY

The presently disclosed subject matter provides prodrugs of glutamine antagonists, and pharmaceutically acceptable salts and esters thereof. In some aspects, the presently disclosed subject matter provides a prodrug of a glutamine antagonist, or a pharmaceutically acceptable salt, the prodrug having a structure of formula (I):

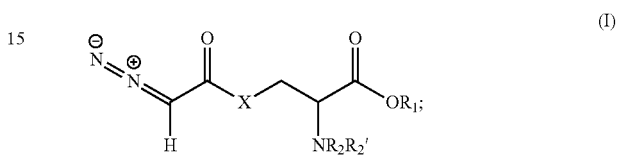

wherein: X is selected from the group consisting of a bond, —O—, and —$(CH_2)_n$—, wherein n is an integer selected from the group consisting of 1, 2, 3, 4, 5, 6, 7, and 8; $R_1$ is selected from the group consisting of H and a first prodrug-forming moiety capable of forming a salt or an ester; and $R_2$ is H or a second prodrug-forming moiety capable of forming an amide linkage, a carbamate linkage, a phosphoramidate linkage or a phosphorodiamidate linkage with the nitrogen adjacent to $R_2$; $R_2'$ is selected from the group consisting of H, $C_1$-$C_6$ alkyl, substituted $C_1$-$C_6$ alkyl, or $R_2$ and $R_2'$ together form a ring structure comprising —C(=O)-G-C(=O)—, wherein G is selected from the group consisting of $C_1$-$C_8$ alkylene, $C_1$-$C_8$ heteroalkylene, $C_5$-$C_8$ cycloalkylene, $C_6$-$C_{12}$ arylene, $C_5$-$C_{14}$ heteroarylene, bivalent $C_4$-$C_{10}$ heterocycle, each of which can be optionally substituted; or $R_1$ and $R_2'$ together form a 4-to 6-membered heterocylic ring comprising the oxygen atom adjacent to $R_1$ and the nitrogen atom adjacent to $R_2'$; provided that the compound has at least one prodrug-forming moiety selected from the group consisting of the first and the second prodrug-forming moieties.

In some aspects, the presently disclosed subject matter provides a prodrug of a glutamine antagonist, or a pharmaceutically acceptable salt, the prodrug having a structure of formula (IIA) or formula (IIB):

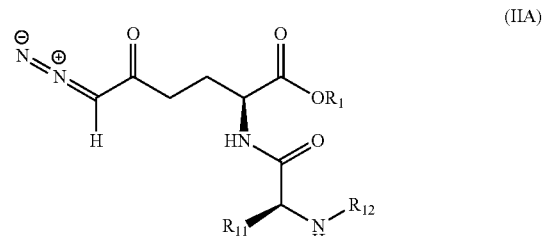

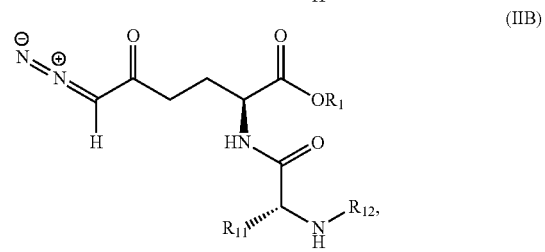

wherein:
R1 is selected from the group consisting of H and C1-6 alkyl;

R11 is selected from the group consisting of H, methyl, isopropyl, sec-butyl, benzyl, p-hydroxybenzyl —CH2CH(CH3)2, —CH2OH, —CH(OH)CH3, —CH2-3-indoyl, —CH2COOH, —CH2CH2COOH, —CH2C(O)NH2, —CH2CH2C(O)NH2, —CH2SH, —CH2CH2SCH3, —(CH2)4NH2, —(CH2)3NHC(═NH)NH2, and —CH2-3-imidazoyl;

R12 is selected from the group consisting of H, C1-4 alkyl, and —C(═O)R13; and

R13 is $C_{1-4}$ alkyl.

In some aspects, the presently disclosed subject matter provides a prodrug of a glutamine antagonist, or a pharmaceutically acceptable salt, the prodrug having a structure of formula (III):

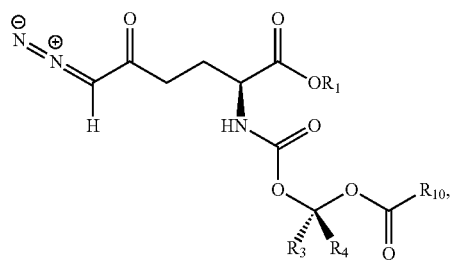

(III)

wherein:
$R_1$ is selected from the group consisting of H and $C_{1-6}$ alkyl;

$R_3$ and $R_4$ are independently selected from the group consisting of H, $C_1$-$C_6$ alkyl, substituted $C_1$-$C_6$ alkyl, aryl, and substituted aryl; and $R_{10}$ is $C_{1-6}$ alkyl.

In other aspects, the presently disclosed subject matter provides a pharmaceutical composition comprising a compound of any one of formula (I), formula (IIA), formula (IIB), or formula (III), and a pharmaceutically acceptable carrier, diluent, or excipient.

In certain aspects, the presently disclosed subject matter provides a method for treating a disease or a condition, the method comprising administering to a subject in need of treatment thereof, a compound of any one of formula (I), formula (IIA), formula (IIB), or formula (III), or a pharmaceutical composition thereof, in an amount effective for treating the disease or condition. In still other aspects, the presently disclosed subject matter provides the use of a compound of any one of formula (I), formula (IIA), formula (IIB), or formula (III), or a pharmaceutical composition thereof, for treating a disease or condition. In some embodiments, the disease or condition is selected from the group consisting of an infection, cancer, an autoimmune disease, an inflammatory disease, and a neurodegenerative or neurological disease.

In yet another aspect, the presently disclosed subject matter provides a compound of any one of formula (I), formula (IIA), formula (IIB), or formula (III), or a pharmaceutically composition thereof, for use as a medicament.

In yet another aspect, the presently disclosed subject matter provides a compound of any one of formula (I), formula (IIA), formula (IIB), or formula (III), or a pharmaceutically composition thereof, for use in the treatment of a disease or condition, preferably the disease or condition is selected from the group consisting of an infection, cancer, an autoimmune disease, an inflammatory disease, and a neurodegenerative or neurological disease.

In yet another aspect, the presently disclosed subject matter provides a compound of any one of formula (I), formula (IIA), formula (IIB), or formula (III), or a pharmaceutically composition thereof, for use in the treatment of the excess and/or aberrant glutamine activity.

Applicant has found that compounds of the disclosure having formula (I), formula (IIA), formula (IIB), and formula (III) are stable in plasma, liver microsomes, liver tissue, and gastrointestinal tissue, yet these compounds are cleaved in tumor cells to liberate DON in tumor tissue. The unexpected tumor-targeted properties of compounds having formula (I), formula (IIA), formula (IIB), and formula (III) result in a surprising improvement in therapeutic index for treating cancer with DON and provide the maximum therapeutic benefit to a subject in need of such treatment.

Applicant has also found unexpectedly that compounds of the disclosure having formula (I), formula (IIA), formula (IIB), and formula (III) exhibit unexpected enhanced CSF to plasma partitioning after administration, making them uniquely useful for the treatment of CNS cancers such as glioblastoma, oligodendroglioma, neuroblastoma, meningioma, spinal cord tumor and metastatic cancer that has spread to the central nervous system (CNS).

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
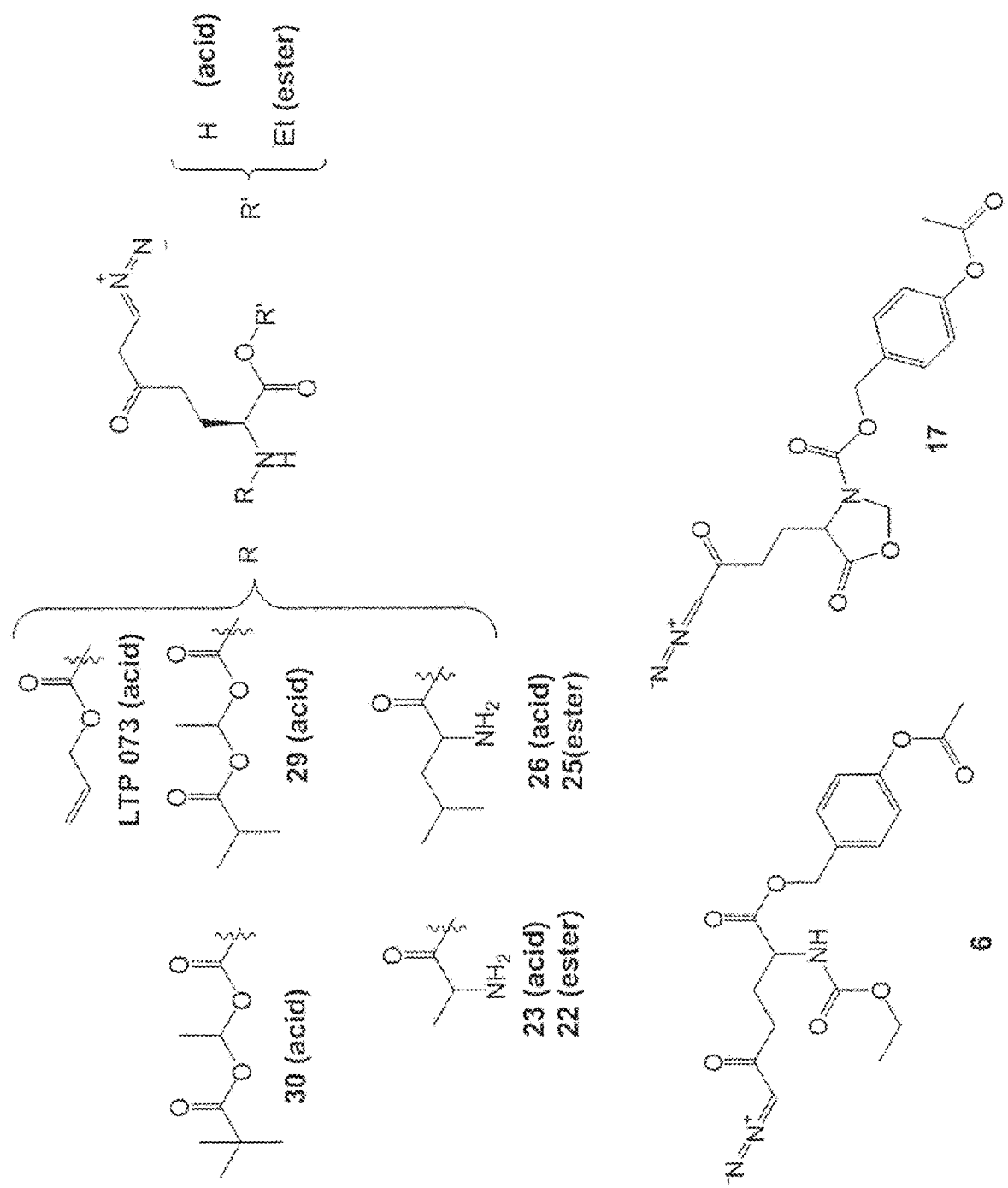

Having thus described the presently disclosed subject matter in general terms, reference will now be made to the accompanying Figures, which are not necessarily drawn to scale, and wherein:

FIG. 1 is an illustration showing exemplary amino (R) and carboxy (R') modifications made to DON in an attempt to synthesize various slow release DON prodrugs.

Figure 2A:
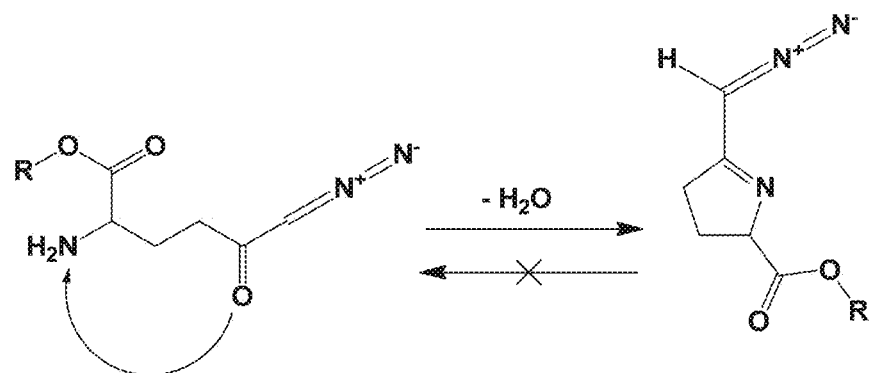
Figure 2B:
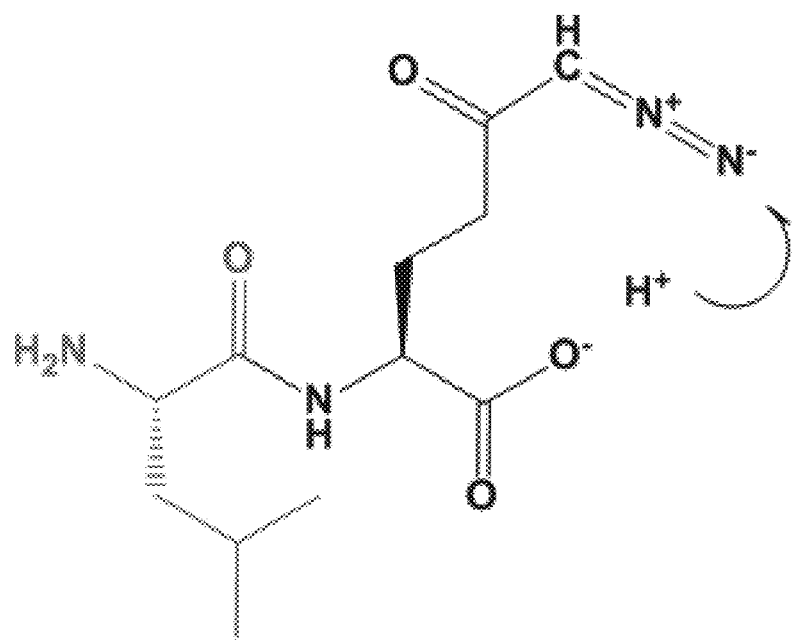
Figure 3A:
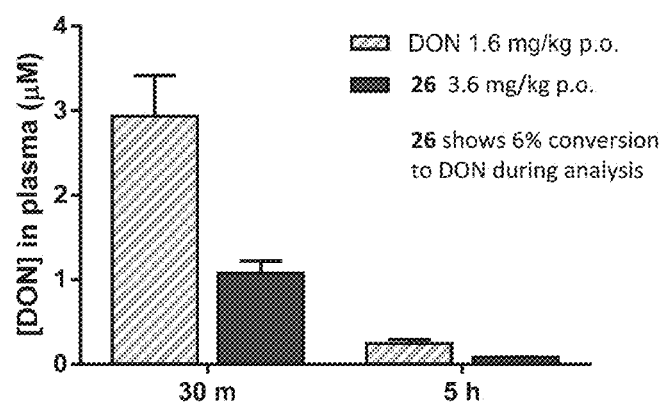
Figure 3B:
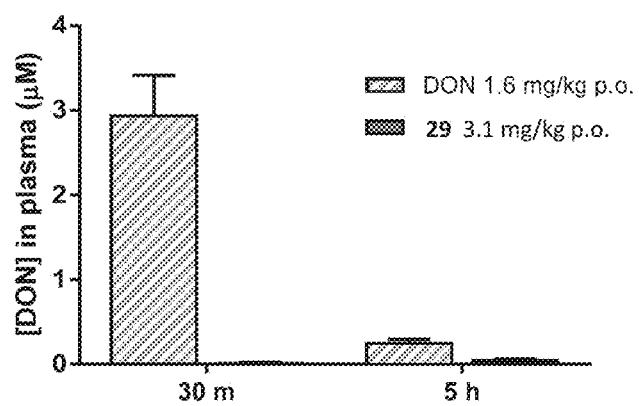
Figure 3C:
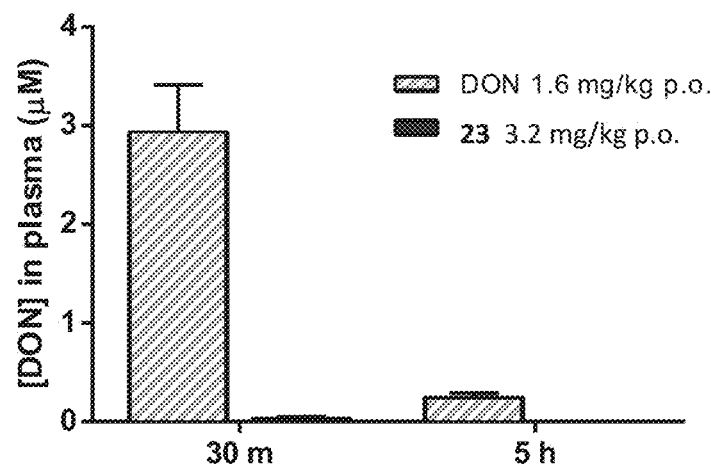
Figure 3D:
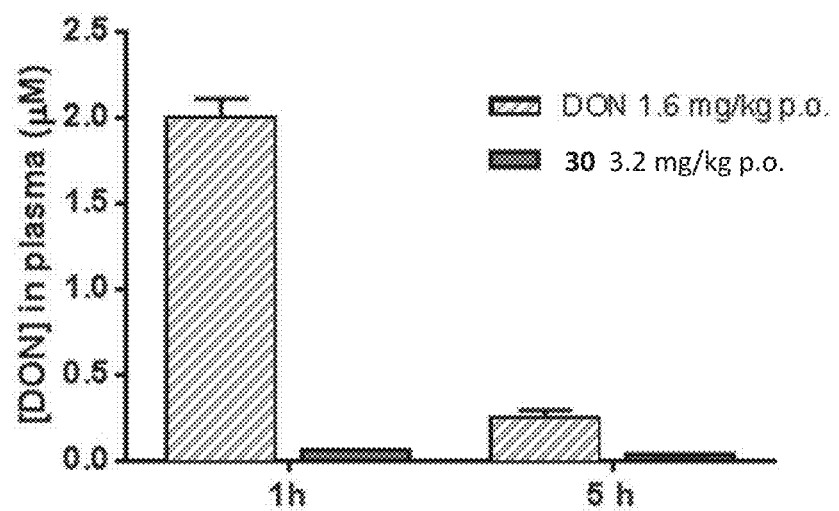
Figure 4A:
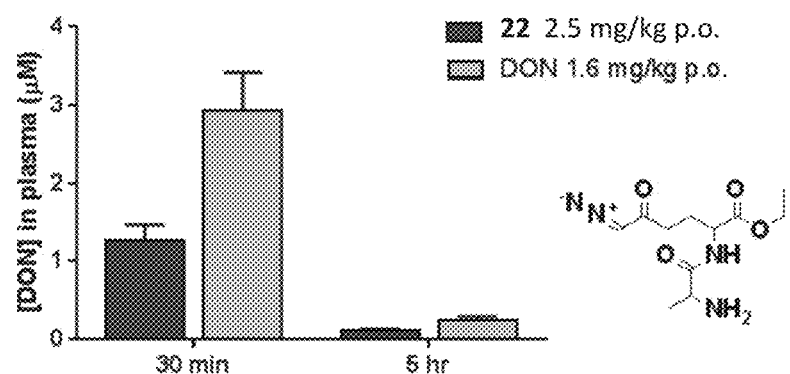
Figure 4B:
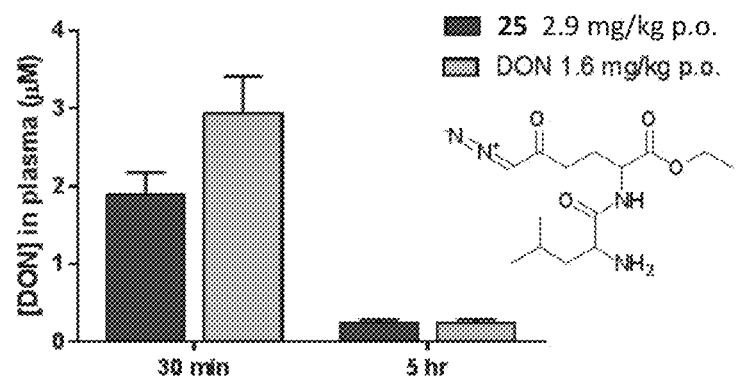
Figure 4C:
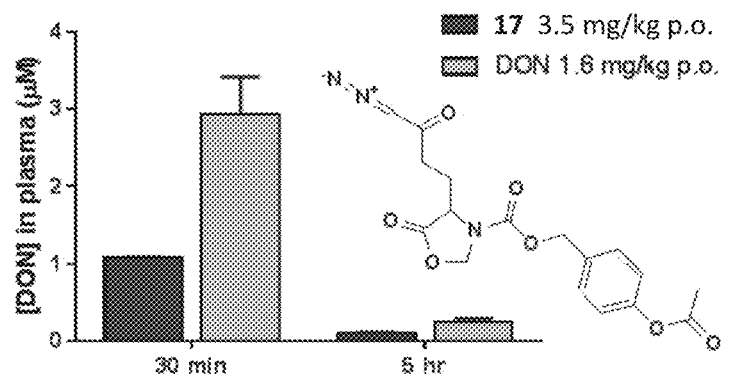
Figure 4D:
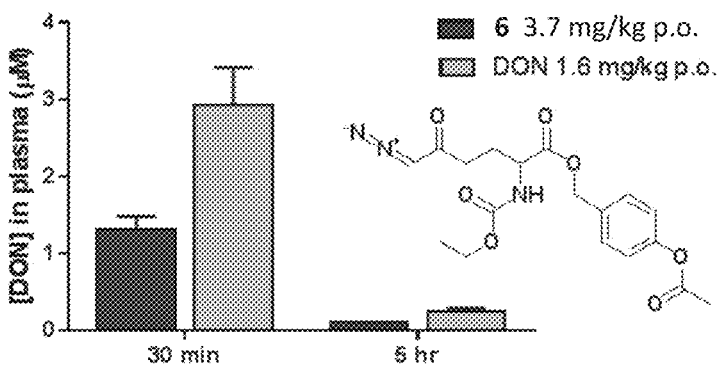

FIG. 2A and FIG. 2B are illustrations demonstrating the chemical stability challenges encountered when attempting to synthesize DON prodrugs, including stability issues presented by DON esters (FIG. 2A), and DON compounds possessing a free terminal carboxylate (FIG. 2B).

FIG. 3A, FIG. 3B, FIG. 3C and FIG. 3D are bar graphs demonstrating the failed chemistry and poor pharmacokinetics of certain attempts to design DON prodrugs. FIG. 3A, FIG. 3B, FIG. 3C and FIG. 3D show that most DON prodrugs having a free carboxylate group exhibited negligible exposure compared to DON (except for 26, which showed some release; FIG. 3A) when administered orally in mice, including 29 (FIG. 3B), 23 (FIG. 3C) and 30 (FIG. 3D), which showed little DON release in mouse plasma upon oral administration. Note that release of DON prodrug LTP073 was below the limit of quantitation in all mouse plasma samples at 30 minutes and 5 hours after dosing (not shown).

FIG. 4A, FIG. 4B, FIG. 4C and FIG. 4D are line graphs showing percentages of DON released in plasma after 0.5 h and 5 h following administration of exemplary DON-releasing as compared to DON. FIG. 4A and FIG. 4B show the results of a pharmacokinetic study in mice showing plasma DON concentrations following administration of DON (1.6 mg/kg p.o.) and DON prodrugs dosed at 1.6 mg/kg equivalent of DON, such as 22 (FIG. 4A; 2.5 mg/kg p.o.) and 25 (FIG. 4B; 2.9 mg/kg p.o.). Compound 22 showed lesser release at 0.5 h (65% of DON), however, the levels were similar at 5 h (almost 100%) to that of DON. FIG. 4C and FIG. 4D show the results of a pharmacokinetic study in mice showing plasma DON concentrations following administration of DON (1.6 mg/kg i.p.) and DON prodrugs 17 (FIG. 4C; 3.5 mg/kg p.o.) and 6 (FIG. 4D; 3.7 mg/kg p.o.).

Figure 5:
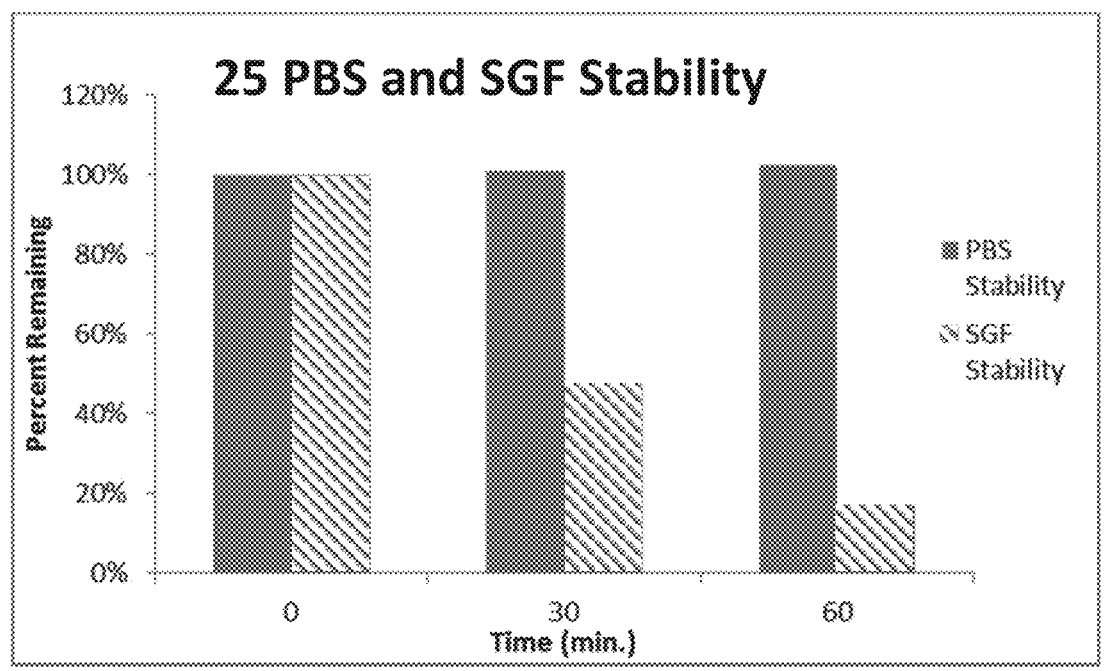

FIG. 5 is a bar graph showing the stability of DON prodrug 25 in phosphate-buffered saline (PBS) and simulated gastric fluid (SGF) after 30 min and 60 min.

Figure 6:
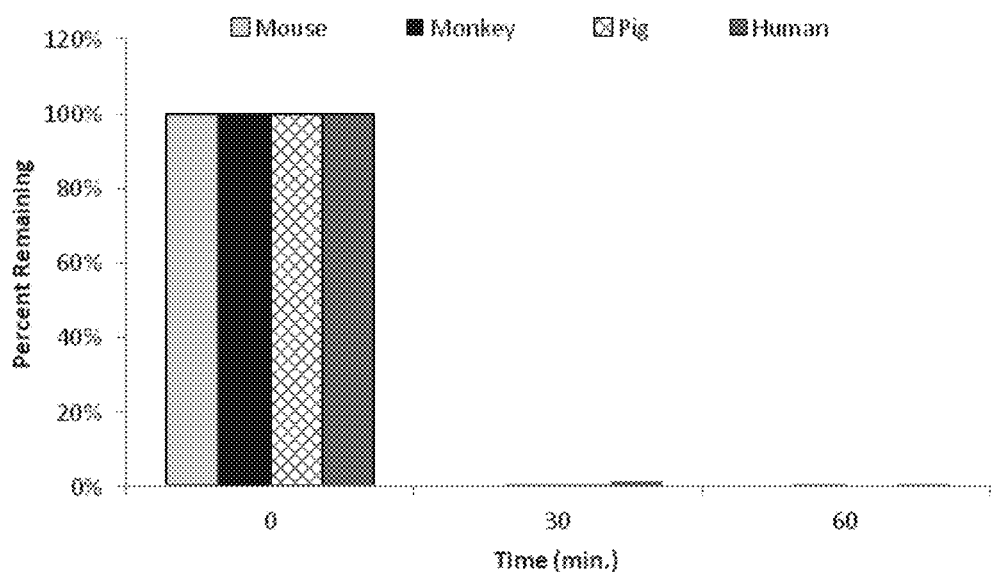

FIG. 6 is a bar graph showing the results of an in vitro metabolic stability screen of DON prodrug 25 in mouse, monkey, pig, and human plasma after 30 min and 60 min. 25 was found to be unstable in plasma in all tested species as both the ethyl ester and leucine ester were hydrolysed by plasma esterases.

Figure 7:
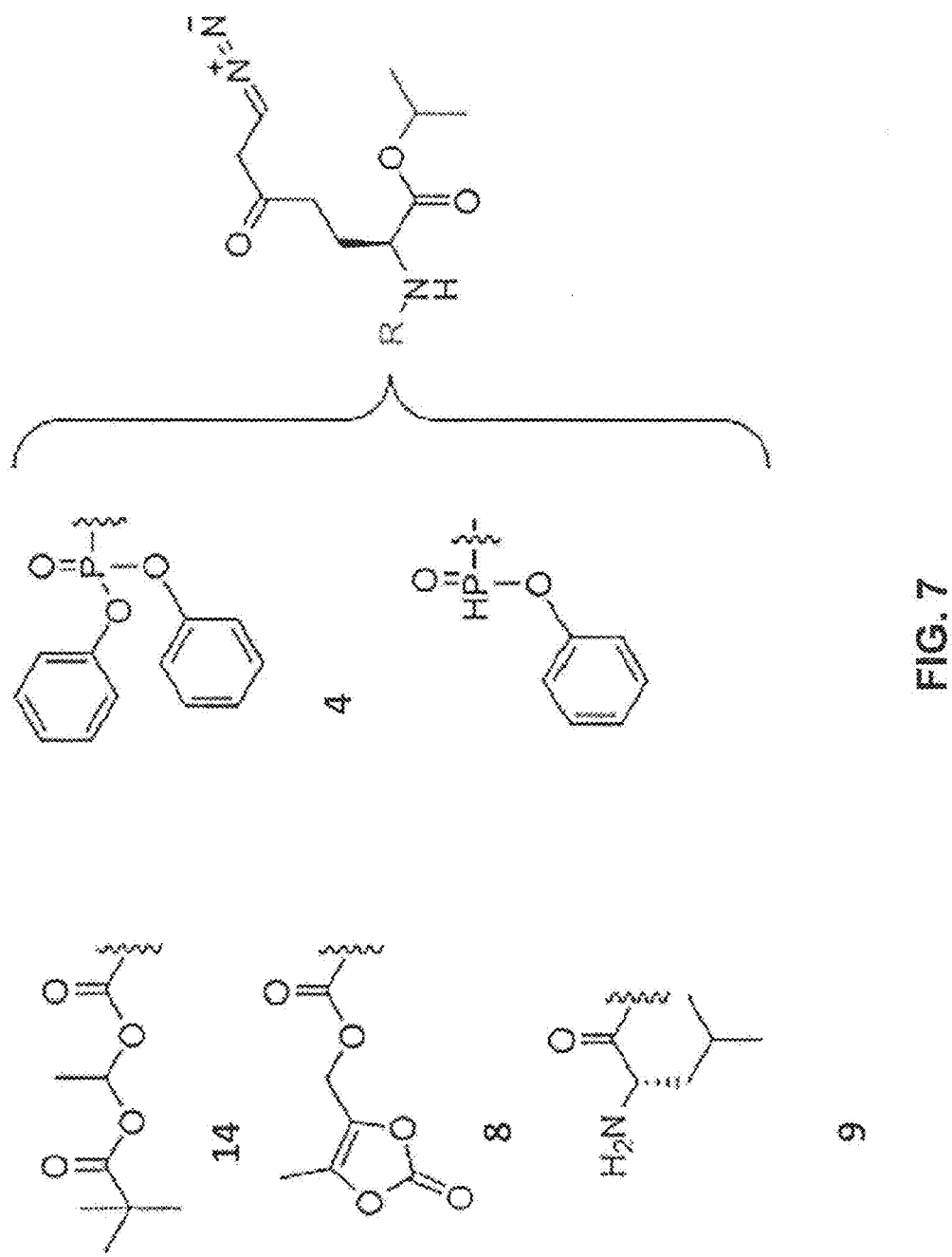

FIG. 7 is an illustration showing the generic structure of certain cell targeting DON prodrugs that comprise an isopropyl ester carboxy modification.

Figure 8:
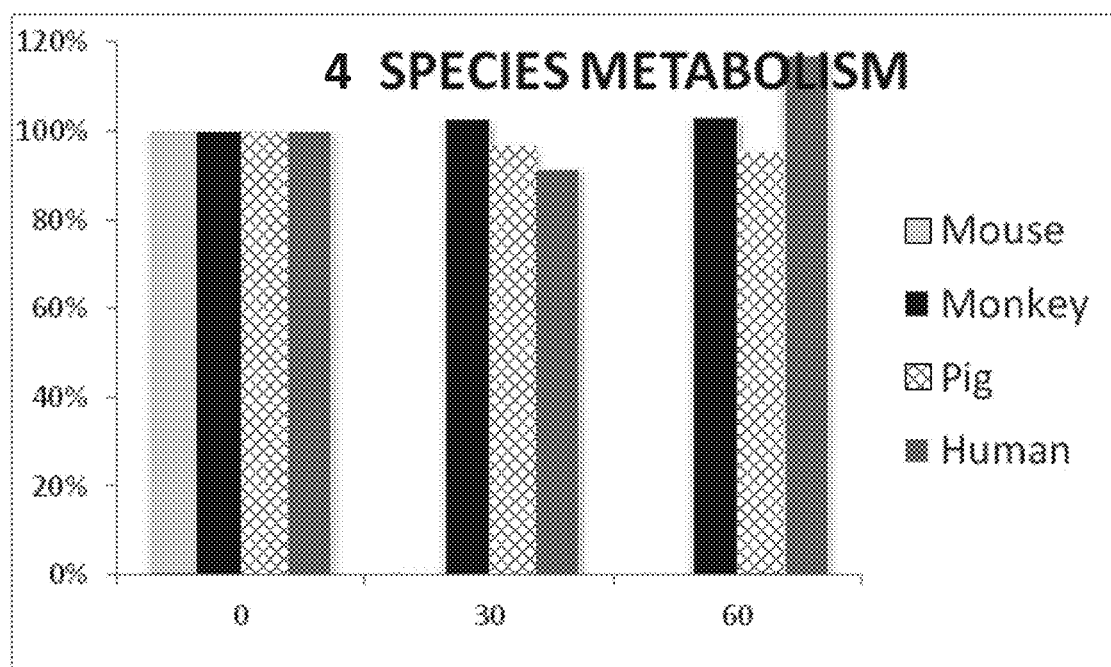

FIG. 8 is a bar graph showing the results of an in vitro metabolic stability screen of cell targeted phosphamide DON prodrug 4 in mouse, monkey, pig, and human plasma after 30 min and 60 min. Compound 4 was found to be unstable in mouse plasma, but stable in the plasma of all other tested species.

Figure 9:
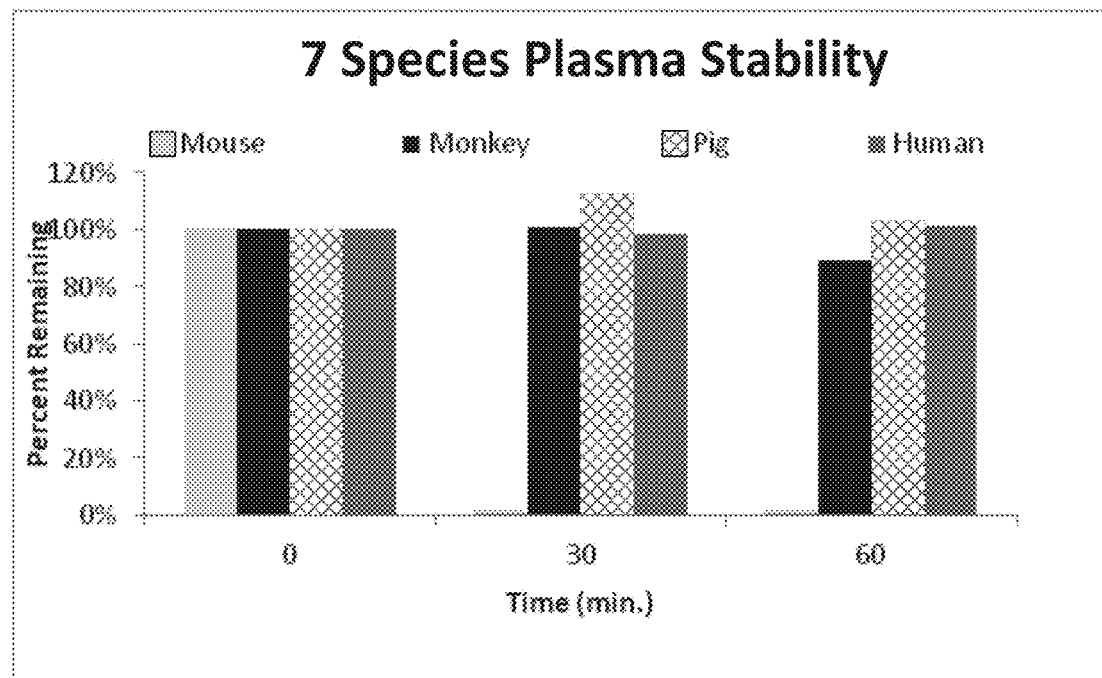

FIG. 9 is a bar graph showing the results of an in vitro metabolic stability screen of DON prodrug 7 in mouse, monkey, pig, and human plasma after 30 min and 60 min. Compound 7 was found to be unstable in mouse plasma, but stable in plasma of all other tested species.

Figure 10:
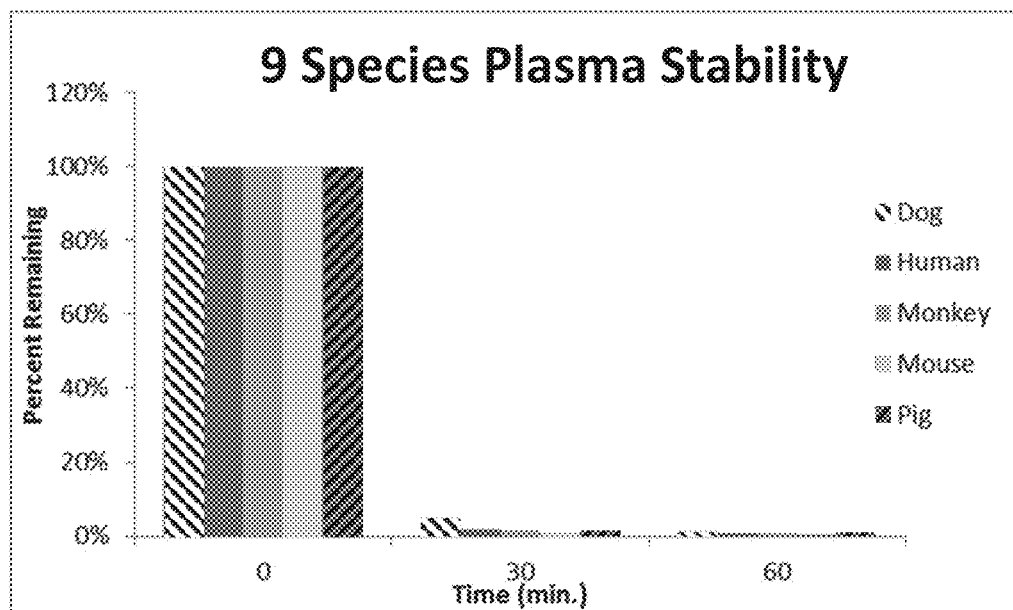
Figure 11A:
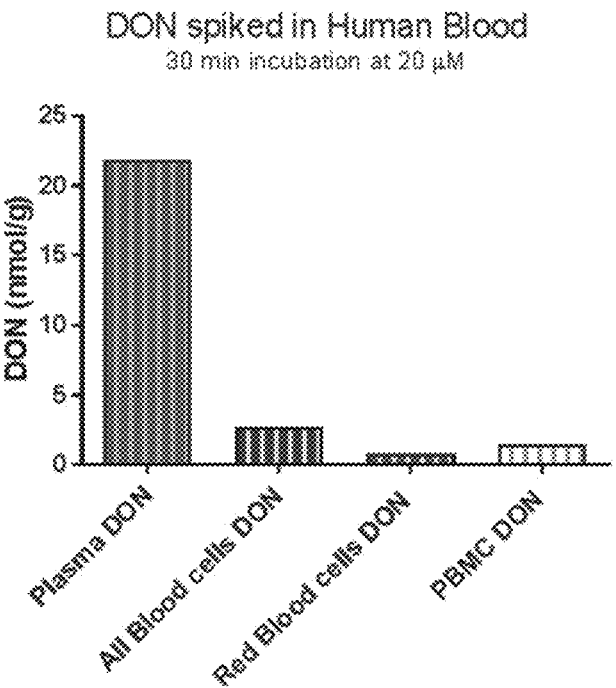
Figure 11B:
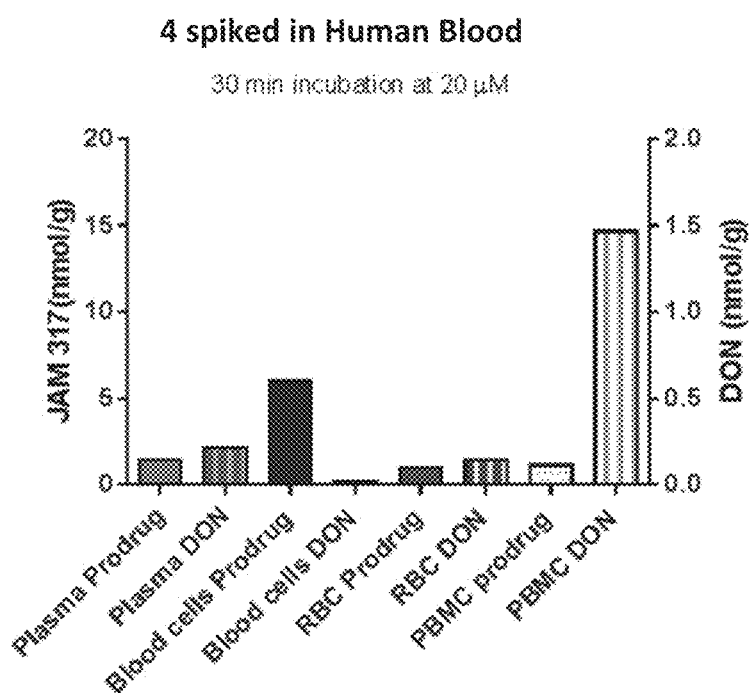
Figure 11C:
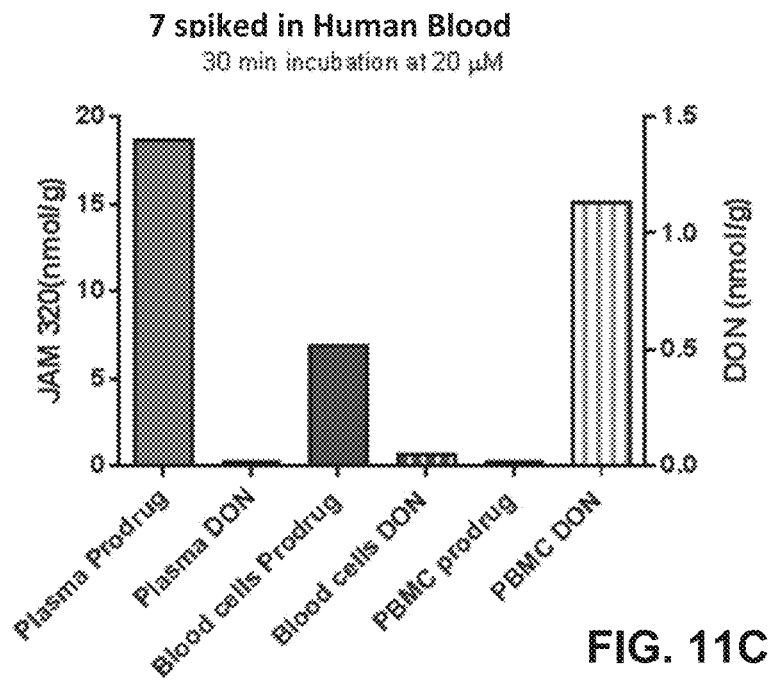
Figure 11D:
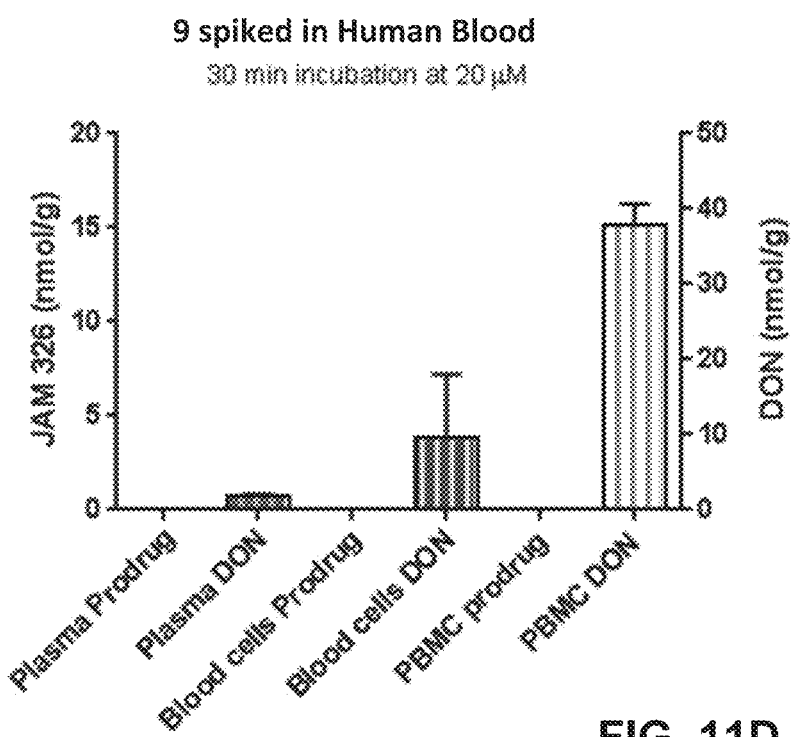
Figure 11E:
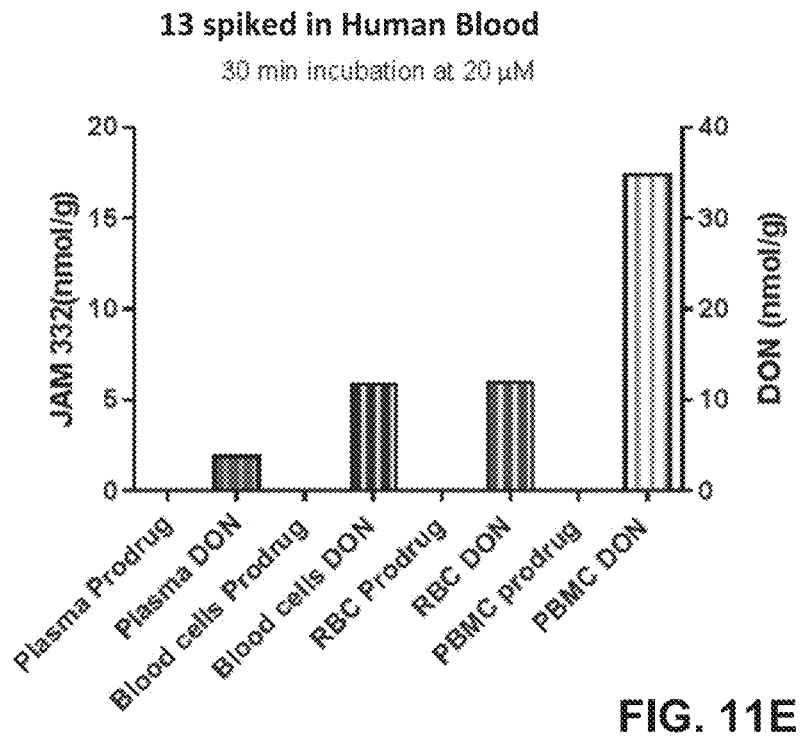
Figure 11F:
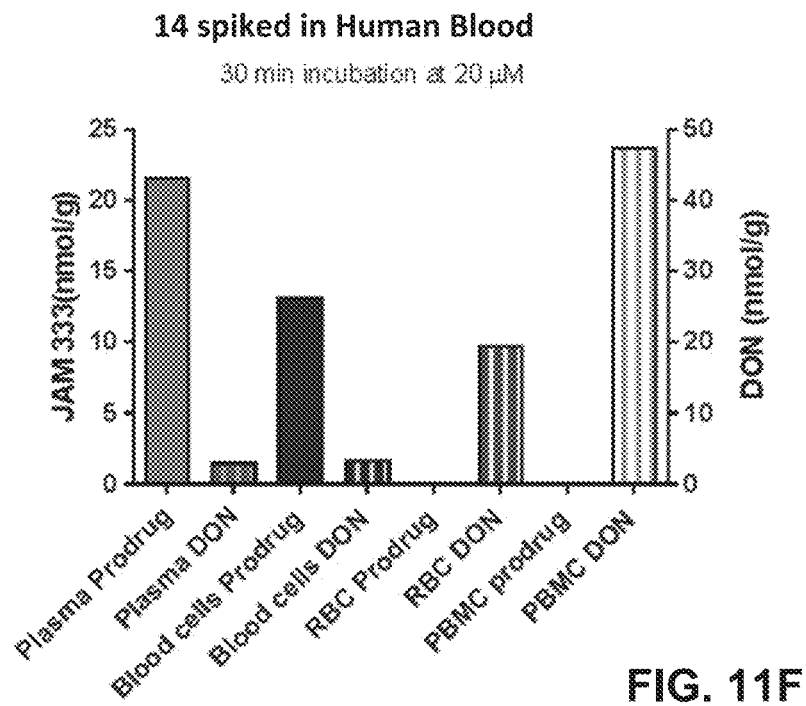
Figure 12A:
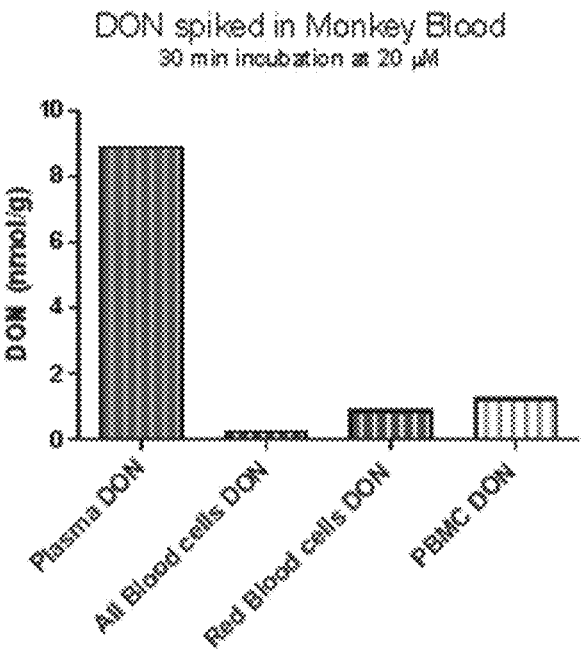
Figure 12B:
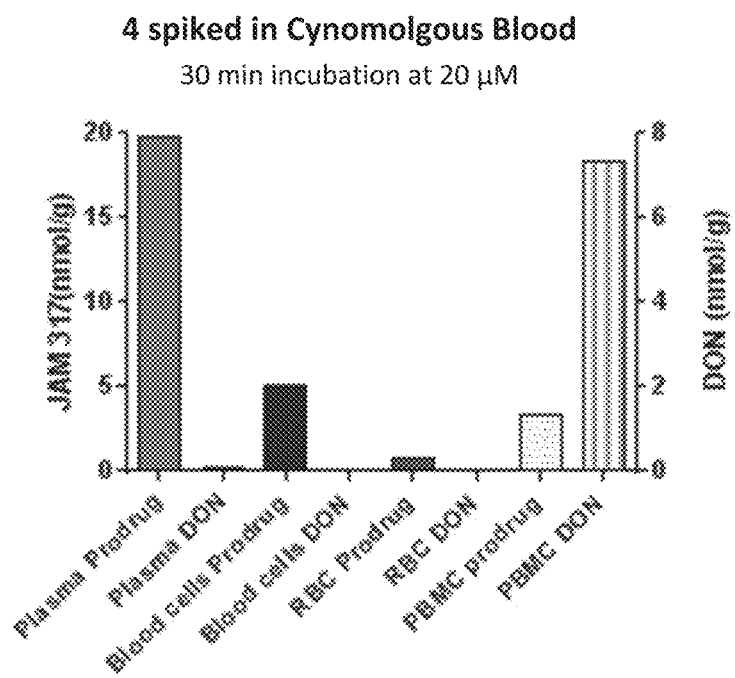
Figure 12C:
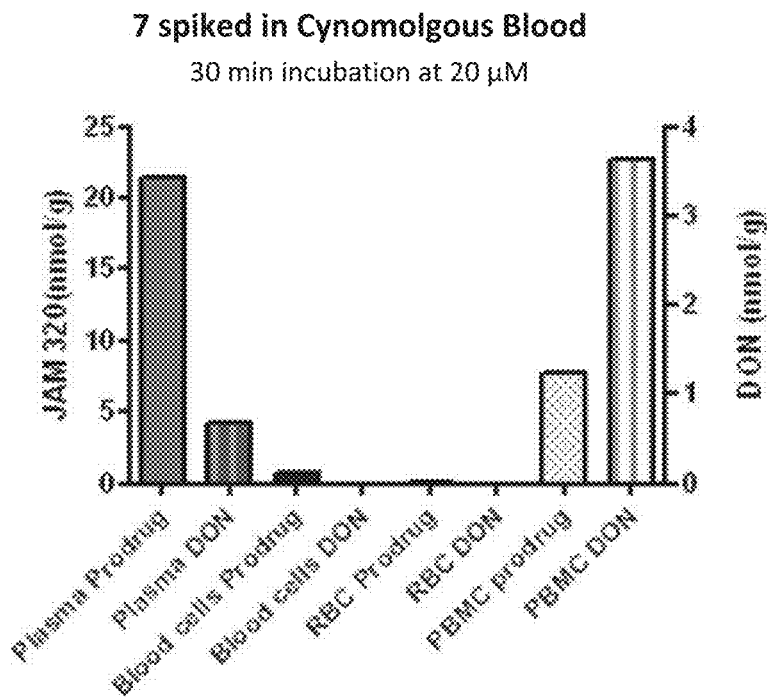
Figure 12D:
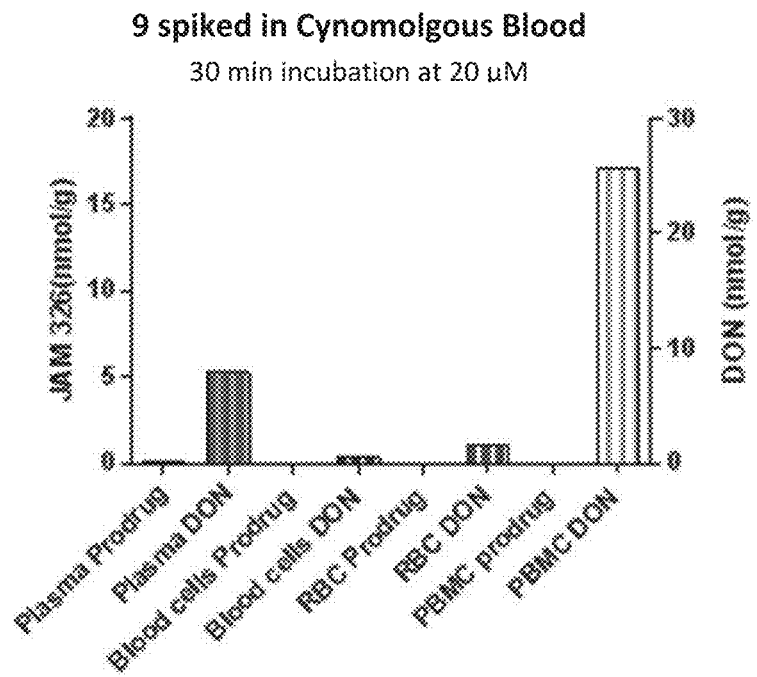

FIG. 10 is a bar graph showing the results of an in vitro metabolic stability screen of DON prodrug 9 in dog, mouse, monkey, pig, and human plasma after 30 min and 60 min. Compound 9 was found to be unstable in plasma off all tested species. Metabolic identification suggested hydrolysis of leucine, but stable isopropyl ester for specific release inside lymphoid cells.

FIG. 11A, FIG. 11B, FIG. 11C, FIG. 11D, FIG. 11E and FIG. 11F are bar graphs demonstrating the results of an ex vivo study comparing the accumulation of DON and DON prodrugs in plasma, blood cells, red blood cells (RBC), and peripheral blood mononuclear cells (PBMC) after 30 minutes of incubation of 20 μM of DON (FIG. 11A) and DON prodrugs 4 (FIG. 11B), 7 (FIG. 11C), 9 (FIG. 11D), 13 (FIG. 11E) and 14 (FIG. 11F) in whole human blood;

FIG. 12A, FIG. 12B, FIG. 12C, and FIG. 12D are bar graphs demonstrating the results of ex vivo studies comparing the accumulation of DON and DON prodrugs in Cynomolgous monkey plasma, blood cells, RBC and PBMC after 30 minutes of incubation of 20 μM DON (FIG. 12A) and DON prodrugs, including 20 μM 4 (FIG. 12B), 7 (FIG. 12C) and 9 (FIG. 12C), in monkey whole blood samples.

Figure 13A:
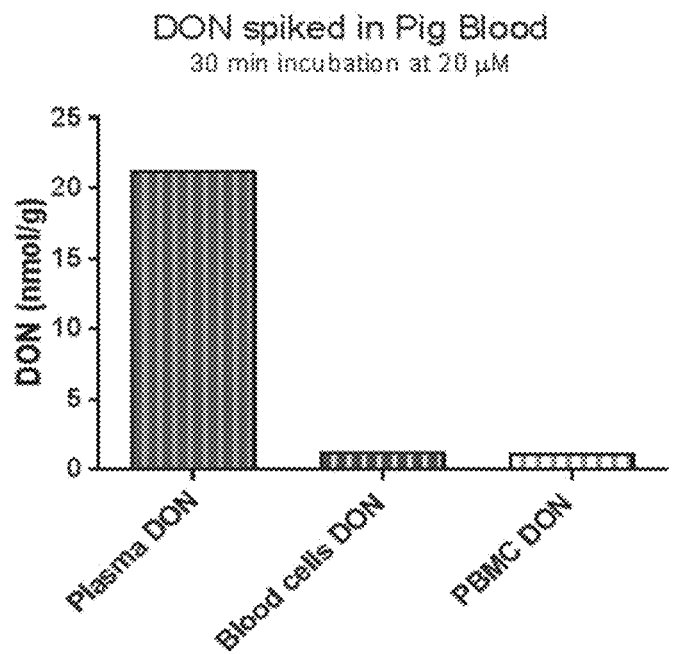
Figure 13B:
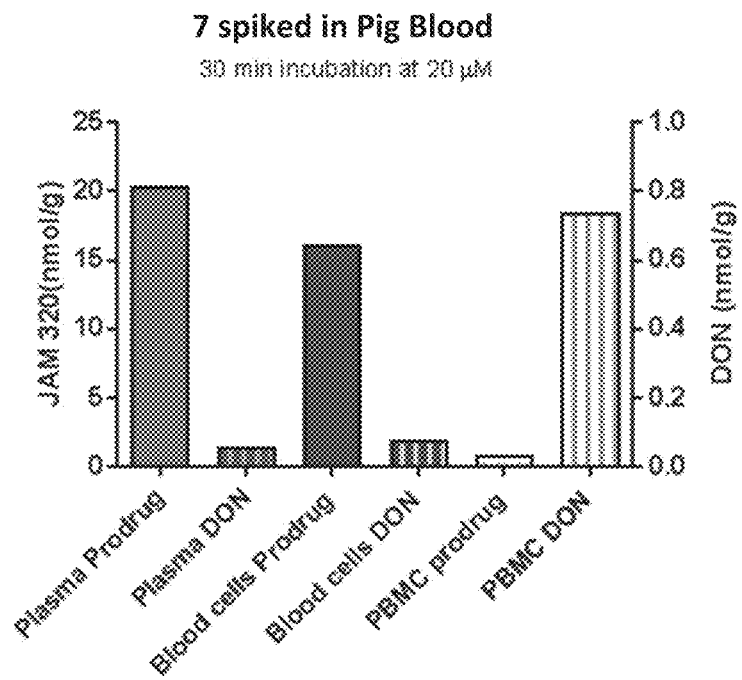
Figure 13C:
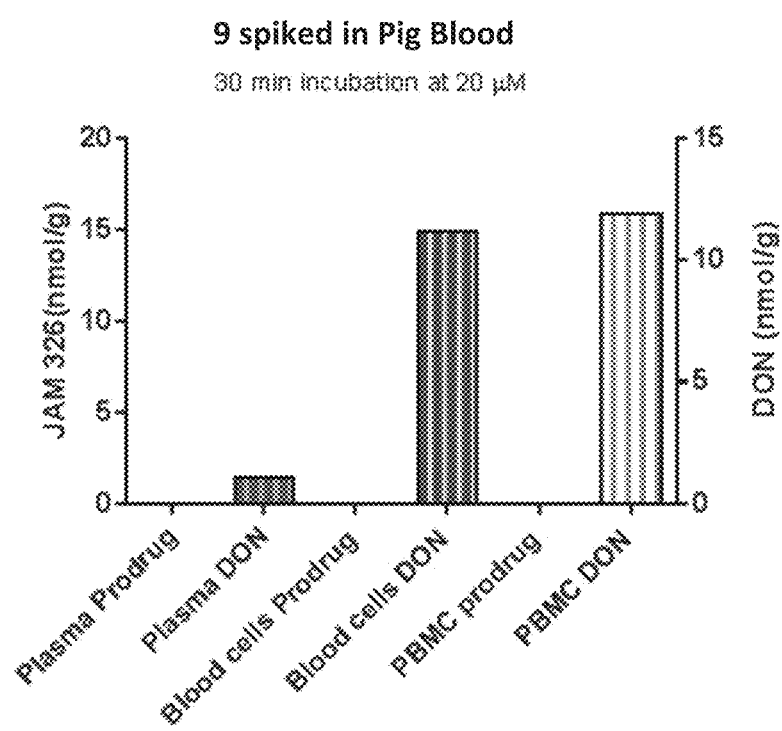

FIG. 13A, FIG. 13B, and FIG. 13C are bar graphs demonstrating the results of ex vivo studies comparing the accumulation of DON and DON prodrugs in pig plasma, blood cells, RBC and PBMC after 30 minutes of incubation of 20 μM DON (FIG. 13A) and DON prodrugs, including 20 μM 7 (FIG. 13B) and 9 (FIG. 13C), in pig whole blood samples.

Figure 14:
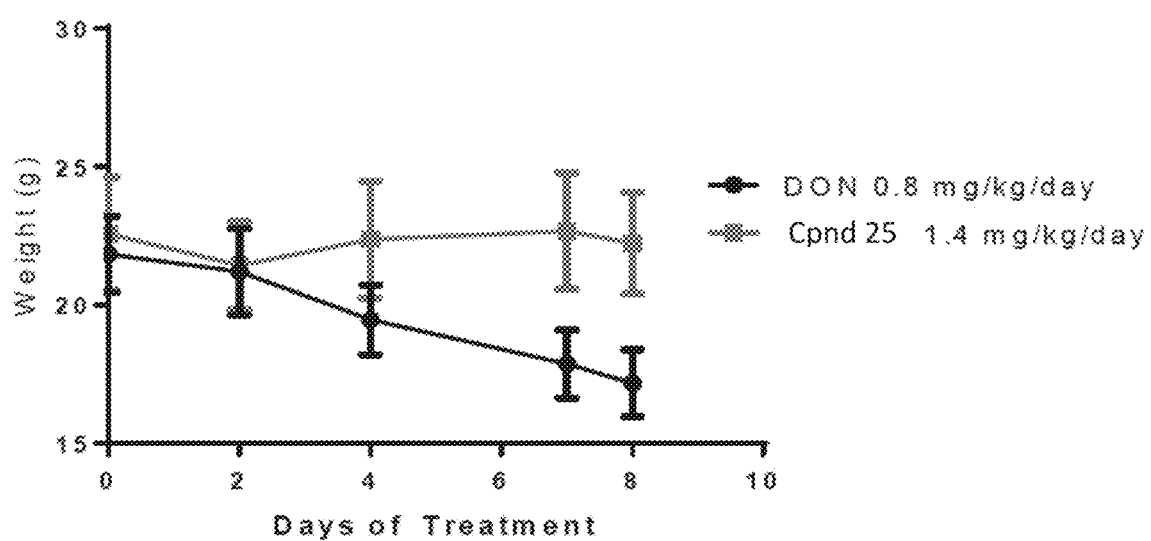

FIG. 14 is a line graph showing that daily high dose treatment leads to weight loss in DON treated mice. No weight loss was observed in 25 treated mice.

FIG. 15 is a table showing that daily high dose treatment leads to pan-cytopeniain DON treated mice. Mice treated with 25 exhibited some leukopenia.

FIG. 16 is a table showing that renal and liver function in mice treated with either high dose DON or 25 was unaffected.

Figure 17A:
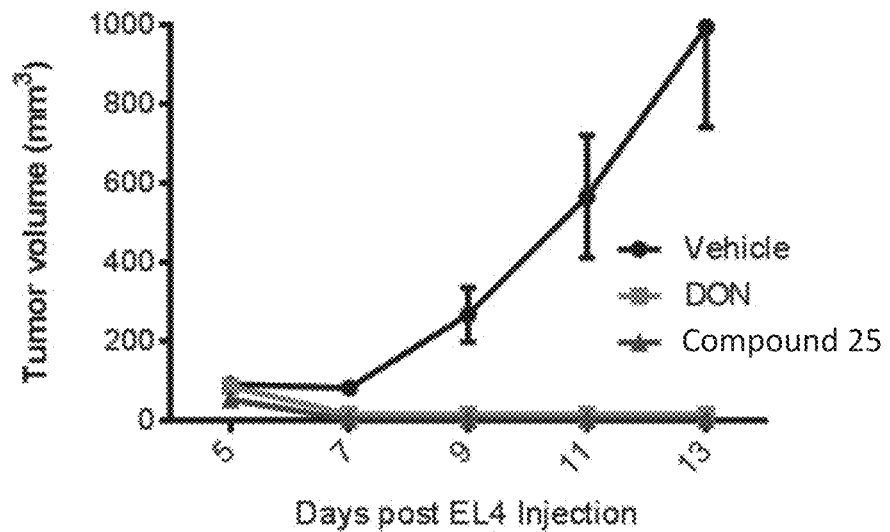
Figure 17B:
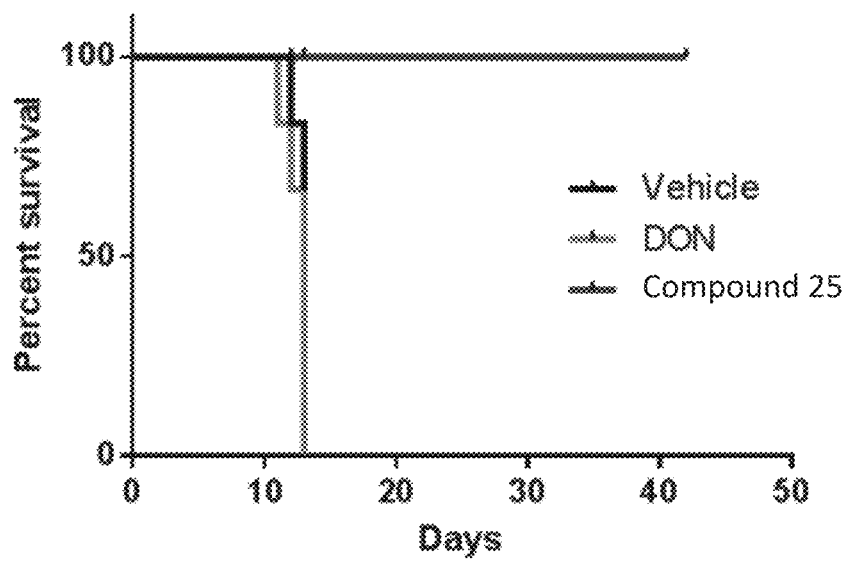

FIG. 17A, and FIG. 17B are line graphs showing that 25 and DON treatment cure lymphoma; DON mice die from treatment with DON while 25 is well tolerated.

Figure 18A:
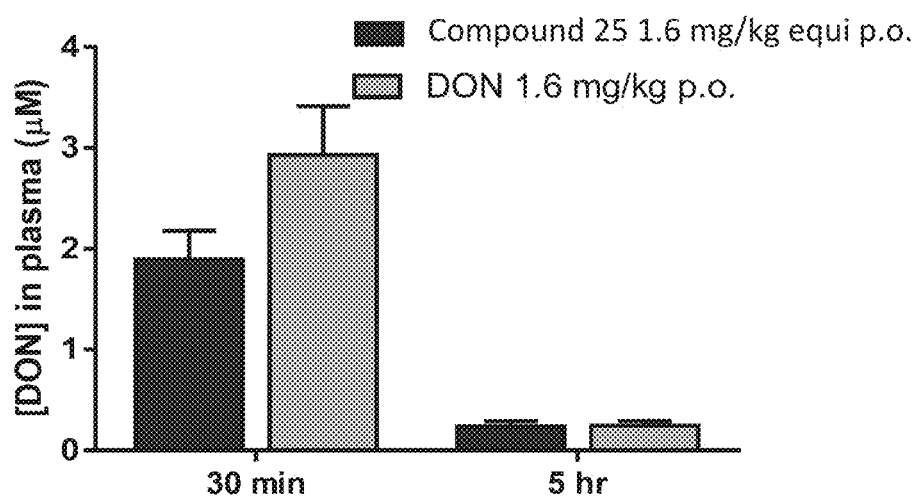
Figure 18B:
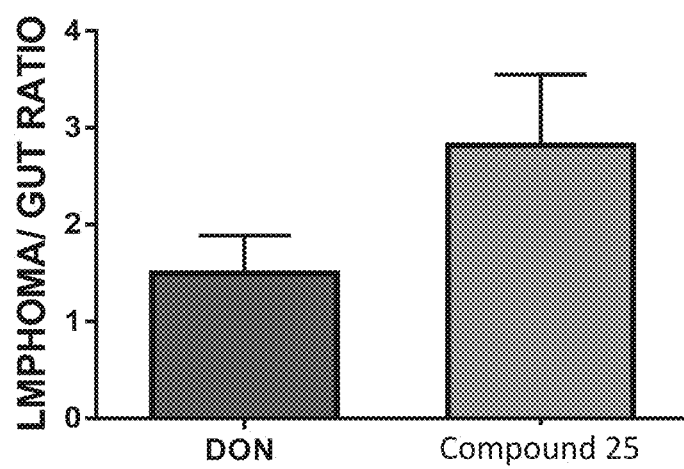
Figure 18C:
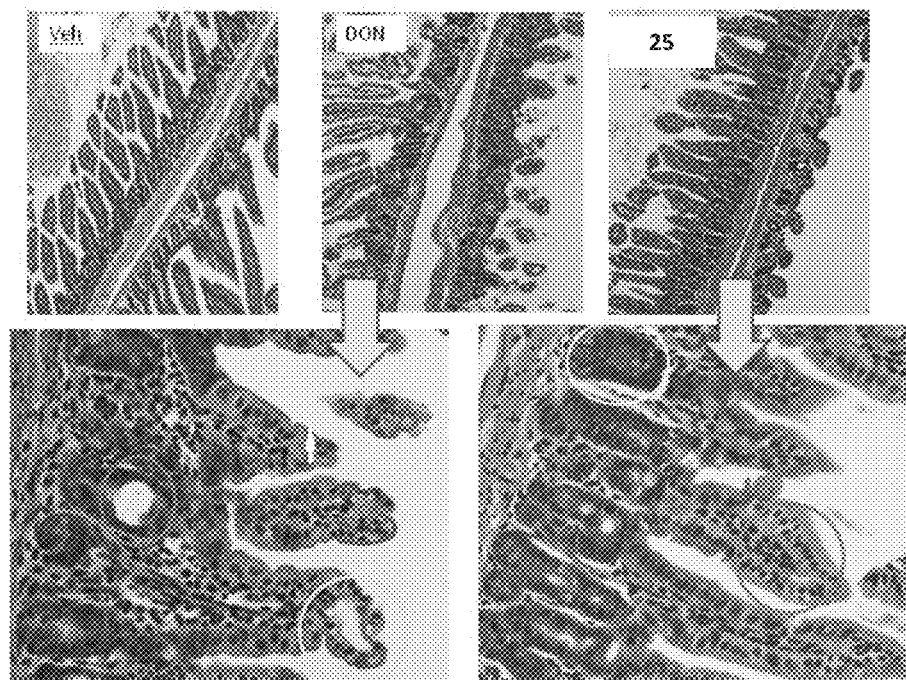
Figure 24:
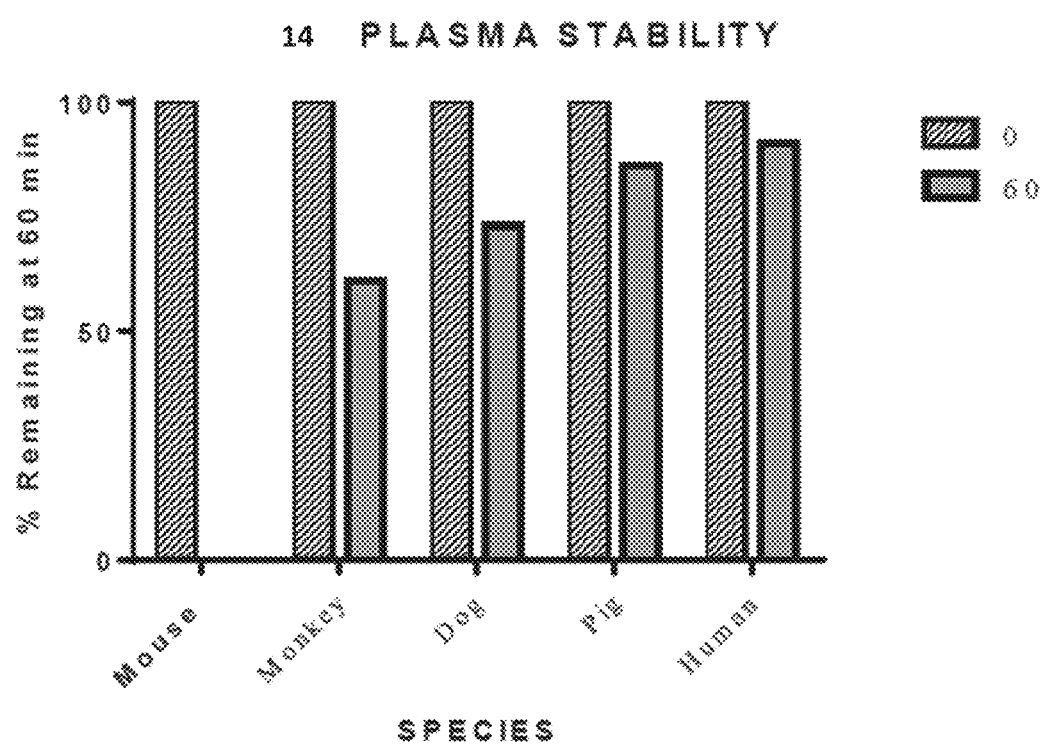
Figure 25:
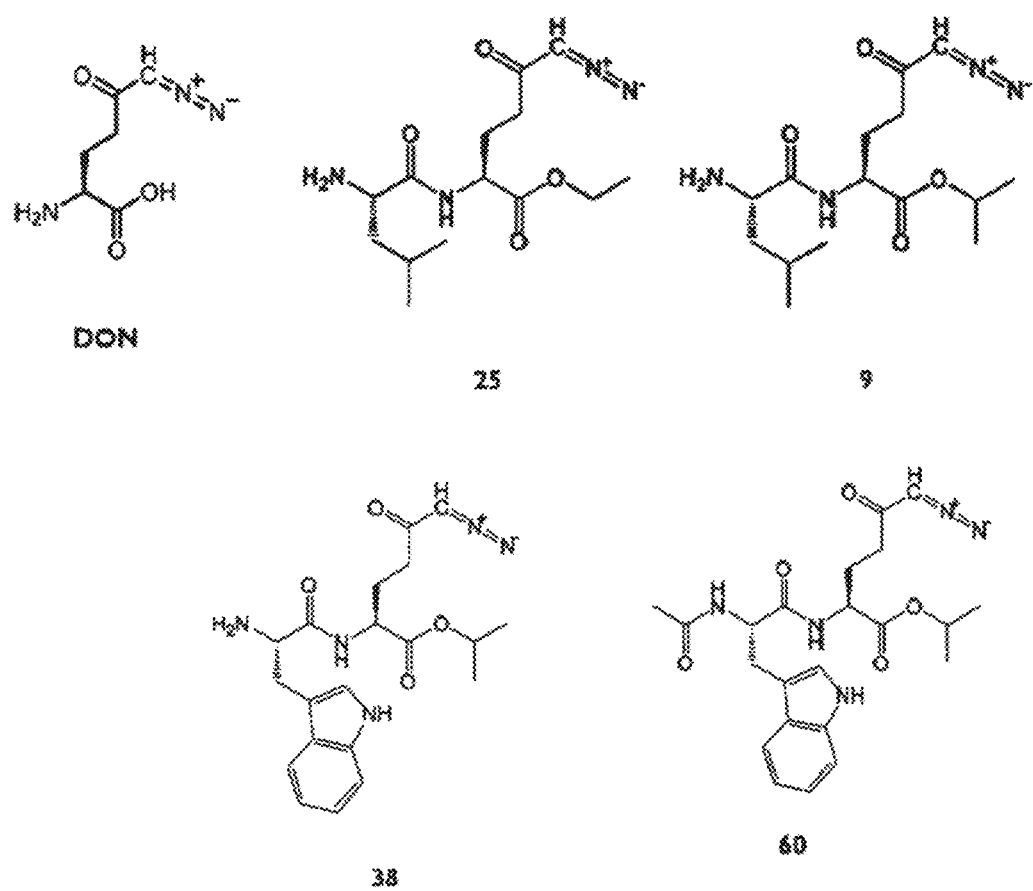
Figure 26A:
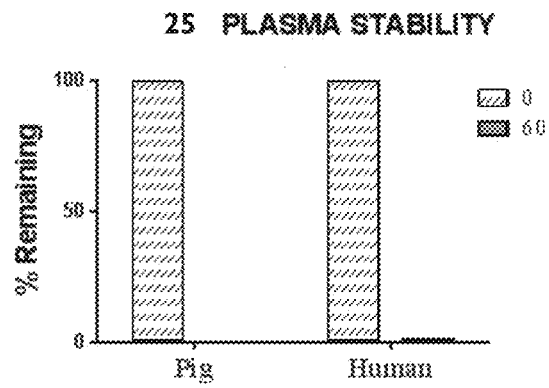
Figure 26B:
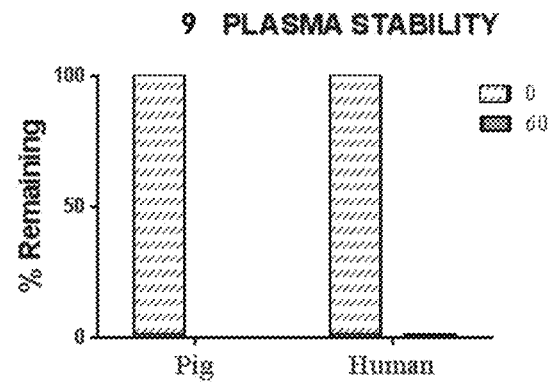
Figure 26C:
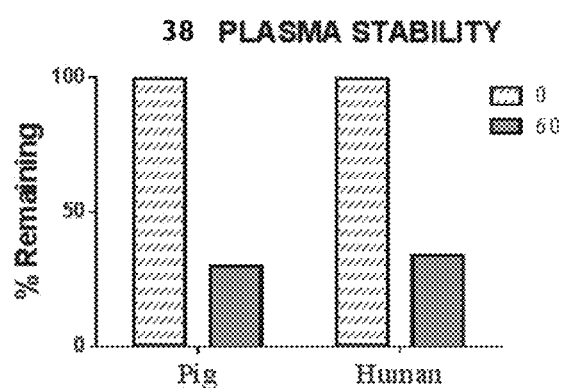
Figure 26D:
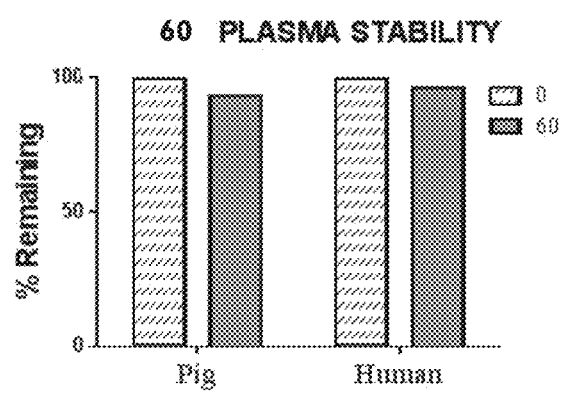
Figure 27A:
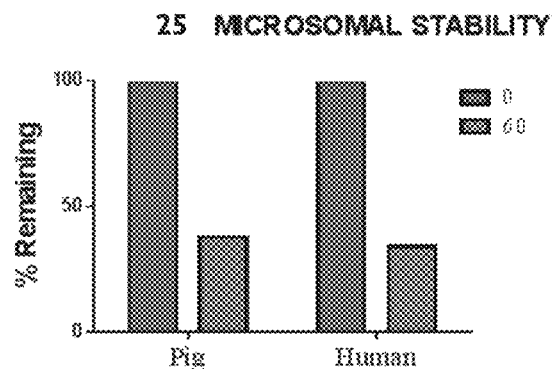
Figure 27B:
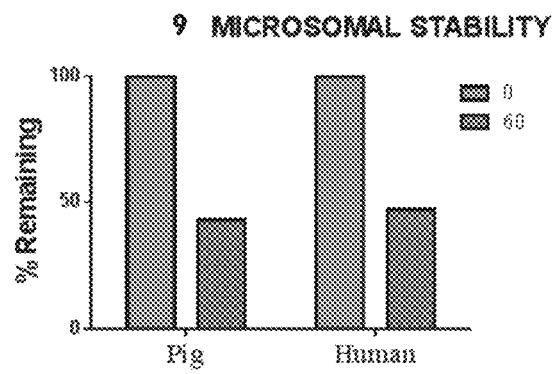
Figure 27C:
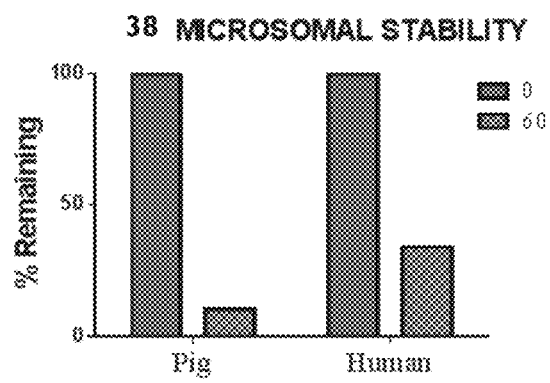
Figure 27D:
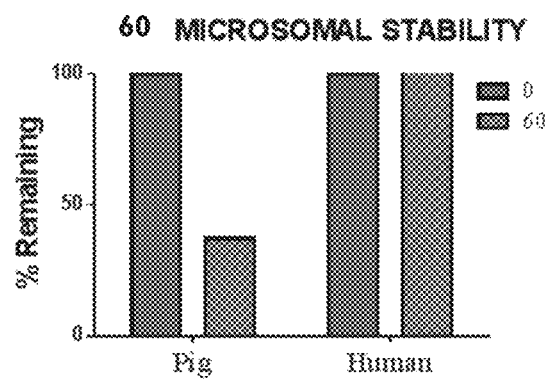
Figure 28A:
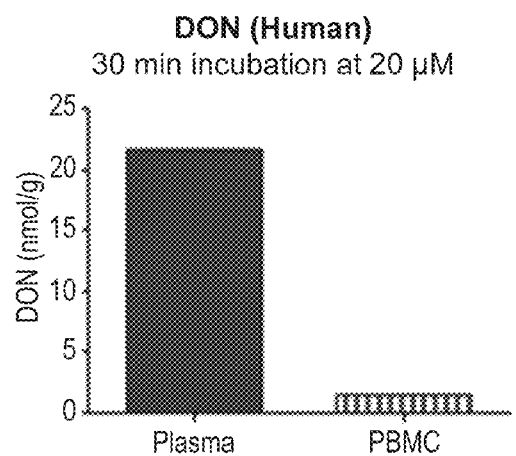
Figure 28B:
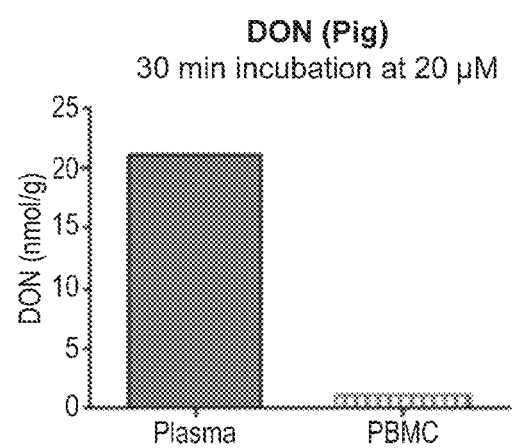
Figure 28C:
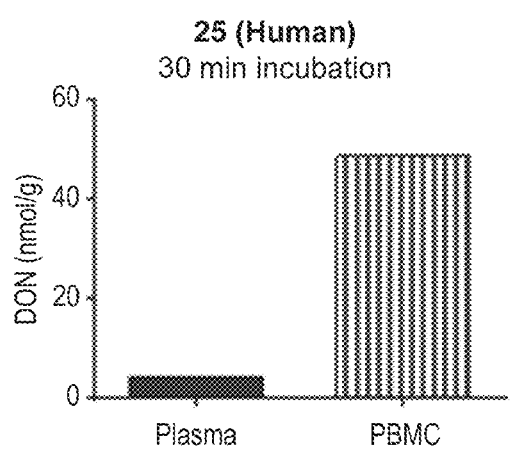
Figure 28D:
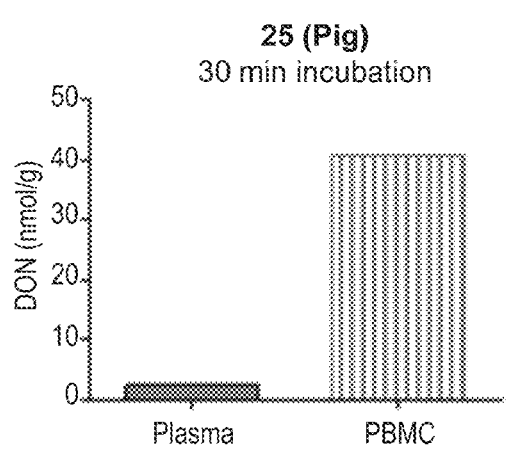
Figure 28E:
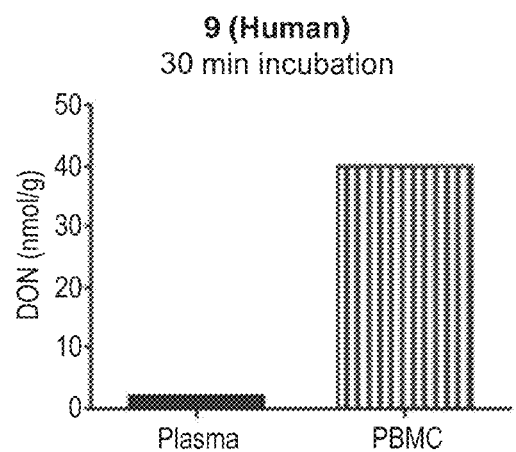
Figure 28F:
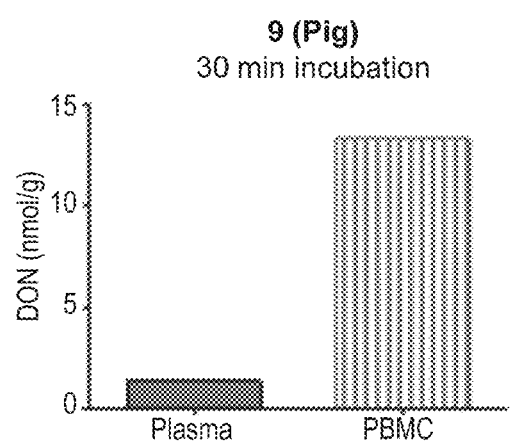
Figure 28G:
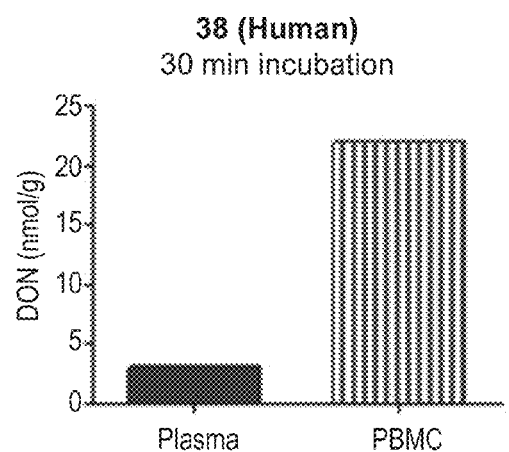
Figure 28H:
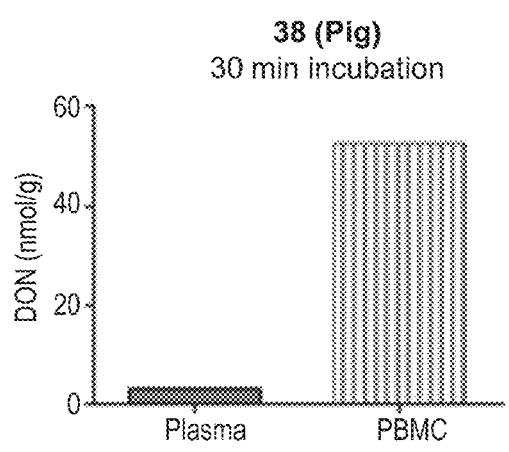
Figure 28I:
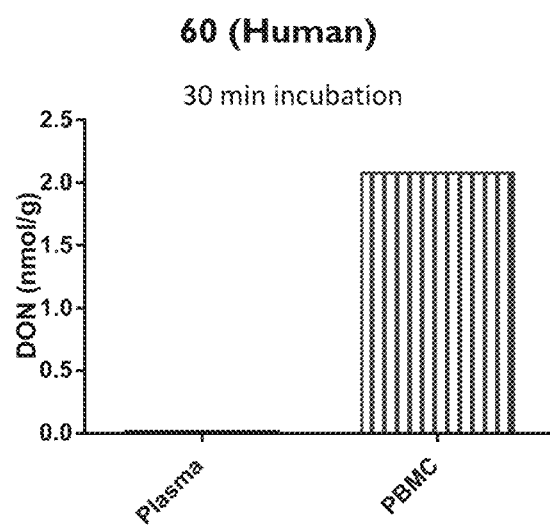
Figure 28J:
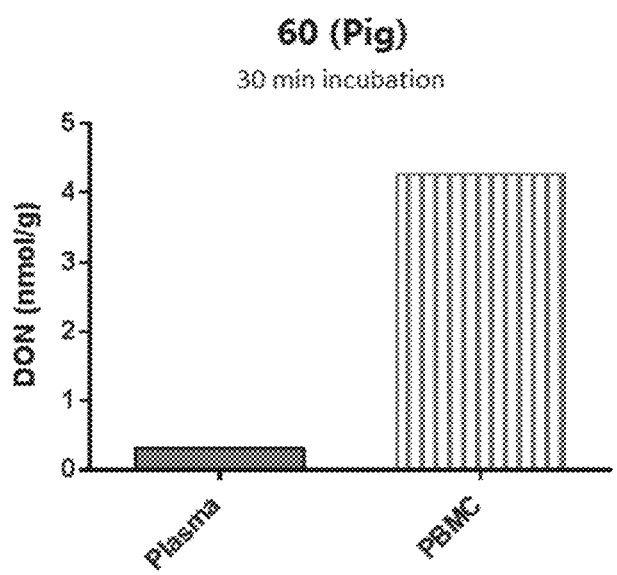
Figure 29A:
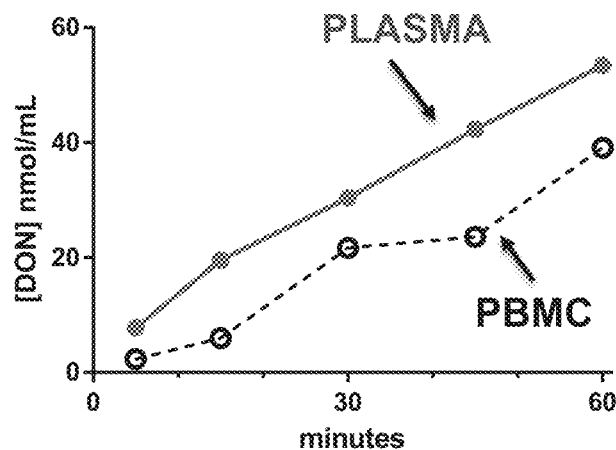
Figure 29B:
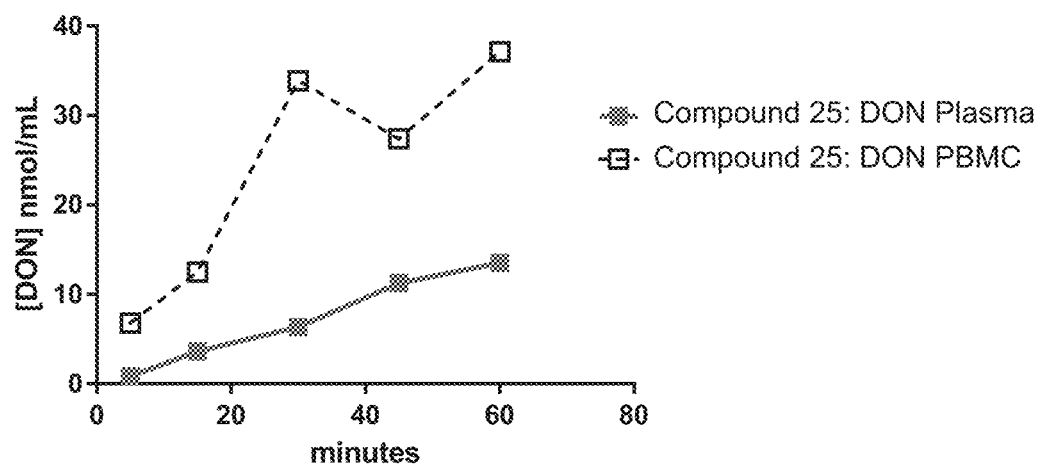
Figure 29C:
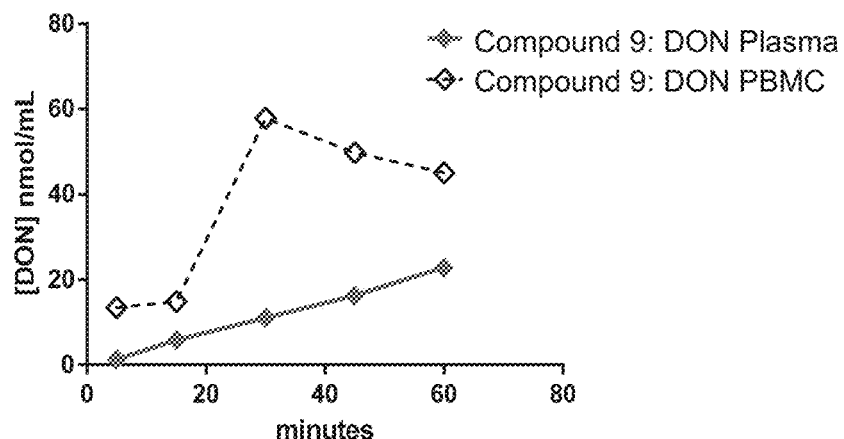
Figure 29D:
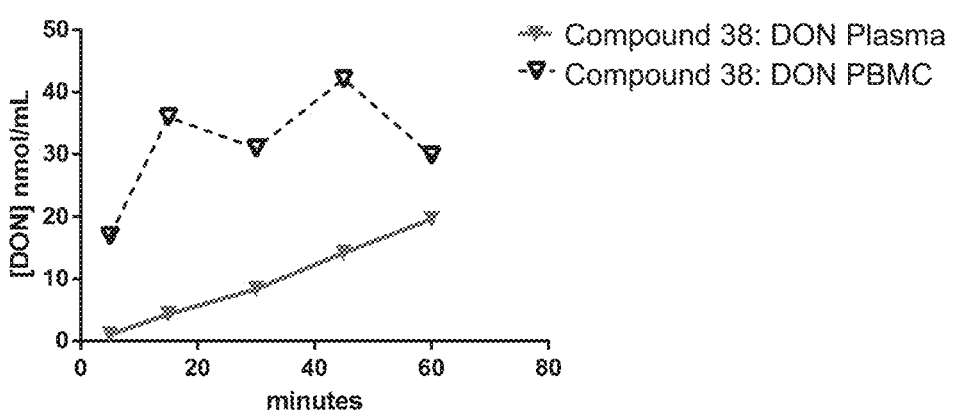
Figure 29E:
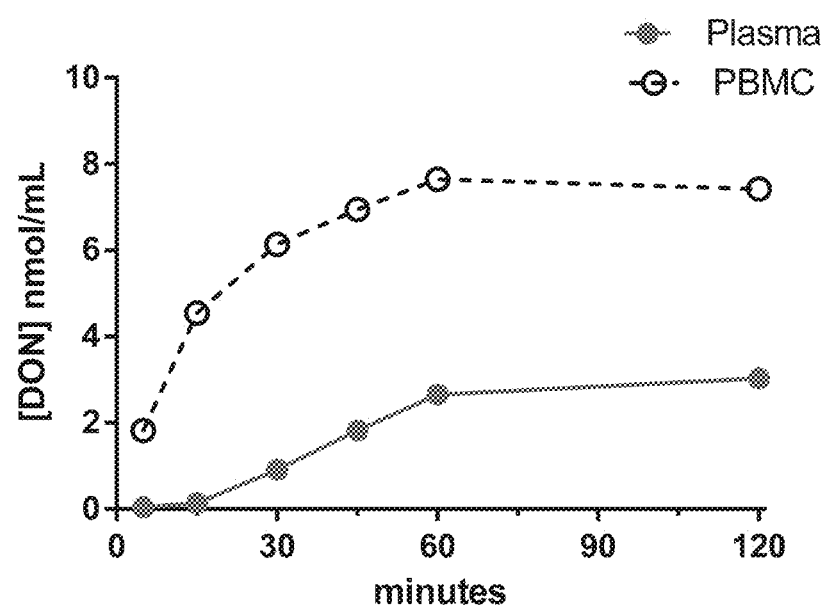
Figure 30A:
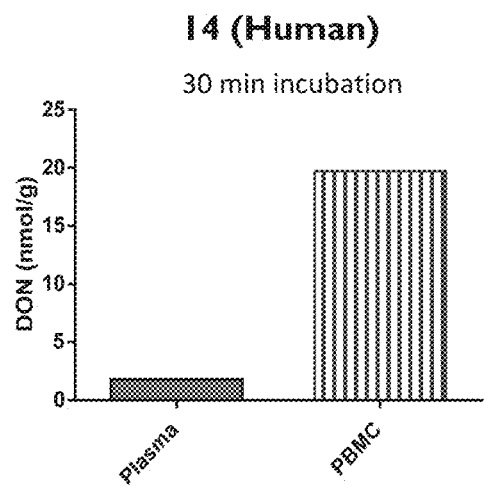
Figure 30B:
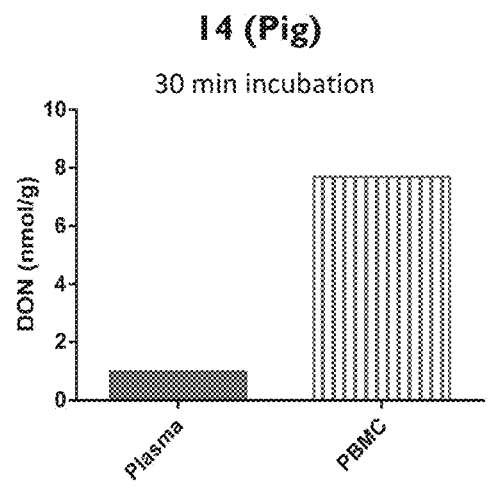
Figure 30C:
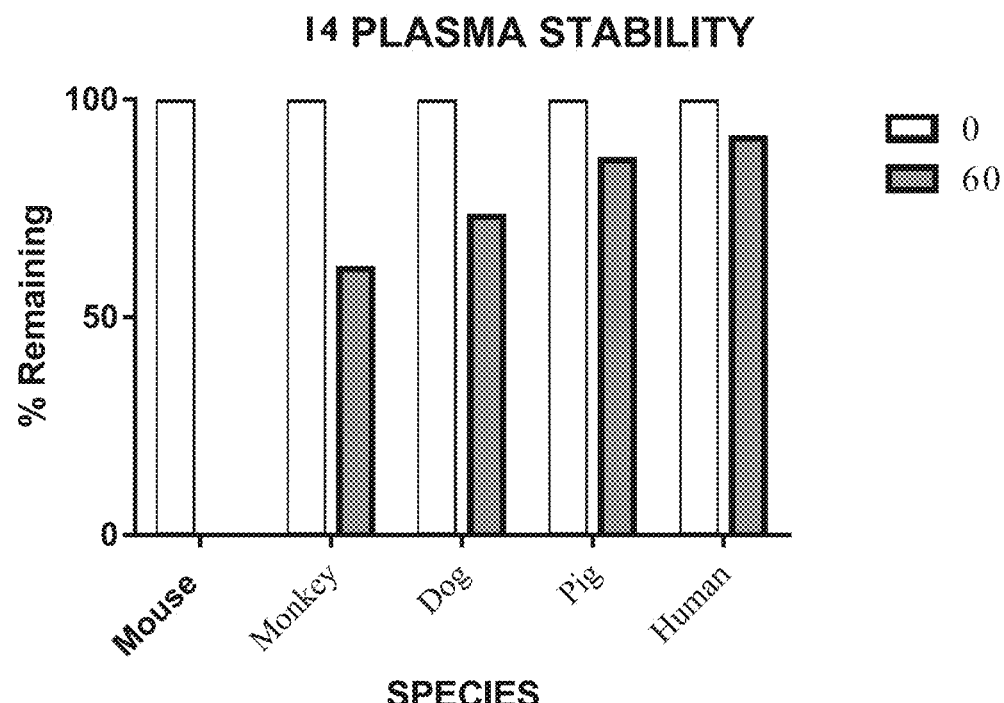
Figure 31:
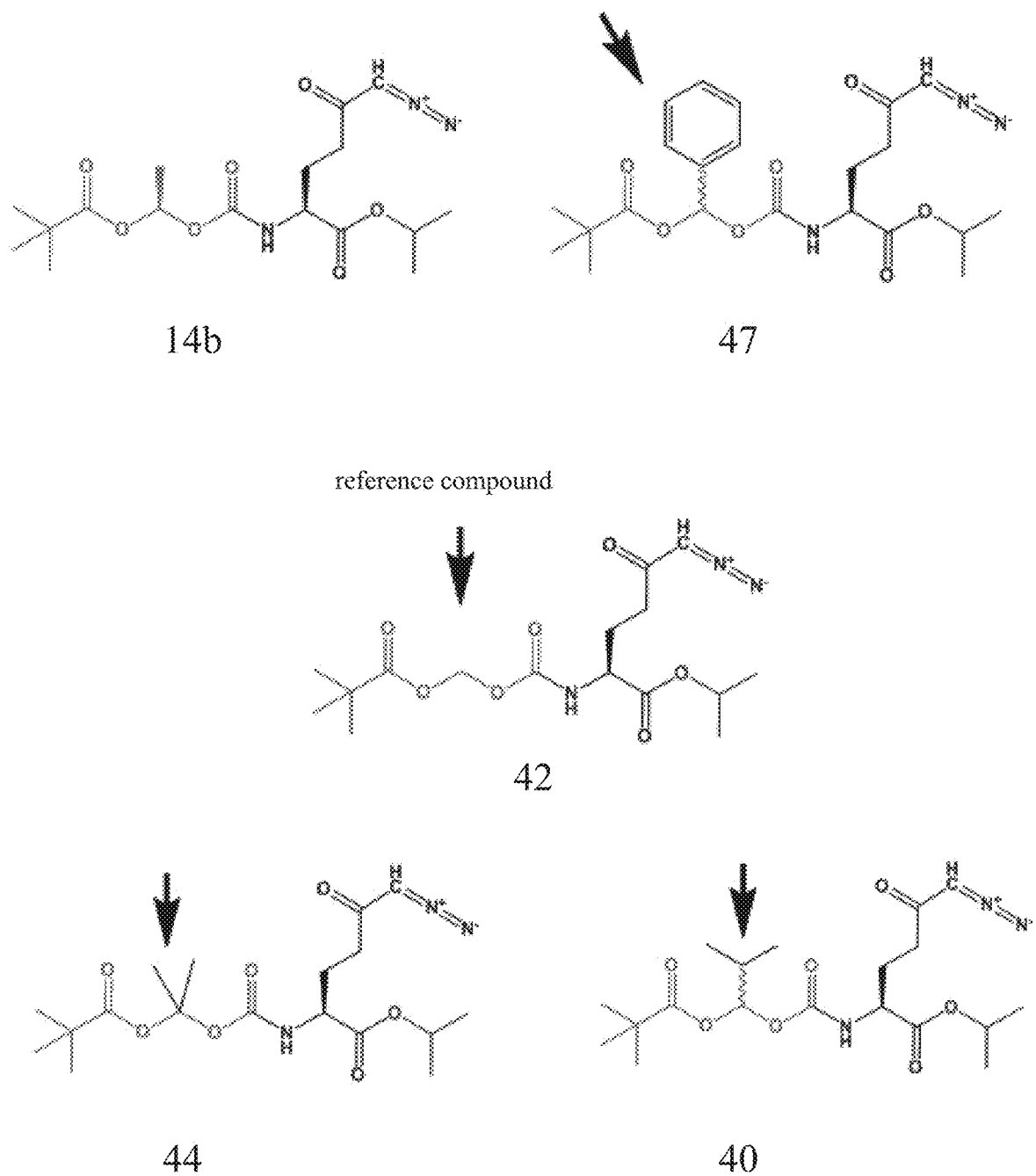
Figure 32A:
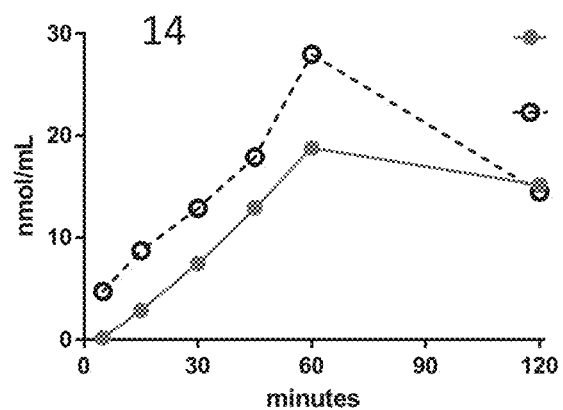
Figure 32B:
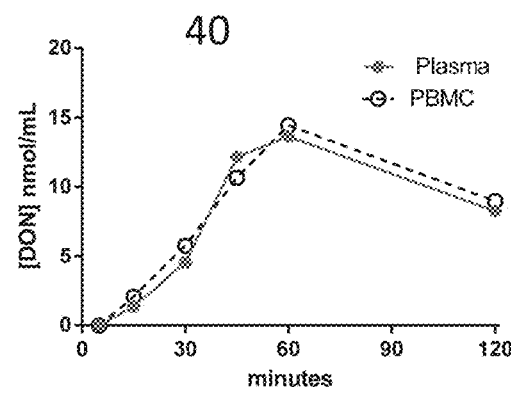
Figure 32C:
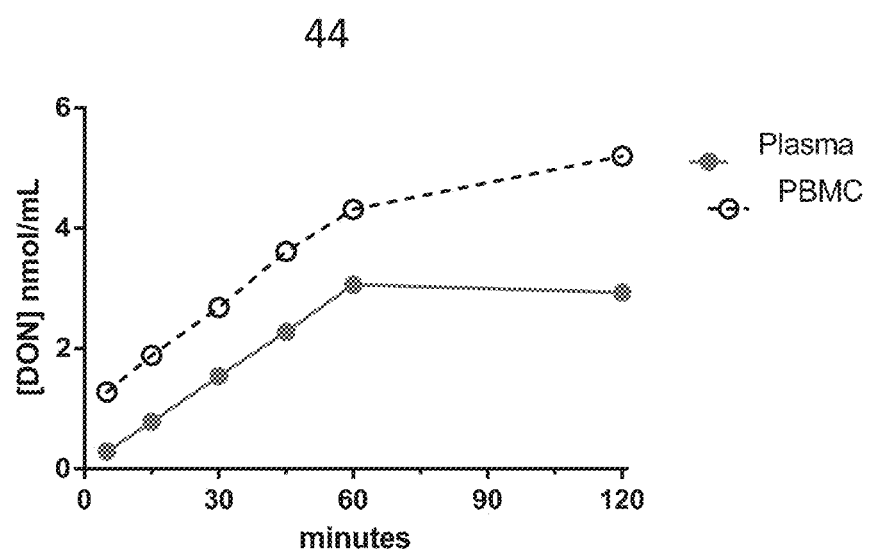
Figure 33:
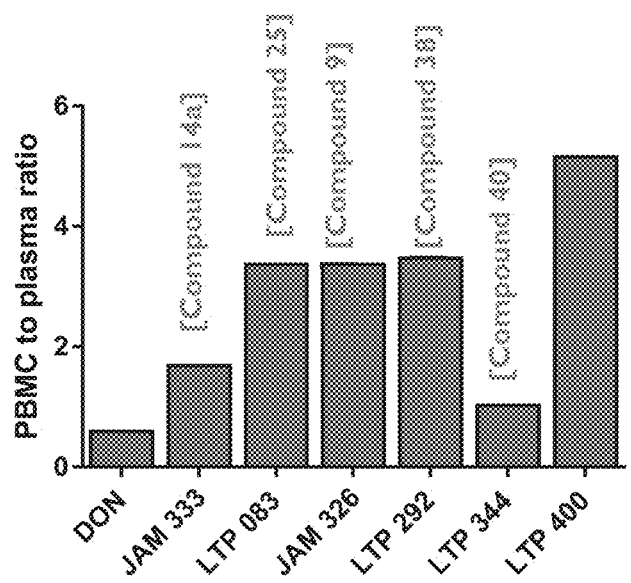
Figure 34A:
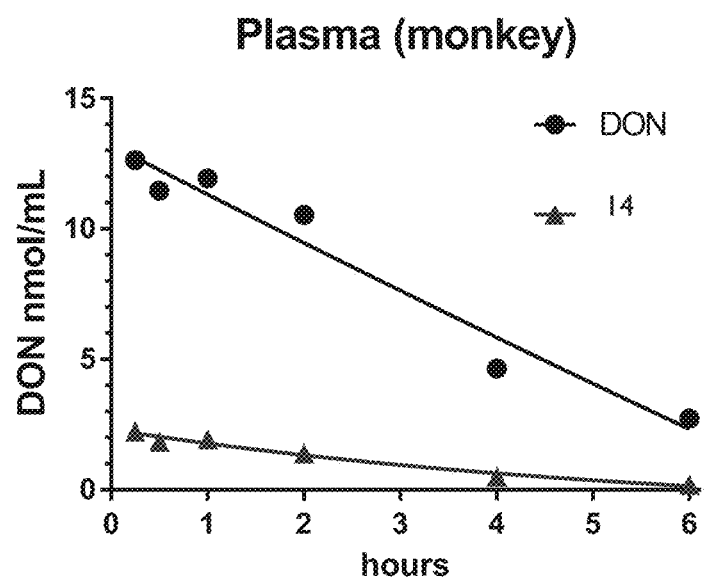
Figure 34B:
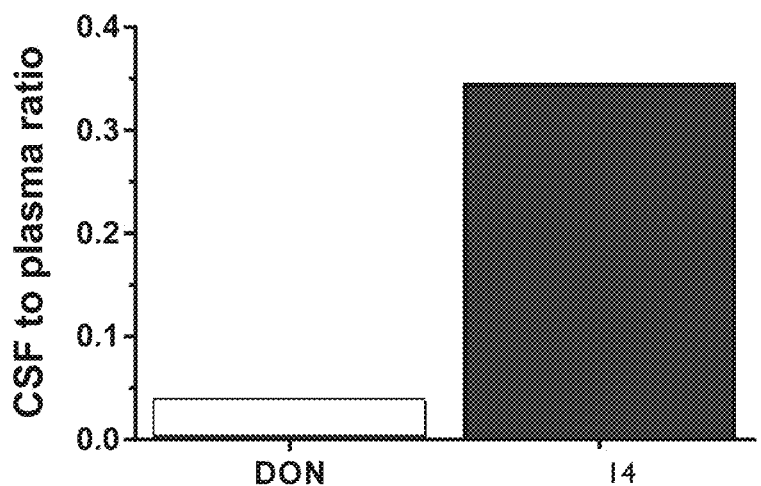
Figure 35:
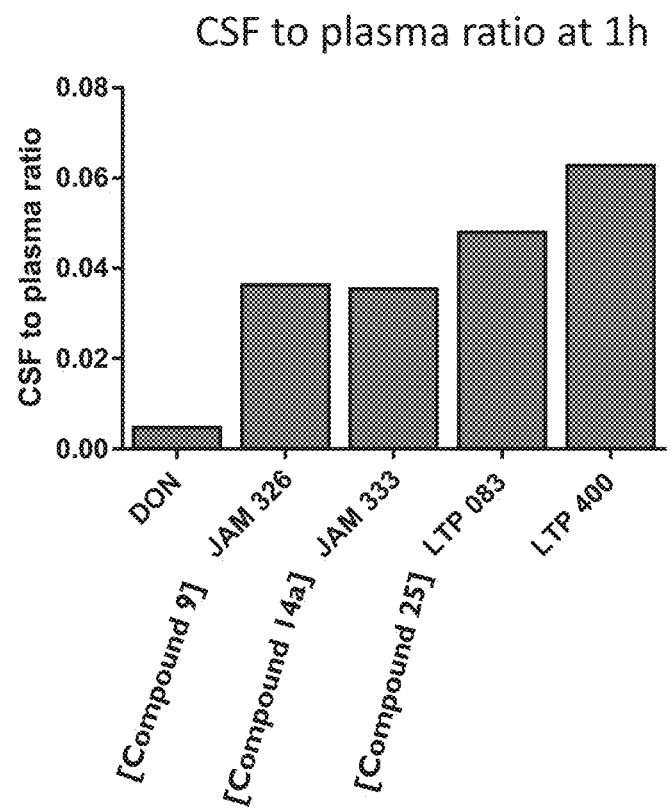
Figure 37A:
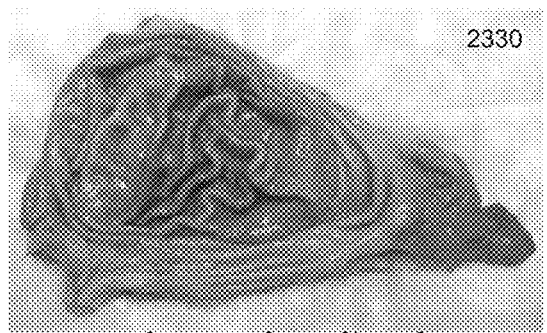
Figure 37B:
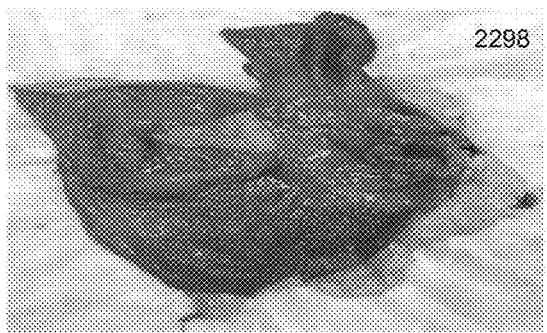
Figure 37C:
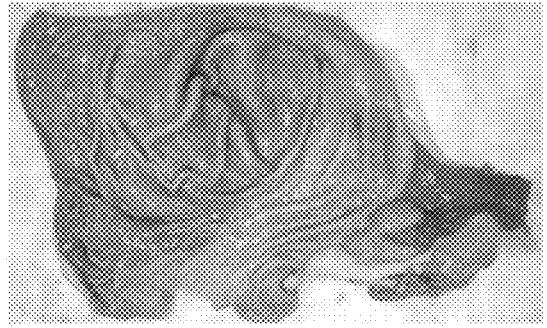
Figure 37D:
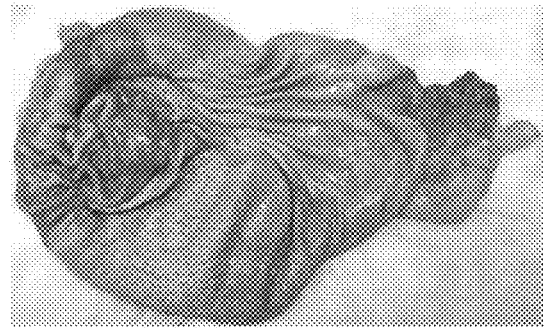
Figure 38:
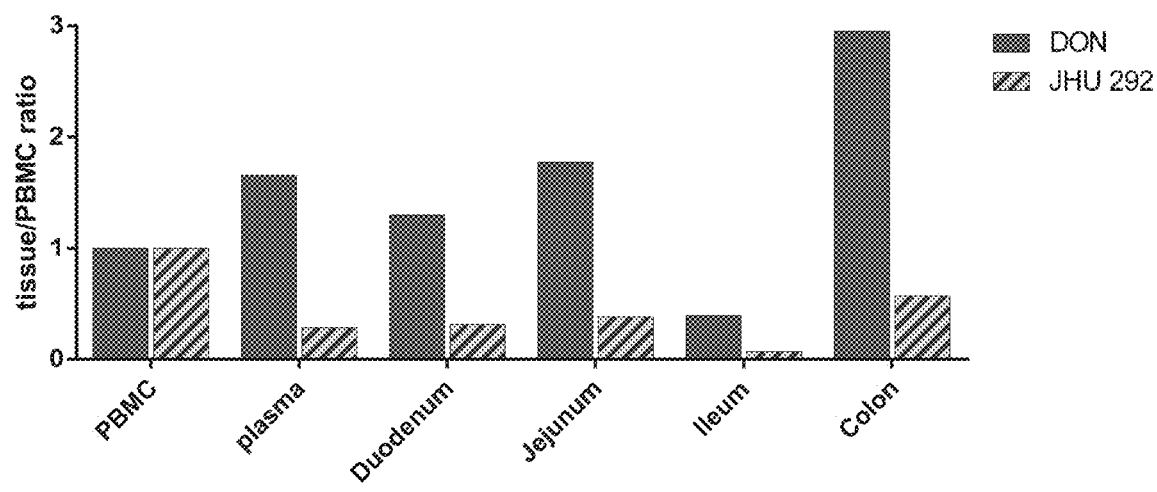
Figure 39:
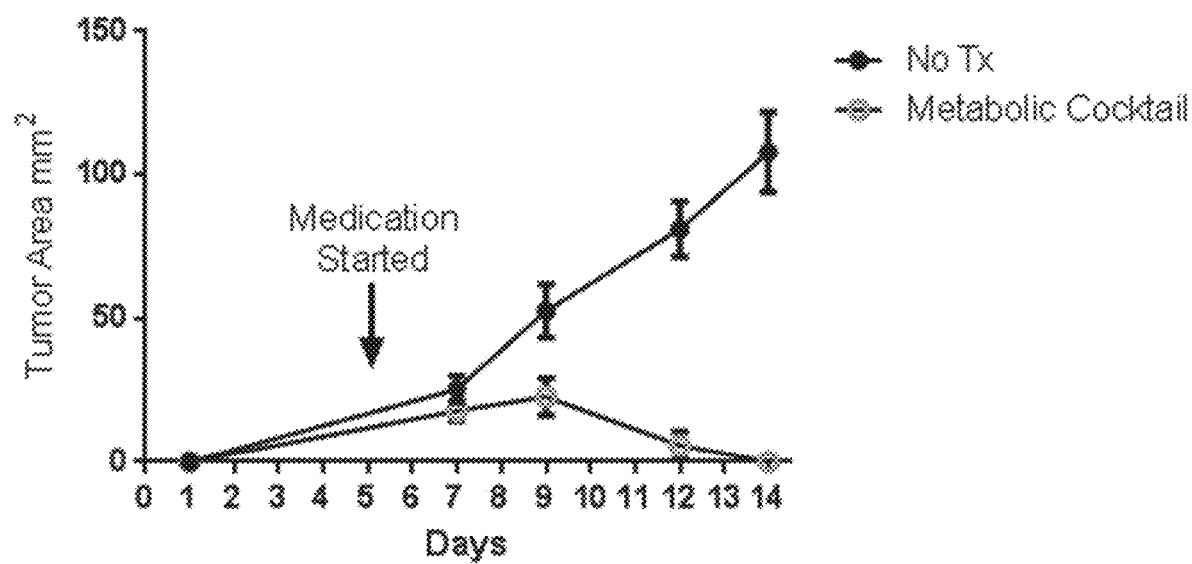
Figure 40:
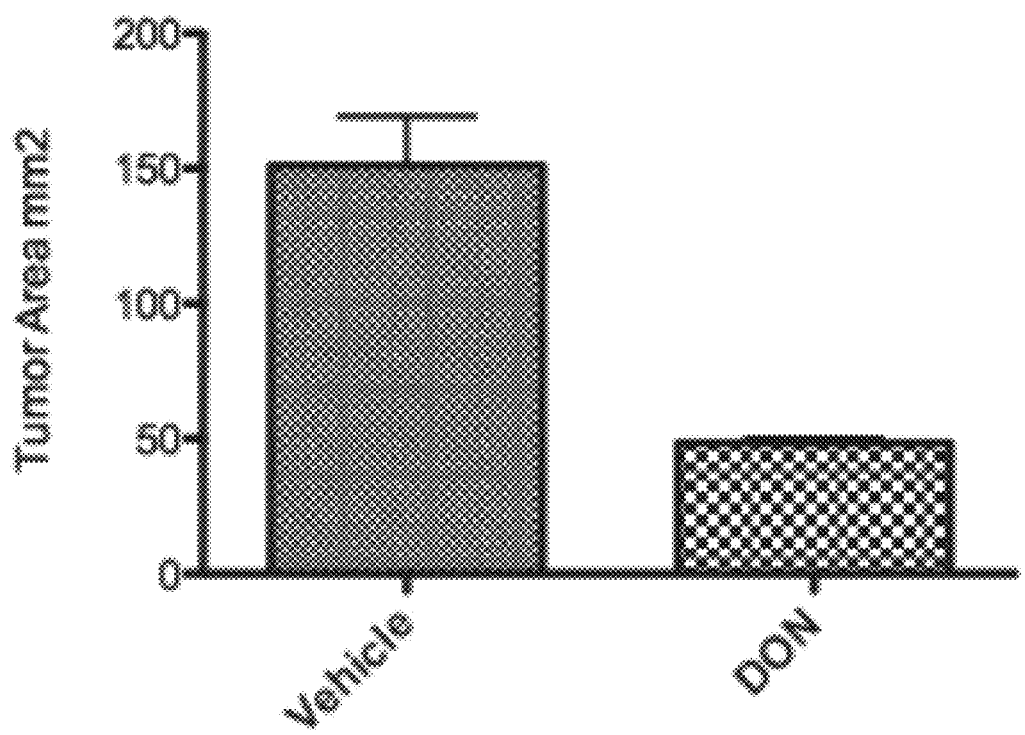
Figure 42:
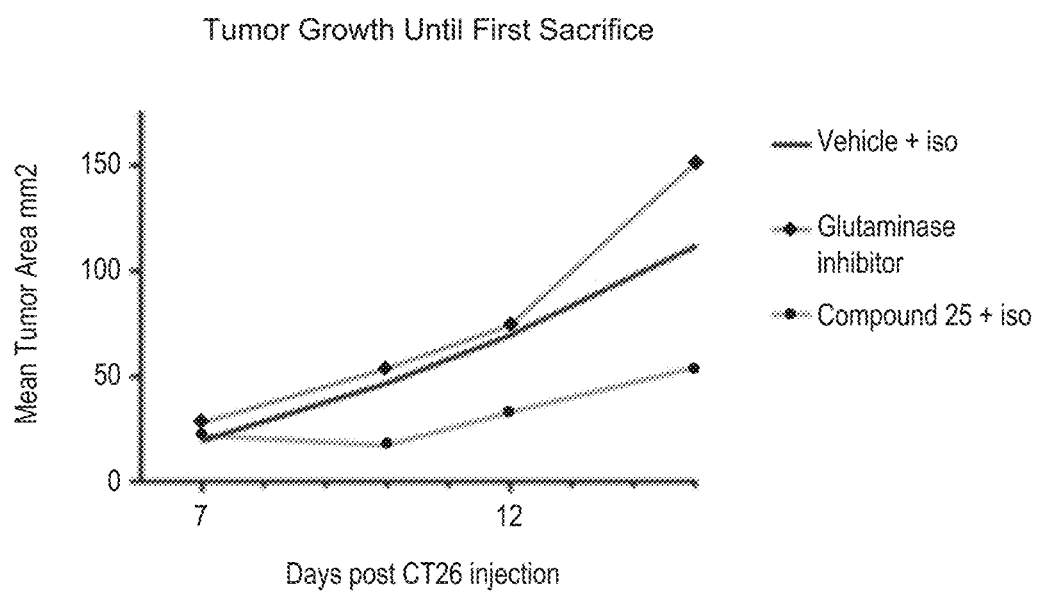
Figure 43:
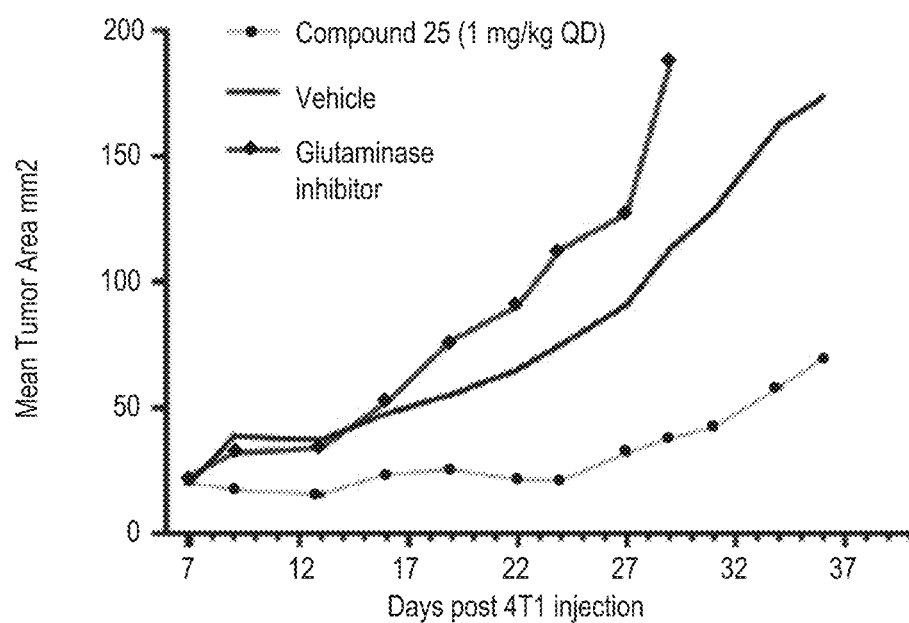
Figure 44A:
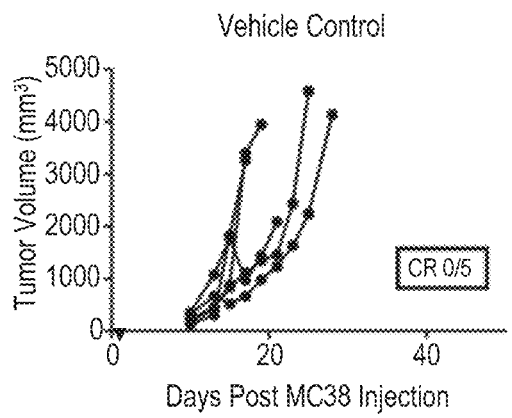
Figure 44B:
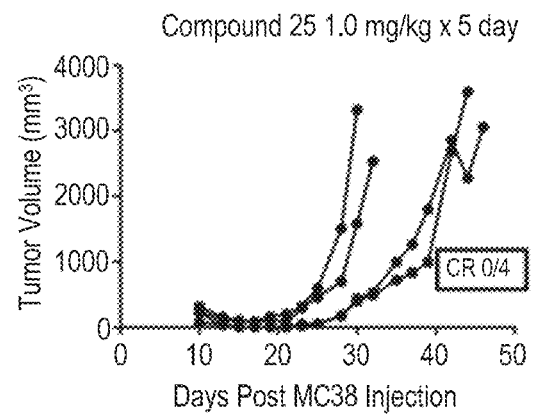
Figure 44C:
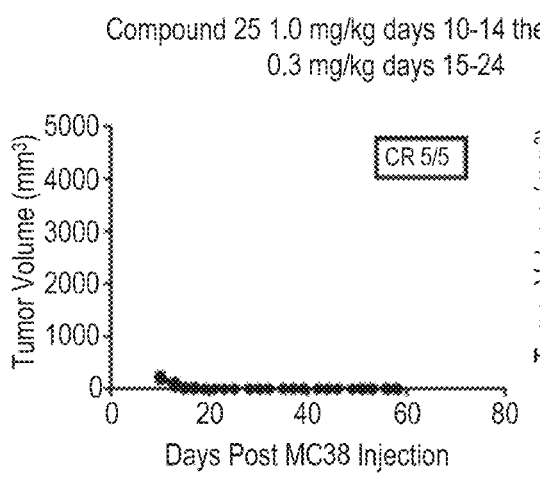
Figure 44D:
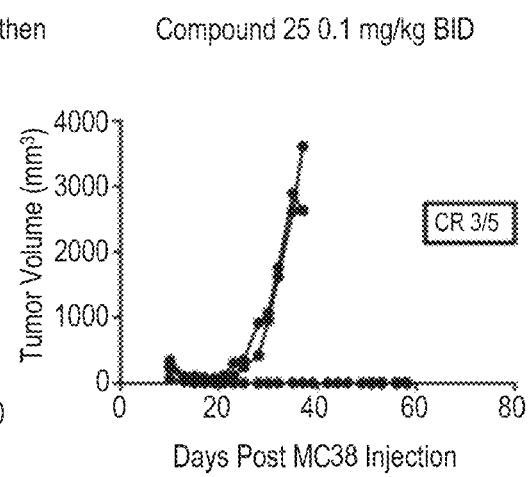
Figure 44E:
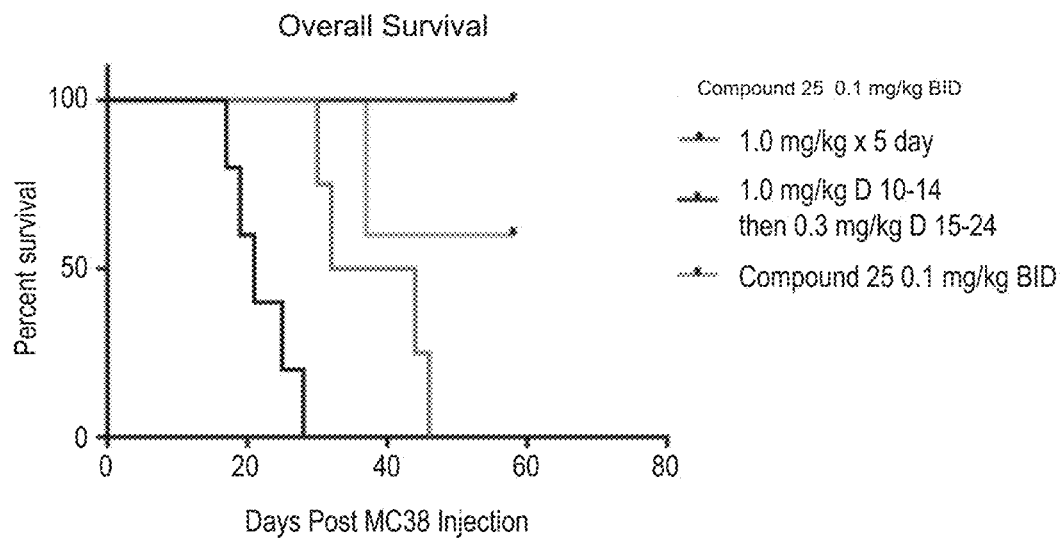
Figure 44F:
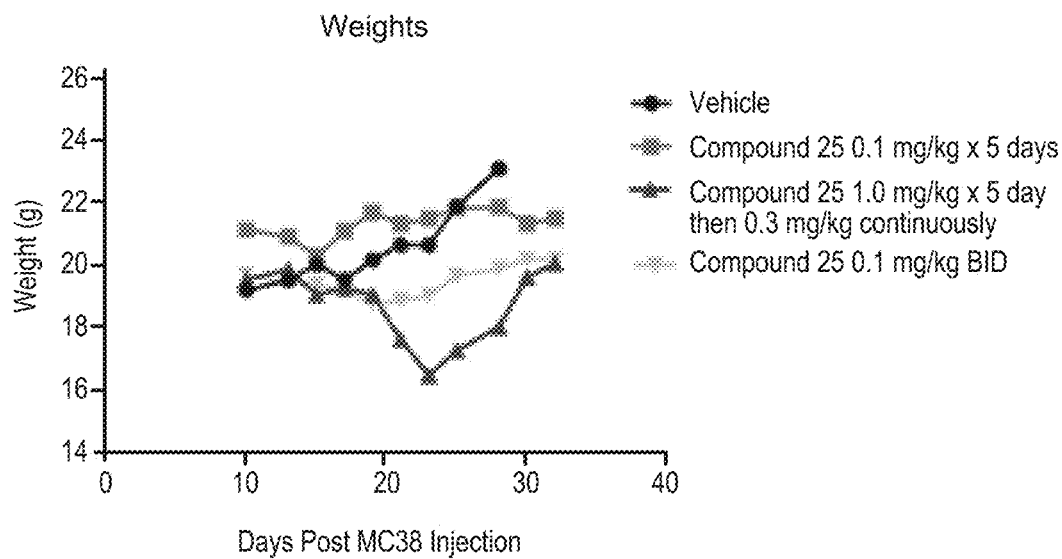
Figure 45A:
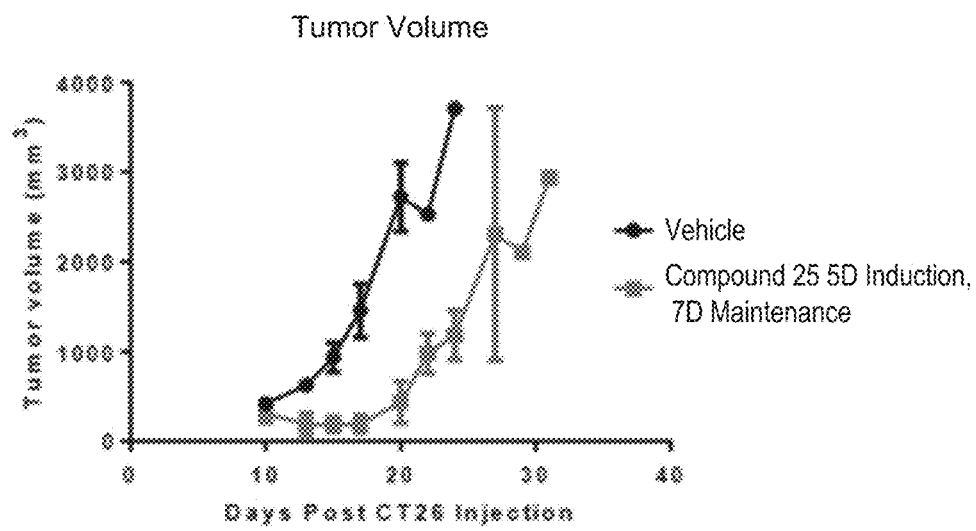
Figure 45B:
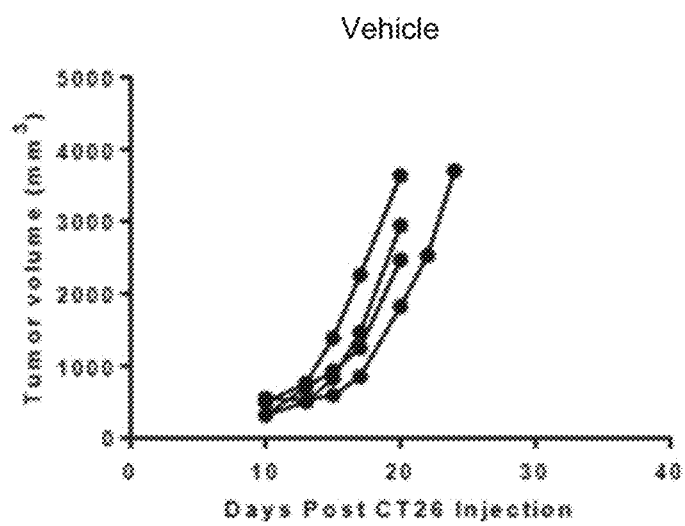
Figure 45C:
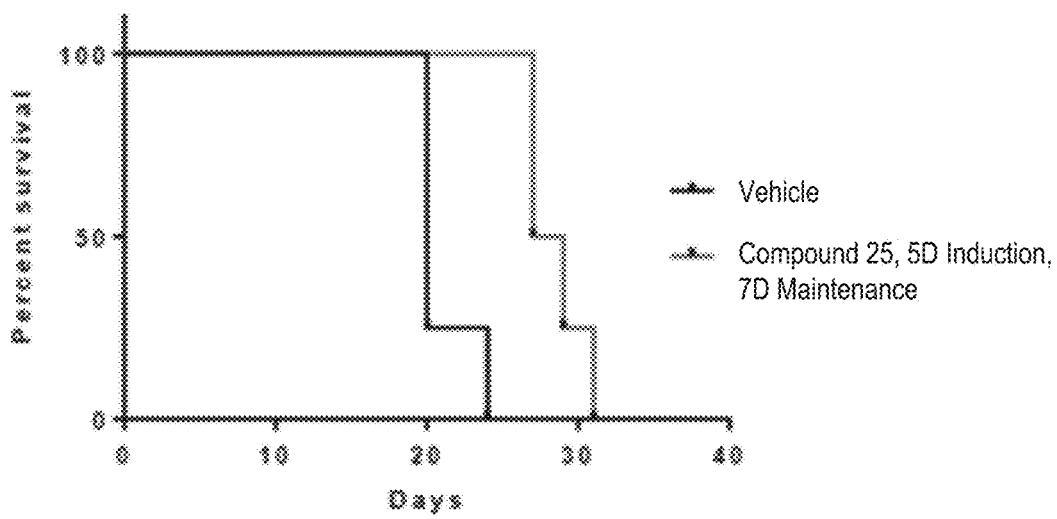
Figure 45D:
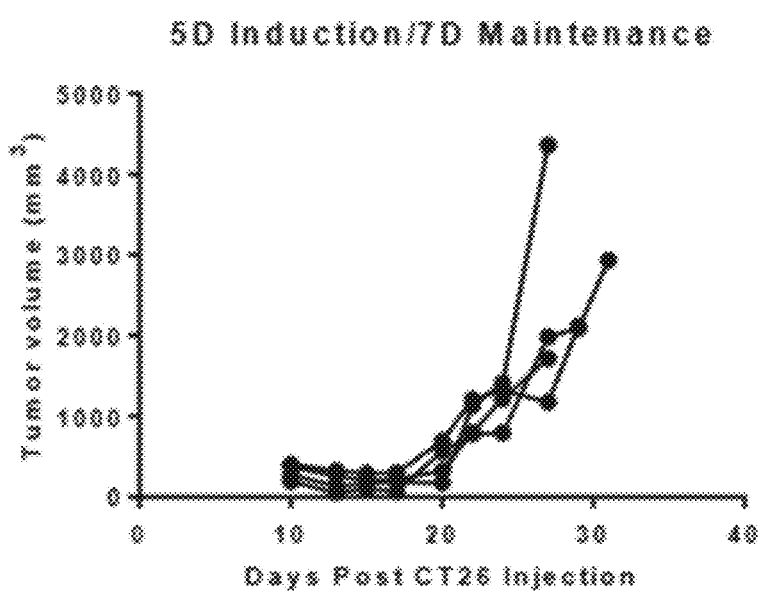
Figure 46A:
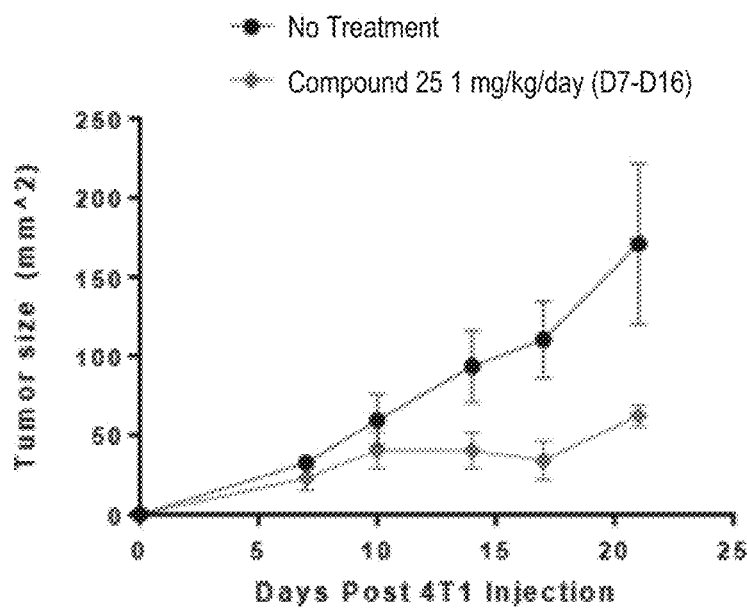
Figure 46B:
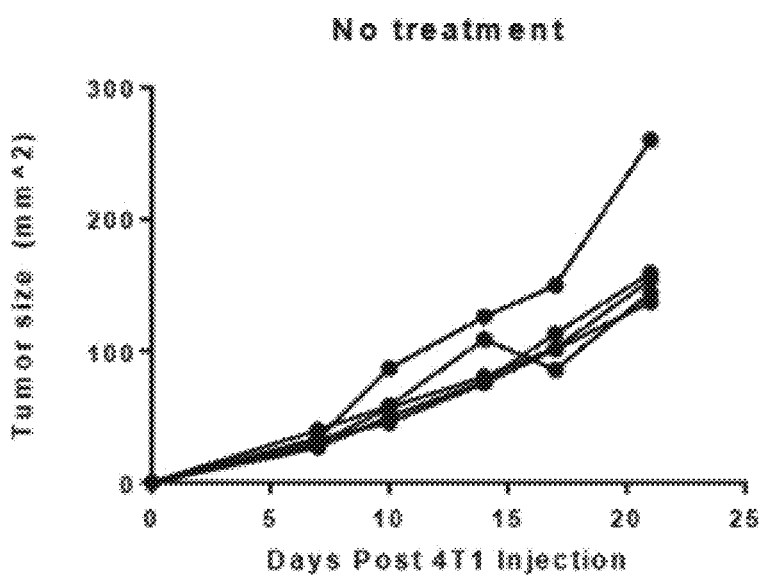
Figure 46C:
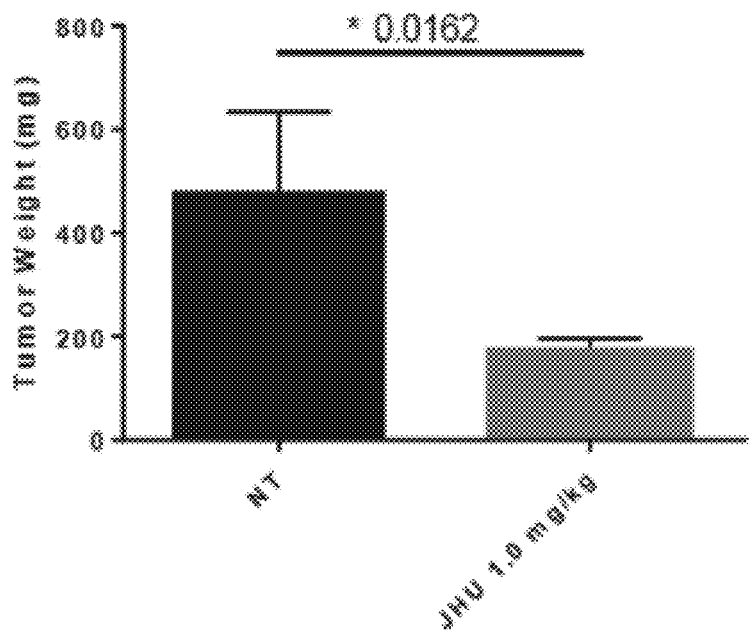
Figure 46D:
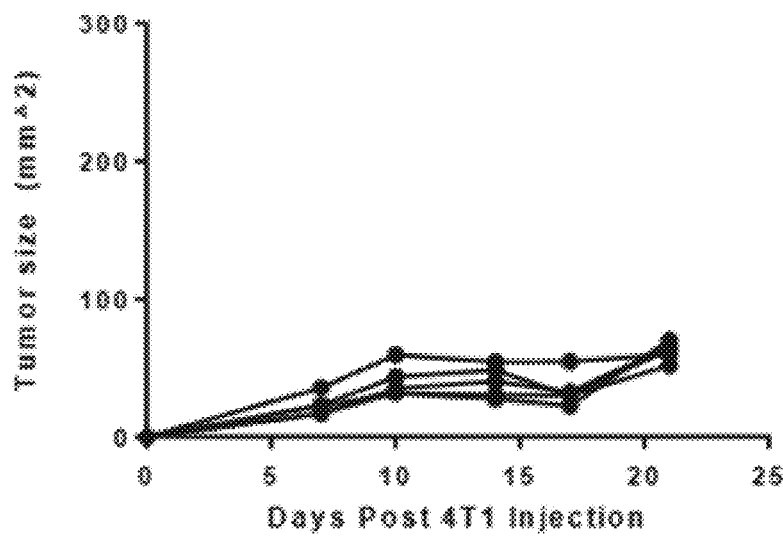
Figure 47A:
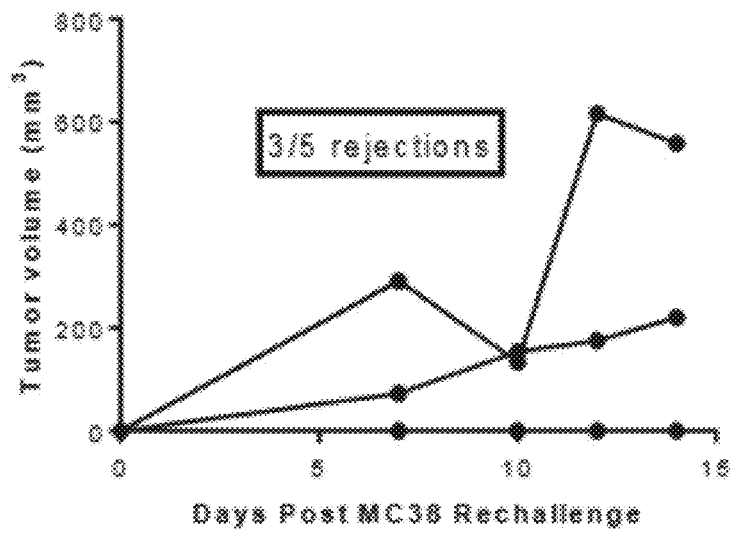
Figure 47B:
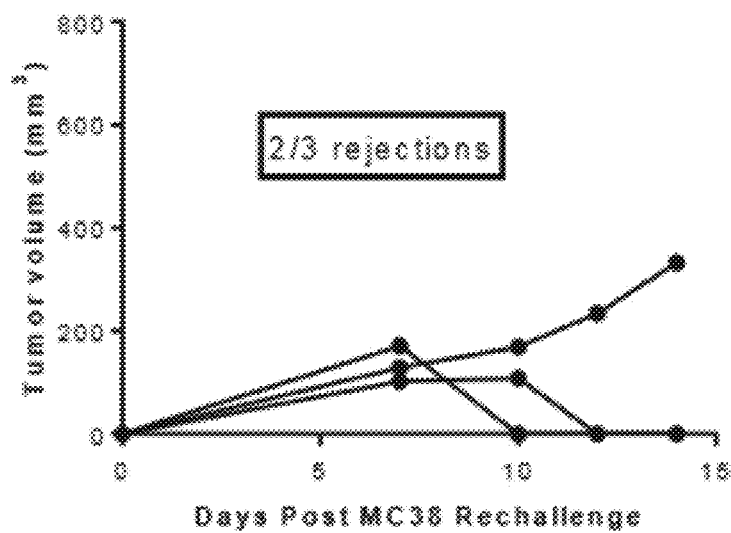
Figure 47C:
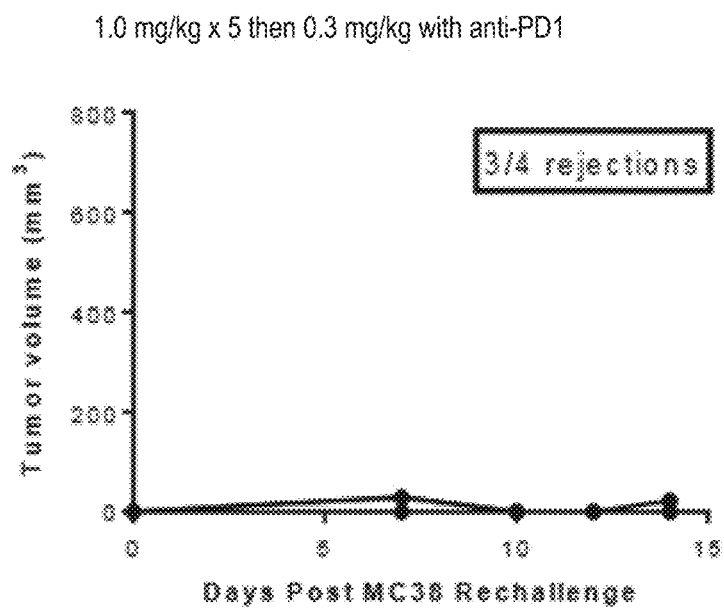
Figure 47D:
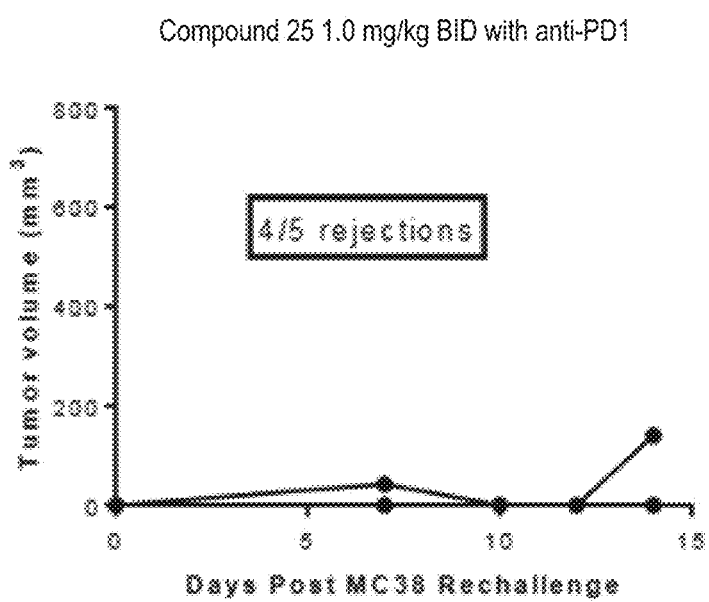
Figure 47E:
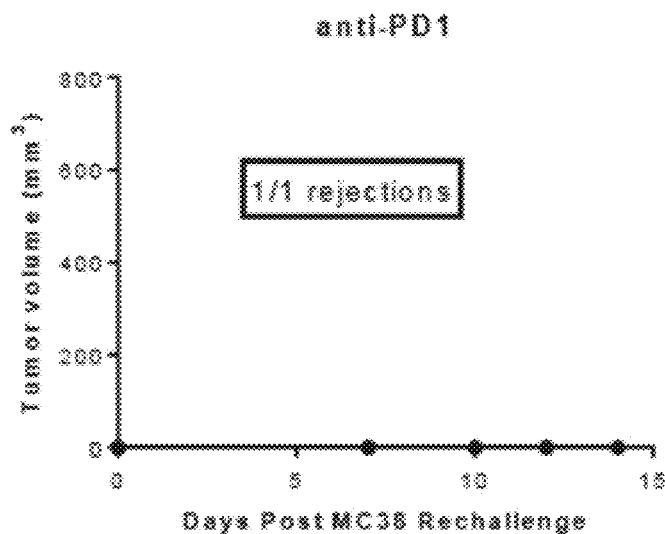
Figure 47F:
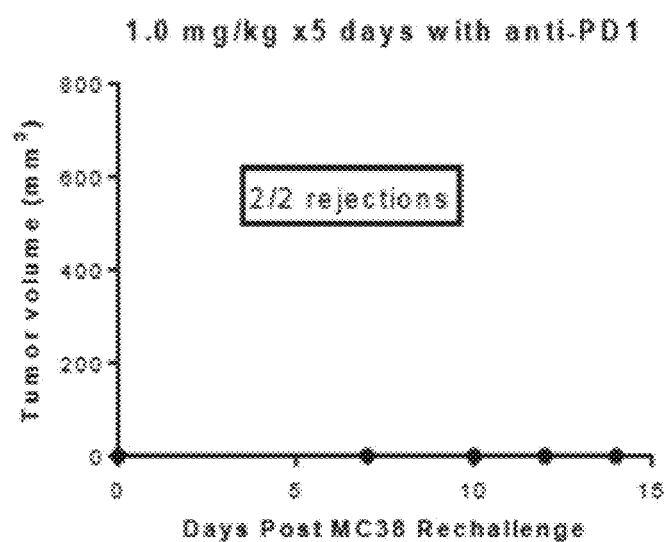
Figure 47G:
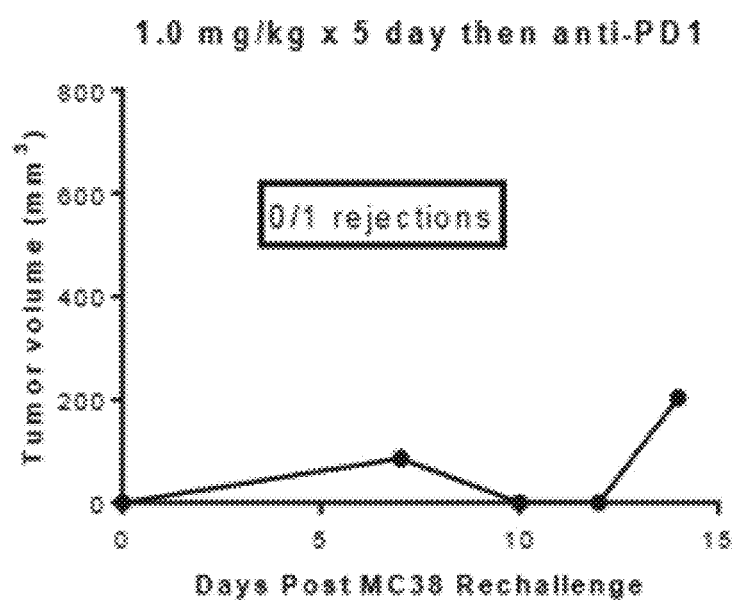
Figure 48A:
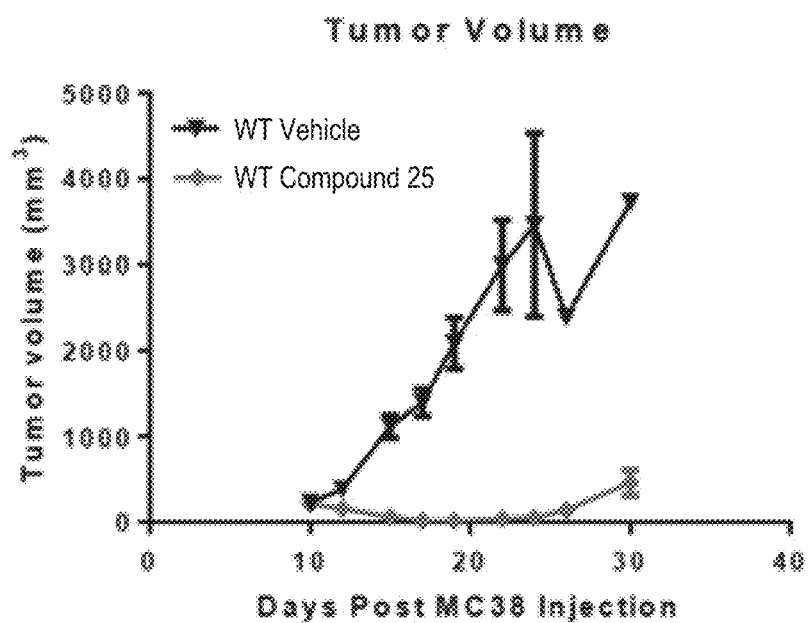
Figure 48B:
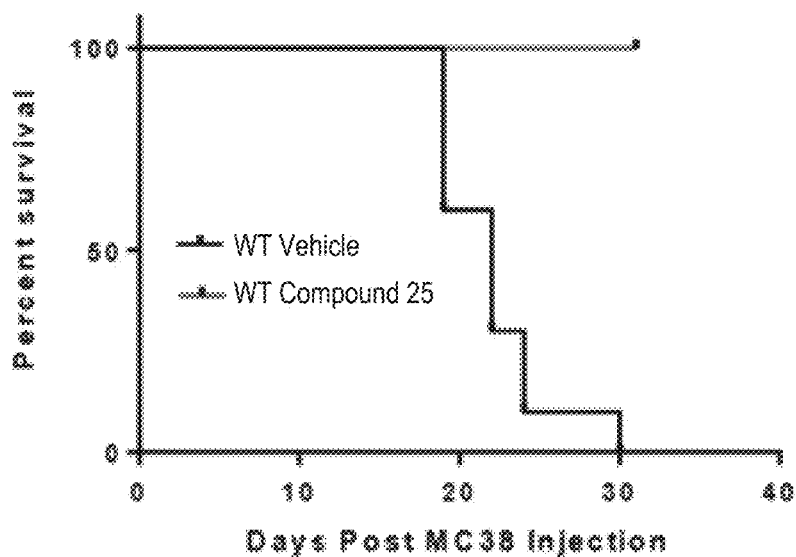
Figure 48C:
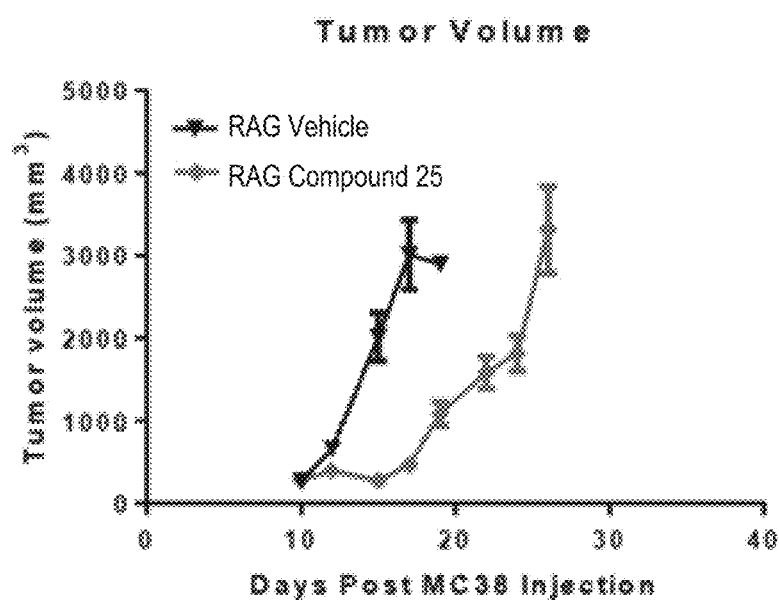
Figure 48D:
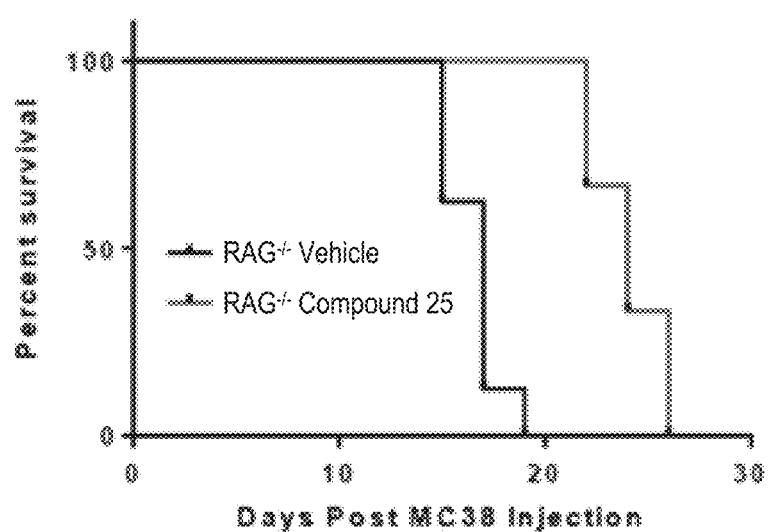
Figure 49A:
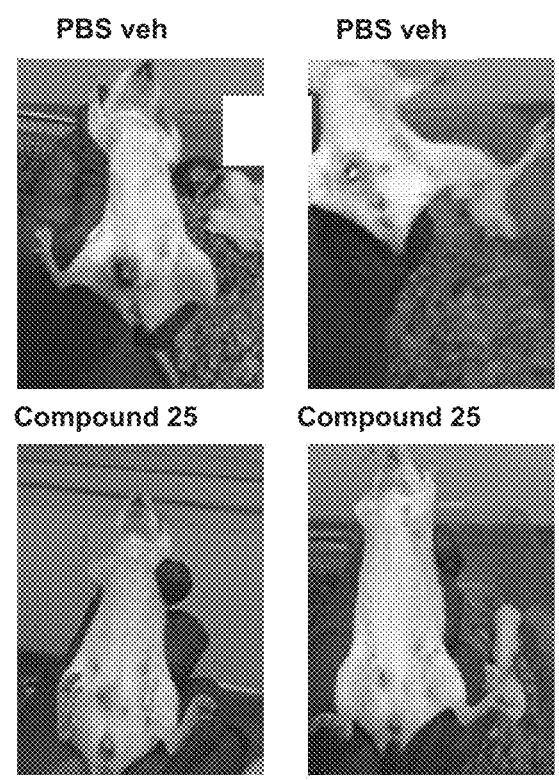
Figure 49B:
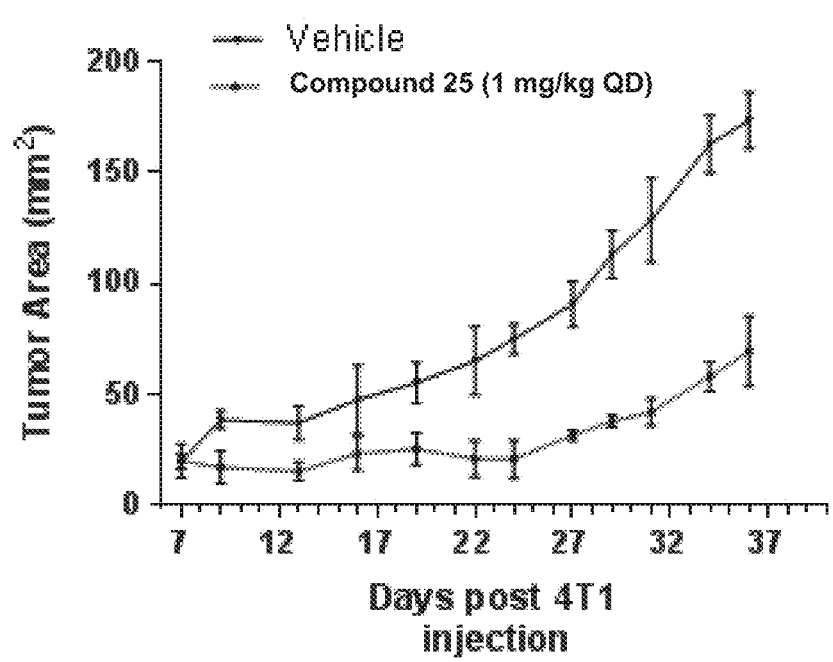

FIG. 18A and FIG. 18B are bar graphs and FIG. 18C is an illustration showing that compound 25 (FIG. 18A) reduces $C_{max}$; (FIG. 18B) enhances tumor to gut ratio; and (FIG. 18C) causes less GI toxicity in mice vs DON at equimolar doses in mice. Ova vaccinia virus infection was given followed by daily treatment with vehicle (Veh), DON (0.8 mg/kg), and 25 (0.8 mg/kg equivalent) for 5 days. At 1 hr after last dose, animals were sacrificed, small intestines removed, perfused with DPBS pH 7.4, and rolled longitudinally using the "swiss role" technique, and fixative for paraffin wax embedding. Upper panels show hematoxylin and eosin (H&E) stained sections of jejunum-ileum at 4× magnification; lower panel shows same sections at 10× magnification. DON caused significant inflammation, consisting of multifocal crypt distortion (left circle on the bottom left picture) and dilatation with loss of columnar epithelial morphology (rightcircle circle on the bottom left picture). DON prodrug looked more similar to vehicle-treated mice, with slightly hypercellular crypts, but no distortion (left circle on the bottom right picture) and normal columnar morphology (right circle on the bottom right picture).

FIG. 19A and FIG. 19B are tables showing that no bone marrow suppression was observed (FIG. 19A) following 25 at two 14-day effective dosing schemes; (FIG. 19B) employing long term 25 dosing schemes (48 days).

FIG. 20 is an illustration showing exemplary structures of DON and DON-based prodrugs.

FIG. 21A is a bar graph and FIG. 21B is a line graph showing that DON (1) inhibits glutamine metabolism and glioblastoma multiform (GBM) tumor growth in vivo. FIG. 21A shows compound DON (1) (0.8 mg/kg, i.p.) inhibited glutamine metabolism as evidenced by increased endogenous glutamine concentrations in flank GBM tumors 2 hours post-administration relative to vehicle-treated controls; *p<0.05. FIG. 21B shows in efficacy studies, compared to Day 0 baseline, vehicle-treated mice exhibited significant growth of flank GBM tumors during the course of the experiment. By contrast, systemic administration of 1 (0.8 mg/kg, i.p, q.d. days 1-6) caused a dramatic reduction in tumor size; *p<0.001, **p<0.0001.

FIG. 22A and FIG. 22B are line graphs and FIG. 22C is a table showing in vivo brain and plasma pharmacokinetics of compound DON (1) following oral administration of DON (1) and 14b in mice. 1 and 14b were dosed in mice at 0.8 mg/kg equivalent, via oral gavage and plasma and brain concentrations of compound 1 were evaluated via LC/MS. Oral administration of compound 1 and 14b exhibited similar plasma and brain pharmacokinetic profiles due to complete and rapid metabolism of 14b to 1 in mouse plasma.

FIG. 23A is a bar graph, FIG. 23B is a bar graph, and FIG. 23C is a table showing in vivo pharmacokinetics of DON following intravenous (i.v.) administration of DON (1) and 14 in monkey plasma and cerebrospinal fluid (CSF). 1 and 14b were dosed in two pigtail macaques at 1.6 mg/kg equivalent of 1 via i.v. administration and plasma (0.25-6 h) and CSF (30 min) concentrations of DON were evaluated via LC/MS. Relative to 1, 14b delivered substantially lower DON plasma concentration. The reverse was observed in CSF, where 14b delivered significantly higher DON CSF concentrations, achieving a 10-fold enhanced CSF to plasma ratio at 30 minute post dose.

FIG. 24 is a bar graph showing species specific plasma stability of 14b; 14b is stable in plasma of human, pig, dog and monkeys, but rapidly metabolized in mice;

FIG. 25 is an illustration showing exemplary structures of DON and DON-based prodrugs 25, 9, 38 and 60; different N-amino acid promoieties (e.g., leucine, tryptophan) provide differential plasma and microsomal stability.

FIG. 26A, FIG. 26B, FIG. 26C, and FIG. 26D are bar graphs showing in vitro plasma stability of DON prodrugs 9, 25, 38 and 60. Metabolism occurs via removal of the N-protecting group; both ethyl and isopropyl esters are stable in plasma of pigs and humans.

FIG. 27A, FIG. 27B, FIG. 27C, and FIG. 27D are bar graphs showing in vitro liver microsomal stability of DON prodrugs 9, 25, 38 and 60; all prodrugs showed moderate-high stability in human and pig microsomes.

FIG. 28A, FIG. 28B, FIG. 28C, FIG. 28D, FIG. 28E, FIG. 28F, FIG. 28G, FIG. 28H, FIG. 28I, and FIG. 28J are bar graphs showing ex-vivo studies in whole human and pig blood of 9, 25, 38 and 60; DON prodrugs selectively deliver DON to PBMCs in both humans and pigs vs plasma; compared to DON, the PBMC/plasma ratio was enhanced 10-100+ fold;

FIG. 29A FIG. 29B, FIG. 29C, FIG. 29D and FIG. 29E are line graphs showing pig in vivo studies with DON prodrugs of 9, 25, 38 and 60; DON prodrugs selectively deliver DON to PBMCs vs plasma; compared to DON, the PBMC/plasma ratio was enhanced 6- to 10-fold.

FIG. 30A, FIG. 30B, and FIG. 30C are bar graphs showing plasma stability of compound Methyl-POM 14b and its derivatives.

FIG. 31 is an illustration showing exemplary structures of N-acylalkyloxy DON-based prodrug analogs for intracellular targeting and brain penetration; the addition of steric bulk to the "bridge" might result in a slower hydrolysis.

FIG. 32A, FIG. 32B, and FIG. 32C are line graphs showing pig i.v. studies with DON prodrugs: in vivo in pigs DON prodrugs selectively deliver DON to PBMCs vs DON.

FIG. 33 is a bar graph and two tables showing PBMC to plasma AUC($_{0-t}$) ratio comparison DON prodrugs achieve >6 fold better ratio (based on $AUC_{0-t}$) vs DON.

FIG. 34A is a line graph and FIG. 34B is a bar graph showing monkey IV studies with DON prodrug 14b shows lower plasma but higher CSF concentrations achieving ~6-7 fold >CSF/plasma ratio vs DON.

FIG. 35 is a bar graph showing CSF to plasma ratio at 1 h after i.v. infusion with compounds 1, 9, 14b, 25 and 60.

FIG. 36 is an illustration showing clinical findings for DON (1) and 38 over 5 days observation period DON-treated pigs exhibited more adverse clinical signs versus 38; DON (1.6 mg/kg) and 38 (1.5 mg/kg) doses were chosen to provide equivalent PBMC exposure; drugs were dosed i.v. for 2 h/day for 5 days (n=2 pigs); close clinical monitoring was performed to evaluate drug toxicity (e.g. lethargy, anorexia, diarrhea, GI-bleeding, etc); after 5 days of dosing, pigs were euthanized and tissues were harvested for PK and histopathology.

FIG. 37A, FIG. 37B, FIG. 37C, and FIG. 37D are illustrations showing that macroscopically, DON-treated pigs exhibited more severe stomach toxicity versus 38; histopathologic toxicity scoring for gastro-intestinal and other tissues is pending; and FIG. 38 is a bar graph showing that at equivalent PBMC exposures, 38 administration delivers less DON to GI tissues versus DON administration. DON administration appeared to cause more adverse clinical effects versus 38.

FIG. 39 is a line graph illustrating that administration of DON markedly inhibits lymphoma growth in a EL4 mouse lymphoma model.

FIG. 40 is a bar graph illustrating that administration of DON has a modest effect on inhibiting melanoma growth, which is a not a bone marrow derived tumor.

FIG. 41A is a Kaplan-Meier graph and FIGS. 41B-E are line graphs showing that compound 25 (5 day dosing starting on day 7) is superior to CB-839 (a glutamase inhibitor) (30 day dosing starting day 1) in CT26 tumor model. These unexpected results suggest that 25 can be used as a single agent to treat colon cancer.

FIG. 42 is a line graph illustrating that compound 25 (4 days starting on day 6) is superior to CB-839 (continuous twice daily dosing starting on day 1 prior to engraftment) in a CT26 tumor model. FIG. 42 shows mice received daily compound 25 (1.9 mg/kg) on days 6-9 vs BID CB-839 on days 1-15. These results again demonstrate the compound 25 is superior to CB-839 and unexpectedly that compound 25 can be used as a single agent to treat cancers such as colon cancer.

FIG. 43 is a line graph illustrating that compound 25 (daily days 7-22) is superior to CB-839 (continuous twice daily dosing days 1-29) in a 4T1 breast cancer model. Mice received daily compound 25 (1.0 mg·kg/d) for days 7-22 as compared to BID CB-839 for days 1-29. These results again demonstrate the compound 25 is superior to glutamase inhibitor CB-839 and unexpectedly that compound 25 can be used as a single agent to treat cancers such as breast cancer.

FIGS. 44A-D and F are line graphs and FIG. 44E is a Kaplan-Meier graph illustrating that compound 25 dosing of 1 mg/kg following by 0.3 mg/kg leads to a complete and durable response in the MC38 tumor model. These results again demonstrate the compound 25 unexpectedly that compound 25 can be used as a single agent to treat cancers such as colon cancer FIGS. 45A, B, and D are line graphs and FIG. 45C is a Kaplan-Meier graph illustrating that compound 25 gives a robust response and improved overall survival as compared to vehicle-treated animals in the CT26 colon cancer model.

FIGS. 46A, B, and D are line graphs and FIG. 46C is a bar graph illustrating that compound 25 provides a robust response and improved overall survival the 4T1 breast cancer model.

FIGS. 47A-47G are line graphs illustrating that mice treated with compound 25 when administered as a single agent prevents colon cancer cell proliferation upon rechallenge, demonstrating that compound 25 unexpectedly immunostimulates the mouse.

FIGS. 48A and 48C are line graphs and FIGS. 48B and 48D are Kaplan-Meier graphs showing that compound 25 inhibits colon cell proliferation and extends the survival of mice in the MC38 model.

FIG. 49A is an illustration of mice and FIG. 49B is a line graph illustrating that compound inhibits tumor growth. FIG. 49A shows mice after 30 days inoculation (8 days drug free). FIG. 49B shows tumor area vs. days post injection with 4T1 tumor cells. Mice were treated with compound 25 1 mg/kg every day (from d5-d22) or vehicle. 4T1 tumor cells (0.1 million) were injected into the mammary fat pads of 8-week-old female BALB/c mice. Mice received vehicle (PBS) or 1 mg/kg compound 25 daily from day 5 to day 22. Photos were taken on day 30 after tumor inoculation (FIG. 57A). Tumor volume was measured 2-3 times weekly until WT mice were sacrificed (when size reached to 20 mm length or necrosis occurred). Day 0: 100K 4T1 cells s.c. in 4th mammary pad. Day 5-22: Daily compound 25. The results show that compound 25 inhibited the growth of mammary carcinoma tumor cells.

Figure 50A:
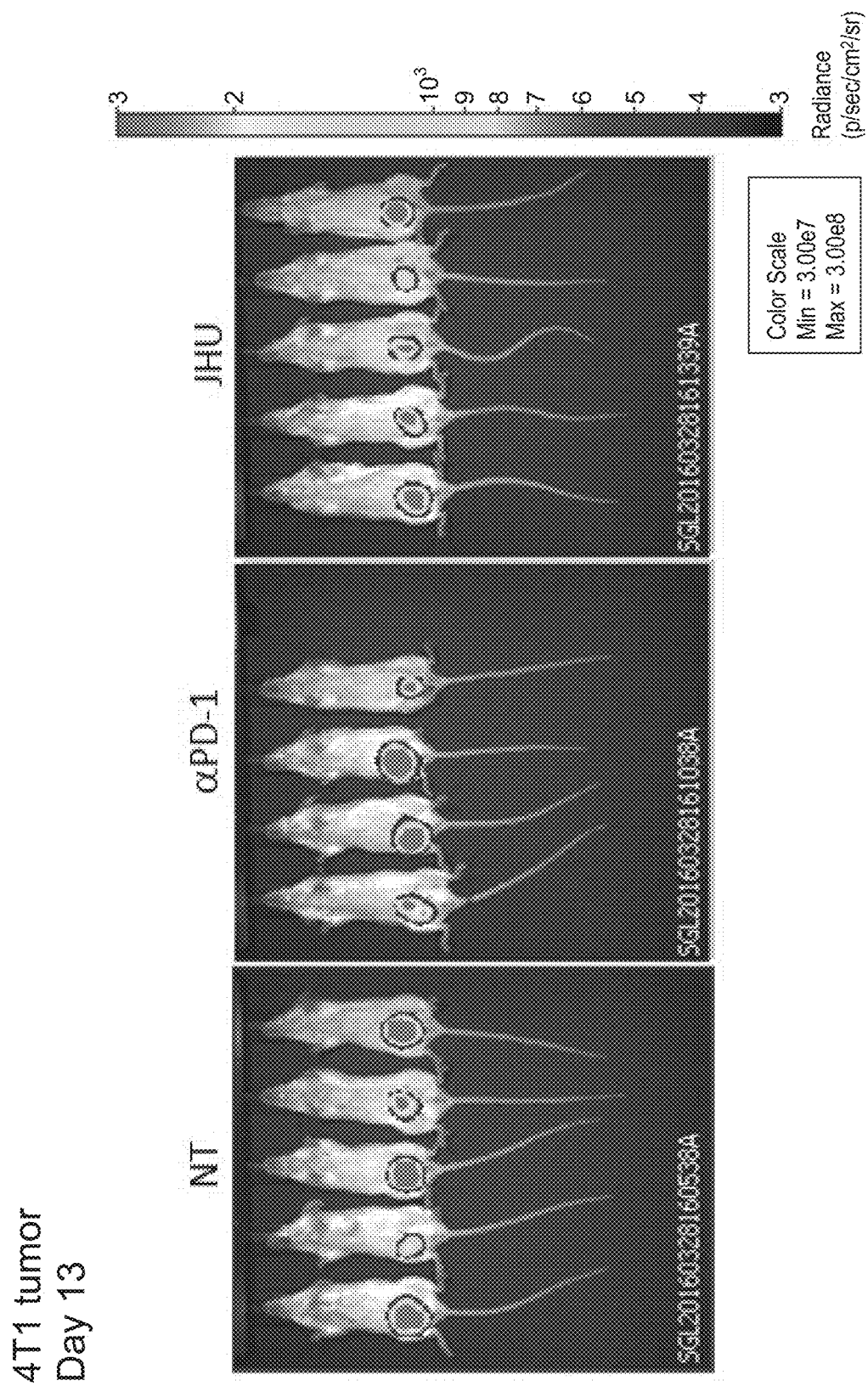
Figure 50B:
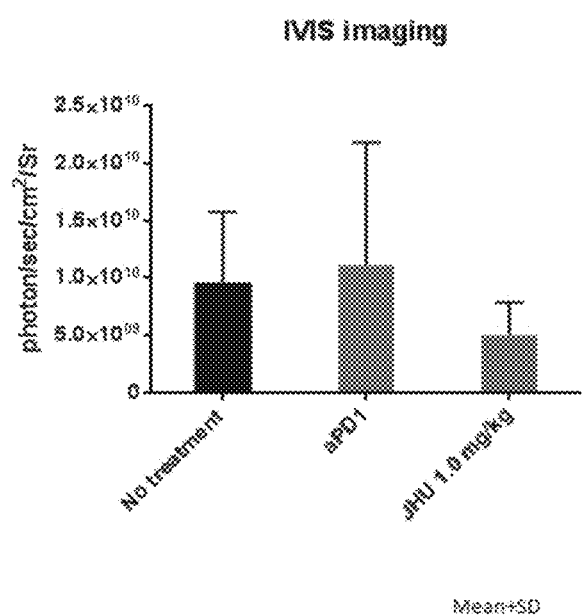

FIG. 50A is an illustration of mice and FIG. 50B is a bar graph illustrating that glutamine analogue (6-diazo-5-oxo-L-norleucine (L-DON) derivative compound 25 referred to in FIGS. 50A and 50B as "JHU") inhibits tumor growth. 4T1-Luc tumor cells (0.1 million) were injected into the mammary fat pads of 8-week-old female BALB/c mice. Mice received vehicle (PBS) or 1 mg/kg compound 25 daily from day 7. Anti-PD1 (5 mg/Kg) was administered on day 5, 8, and 12. Mice carrying 4T1-luc tumors are injected with Luciferin to measure luminescence from the tumor. IVIS imaging were taken on day 13.

Figure 51A:
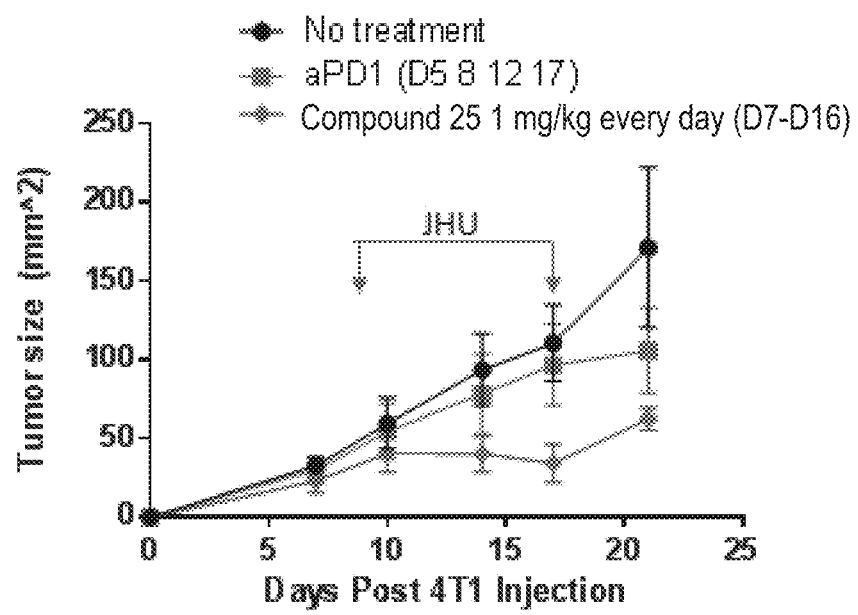
Figure 51B:
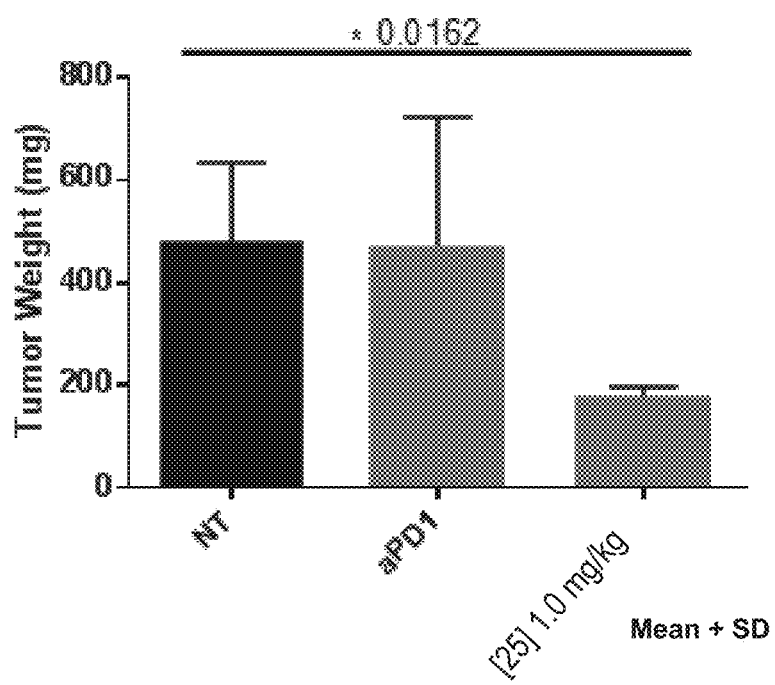

FIG. 51A is a line graph and FIG. 51B is a bar graph illustrating that compound 25 inhibits tumor growth. FIG. 51B shows tumor weight (mg) on harvest day 21. 4T1-Luc tumor cells (0.1 million) were injected into the mammary fat pads of 8-week-old female BALB/c mice. Mice received vehicle (PBS) or 1 mg/kg compound 25 daily from day 7 to day 16. Anti-PD1 (5 mg/Kg) was administered on day 5, 8, 12 and 17. Tumor volume was measured 2-3 times weekly until tumors were evaluated for tumor infiltrating cells on day 21. Tumor weights were measured on day 21. On day 21, the PD1 group tumor size looks like it was reduced, however, the result was not due to a tumor size reduction, but rather because one of the large tumor mice died.

Figure 52:
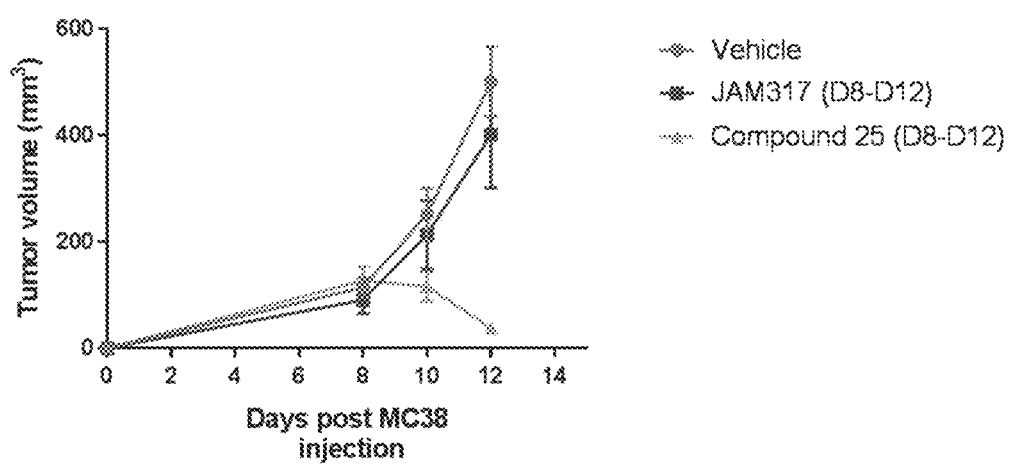

FIG. 52 is a line graph showing that compound 25 is efficacious in the MC38 tumor model. These data show unexpectedly that compound 25 is highly effective at killing colon cancer cells as a single agent.

Figure 53:
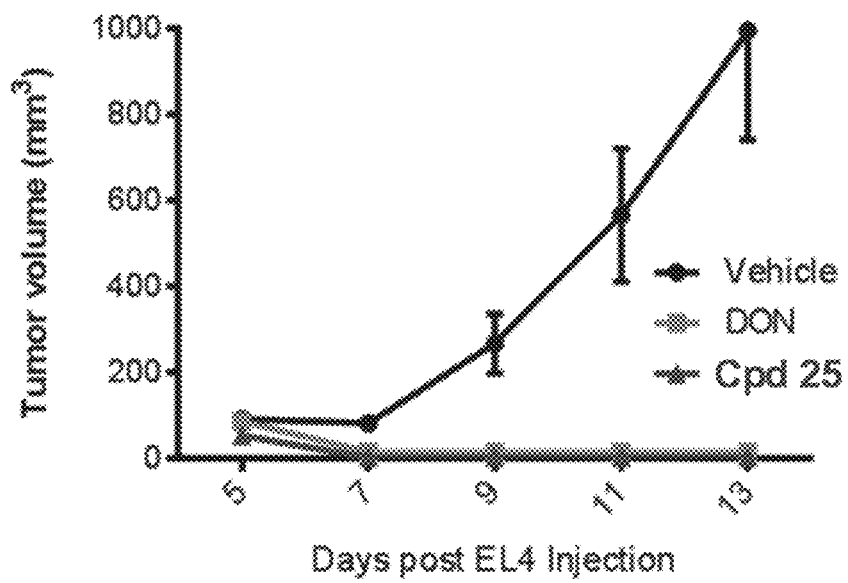

FIG. 53 is a line graph showing compound 25 and DON are efficacious in the EL4 mouse lymphoma model. These data show unexpectedly that compound 25 is highly effective at killing lymphoma cancer cells as a single agent.

Figure 54:
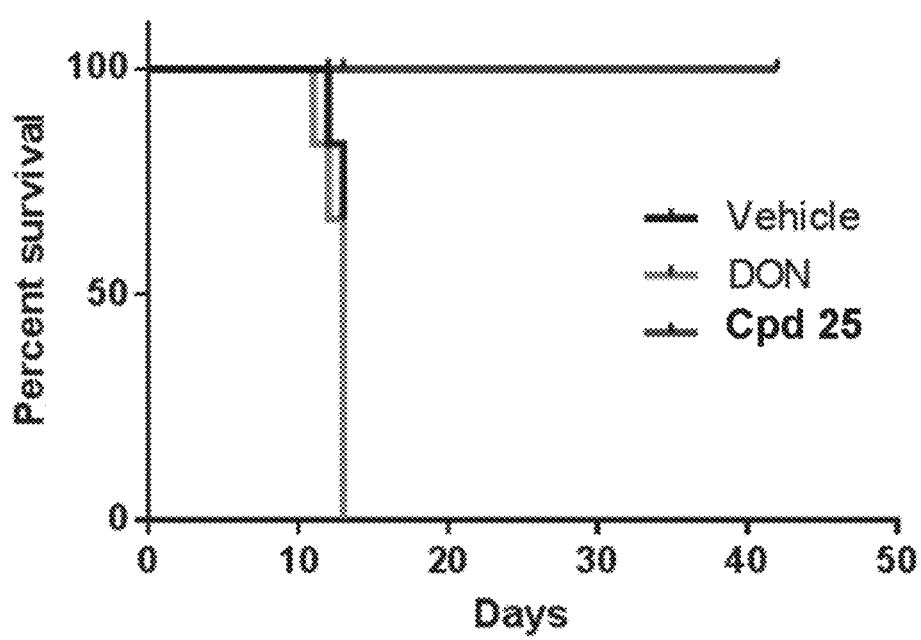

FIG. 54 is a Kaplan-Meier graph showing that DON treated mice die of toxicity, and compound 25 treated mice show no signs of toxicity in the EL4 mouse lymphoma model. These results show unexpectedly that compound 25 is highly effective at killing cancer cells but with significantly improved tolerability compared to DON.

Figure 55:
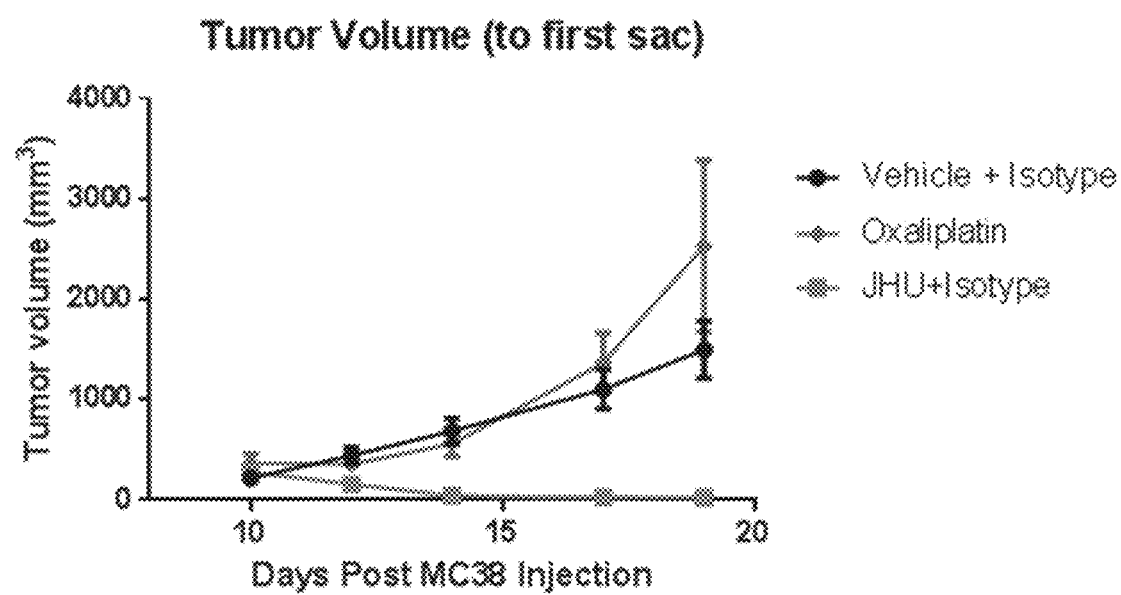

FIG. 55 a line graph showing compound 25 administered as a single agent is more efficacious than oxaliplatin in the MC38 tumor model. These results show unexpectedly that compound 25 (referred to as "JHU") is highly effective at killing colon cancer cells as a single agent.

Figure 56A:
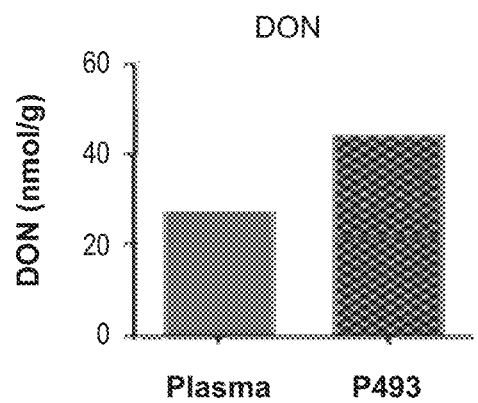
Figure 56B:
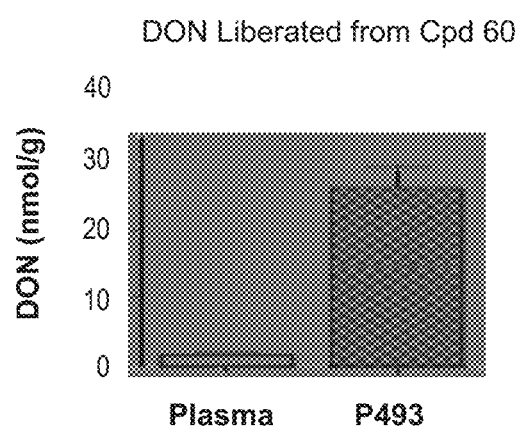
Figure 56C:
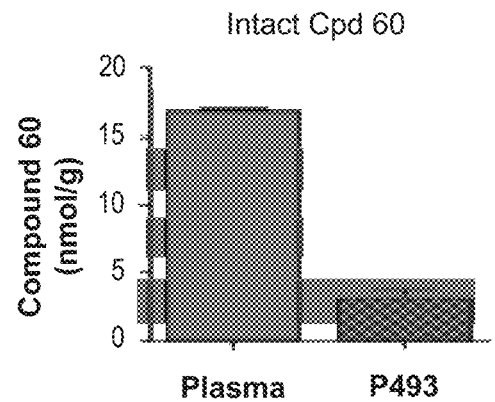

FIGS. 56A-C are bar graphs showing compound 60 preferentially delivers DON to P493 tumor cells versus plasma.

Figure 57:
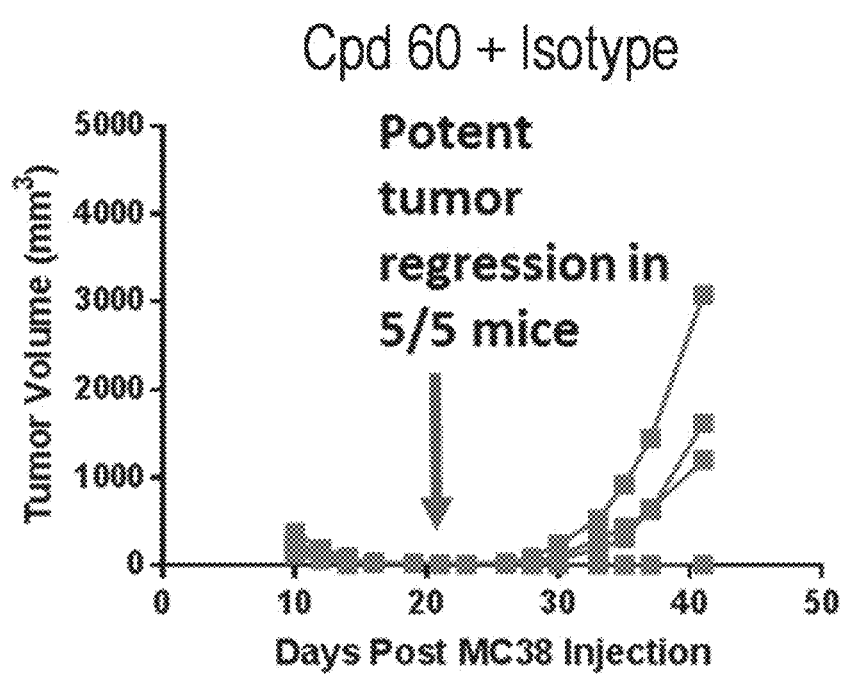

FIG. 57 is a line graph showing subcutaneous administration of compound 60 unexpectedly promoted tumor regression in the MC38 tumor model as a single agent.

Figure 58A:
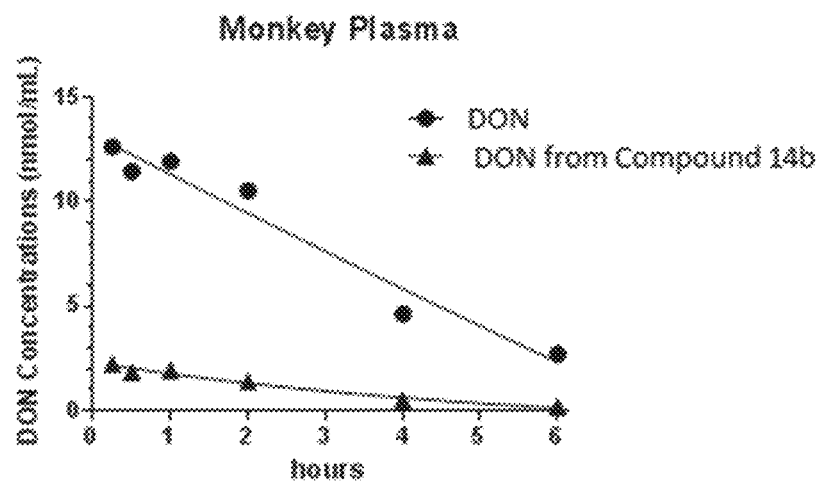

FIG. 58A is a line graph demonstrating different DON plasma profiles in Monkey for DON and compound 14b.

Figure 58B:
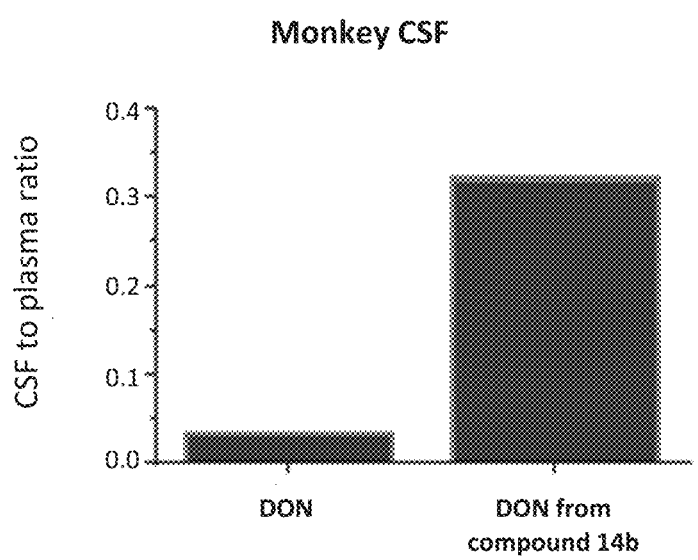

FIG. 58B is a bar graph showing that compound 14b exhibited enhanced CSF:plasma ratio of DON in Monkey.

Figure 59A:
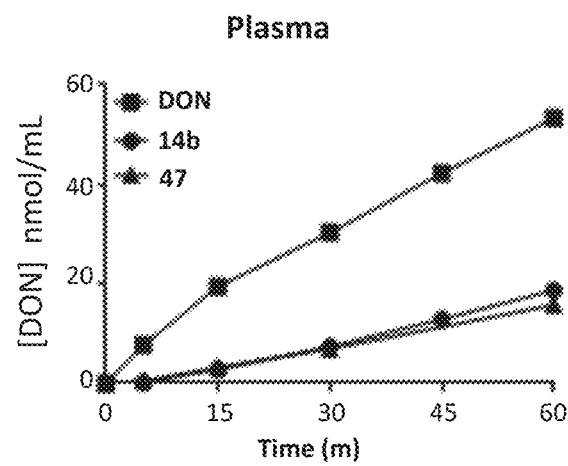

FIG. 59A is a line graph demonstrating different DON plasma profiles in swine for DON, compound 14b and compound 47.

Figure 59B:
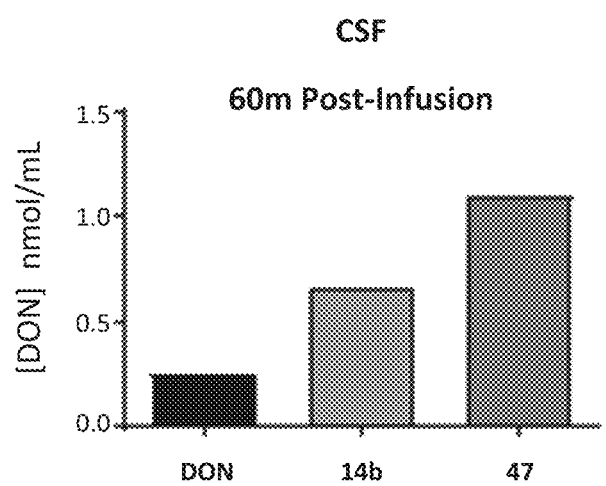
Figure 59C:
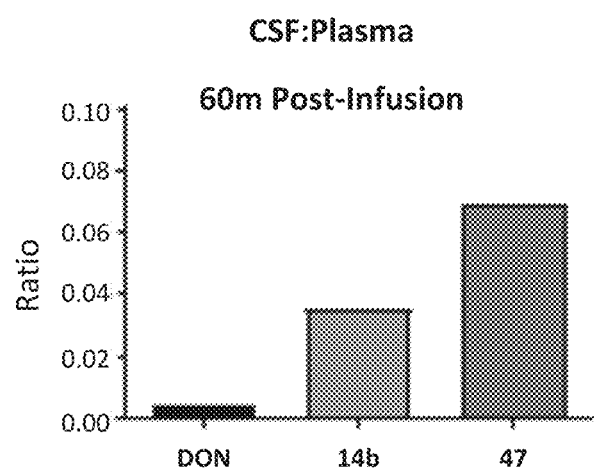

FIG. 59B is a bar graph showing that compounds 14b and 47 exhibited enhanced CSF delivery of DON at 60 min post-administration in swine FIG. 59C is a bar graph showing that compounds 14b and 47 exhibited enhanced CSF:plasma ratio of DON at 60 min post-administration in swine.

The patent or application file contains at least one figure executed in color. Copies of this patent or patent application publication with color figures will be provided by the Office upon request and payment of the necessary fee.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Prodrugs of Glutamine Antagonists

DON is an antibiotic that was isolated from *Streptomyces* in 1953. DON is a diazo analog of L-glutamine, which interferes in various reactions in the synthesis of nucleic acids and proteins in which L-glutamine donates nitrogen, blocks various glutamine recognizing enzymes, such as glutaminase, modulates brain glutamate levels, and is involved in energy metabolism, amongst others.

One strategy to improve the therapeutic index of DON for various treatment regimes, including GBM therapy, would be to increase its brain exposure while limiting its systemic exposure and thus toxicity (Upadhyay, 2014). The prodrug approach is a well-established strategy to alter the pharmacokinetic and tissue distribution of drug molecules, however synthetically this approach is challenging with DON. Given that DON's labile diazo group is critical to its glutamine antagonizing activity, the addition of promoeities must be performed under mild conditions to preserve the diazo ketone group.

The presently disclosed subject matter provides novel compositions of matter wherein pro-moieties have been added to glutamine antagonists, such as 6-diazo-5-oxo-norleucine (DON), and aza-serine.

The presently disclosed prodrugs of glutamine antagonists were prepared by masking the amine and/or the carboxylate functionalities to alter the pharmacokinetics of DON providing slower release kinetics and cellular targeting to enhance tolerability. Further, the presently disclosed prodrugs, in some embodiments, selectively target the active glutamine antagonists to specific cells or provide a slower release of DON and thus decrease the toxicity of the drug molecule.

The presently disclosed subject matter demonstrates that masking both the α-amino group and the carboxy-functionality to be derivatized enhances prodrug stability and oral bioavailability. The presently disclosed prodrugs also exhibit a stability that is comparable to free DON.

Structures of representative DON prodrugs are provided in Table 1.

TABLE 1

Structures of Representative DON Prodrugs

| IOCB No./ Compound No. | Structure | MW |
|---|---|---|
| Compound 1 (DON) | 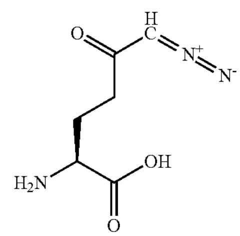 [SMILES: [N-]=[N+]=CC(=O)CC[C@H](N)C(=O)O] | 171.15 |
| Compound 3 | 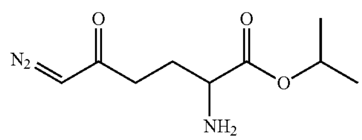 | 213.24 |
| Compound 4 (or JAM317) | 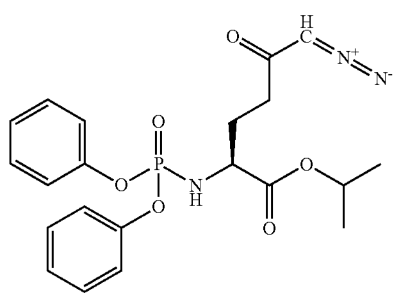 [SMILES: CC(C)OC(=O)[C@H](CCC(=O)C=[N+]=[N-])NP(=O)(Oc1ccccc1)Oc1ccccc1] | 445.41 |
| Compound 6 | 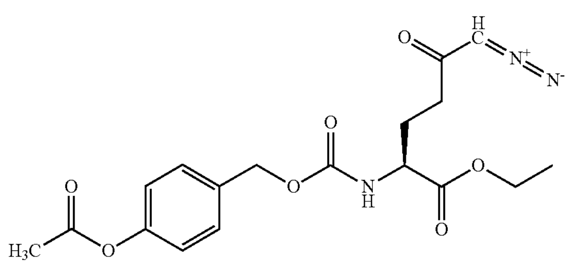 [SMILES: CCOC(=O)[C@H](CCC(=O)C=[N+]=[N-])NC(=O)OCc1ccc(OC(C)=O)cc1] | 391.38 |
| Compound 7 | 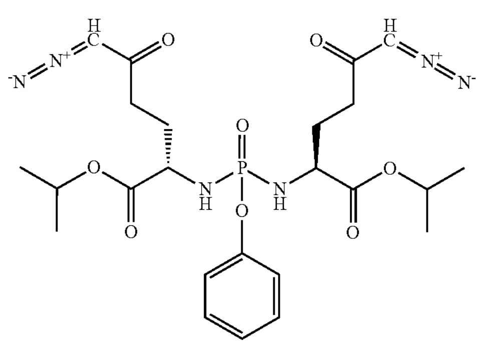 | 564.53 |

TABLE 1-continued

Structures of Representative DON Prodrugs

| IOCB No./ Compound No. | Structure | MW |
|---|---|---|
| Compound 9 | 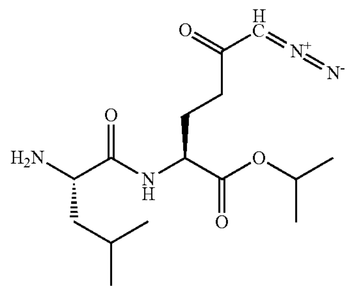 [SMILES: CC(C)C[C@H](N)C(=O)N[C@@H](CCC(=O)C=[N+]=[N-])C(=O)OC(C)C] | 326.39 |
| Compound 11 | 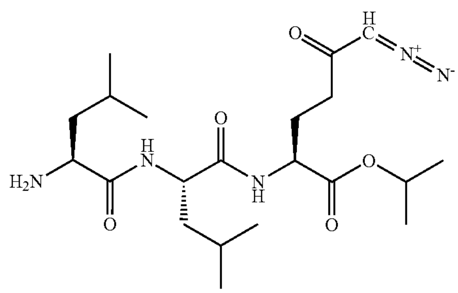 [SMILES: CC(C)C[C@H](NC(=O)[C@@H](N)CC(C)C)C(=O)N[C@@H](CCC(=O)C=[N+]=[N-])C(=O)OC(C)C] | 439.55 |
| Compound 13 | 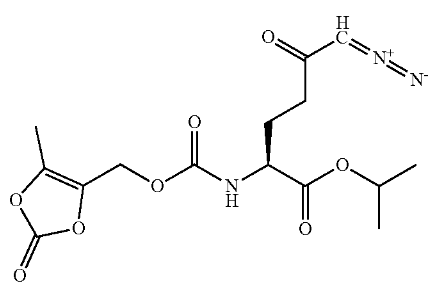 [SMILES: Cc1oc(=O)oc1COC(=O)N[C@@H](CCC(=O)C=[N+]=[N-])C(=O)OC(C)C] | 369.18 |
| Compound 14a | 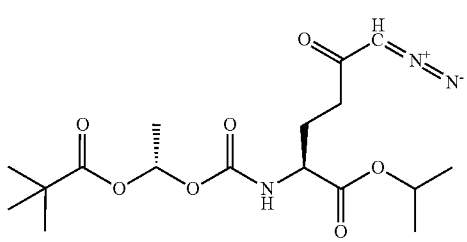 [SMILES: CC(C)OC(=O)[C@H](CCC(=O)C=[N+]=[N-])NC(=O)O[C@@H](C)OC(=O)C(C)(C)C] | 385.41 |
| Compound 14b (or 5c) | 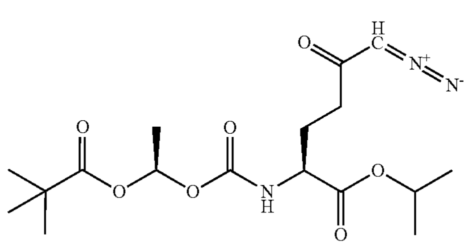 [SMILES: CC(C)OC(=O)[C@H](CCC(=O)C=[N+]=[N-])NC(=O)O[C@H](C)OC(=O)C(C)(C)C] | |

TABLE 1-continued

Structures of Representative DON Prodrugs

| IOCB No./ Compound No. | Structure | MW |
|---|---|---|
| Compound 15 | 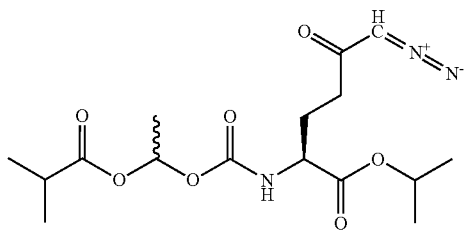 [SMILES: CC(C)OC(=O)[C@H](CCC(=O)C=[N+]=[N-])NC(=O)OC(C)OC(=O)C(C)C] | 371.39 |
| Compound 17 | 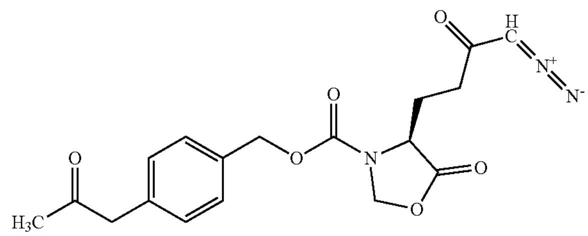 [SMILES: CC(=O)Cc1ccc(COC(=O)N2COC(=O)[C@@H]2CCC(=O)C=[N+]=[N-])cc1] | 375.33 |
| Compound 20 | 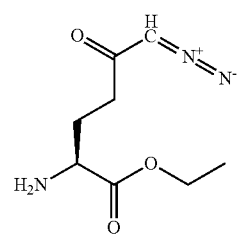 | 199.21 |
| Compound 22 | 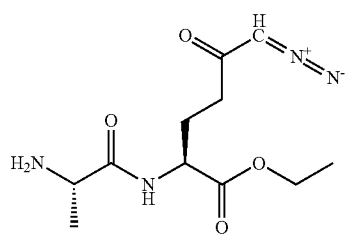 [SMILES: CCOC(=O)[C@H](CCC(=O)C=[N+]=[N-])NC(=O)[C@H](C)N] | 270.28 |
| Compound 23 | ·Et$_3$N | 343.42 |
| Compound 25 | 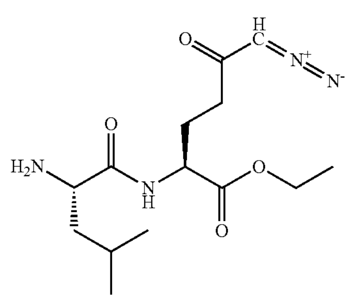 [SMILES: CCOC(=O)[C@H](CCC(=O)C=[N+]=[N-])NC(=O)[C@@H](N)CC(C)C] | 312.36 |

TABLE 1-continued

Structures of Representative DON Prodrugs

| IOCB No./<br>Compound No. | Structure | MW |
|---|---|---|
| Compound 26 | (structure: H-Leu-DON with free acid, ·Et₃N salt) | 385.50 |
| Compound 28 | (structure: H-Leu-Leu-DON ethyl ester) | 425.52 |
| Compound 29 | (structure: isobutyryloxymethyl carbamate of DON free acid) | 329.31 |
| Compound 30 | (structure: pivaloyloxymethyl carbamate of DON free acid) | 343.33 |
| Compound 31 | (structure: isobutyryloxymethyl carbamate of DON ethyl ester) | 357.37 |
| Compound 32 | (structure: pivaloyloxymethyl carbamate of DON ethyl ester) | 371.39 |

TABLE 1-continued

Structures of Representative DON Prodrugs

| IOCB No./Compound No. | Structure | MW |
|---|---|---|
| Compound 34 | 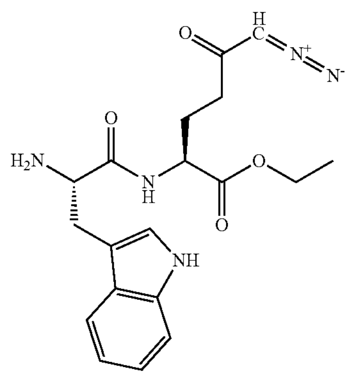 [SMILES: CCOC(=O)[C@H](CCC(=O)C=[N+]=[N-])NC(=O)[C@@H](N)Cc1c[nH]c2ccccc12] | 385.42 |
| Compound 35 | 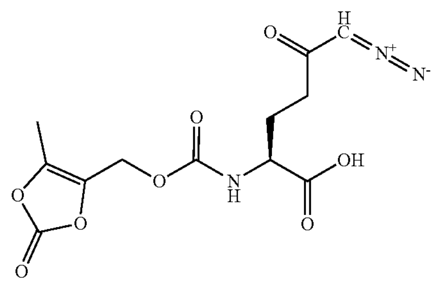 [SMILES: Cc1oc(=O)oc1COC(=O)N[C@@H](CCC(=O)C=[N+]=[N-])C(=O)O] | 327.25 |
| Compound 36 | 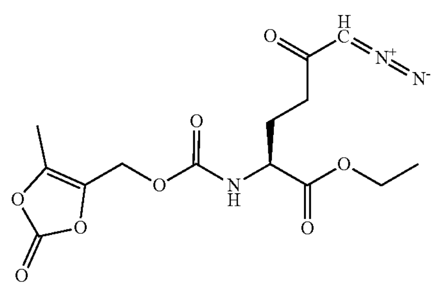 [SMILES: CCOC(=O)[C@H](CCC(=O)C=[N+]=[N-])NC(=O)OCc1oc(=O)oc1C] | 355.30 |
| Compound 38 | 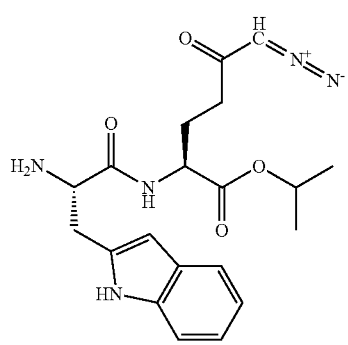 [SMILES: CC(C)OC(=O)[C@H](CCC(=O)C=[N+]=[N-])NC(=O)[C@@H](N)Cc1cc2ccccc2[nH]1] | 399.45 |
| Compound 40 | 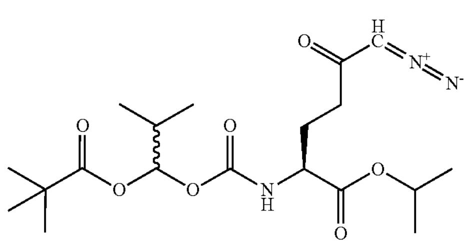 [SMILES: CC(C)OC(=O)[C@H](CCC(=O)C=[N+]=[N-])NC(=O)OC(OC(=O)C(C)(C)C)C(C)C] | 413.47 |

TABLE 1-continued

Structures of Representative DON Prodrugs

| IOCB No./Compound No. | Structure | MW |
|---|---|---|
| Compound 42 | 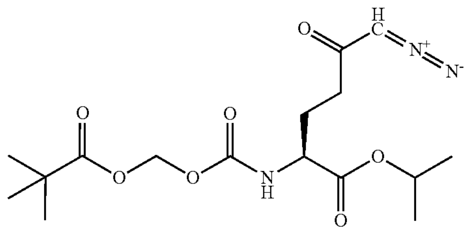 [SMILES: CC(C)OC(=O)[C@H](CCC(=O)C=[N+]=[N-])NC(=O)OCOC(=O)C(C)(C)C] | 371.39 |
| Compound 44 | 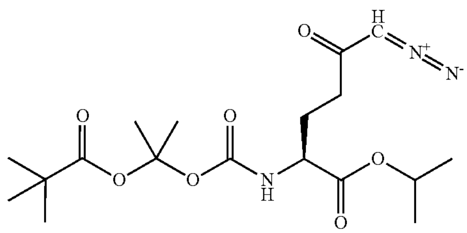 [SMILES: CC(C)OC(=O)[C@H](CCC(=O)C=[N+]=[N-])NC(=O)OC(C)(C)OC(=O)C(C)(C)C] | 2.44 |
| Compound 47 | 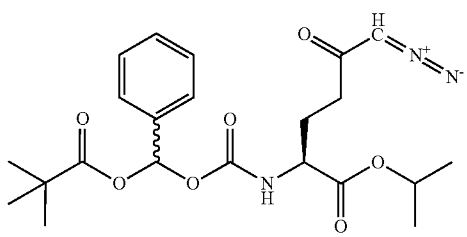 [SMILES: CC(C)OC(=O)[C@H](CCC(=O)C=[N+]=[N-])NC(=O)OC(OC(=O)C(C)(C)C)c1ccccc1] | 447.49 |
| Compound 47a | 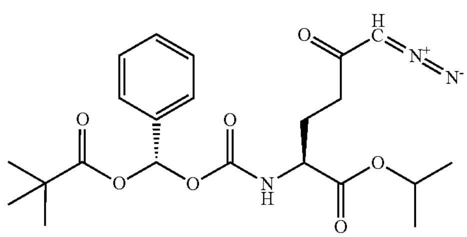 [SMILES: CC(C)OC(=O)[C@H](CCC(=O)C=[N+]=[N-])NC(=O)O[C@H](OC(=O)C(C)(C)C)c1ccccc1] | |
| Compound 47b | 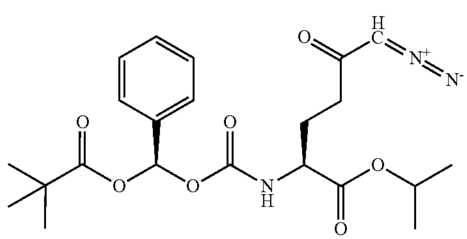 [SMILES: CC(C)OC(=O)[C@H](CCC(=O)C=[N+]=[N-])NC(=O)O[C@@H](OC(=O)C(C)(C)C)c1ccccc1] | |
| Compound 49 | 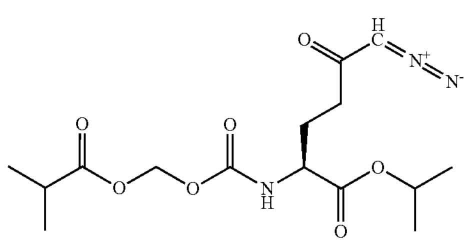 [SMILES: CC(C)OC(=O)[C@H](CCC(=O)C=[N+]=[N-])NC(=O)OCOC(=O)C(C)C] | 357.36 |

TABLE 1-continued

Structures of Representative DON Prodrugs

| IOCB No./Compound No. | Structure | MW |
|---|---|---|
| Compound 51 | 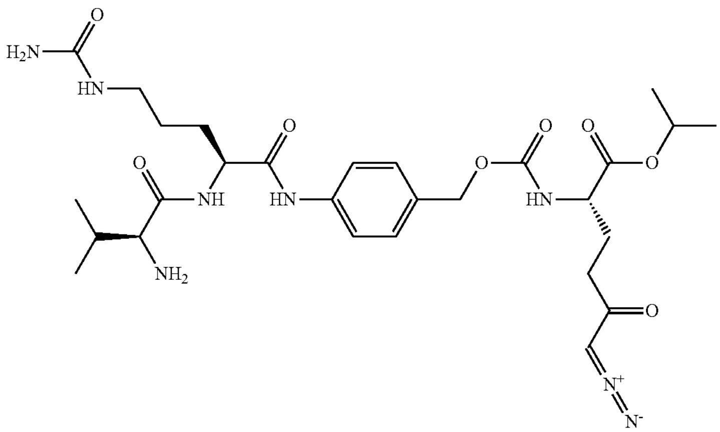 [SMILES: CC(C)OC(=O)[C@H](CCC(=O)C=[N+]=[N-])NC(=O)OCc1ccc(NC(=O)[C@H](CCCNC(N)=O)NC(=O)[C@@H](N)C(C)C)cc1] | 618.69 |
| Compound 52 | 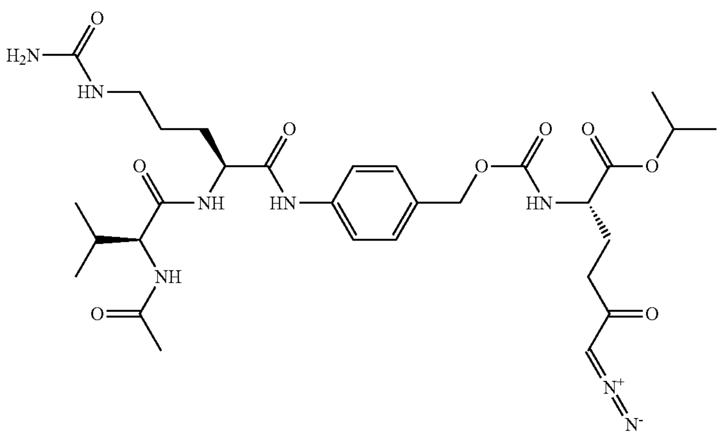 [SMILES: CC(=O)N[C@H](C(=O)N[C@@H](CCCNC(N)=O)C(=O)Nc1ccc(COC(=O)N[C@@H](CCC(=O)C=[N+]=[N-])C(=O)OC(C)C)cc1)C(C)C] | 660.73 |
| Compound 56 | 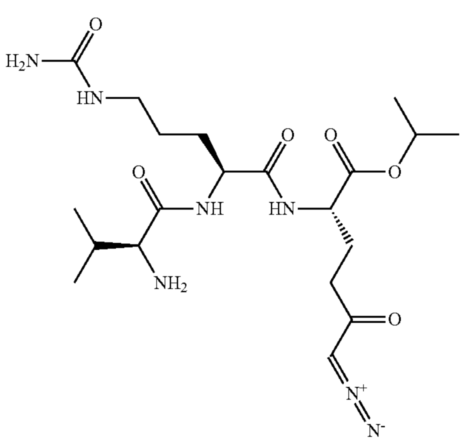 [SMILES: CC(C)OC(=O)[C@H](CCC(=O)C=[N+]=[N-])NC(=O)[C@H](CCCNC(N)=O)NC(=O)[C@@H](N)C(C)C] | 469.54 |

TABLE 1-continued

Structures of Representative DON Prodrugs

| IOCB No./ Compound No. | Structure | MW |
|---|---|---|
| Compound 57 | 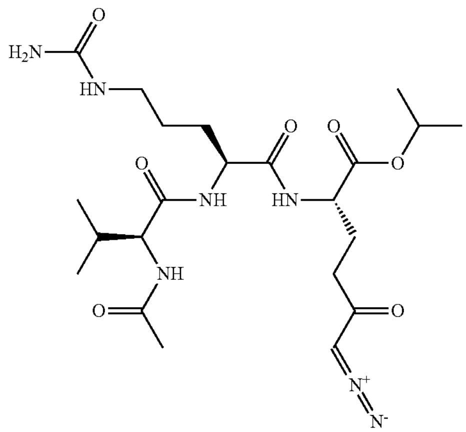 [SMILES: CC(=O)N[C@H](C(=O)N[C@@H](CCCNC(N)=O)C(=O)N[C@@H](CCC(=O)C=[N+]=[N-])C(=O)OC(C)C)C(C)C] | 511.58 |
| Compound 59 | 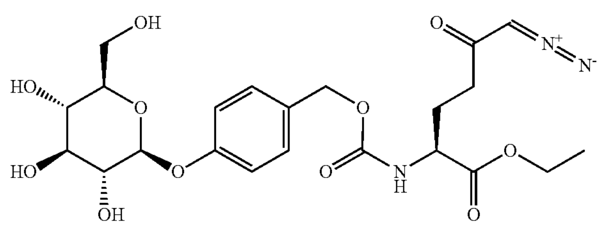 [SMILES: CCOC(=O)[C@H](CCC(=O)C=[N+]=[N-])NC(=O)OCc1ccc(O[C@@H]2O[C@H](CO)[C@@H](O)[C@H](O)[C@H]2O)cc1] | 511.48 |
| Compound 60 | 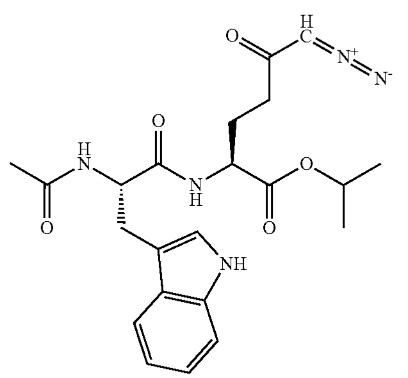 [SMILES: CC(=O)N[C@@H](Cc1c[nH]c2ccccc12)C(=O)N[C@@H](CCC(=O)C=[N+]=[N-])C(=O)OC(C)C] | 464.19 |
| A | 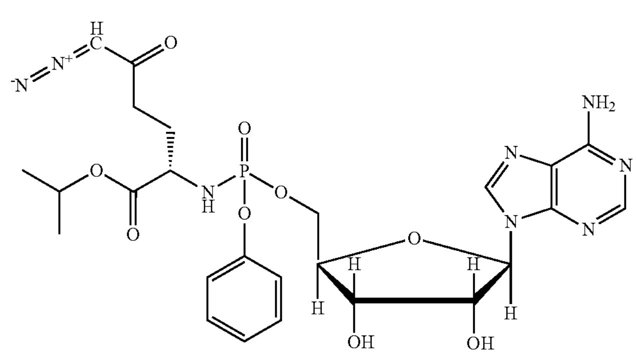 | 618.54 |

TABLE 1-continued

Structures of Representative DON Prodrugs

| IOCB No./ Compound No. | Structure | MW |
| --- | --- | --- |
| B | 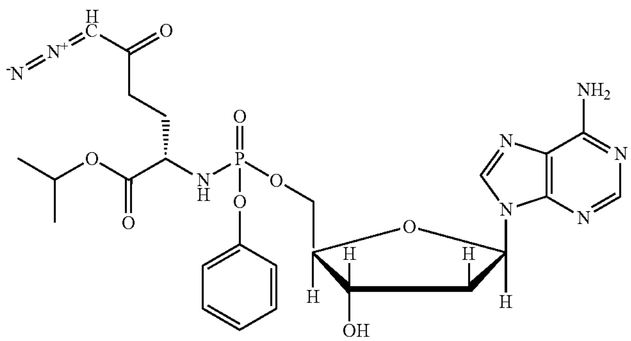 | 602.54 |
| C | 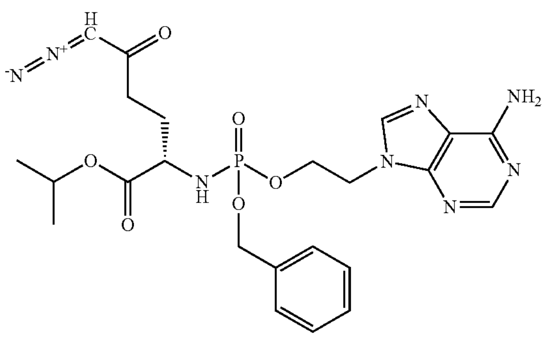 | 530.47 |
| D | 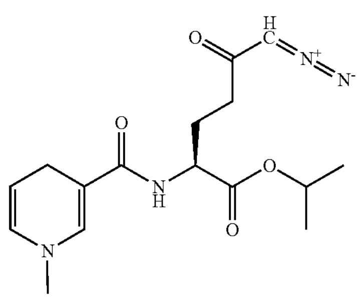 [SMILES: CC(C)OC(=O)[C@H](CCC(=O)C=[N+]=[N-])NC(=O)C1=CN(C)C=CC1] | 334.38 |
| E | 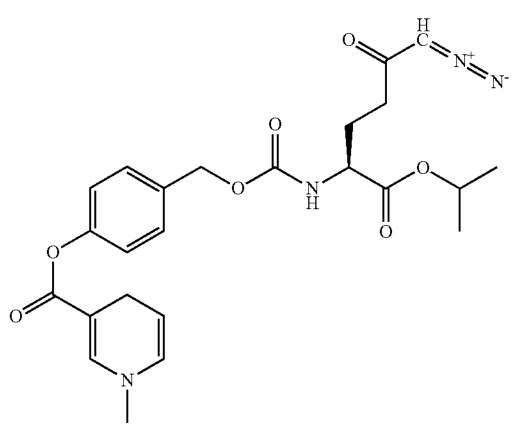 [SMILES: CC(C)OC(=O)[C@H](CCC(=O)C=[N+]=[N-])NC(=O)OCc1ccc(OC(=O)C2=CN(C)C=CC2)cc1] | 484.51 |

TABLE 1-continued

Structures of Representative DON Prodrugs

| IOCB No./Compound No. | Structure | MW |
|---|---|---|
| F | 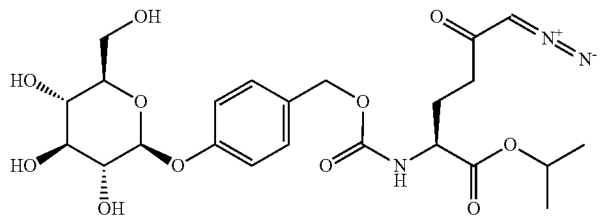 [SMILES: CC(C)OC(=O)[C@H](CCC(=O)C=[N+]=[N-])NC(=O)OCc1ccc(O[C@@H]2O[C@H](CO)[C@@H](O)[C@H](O)[C@H]2O)cc1] | 525.51 |
| G | 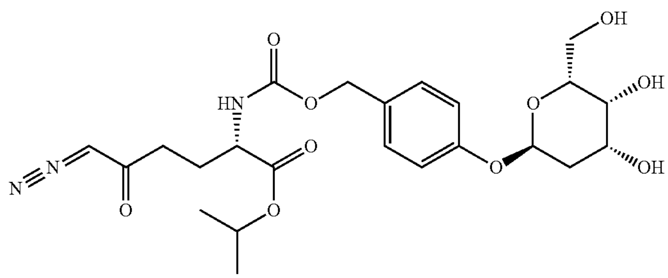 [SMILES: CC(C)OC(=O)[C@H](CCC(=O)C=[N+]=[N-])NC(=O)OCc1ccc(O[C@@H]2C[C@@H](O)[C@@H](O)[C@@H](CO)O2)cc1] | 509.51 |
| LTP 073 | 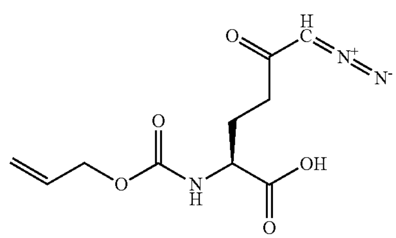 [SMILES: C=CCOC(=O)N[C@@H](CCC(=O)C=[N+]=[N-])C(=O)O] | 255.23 |
| JAM0351 | 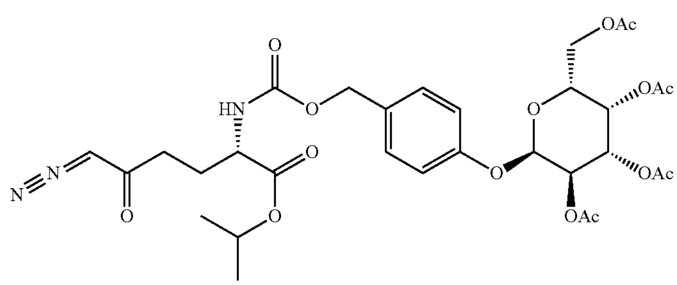 [SMILES: CC(=O)OC[C@H]1O[C@H](Oc2ccc(COC(=O)N[C@@H](CCC(=O)C=[N+]=[N-])C(=O)OC(C)C)cc2)[C@H](OC(C)=O)[C@@H](OC(C)=O)[C@H]1OC(C)=O] | 693.66 |
| JAM0359 | 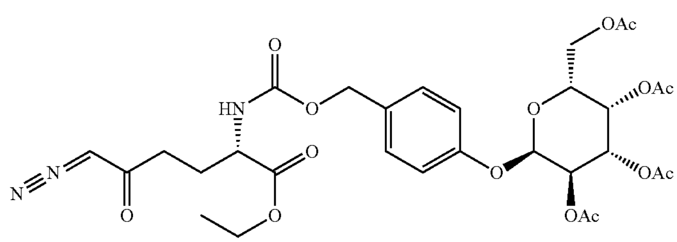 [SMILES: CCOC(=O)[C@H](CCC(=O)C=[N+]=[N-])NC(=O)OCc1ccc(O[C@H]2O[C@H](COC(C)=O)[C@H](OC(C)=O)[C@H](OC(C)=O)[C@H]2OC(C)=O)cc1] | 679.63 |

Those skilled in the art will appreciate that the representative struct

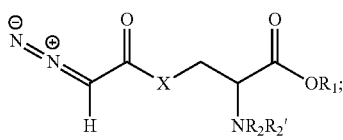 (I)

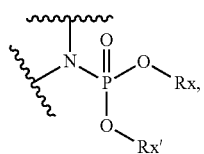

wherein $R_x$ and $R_x'$ are each independently selected from the group consisting of alkyl, substituted alkyl, cycloalkyl, substituted cycloalkyl, aryl, substituted aryl, aralkyl, substituted aralkyl, heterocyclyl, substituted heterocyclyl, alkenyl, substituted alkenyl, cycloalkenyl, substituted cycloalkenyl, alkylamine, substituted alkylamine, heteroaryl, and substituted heteroaryl.

As used herein, the term "phosphorodiamidate linkage" comprises a structure represented by the formula:

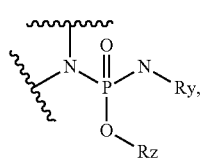

wherein $R_y$ and $R_z$ are each independently selected from the group consisting of H, alkyl, substituted alkyl, cycloalkyl, substituted cycloalkyl, heterocyclyl, substituted heterocyclyl, alkenyl, substituted alkenyl, cycloalkenyl, substituted cycloalkenyl, —(CR$_3$R$_4$)$_m$—Z, —(CR$_3$R$_4$)$_m$-Q-Z, aryl, substituted aryl, alkylamine, substituted alkylamine, heteroaryl, substituted heteroaryl, and

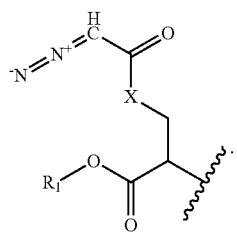

wherein: X is selected from the group consisting of a bond, —O—, and —(CH$_2$)$_n$—, wherein n is an integer selected from the group consisting of 1, 2, 3, 4, 5, 6, 7, and 8; $R_1$ is selected from the group consisting of H and a first prodrug-forming moiety capable of forming a salt or an ester; and $R_2$ is H or a second prodrug-forming moiety capable of forming an amide linkage, a carbamate linkage, a phosphoramidate linkage or a phosphorodiamidate linkage with the nitrogen adjacent to $R_2$; $R_2'$ is selected from the group consisting of H, $C_1$-$C_6$ alkyl, substituted $C_1$-$C_6$ alkyl, or $R_2$ and $R_2'$ together form a ring structure comprising —C(=O)-G-C(=O)—, wherein G is selected from the group consisting of $C_1$-$C_8$ alkylene, $C_1$-$C_8$ heteroalkylene, $C_5$-$C_8$ cycloalkylene, $C_6$-$C_{12}$ arylene, $C_5$-$C_{14}$ heteroarylene, bivalent $C_4$-$C_{10}$ heterocycle, each of which can be optionally substituted; or $R_1$ and $R_2'$ together form a 4-to 6-membered heterocylic ring comprising the oxygen atom adjacent to $R_1$ and the nitrogen atom adjacent to $R_2'$; provided that the compound has at least one prodrug-forming moiety selected from the group consisting of the first and the second prodrug-forming moieties.

As used herein, the term "amide linkage" comprises a structure represented by the formula:

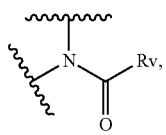

wherein $R_v$ is selected from the group consisting of alkyl, substituted alkyl, cycloalkyl, substituted cycloalkyl, aryl, substituted aryl, aralkyl, substituted aralkyl, heterocyclyl, substituted heterocyclyl, alkenyl, substituted alkenyl, cycloalkenyl, substituted cycloalkenyl, alkylamine, substituted alkylamine, heteroaryl, and substituted heteroaryl.

As used herein, the term "carbamate linkage" comprises a structure represented by the formula:

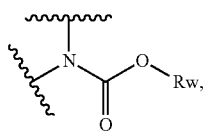

wherein $R_w$ is selected from the group consisting of alkyl, substituted alkyl, cycloalkyl, substituted cycloalkyl, aryl, substituted aryl, aralkyl, substituted aralkyl, heterocyclyl, substituted heterocyclyl, alkenyl, substituted alkenyl, cycloalkenyl, substituted cycloalkenyl, alkylamine, substituted alkylamine, heteroaryl, and substituted heteroaryl.

As used herein, the term "phosphoramidate linkage" comprises a structure represented by the formula:

In some embodiments, X is —CH$_2$—, and n is 1.

In other embodiments, X is —O—. In some embodiments, the prodrug compound has both the first prodrug-forming moiety and the second prodrug-forming moiety. In some embodiments, the glutamine analog is a glutamine antagonist, i.e., the prodrug is a prodrug of a glutamine analog that antagonizes a glutamine pathway. Exemplary glutamine antagonists include, without limitation, 6-diazo-5-oxo-norleucine (DON), and aza-serine, and 5-diazo-4-oxo-L-norvaline (L-DONV).

In some embodiments, the presently disclosed subject matter provides a prodrug of DON. In some embodiments, the prodrug of DON has a structure of formula (I). In some embodiments, the presently disclosed subject matter provides a prodrug of L-DONV. In some embodiments, the prodrug of L-DONV has a structure of formula (I). In some embodiments, the presently disclosed subject matter provides a prodrug of azaserine. In some embodiments, the prodrug of azaserine has a structure of formula (I).

In some embodiments, $R_1$ of formula (I) comprises a residue PRO$_1$ of the prodrug-forming moiety, which, together with a basic moiety and the terminal hydroxyl group forms a salt.

In some embodiments, $R_1$ of formula (I) comprises a residue $PRO_1$ of the prodrug-forming moiety, which, together with an alkyl group and the oxygen of an adjoining hydroxyl group forms an ester.

In some embodiments, $R_1$ of formula (I) comprises a residue $PRO_1$ of the prodrug-forming moiety, which, together with an alkyl group and the nitrogen adjoining the $R_2'$ group, forms an azlactone or an oxazolidone.

In some embodiments, $R_1$ of formula (I) is selected from the group consisting of H, alkyl, substituted alkyl, cycloalkyl, substituted cycloalkyl, alkenyl, substituted alkenyl, alkynyl, substituted alkynyl, cycloalkenyl, substituted cycloalkenyl, tri(hydrocarbyl)ammonium, and tetra(hydrocarbyl)ammonium. Preferred alkyl group, cycloalkyl group, alkenyl group, alkynyl group, and cycloalkenyl group substituents include alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl.

In some embodiments, $R_1$ of formula (I) is not H. In some embodiments, $R_1$ of formula (I) is not H when $R_2$ and $R_2'$ are H. In some embodiments, $R_2$ and $R_2'$ of formula (I) are each H when and $R_1$ is not H.

In some embodiments, $R_1$ of formula (I) is selected from the group consisting of a $C_{1-6}$ straight-chain alkyl, a substituted $C_{1-6}$ straight-chain alkyl, a $C_{1-6}$ branched alkyl, a substituted $C_{1-6}$ branched alkyl, tri($C_1$-$C_8$-alkyl)ammonium, tetra($C_1$-$C_8$-alkyl)ammonium, triphenylammonium, tri(hydroxy-$C_1$-$C_8$-alkyl)ammonium, and tetra(hydroxy-$C_1$-$C_8$-alkyl)ammonium.

In some embodiments, $R_1$ of formula (I) is selected from the group consisting of methyl, ethyl, isopropyl, cyclopentyl, cyclohexyl, trimethylammonium, triethylammonium, tri(hydroxyethyl)ammonium, tripropylammonium, and tri(hydroxypropyl)ammonium. In some embodiments, $R_1$ of formula (I) is methyl. In some embodiments, $R_1$ of formula (I) is ethyl. In some embodiments, $R_1$ of formula (I) is isopropyl.

In some embodiments, $R_2$ of formula (I) comprises a residue $PRO_2$ of the second prodrug-forming moiety, which, together with a carbonyl, oxy carbonyl, or phosphonyl group and the nitrogen of the adjoining NH, forms an amide, a carbamate, phosphoramidate, or phosphorodiamidate linkage.

In some embodiments, $R_2$ of formula (I) comprises a moiety selected from the group consisting of an amino acid, an N-substituted amino acid, a peptide, a substituted peptide, a monocyclic ring, a substituted monocyclic ring, a bicyclic ring, a substituted bicyclic ring, a purine nucleoside, a substituted purine nucleoside, a pyrimidine nucleoside, and a substituted pyrimidine nucleoside.

In another embodiment, the disclosure provides a compound having formula (I), or a pharmaceutically acceptable salt thereof, wherein:

X is selected from the group consisting of a bond, —O—, and —$(CH_2)_n$—, wherein n is an integer selected from the group consisting of 1, 2, 3, 4, 5, 6, 7, and 8;

$R_1$ is selected from the group consisting of H, $C_{1-6}$ alkyl, and substituted $C_{1-6}$ alkyl;

$R_2$ is an amino acid, an N-substituted amino acid, or —C(=O)—O—$(CR_3R_4)_m$—O—C(=O)—$R_{10}$;

$R_2'$ is selected from the group consisting of H, $C_1$-$C_6$ alkyl, and substituted $C_1$-$C_6$ alkyl;

each $R_3$ and $R_4$ are independently H, $C_1$-$C_6$ alkyl, substituted $C_1$-$C_6$ alkyl, aryl, substituted aryl, —$(CR_3R_4)_m$—$NR_5R_6$, or

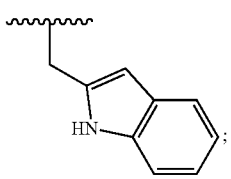 [SMILES: *Cc1cc2ccccc2[nH]1]

m is an integer selected from the group consisting of 1, 2, 3, 4, 5, 6, 7, and 8;

$R_5$ and $R_6$ are independently H or alkyl; and $R_{10}$ is selected from the group consisting of alkyl, substituted alkyl, cycloalkyl, substituted cycloalkyl, monosaccharide, acylated monosaccharide, aryl, substituted aryl, heteroaryl, and substituted heteroaryl.

In another embodiment, the disclosure provides a compound having formula (I), or a pharmaceutically acceptable salt thereof, wherein X is —$CH_2$—.

In another embodiment, the disclosure provides a compound having formula (I), or a pharmaceutically acceptable salt thereof, having formula (I), wherein X is —O—.

In another embodiment, the disclosure provides a compound having formula (I), or a pharmaceutically acceptable salt thereof, wherein $R_1$ is selected from the group consisting of methyl, ethyl, isopropyl, cyclopentyl, cyclohexyl, trimethylammonium, triethylammonium, tri(hydroxyethyl)ammonium, tripropylammonium, and tri(hydroxypropyl)ammonium.

In another embodiment, the disclosure provides a compound having formula (I), or a pharmaceutically acceptable salt thereof, wherein:

$R_2$ is selected from the group consisting of —C(=O)—Y—$(CR_3R_4)_m$—$NR_5R_6$, and —C(=O)—O—$(CR_3R_4)_m$—O—C(=O)—$R_{10}$;

wherein:

Y is —O— or a bond;

m is an integer selected from the group consisting of 1, 2, 3, 4, 5, 6, 7, and 8; and each $R_3$ and $R_4$ is independently H, $C_1$-$C_6$ alkyl, substituted $C_1$-$C_6$ alkyl, aryl, or substituted aryl;

$R_{10}$ is selected from the group consisting of alkyl, substituted alkyl, cycloalkyl, substituted cycloalkyl, aryl, substituted aryl, heteroaryl, and substituted heteroaryl.

In another embodiment, the disclosure provides a compound having formula (I), or a pharmaceutically acceptable salt thereof, wherein Y is a bond; m is 1; $R_5$ and $R_6$ are each H.

In another embodiment, the disclosure provides a compound having formula (I), or a pharmaceutically acceptable salt thereof, wherein $R_2$ is an amino acid.

In another embodiment, the disclosure provides a compound having formula (I), or a pharmaceutically acceptable salt thereof, wherein the amino acid is tryptophan.

In another embodiment, the disclosure provides a compound having formula (I), or a pharmaceutically acceptable salt thereof, wherein $R_2$ is a N-acyl amino acid.

In another embodiment, the disclosure provides a compound having formula (I), or a pharmaceutically acceptable salt thereof, wherein the amino acid is tryptophan.

In another embodiment, the disclosure provides a compound having formula (IIA):

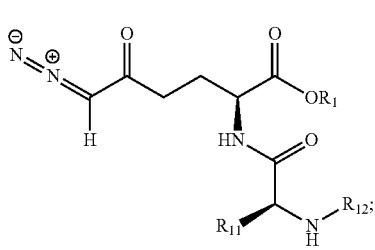

(IIA)

or a pharmaceutically acceptable salt thereof, wherein:

$R_1$ is selected from the group consisting of H and $C_{1-6}$ alkyl;

$R_{11}$ is selected from the group consisting of H, methyl, isopropyl, sec-butyl, benzyl, p-hydroxybenzyl —$CH_2CH(CH_3)_2$, —$CH_2OH$, —$CH(OH)CH_3$, —$CH_2$-3-indoyl, —$CH_2COOH$, —$CH_2CH_2COOH$, —$CH_2C(O)NH_2$, —$CH_2CH_2C(O)NH_2$, —$CH_2SH$, —$CH_2CH_2SCH_3$, —$(CH_2)_4NH_2$, —$(CH_2)_3NHC(=NH)NH_2$, and —$CH_2$-3-imidazoyl;

$R_{12}$ is selected from the group consisting of H, $C_{1-4}$ alkyl, and —$C(=O)R_{13}$; and $R_{13}$ is $C_{1-4}$ alkyl.

In another embodiment, the disclosure provides a compound having formula (IIB):

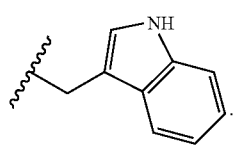 [SMILES: *Cc1c[nH]c2ccccc12]

(IIB)

or a pharmaceutically acceptable salt thereof, wherein:

$R_1$ is selected from the group consisting of H and $C_{1-6}$ alkyl;

$R_{11}$ is selected from the group consisting of H, methyl, isopropyl, sec-butyl, benzyl, p-hydroxybenzyl —$CH_2CH(CH_3)_2$, —$CH_2OH$, —$CH(OH)CH_3$, —$CH_2$-3-indoyl, —$CH_2COOH$, —$CH_2CH_2COOH$, —$CH_2C(O)NH_2$, —$CH_2CH_2C(O)NH_2$, —$CH_2SH$, —$CH_2CH_2SCH_3$, —$(CH_2)_4NH_2$, —$(CH_2)_3NHC(=NH)NH_2$, and —$CH_2$-3-imidazoyl;

$R_{12}$ is selected from the group consisting of H, $C_{1-4}$ alkyl, and —$C(=O)R_{13}$; and $R_{13}$ is $C_{1-4}$ alkyl.

In another embodiment, the disclosure provides a compound having formula (IIA) or formula (IIB), or a pharmaceutically acceptable salt thereof, wherein $R_1$ is selected from the group consisting of methyl, ethyl, and isopropyl.

In another embodiment, the disclosure provides a compound having formula (IIA) or formula (IIB), or a pharmaceutically acceptable salt thereof, wherein $R_{11}$ is selected from the group consisting of methyl, sec-butyl, benzyl, —$CH_2CH(CH_3)_2$, —$CH(OH)CH_3$ and —$CH_2$-3-indoyl. In another embodiment, $R_{11}$ is —$CH_2$-3-indoyl, i.e., In another embodiment, the disclosure provides a compound having formula (IIA) or formula (IIB), or a pharmaceutically acceptable salt thereof, wherein $R_{12}$ is selected from the group consisting of H and —$C(=O)R_{13}$. In another embodiment, $R_{12}$ is —$C(=O)R_{13}$ and $R_{13}$ is methyl.

In another embodiment, the disclosure provides a compound having formula (I), or a pharmaceutically acceptable salt thereof, selected from the group consisting of:

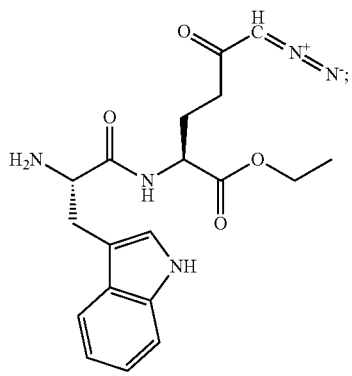

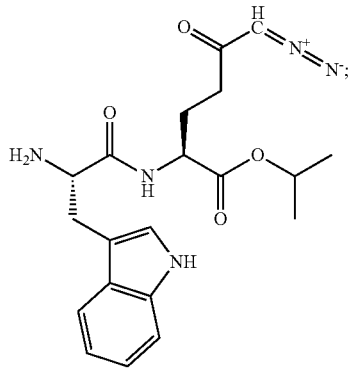

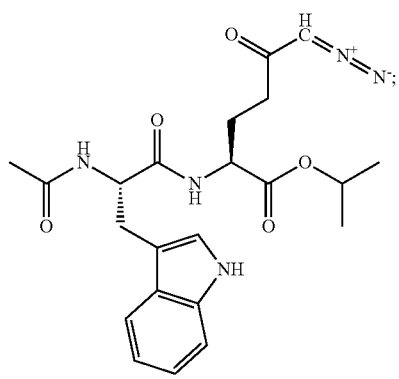

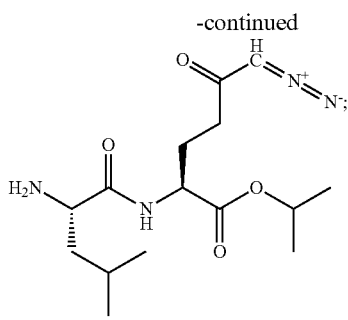

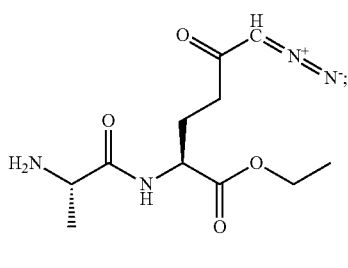

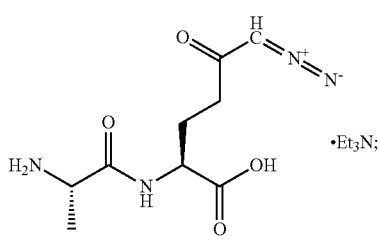

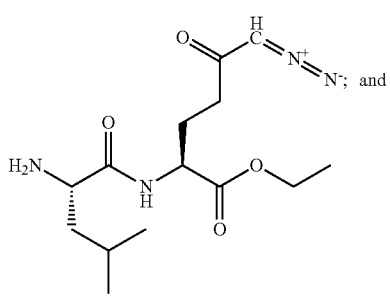

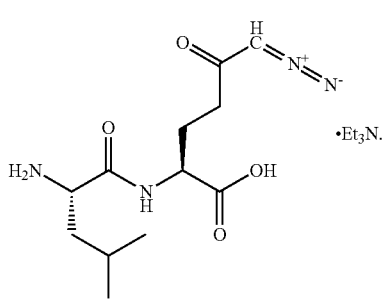

In another embodiment, the disclosure provides a compound having formula (I), or a pharmaceutically acceptable salt thereof, which is:

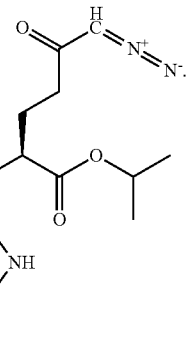

In another embodiment, the disclosure provides a compound having formula (III):

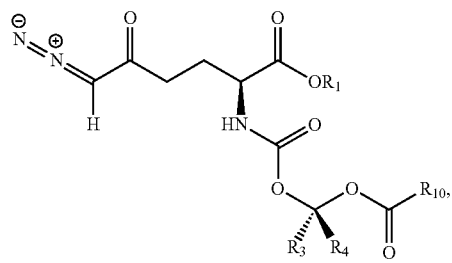

or a pharmaceutically acceptable salt thereof, wherein:

$R_1$ is selected from the group consisting of H and $C_{1-6}$ alkyl;

$R_3$ and $R_4$ are independently selected from the group consisting of H, $C_1$-$C_6$ alkyl, substituted $C_1$-$C_6$ alkyl, aryl, and substituted aryl; and $R_{10}$ is $C_{1-6}$ alkyl.

In another embodiment, the disclosure provides a compound having formula (III), or a pharmaceutically acceptable salt thereof, wherein $R_1$ is selected from the group consisting of methyl, ethyl, and isopropyl.

In another embodiment, the disclosure provides a compound having formula (III), or a pharmaceutically acceptable salt thereof, wherein $R_3$ is selected from the group consisting of methyl and phenyl; and $R_4$ is H.

In another embodiment, the disclosure provides a compound having formula (III), or a pharmaceutically acceptable salt thereof, wherein $R_3$ is H and $R_4$ is selected from the group consisting of methyl and phenyl.

In another embodiment, the disclosure provides a compound having formula (III), or a pharmaceutically acceptable salt thereof, wherein $R_{10}$ is selected from the group consisting of isopropyl and tert-butyl.

In another embodiment, the disclosure provides a compound having formula (I), or a pharmaceutically acceptable salt thereof, selected from the group consisting of:

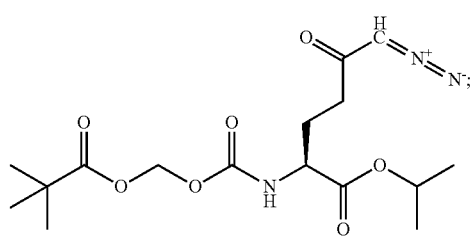
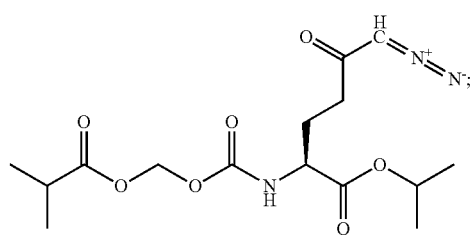
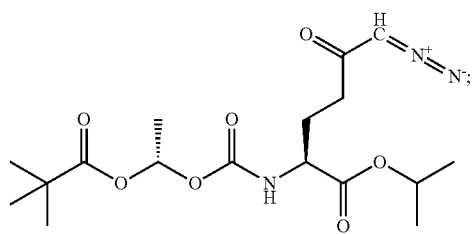
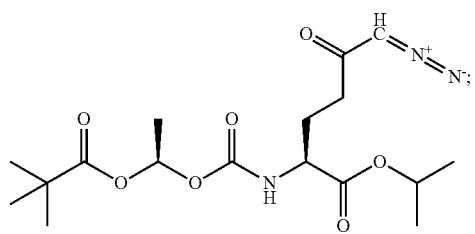
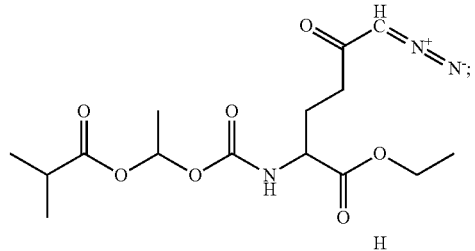
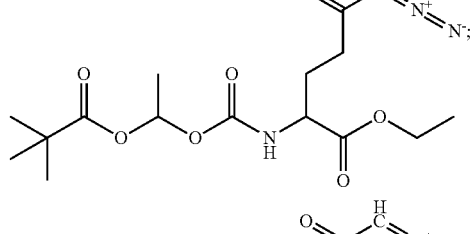
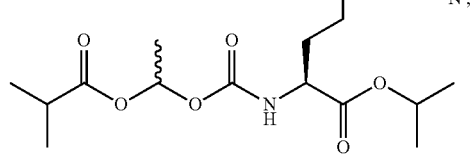
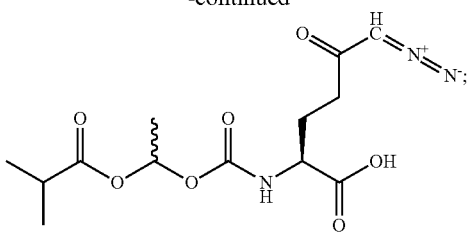
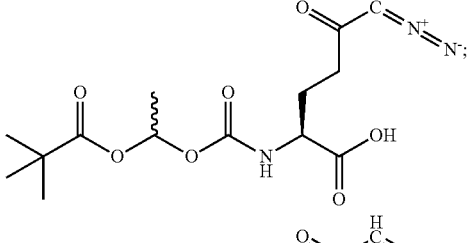
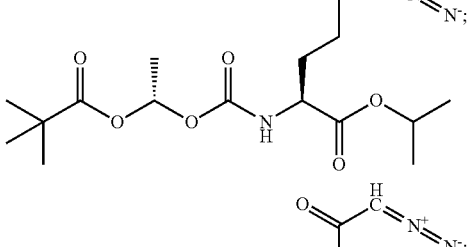
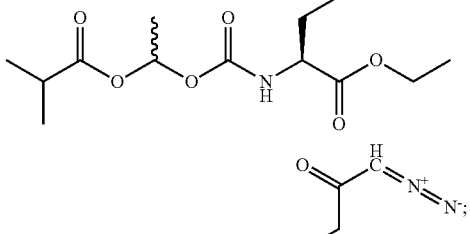
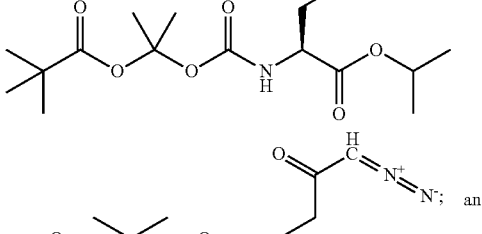
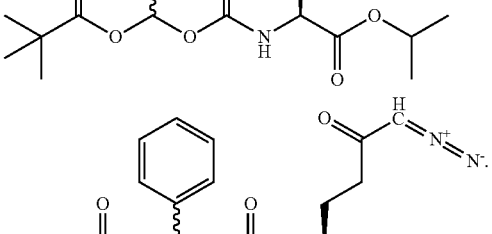
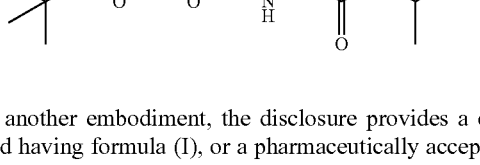
In another embodiment, the disclosure provides a compound having formula (I), or a pharmaceutically acceptable salt thereof, selected from the group consisting of:

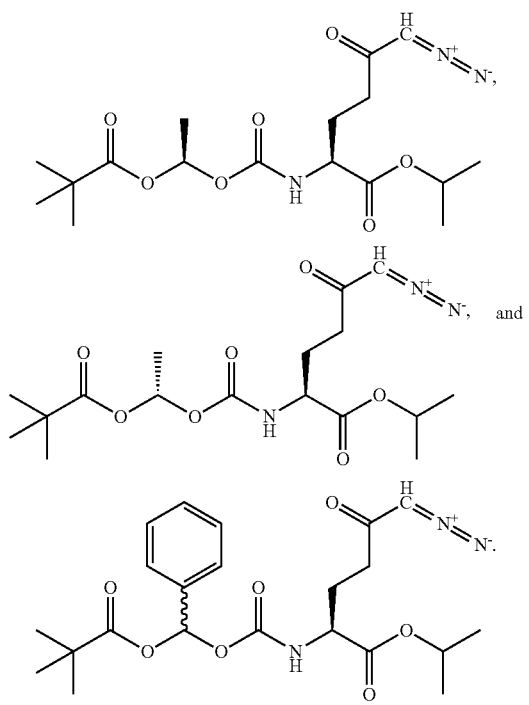
In another embodiment, the disclosure provides a compound, or a pharmaceutically acceptable salt thereof, selected from the group consisting of:
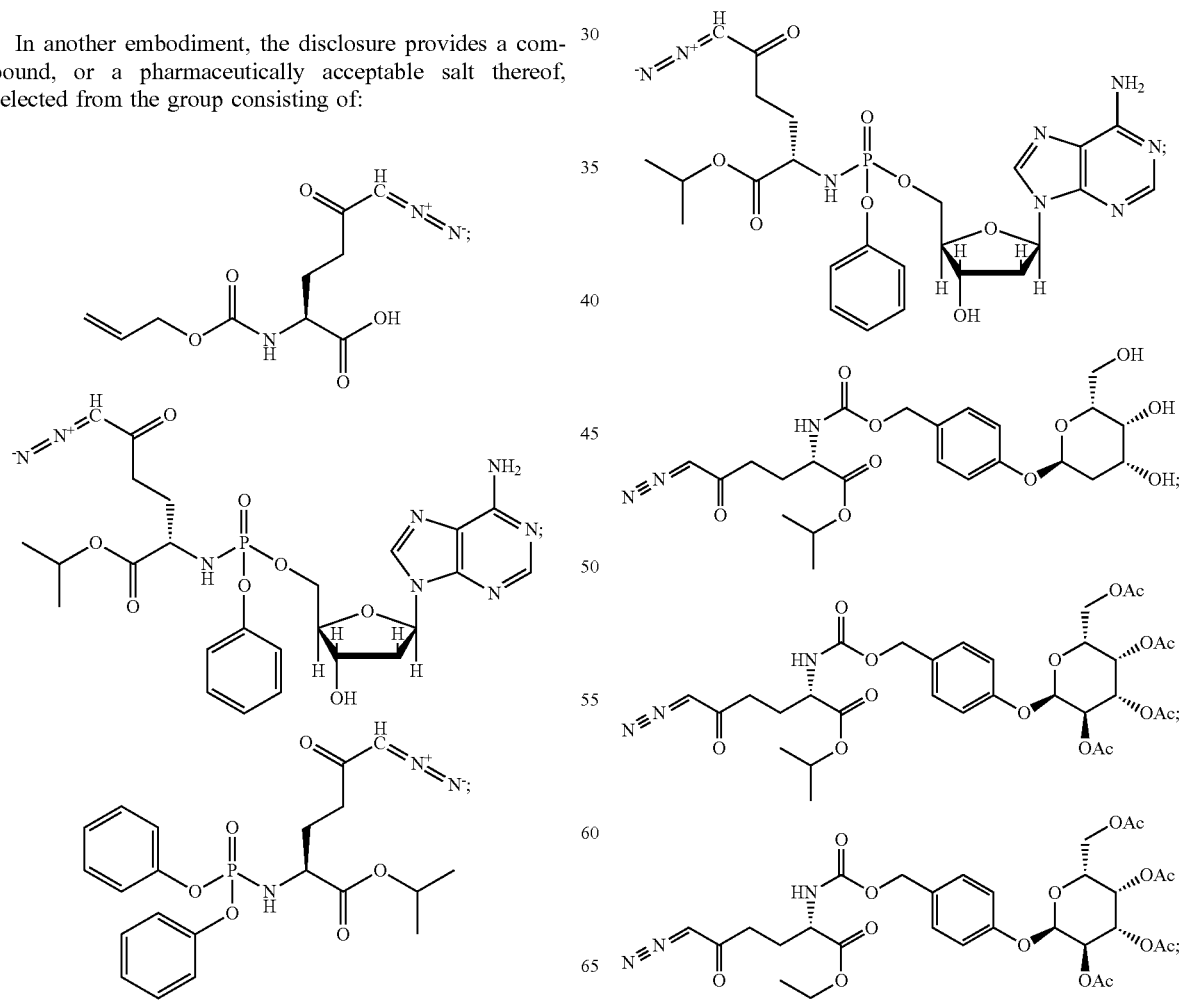
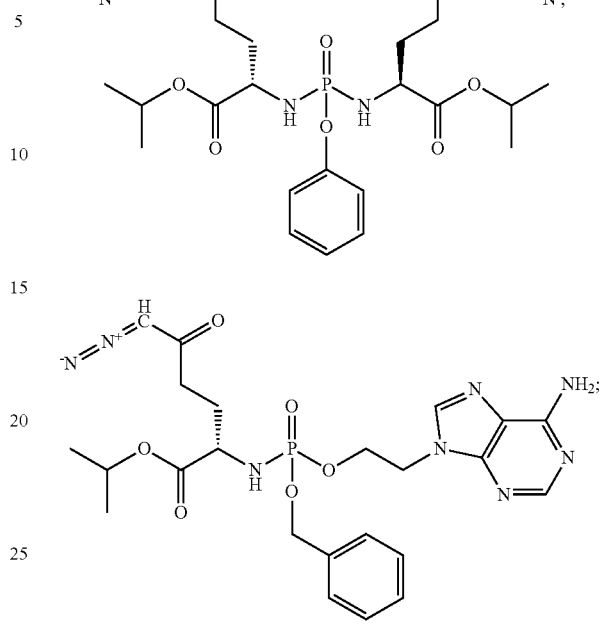

43
-continued
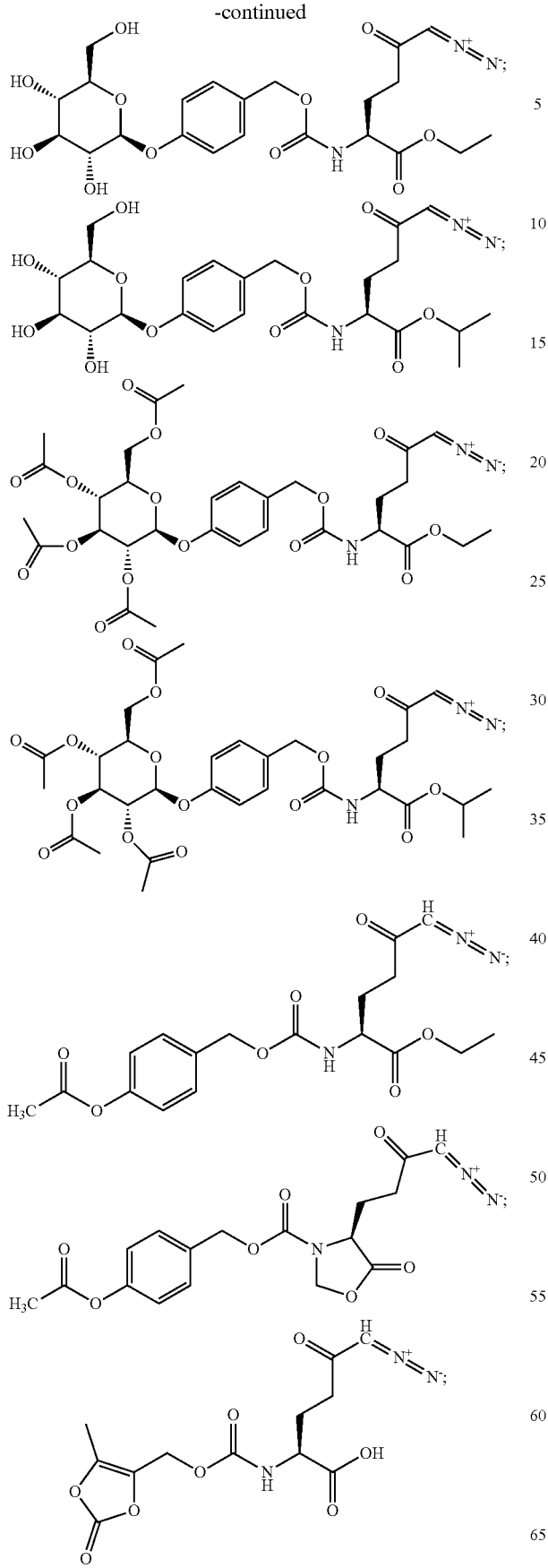
44
-continued
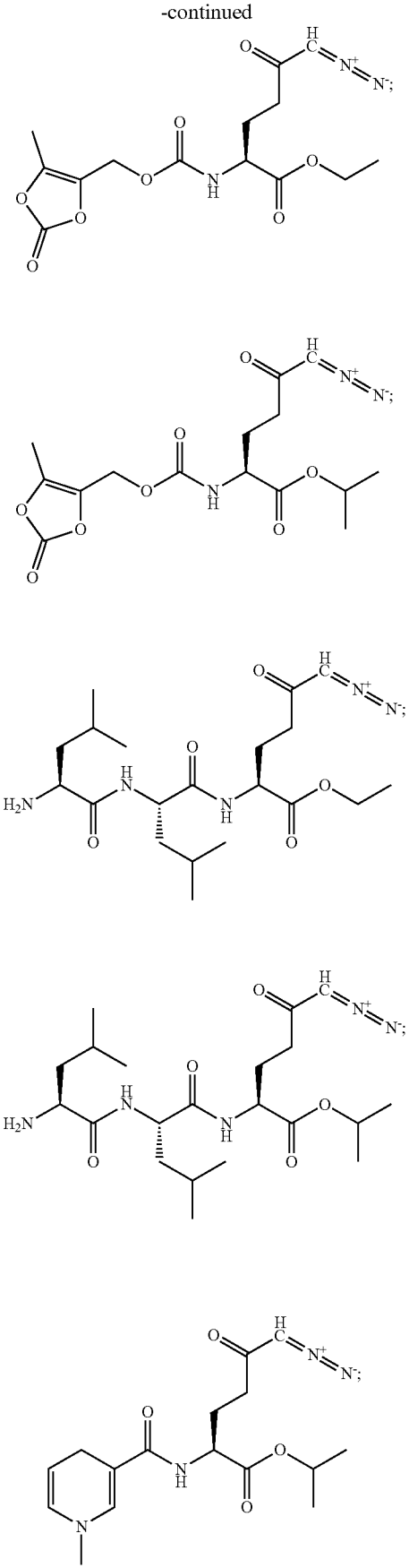

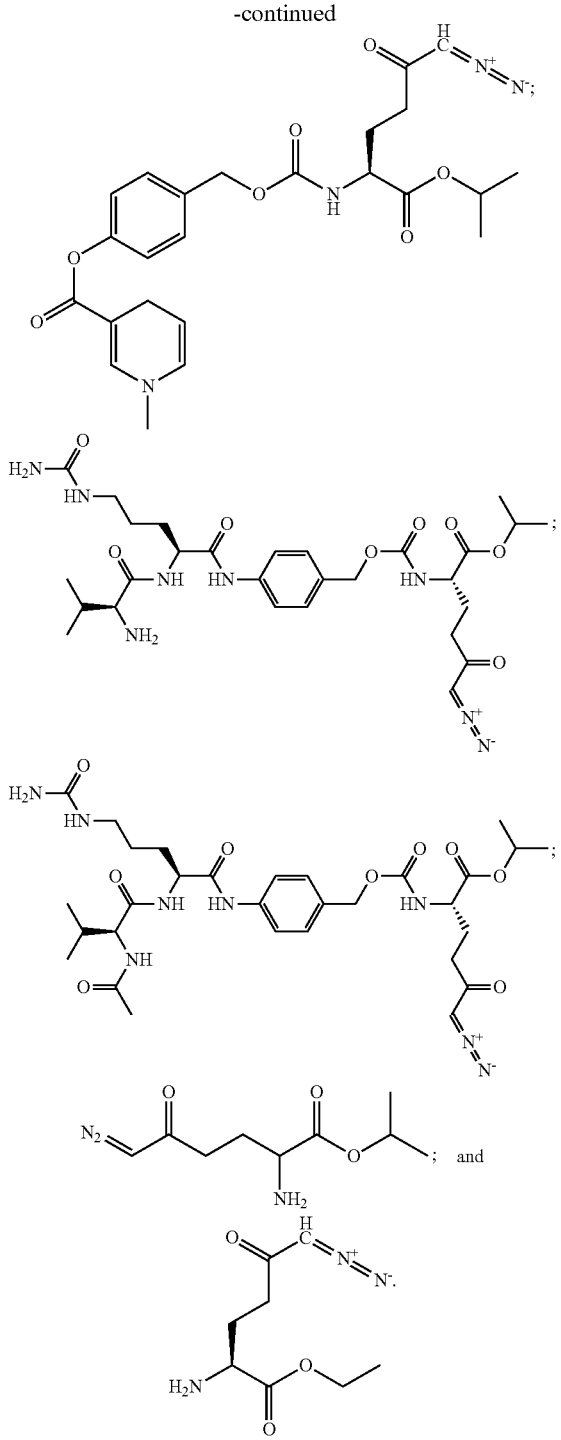

In another embodiment, the disclosure provides a pharmaceutical composition comprising the compound of any one of formula (I), formula (IIA), formula (IIB), or formula (II), or a pharmaceutically acceptable salt thereof, and a pharmaceutically acceptable carrier, diluent, or excipient.

In another embodiment, the disclosure provides a method of treating cancer in a subject, the method comprising administering to the subject in need thereof a compound of any one of formula (I), formula (IIA), formula (IIB), or formula (III), or a pharmaceutically acceptable salt thereof. In another embodiment, compound of any one of formula (I), formula (IIA), formula (IIB), or formula (III), or a pharmaceutically acceptable salt thereof, is administered subcutaneously to the subject. In another embodiment, the compound of formula (I), formula (IIA), formula (IIB), or formula (III) is administered in combination with one or more additional anticancer agents. The term "anticancer agent" refers to radiotherapy, e.g., gamma-radiation, neutron beam radiotherapy, and/or any chemotherapeutic drug. In another embodiment, the compound of formula (I), formula (IIA), formula (IIB), or formula (III) is administered as the only anticancer agent to the subject, i.e., the compound of formula (I), formula (TIA), formula (IIB), or formula (III) is administered to the subject as a single anticancer agent. In another embodiment, $R_1$ is $C_{1-6}$ alkyl. In another embodiment, the cancer is selected from the group consisting of non-small cell lung cancer, melanoma, squamous cell carcinoma, kidney cancer, liver cancer, pancreatic cancer, colon cancer, triple negative breast cancer, and glioma. In another embodiment, the cancer is glioblastoma.

As used herein, the term "amino acid" includes moieties having a carboxylic acid group and an amino group. The term amino acid thus includes both natural amino acids (including proteinogenic amino acids) and non-natural amino acids. The term "natural amino acid" also includes other amino acids that can be incorporated into proteins during translation (including pyrrolysine and selenocysteine). Additionally, the term "natural amino acid" also includes other amino acids, which are formed during intermediary metabolism, e.g., ornithine generated from arginine in the urea cycle. The natural amino acids are summarized in Table 2:

TABLE 2

Natural Amino Acids (Used For Protein Biosynthesis)

| Amino acid | 3 letter code | 1-letter code |
|---|---|---|
| Alanine | ALA | A |
| Cysteine | CYS | C |
| Aspartic Acid | ASP | D |
| Glutamic Acid | GLU | E |
| Phenylalanine | PHE | F |
| Glycine | GLY | G |
| Histidine | HIS | H |
| Isoleucine | ILE | I |
| Lysine | LYS | K |
| Leucine | LEU | L |
| Methionine | MET | M |
| Asparagine | ASN | N |
| Proline | PRO | P |
| Glutamine | GLN | Q |
| Arginine | ARG | R |
| Serine | SER | S |
| Threonine | THR | T |
| Valine | VAL | V |
| Tryptophan | TRP | W |
| Tyrosine | TYR | Y |

The natural or non-natural amino acid may be optionally substituted. In one embodiment, the amino acid is selected from proteinogenic amino acids. Proteinogenic amino acids include glycine, alanine, valine, leucine, isoleucine, aspartic acid, glutamic acid, serine, threonine, glutamine, asparagine, arginine, lysine, proline, phenylalanine, tyrosine, tryptophan, cysteine, methionine and histidine. The term amino acid includes alpha amino acids and beta amino acids, such as, but not limited to, beta alanine and 2-methyl beta alanine. The term amino acid also includes certain lactam analogues of natural amino acids, such as, but not limited to, pyroglutamine. The term amino acid also includes amino acids homologues including homocitrulline, homoarginine, homoserine, homotyrosine, homoproline and homophenylalanine.

The terminal portion of the amino acid residue or peptide may be in the form of the free acid i.e., terminating in a —COOH group or may be in a masked (protected) form, such as in the form of a carboxylate ester or carboxamide. In certain embodiments, the amino acid or peptide residue terminates with an amino group. In an embodiment, the residue terminates with a carboxylic acid group —COOH or an amino group —NH$_2$. In another embodiment, the residue terminates with a carboxamide group. In yet another embodiment, the residue terminates with a carboxylate ester.

As disclosed hereinabove, the term "amino acid" includes compounds having a —COOH group and an —NH$_2$ group. A substituted amino acid includes an amino acid which has an amino group which is mono- or di-substituted. In particular embodiments, the amino group may be mono-substituted. (A proteinogenic amino acid may be substituted at another site from its amino group to form an amino acid which is a substituted proteinogenic amino acid). The term substituted amino acid thus includes N-substituted metabolites of the natural amino acids including, but not limited to, N-acetyl cysteine, N-acetyl serine, and N-acetyl threonine.

For example, the term "N-substituted amino acid" includes N-alkyl amino acids (e.g., $C_{1-6}$ N-alkyl amino acids, such as sarcosine, N-methyl-alanine, N-methyl-glutamic acid and N-tert-butylglycine), which can include $C_{1-6}$ N-substituted alkyl amino acids (e.g., N-(carboxy alkyl) amino acids (e.g., N-(carboxymethyl)amino acids) and N-methylcycloalkyl amino acids (e.g., N-methylcyclopropyl amino acids)); N,N-di-alkyl amino acids (e.g., N,N-di-$C_{1-6}$ alkyl amino acids (e.g., N,N-dimethyl amino acid)); N,N,N-tri-alkyl amino acids (e.g., N,N,N-tri-$C_{1-6}$ alkyl amino acids (e.g., N,N,N-trimethyl amino acid)); N-acyl amino acids (e.g., $C_{1-6}$ N-acyl amino acid); N-aryl amino acids (e.g., N-phenyl amino acids, such as N-phenylglycine); N-amidinyl amino acids (e.g., an N-amidine amino acid, i.e., an amino acid in which an amine group is replaced by a guanidino group).

The term "amino acid" also includes amino acid alkyl esters (e.g., amino acid $C_{1-6}$ alkyl esters); and amino acid aryl esters (e.g., amino acid phenyl esters).

For amino acids having a hydroxy group present on the side chain, the term "amino acid" also includes O-alkyl amino acids (e.g., $C_{1-6}$ O-alkyl amino acid ethers); O-aryl amino acids (e.g., O-phenyl amino acid ethers); O-acyl amino acid esters; and O-carbamoyl amino acids.

For amino acids having a thiol group present on the side chain, the term "amino acid" also includes S-alkyl amino acids (e.g., $C_{1-6}$ S-alkyl amino acids, such as S-methyl methionine, which can include $C_{1-6}$ S-substituted alkyl amino acids and S-methylcycloalkyl amino acids (e.g., S-methylcyclopropyl amino acids)); S-acyl amino acids (e.g., a $C_{1-6}$ S-acyl amino acid); S-aryl amino acid (e.g., a S-phenyl amino acid); a sulfoxide analogue of a sulfur-containing amino acid (e.g., methionine sulfoxide) or a sulfoxide analogue of an S-alkyl amino acid (e.g., S-methyl cystein sulfoxide) or an S-aryl amino acid.

In other words, the presently disclosed subject matter also envisages derivatives of natural amino acids, such as those mentioned above which have been functionalized by simple synthetic transformations known in the art (e.g., as described in "Protective Groups in Organic Synthesis" by T W Greene and P G M Wuts, John Wiley & Sons Inc. (1999)), and references therein.

Examples of non-proteinogenic amino acids include, but are not limited to: citrulline, hydroxyproline, 4-hydroxyproline, β-hydroxyvaline, ornithine, β-amino alanine, albizziin, 4-amino-phenylalanine, biphenylalanine, 4-nitro-phenylalanine, 4-fluoro-phenylalanine, 2,3,4,5,6-pentafluoro-phenylalanine, norleucine, cyclohexylalanine, α-aminoisobutyric acid, α-aminobutyric acid, α-aminoisobutyric acid, 2-aminoisobutyric acid, 2-aminoindane-2-carboxylic acid, selenomethionine, lanthionine, dehydroalanine, γ-amino butyric acid, naphthylalanine, aminohexanoic acid, pipecolic acid, 2,3-diaminoproprionic acid, tetrahydroisoquinoline-3-carboxylic acid, tert-leucine, tert-butylalanine, cyclopropylglycine, cyclohexylglycine, 4-aminopiperidine-4-carboxylic acid, diethylglycine, dipropylglycine and derivatives thereof wherein the amine nitrogen has been mono- or di-alkylated.

The term "peptide" refers to an amino acid chain consisting of 2 to 9 amino acids, unless otherwise specified. In preferred embodiments, the peptide used in the present invention is 2 or 3 amino acids in length. In one embodiment, a peptide can be a branched peptide. In this embodiment, at least one amino acid side chain in the peptide is bound to another amino acid (either through one of the termini or the side chain).

The term "N-substituted peptide" refers to an amino acid chain consisting of 2 to 9 amino acids in which one or more NH groups are substituted, e.g., by a substituent described elsewhere herein in relation to substituted amino groups. Optionally, the N-substituted peptide has its N-terminal amino group substituted and, in one embodiment, the amide linkages are unsubstituted.

In one embodiment, an amino acid side chain is bound to another amino acid. In a further embodiment, side chain is bound to the amino acid via the amino acid's N-terminus, C-terminus, or side chain.

Examples of natural amino acid sidechains include hydrogen (glycine), methyl (alanine), isopropyl (valine), sec-butyl (isoleucine), —CH$_2$CH(CH$_3$)$_2$ (leucine), benzyl (phenylalanine), p-hydroxybenzyl (tyrosine), —CH$_2$OH (serine), —CH(OH)CH$_3$ (threonine), —CH$_2$-3-indoyl (tryptophan), —CH$_2$COOH (aspartic acid), —CH$_2$CH$_2$COOH (glutamic acid), —CH$_2$C(O)NH$_2$ (asparagine), —CH$_2$CH$_2$C(O)NH$_2$ (glutamine), —CH$_2$SH, (cysteine), —CH$_2$CH$_2$SCH$_3$ (methionine), —(CH$_2$)$_4$NH$_2$ (lysine), —(CH$_2$)$_3$NHC(=NH)NH$_2$ (arginine) and —CH$_2$-3-imidazoyl (histidine).

Exemplary monocyclic rings and bicyclic rings include, without limitation, benzene, pyrimidines, and purines, and more generally aryl and heteroaryl rings. Exemplary heteroaryls include, but are not limited to, pyridyl, pyrimidinyl, pyrazinyl, furanyl, thienyl, pyrazolyl, oxazolyl, thiazolyl, isothiazolyl, isoxazolyl, pyrrolyl, imidazolyl, indolyl, indolinolyl, and imidazopyridazinyl. Aryls include phenyl ($C_6$), benzyl, naphthyl ($C_{10}$), and biphenyl ($C_{12}$). Exemplary pyrimidines include, without limitation, cytosine, thymine, and uracil. Exemplary purines include, without limitation, purine, adenine, N-substituted adenine, guanine, hypoxanthine, xanthine, theobromine, caffeine, uric acid, and isoguanine. Exemplary purine nucleosides include, without limitation, adenine and guanine.

In some embodiments, R$_2$ of formula (I) is selected from the group consisting of H, alkyl, —C(=O)—Ar, —C(=O)—Y—(CR$_3$R$_4$)$_m$—Ar, —C(=O)—Y—(CR$_3$R$_4$)$_m$—NR$_5$R$_6$, —P(=O)(OR$_7$)$_n$(NHR$_9$)$_o$, —C(=O)—Y—(CR$_3$R$_4$)—Ar—O—C(=O)—R$_8$, —C(=O)—Y(CR$_3$R$_4$)$_m$—Ar—O—R$_8$, —C(=O)—O—(CR$_3$R$_4$)$_m$—O—C(=O)—R$_{10}$, —C(=O)—O—R$_9$, —C(=O)—Y—(CR$_3$R$_4$)$_m$—Ar—O—C(=O)—Ar, and —C(=O)—Y—(CR$_3$R$_4$)$_m$—Ar—NR$_5$R$_6$; wherein: Y is —O— or a bond; m is an integer selected from the group consisting of 0, 1, 2, 3, 4, 5, 6, 7, and 8; each n and o is an integer from 0 to 2 provided that the sum of n and o is 2; $R_3$ and $R_4$ is independently H, $C_1$-$C_6$ alkyl or substituted $C_1$-$C_6$ alkyl, aryl or substituted aryl. —$(CR_3R_4)_m$—$NR_5R_6$, or

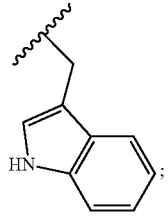 [SMILES: *Cc1c[nH]c2ccccc12]

each $R_5$ and $R_6$ is independently H, alkyl, —C(=O)—$(CR_3R_4)_m$H, —C(=O)—($NR_5R_6$), or —C(=O)—($CR_3R_4)_m$—$NR_5R_6$; each $R_7$ is independently selected from the group consisting of H, alkyl, substituted alkyl, cycloalkyl, substituted cycloalkyl, heterocyclyl, substituted heterocyclyl, alkenyl, substituted alkenyl, cycloalkenyl, substituted cycloalkenyl, —$(CR_3R_4)_m$—Z, —$(CR_3R_4)_m$-Q-Z, wherein Q is a monosaccharide, aryl, substituted aryl, heteroaryl, substituted heteroaryl, and wherein Z is

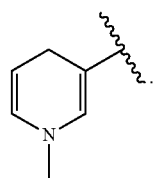

or wherein $R_7$ together with the oxygen atom to which it is attached forms a purine or pyrimidine nucleoside; each $R_9$ is independently selected from the group consisting of H, alkyl, substituted alkyl, cycloalkyl, substituted cycloalkyl, heterocyclyl, substituted heterocyclyl, alkenyl, substituted alkenyl, cycloalkenyl, substituted cycloalkenyl, —$(CR_3R_4)_m$—Z, aryl, substituted aryl, heteroaryl, substituted heteroaryl, and

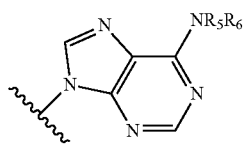

wherein $R_1$ and X are as defined above, provided that $R_1$ is not H; each $R_8$ is independently alkyl, substituted alkyl, cycloalkyl, substituted cycloalkyl, monosaccharide, acylated monosaccharide, aryl, substituted aryl, heteroaryl, substituted heteroaryl; each $R_{10}$ is independently alkyl, substituted alkyl, cycloalkyl, substituted cycloalkyl, monosaccharide, acylated monosaccharide, aryl, substituted aryl, heteroaryl, substituted heteroaryl; and Ar is aryl, substituted aryl, heteroaryl, or substituted heteroaryl. It should be appreciated that in addition to substitutions on the amino group of Z, one or more substitutions $R_3$, $R_4$, $R_5$, and/or $R_6$ can be made to the 5 or 6 membered rings of Z.

In particular embodiments Ar is

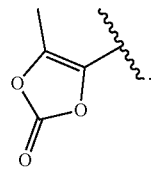 [SMILES: *c1oc(=O)oc1C]

In other particular embodiments, Ar is and

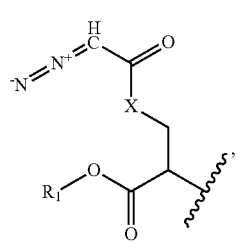

In yet other particular embodiments Ar is benzyl.

In particular embodiments, the prodrug compound of formula (I) is

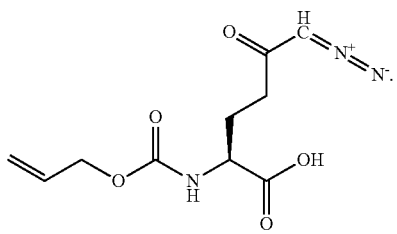

In some embodiments, $R_2$ of formula (I) is —C(=O)—Y—$(CR_3R_4)_m$—$NR_5R_6$; wherein: (i) Y is a bond; m is 1; $R_5$ and $R_6$ are each H; (ii) Y is a bond; m is 1; $R_5$ is H; $R_6$ is —C(=O)—$(CR_3R_4)_m$H.

In particular embodiments, the prodrug compound of formula (I) is selected from the group consisting of:

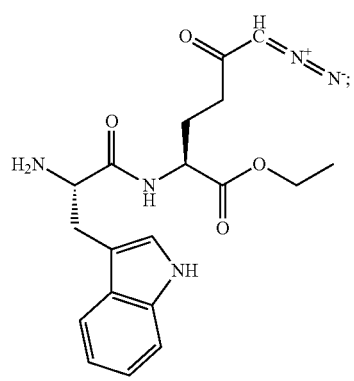

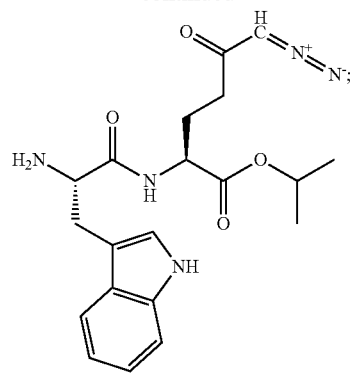

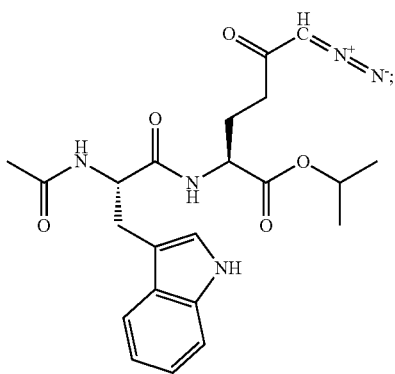

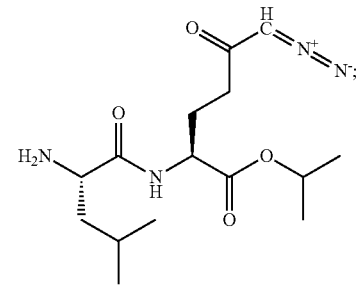

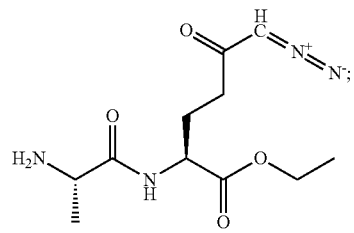

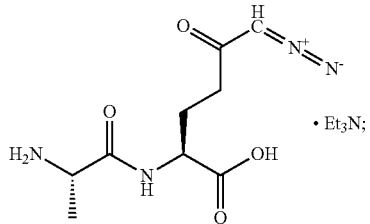

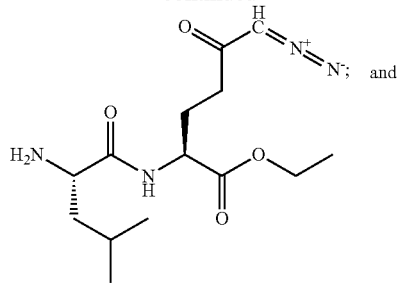

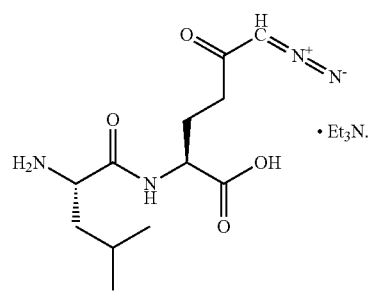

In such embodiments, it should be appreciated that the terminal carboxy groups of the compounds of formula (I) shown above can be used to form salts. In an exemplary embodiment, a salt of any of the compounds of formula (I) shown above can be formed when an H is replaced by NEt$_3$, as will be appreciated by those skilled in the art.

In some embodiments, R$_2$ of formula (I) is —P(=O)(OR$_7$)$_n$(NHR$_9$)$_o$; wherein: n is 2 and o is 0; n is 1 and o is 1; or n is 0 and o is 2.

In particular embodiments, the prodrug compound of formula (I) is selected from the group consisting of:

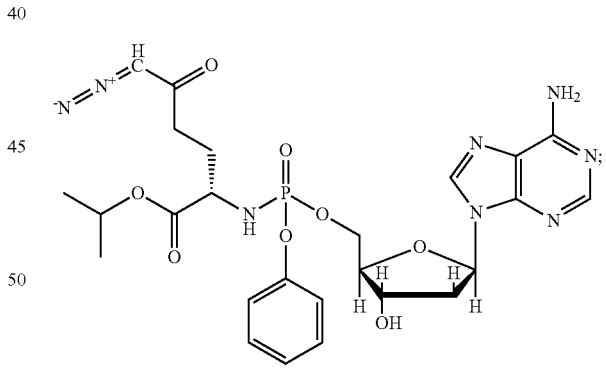

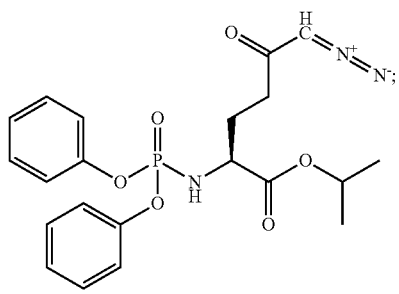

-continued

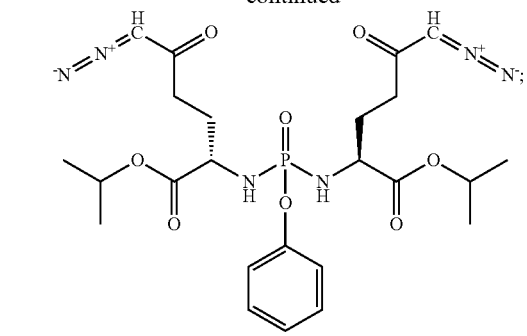

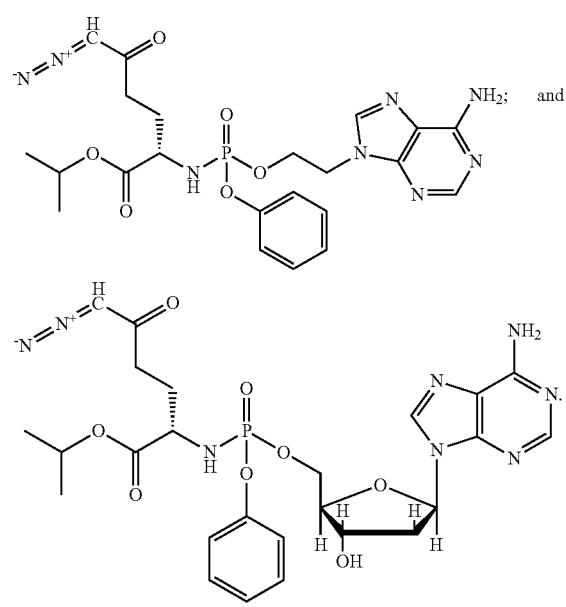

In some embodiments, $R_2$ of formula (I) is —C(=O)—Y—(CR$_3$R$_4$)$_m$—Ar—O—C(=O)—R$_8$ or —C(=O)—Y—(CR$_3$R$_4$)$_m$—Ar—O—R$_8$; wherein: Y is —O—; m is 0; and Ar is benzyl.

In particular embodiments, the prodrug compound of formula (I) is selected from the group consisting of:

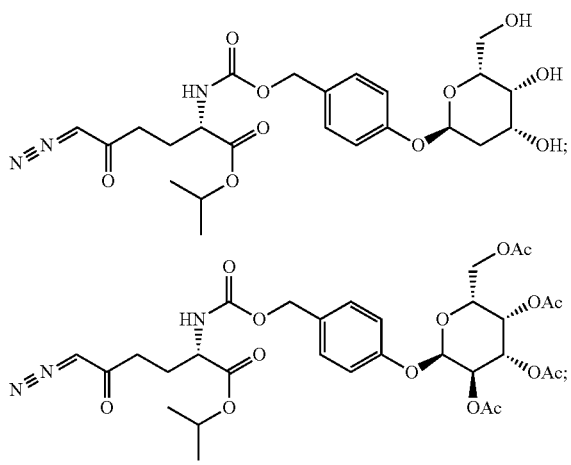

-continued

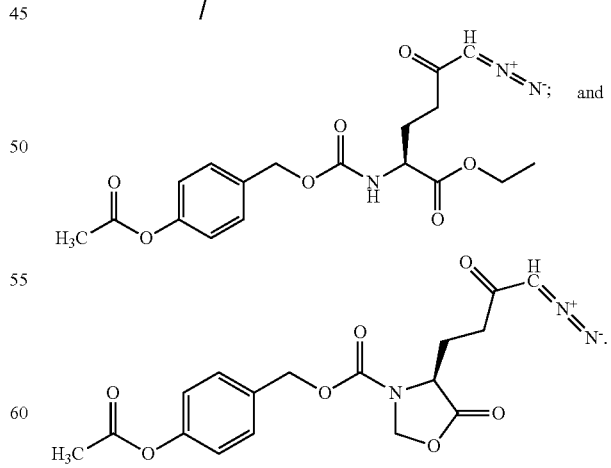

In some embodiments, $R_2$ of formula (I) is —C(=O)—O—(CR$_3$R$_4$)$_m$—O—C(=O)—R$_{10}$; wherein: (i) m is 1; $R_3$ is H; and $R_4$ is methyl, iPr, or aryl; (ii) m is 1; $R_3$ and $R_4$ are each H; or (vi) m is 1; $R_3$ and $R_4$ are each methyl.

In particular embodiments, the prodrug compound of formula (I) is selected from the group consisting of:
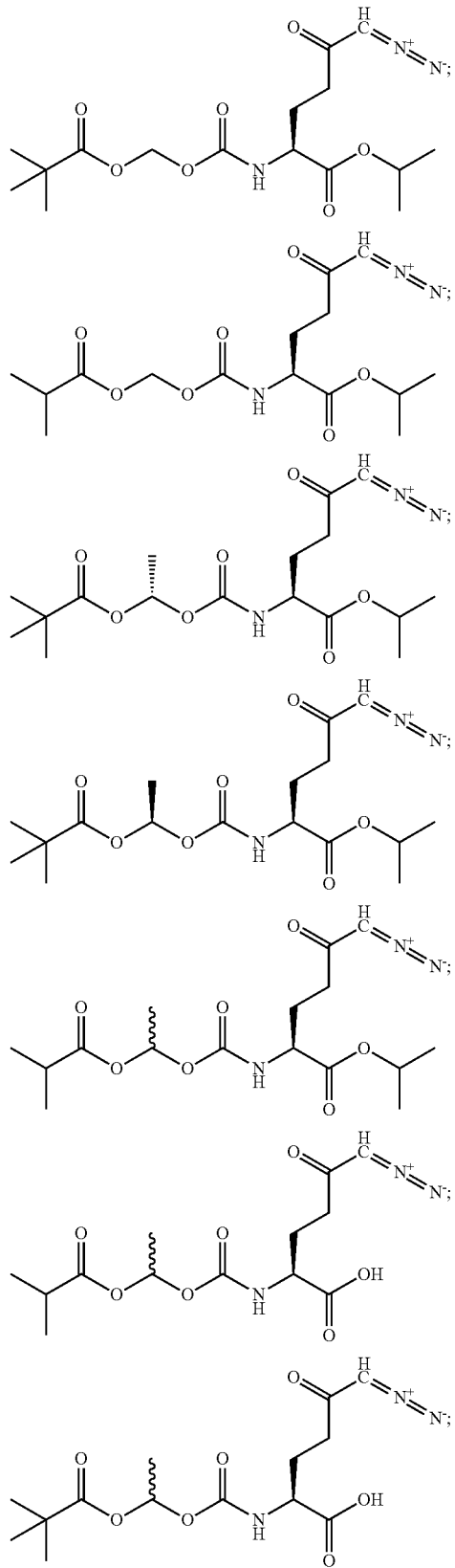
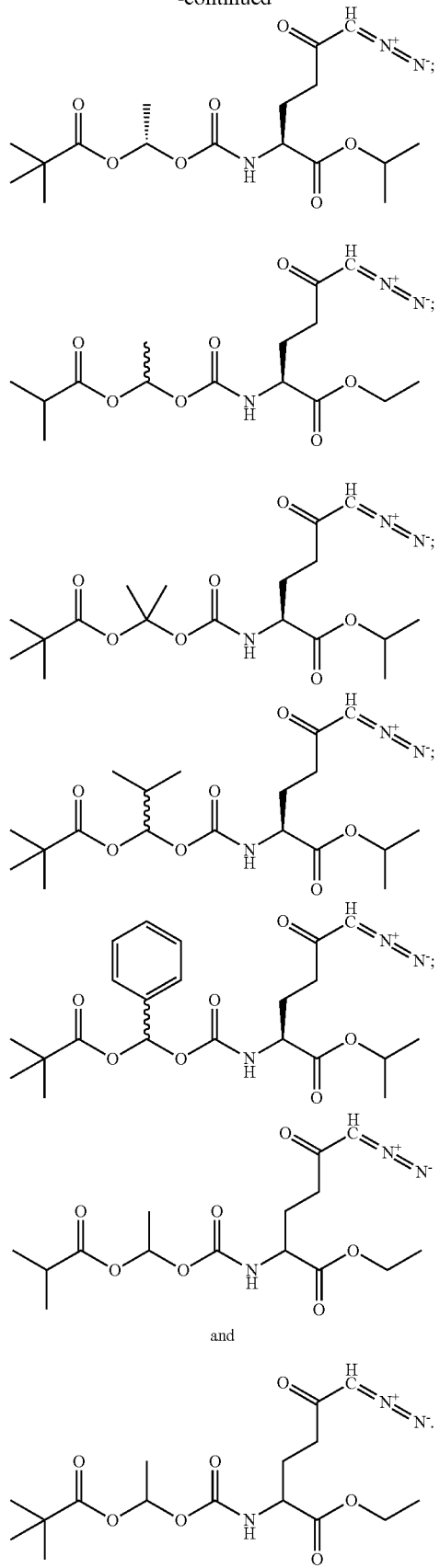
and In particular embodiments, the prodrug compound of formula (I) is of formula:

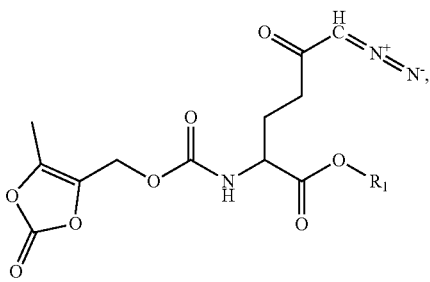

wherein R$_1$ is as defined above.

In particular embodiments, the prodrug compound of formula (I) is selected from the group consisting of:

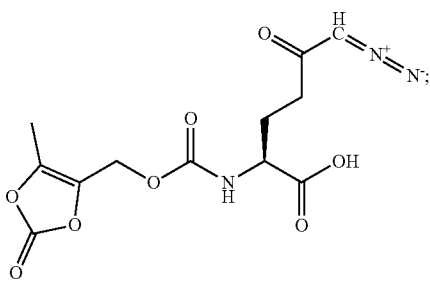

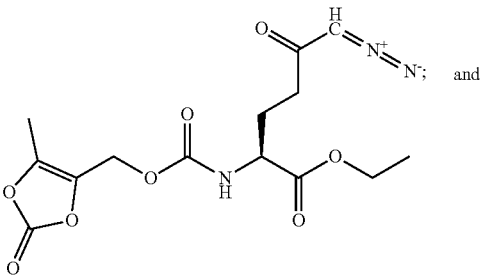

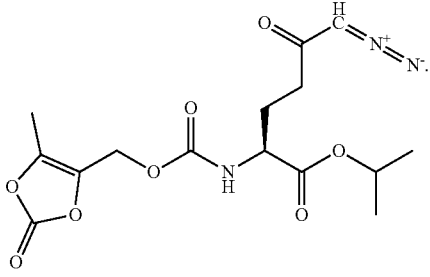

In some embodiments, R$_2$ of formula (I) is —C(=O)—Y—(CR$_3$R$_4$)$_m$—NR$_5$R$_6$; wherein Y is a bond; each m is 1; each R$_5$ is H; each R$_6$ is independently H or —C(=O)—(CR$_3$R$_4$)$_m$—NR$_5$R$_6$.

In particular embodiments, the prodrug compound of formula (I) is selected from the group consisting of:

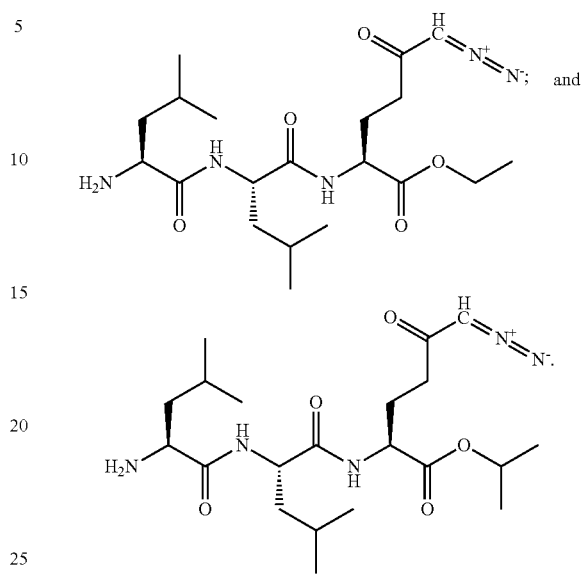

In some embodiments, R$_2$ of formula (I) is —C(=O)—Ar, or —C(=O)—Y—(CR$_3$R$_4$)$_m$—Ar—O—C(=O)—Ar.

In particular embodiments, the prodrug compound of formula (I) is selected from the group consisting of:

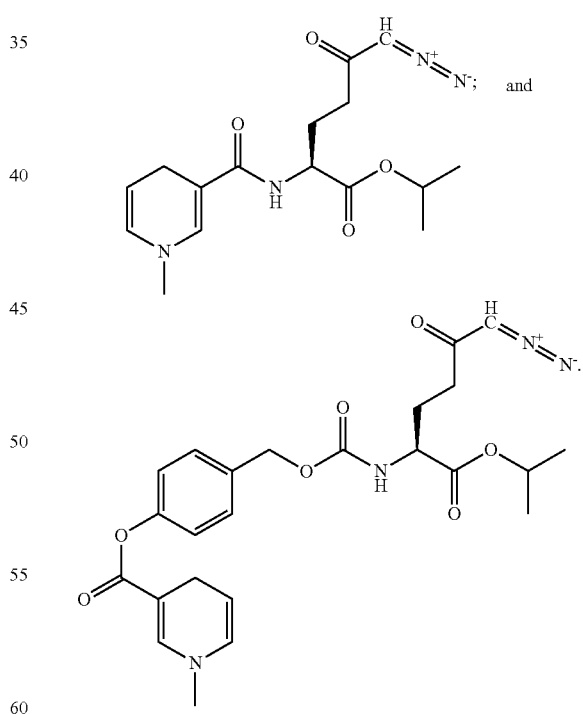

In some embodiments, R$_2$ of formula (I) is —C(=O)—Y—(CR$_3$R$_4$)$_m$—Ar—NR$_5$R$_6$; wherein: Y is O; each m is independently 0, 1, or 3; each R$_3$ is independently H, C$_1$-C$_6$ alkyl, or —(CR$_3$R$_4$)$_m$—NR$_5$R$_6$; each R$_4$ is H; each R$_5$ is independently H, —C(=O)—(CR$_3$R$_4$)$_m$H, —C(=O)—NR$_5$R$_6$, or —C(=O)—(CR$_3$R$_4$)$_m$—NR$_5$R$_6$; each R$_6$ is H.

In particular embodiments, the prodrug compound of formula (I) is selected from the group consisting of:

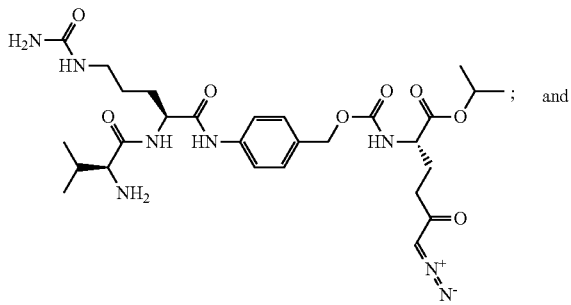
; and

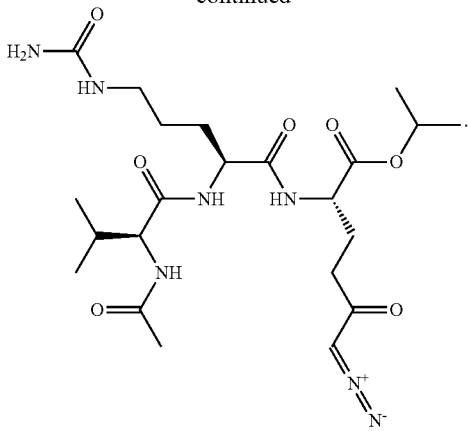

In some embodiments, $R_2$ of formula (I) is H and $R_1$ is selected from the group consisting of alkyl and substituted alkyl.

In particular embodiments, the prodrug compound of formula (I) is selected from the group consisting of:

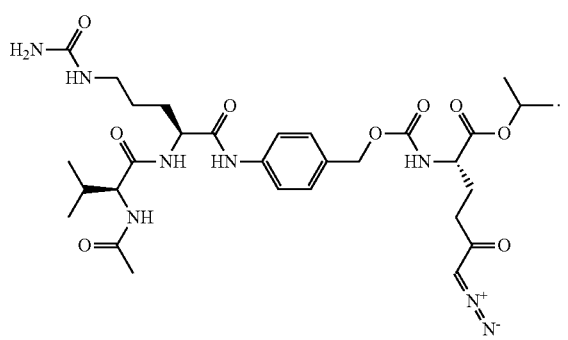

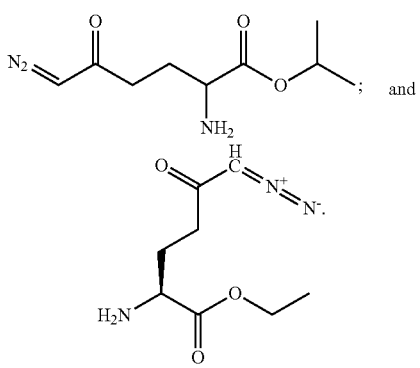
; and

In some embodiments, $R_2$ of formula (I) is —C(=O)—Y—(CR$_3$R$_4$)$_m$—NR$_5$R$_6$, wherein: Y is a bond; m is 1, 2 or 3; each $R_3$ is independently H, $C_1$-$C_6$ alkyl, or —(CR$_3$R$_4$)$_m$—NR$_5$R$_6$; each $R_4$ is H; each $R_5$ is independently H, —C(=O)—(CR$_3$R$_4$)$_m$H, —C(=O)—(NR$_5$R$_6$), or —C(=O)—(CR$_3$R$_4$)$_m$—NR$_5$R$_6$; each $R_6$ is H.

In particular embodiments, the prodrug compound of formula (I) is selected from the group consisting of:

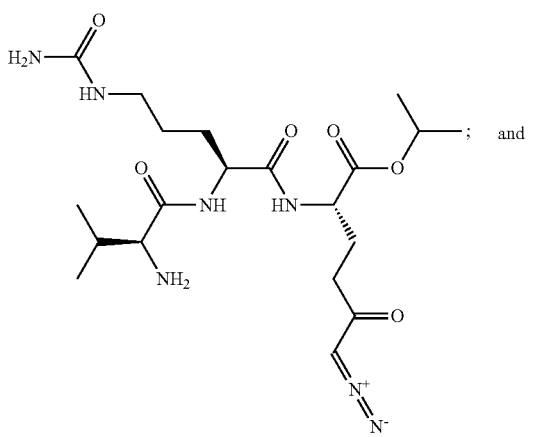

It should be appreciated that all of the compounds of formula (I) depicted in the structural formulas as prodrugs of DON are merely exemplary of prodrugs of glutamine analogs, such as L-DONV and aza-serine, that can be synthesized using the guidance of the presently disclosed subject matter.

The disclosure also provides the following embodiments numbered Embodiments I-XXXIII.

Embodiment I. A prodrug of a glutamine analog, or a pharmaceutically acceptable salt or ester thereof, the prodrug having a structure of formula (I):

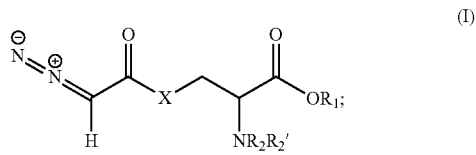

(I)

wherein:
X is selected from the group consisting of a bond, —O—, and —(CH$_2$)$_n$—; wherein n is an integer selected from the group consisting of 1, 2, 3, 4, 5, 6, 7, and 8;
$R_1$ is selected from the group consisting of H and a first prodrug-forming moiety capable of forming a salt or an ester; and R$_2$ is H or a second prodrug-forming moiety capable of forming an amide linkage, a carbamate linkage, a phosphoramidate linkage or a phosphorodiamidate linkage with the nitrogen adjacent to R$_2$;

R$_2$' is selected from the group consisting of H, C$_1$-C$_6$ alkyl, substituted C$_1$-C$_6$ alkyl, or R$_2$ and R$_2$' together form a ring structure comprising —C(═O)—G-C(═O)—, wherein G is selected from the group consisting of C$_1$-C$_8$ alkylene, C$_1$-C$_8$ heteroalkylene, C$_5$-C$_8$ cycloalkylene, C$_6$-C$_{12}$ arylene, C$_5$-C$_{14}$ heteroarylene, bivalent C$_4$-C$_{10}$ heterocycle, each of which can be optionally substituted; or R$_1$ and R$_2$' together form a 4-to 6-membered heterocylic ring comprising the oxygen atom adjacent to R$_1$ and the nitrogen atom adjacent to R$_2$';

provided that the compound has at least one prodrug-forming moiety selected from the group consisting of the first and the second prodrug-forming moieties.

Embodiment II. The prodrug of Embodiment 1, wherein X is —CH$_2$—.

Embodiment III. The prodrug of Embodiment I, wherein X is —O—.

Embodiment IV. The prodrug of Embodiment I, wherein the glutamine analog is a glutamine antagonist selected from the group consisting of 6-diazo-5-oxo-norleucine (DON), 5-diazo-4-oxo-L-norvaline (L-DONV), and aza-serine.

Embodiment V. The prodrug of Embodiment I, wherein R$_1$ comprises a residue PRO$_1$ of the prodrug-forming moiety, which, together with:
(i) a basic moiety and a terminal hydroxyl group forms a salt;
(ii) an alkyl group and the oxygen of an adjoining hydroxyl group forms an ester; or
(iii) an alkyl group and the nitrogen atom adjoining R$_2$' forms an azlactone or an oxazolidone.

Embodiment VI. The prodrug of Embodiment I, wherein R$_1$ is selected from the group consisting of H, alkyl, substituted alkyl, cycloalkyl, substituted cycloalkyl, alkenyl, substituted alkenyl, alkynyl, substituted alkynyl, cycloalkenyl, substituted cycloalkenyl, tri(hydrocarbyl)ammonium, and tetra(hydrocarbyl)ammonium.

Embodiment VII. The prodrug of Embodiment VI, wherein R$_1$ is selected from the group consisting of a C$_{1-6}$ straight-chain alkyl, a substituted C$_{1-6}$ straight-chain alkyl, a C$_{1-6}$ branched alkyl, a substituted C$_{1-6}$ branched alkyl, tri (C$_1$-C$_8$-alkyl)ammonium, tetra(C$_1$-C$_8$-alkyl)ammonium, triphenylammonium, tri(hydroxy-C$_1$-C$_8$-alkyl)ammonium, and tetra(hydroxy-C$_1$-C$_8$-alkyl)ammonium.

Embodiment VIII. The prodrug of Embodiment I, wherein R$_1$ is selected from the group consisting of methyl, ethyl, isopropyl, cyclopentyl, cyclohexyl, trimethylammonium, triethylammonium, tri(hydroxyethyl)ammonium, tripropylammonium, and tri(hydroxypropyl)ammonium.

Embodiment IX. The prodrug of Embodiment I, wherein R$_2$ comprises a residue PRO$_2$ of the second prodrug-forming moiety which comprises a carbonyl, an oxy carbonyl, or a phosphonyl group, wherein the carbonyl, the oxy carbonyl, or the phosphonyl group is bound to the nitrogen of the adjoining NR$_2$' to form an amide, a carbamate, phosphoramidate, or phosphorodiamidate linkage.

Embodiment X. The prodrug of Embodiment IX, wherein PRO$_2$ comprises a moiety selected from the group consisting of an amino acid, an N-substituted amino acid, a peptide, a substituted peptide, a monocyclic ring, a substituted monocyclic ring, a bicyclic ring, a substituted bicyclic ring, a purine nucleoside, a substituted purine nucleoside, a pyrimidine nucleoside, and a substituted pyrimidine nucleoside.

Embodiment XI. The prodrug of Embodiment I, wherein R$_2$ is selected from the group consisting of H, alkyl, —C(═O)—Ar, —C(═O)—Y—(CR$_3$R$_4$)$_m$—Ar, —C(═O)—Y—(CR$_3$R$_4$)$_m$—NR$_5$R$_6$, —P(═O)(OR$_7$)$_n$(NHR$_9$)$_o$, —C(═O)—Y—(CR$_3$R$_4$)$_m$—Ar—O—C(═O)—R$_8$, —C(═O)—Y—(CR$_3$R$_4$)$_m$—Ar—O—R$_8$, —C(═O)—O—(CR$_3$R$_4$)$_m$—O—C(═O)—R$_{10}$, —C(═O)—O—R$_9$, —C(═O)—Y—(CR$_3$R$_4$)$_m$—Ar—O—C(═O)—Ar, and —C(═O)—Y—(CR$_3$R$_4$)$_m$—Ar—NR$_5$R$_6$;

wherein:
Y is —O— or a bond;
m is an integer selected from the group consisting of 0, 1, 2, 3, 4, 5, 6, 7, and 8;
each n and o is an integer from 0 to 2 provided that the sum of n and o is 2;
each R$_3$ and R$_4$ is independently H, C$_1$-C$_6$ alkyl or substituted C$_1$-C$_6$ alkyl, aryl or substituted aryl, —(CR$_3$R$_4$)$_m$—NR$_5$R$_6$, or

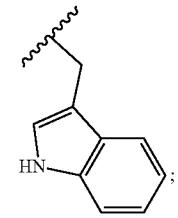

each R$_5$ and R$_6$ is independently H, alkyl, —C(═O)—(CR$_3$R$_4$)$_m$, —C(═O)—(NR$_5$R$_6$), or —C(═O)—(CR$_3$R$_4$)$_m$—NR$_5$R$_6$;

each R$_7$ is independently selected from the group consisting of H, alkyl, substituted alkyl, cycloalkyl, substituted cycloalkyl, heterocyclyl, substituted heterocyclyl, alkenyl, substituted alkenyl, cycloalkenyl, substituted cycloalkenyl, —(CR$_3$R$_4$)$_m$—Z, —(CR$_3$R$_4$)$_m$-Q-Z wherein Q is a monosaccharide, aryl, substituted aryl, heteroaryl, substituted heteroaryl, and wherein Z is

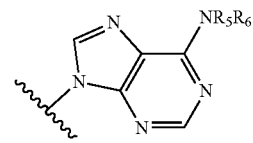

or wherein R$_7$ together with the oxygen atom to which it is attached forms a purine or pyrimidine nucleoside;

each R$_9$ is independently selected from the group consisting of H, alkyl, substituted alkyl, cycloalkyl, substituted cycloalkyl, heterocyclyl, substituted heterocyclyl, alkenyl, substituted alkenyl, cycloalkenyl, substituted cycloalkenyl, —(CR$_3$R$_4$)$_m$—Z, aryl, substituted aryl, heteroaryl, substituted heteroaryl, and

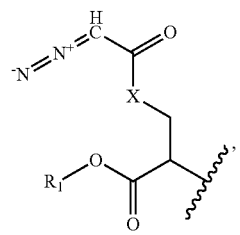

wherein $R_1$ and X are as defined in Embodiment 1, provided that $R_1$ is not H,

- each $R_8$ is independently alkyl, substituted alkyl, cycloalkyl, substituted cycloalkyl, monosaccharide, acylated monosaccharide, aryl, substituted aryl, heteroaryl, substituted heteroaryl;
- each $R_{10}$ is independently alkyl, substituted alkyl, cycloalkyl, substituted cycloalkyl, monosaccharide, acylated monosaccharide, aryl, substituted aryl, heteroaryl, substituted heteroaryl; and
- Ar is aryl, substituted aryl, heteroaryl, or substituted heteroaryl.

Embodiment XII. The prodrug of Embodiment XI, wherein the compound of formula (I) is

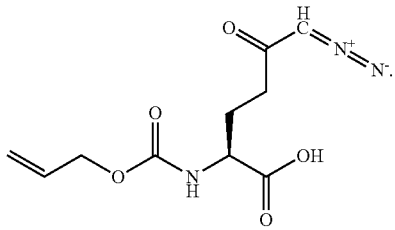

Embodiment XIII. The prodrug of Embodiment XI, wherein $R_2$ is —C(=O)—Y—$(CR_3R_4)_m$—$NR_5R_6$;

wherein:
(i) Y is a bond;
  m is 1;
  $R_5$ and $R_6$ are each H; or
(ii) Y is a bond;
  m is 1;
  $R_5$ is H,
  $R^6$ is —C(=O)—$(CR_3R_4)_m$.

Embodiment XIV. The prodrug of Embodiment XIII, wherein the compound of formula (I) is selected from the group consisting of:

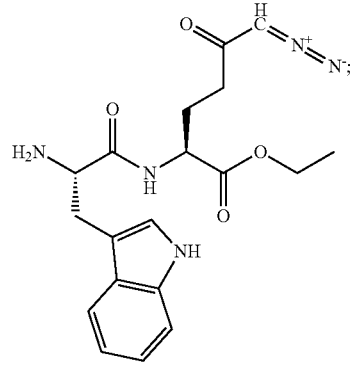

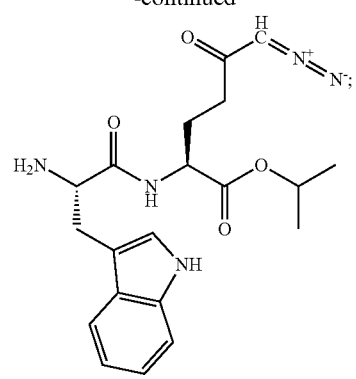

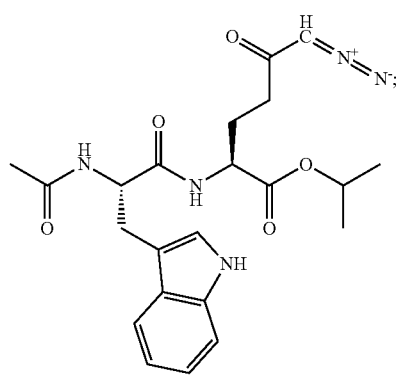

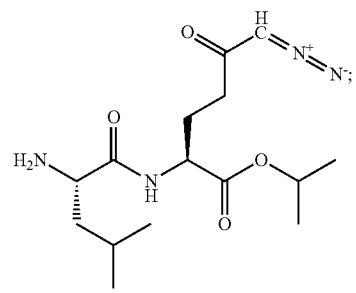

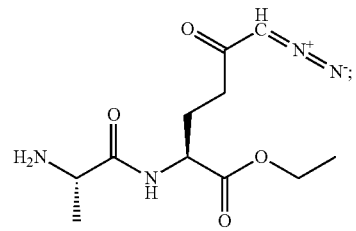

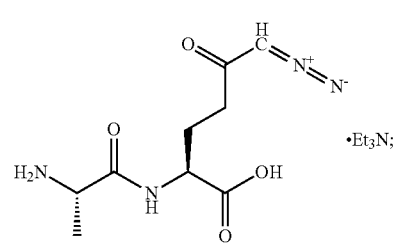

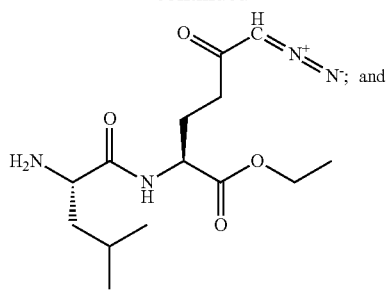

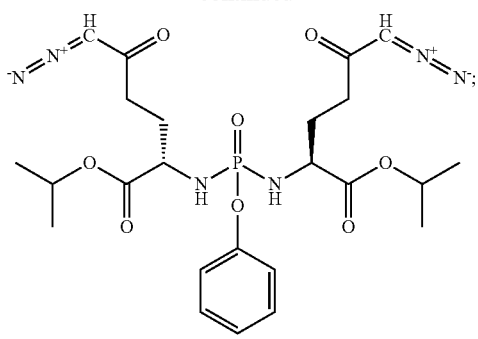

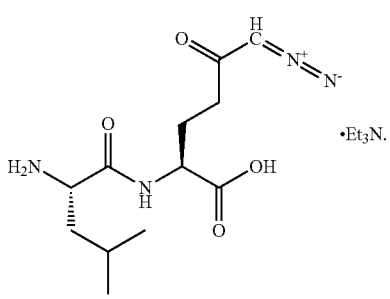

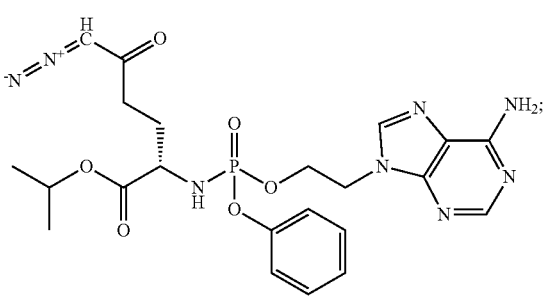

Embodiment XV. The prodrug of Embodiment XI, wherein $R_2$ is —P(=O)(OR$_7$)$_n$(NHR$_9$)$_o$;

wherein:

(i) n is 2 and o is 0;

(ii) n is 1 and o is 1; or (iii) n is 0 and o is 2.

Embodiment XVI. The prodrug of Embodiment XV, wherein the compound of formula (I) is selected from the group consisting of:

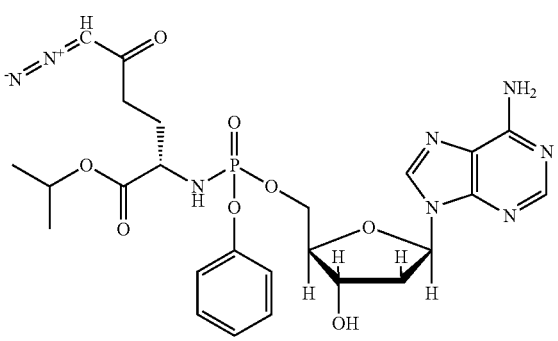

Embodiment XVII. The prodrug of Embodiment XI, wherein: $R_2$ is —C(=O)—Y—(CR$_3$R$_4$)$_m$—Ar—O—C(=O)—R$_8$ or —C(=O)—Y—(CR$_3$R$_4$)$_m$—Ar—O—R$_8$; and Y is —O—;

m is 0; and

Ar is benzyl.

Embodiment XVIII. The prodrug of Embodiment XVII, wherein the compound of formula (I) is selected from the group consisting of:

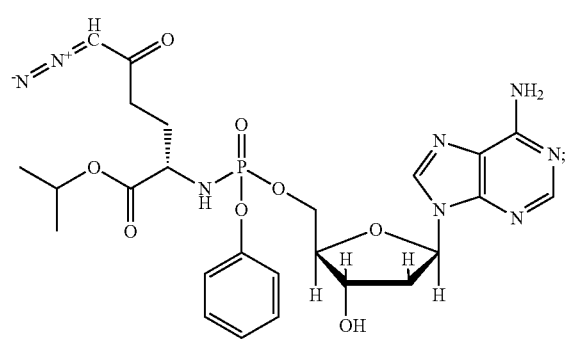

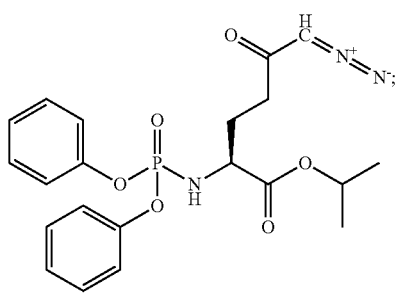

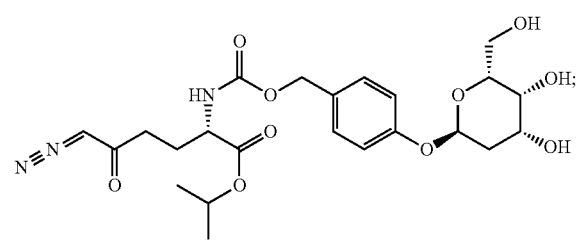

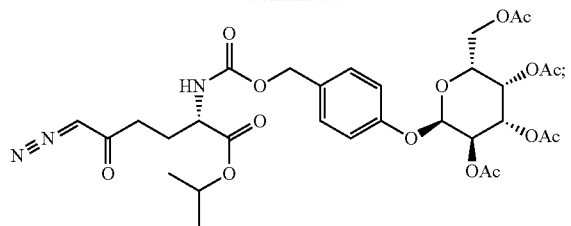
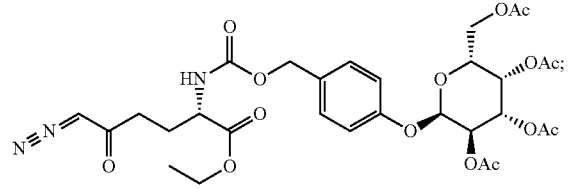
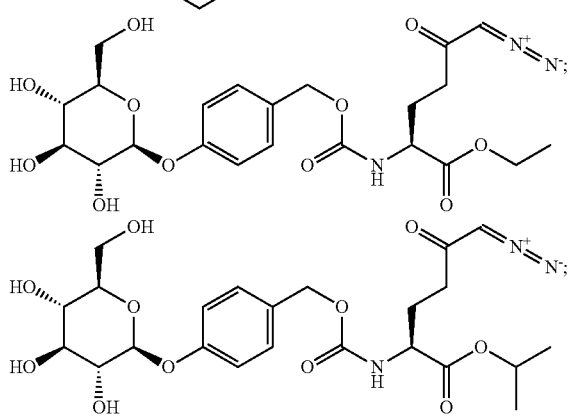
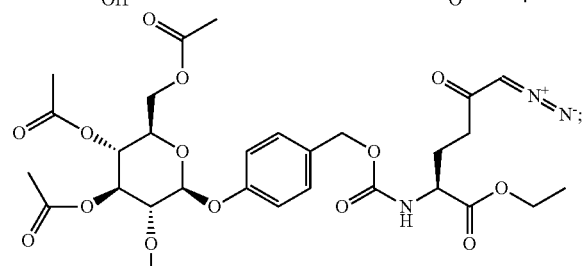
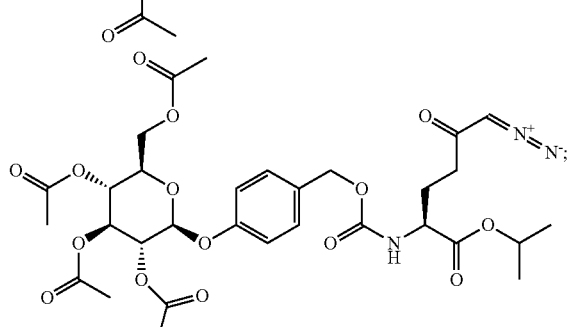
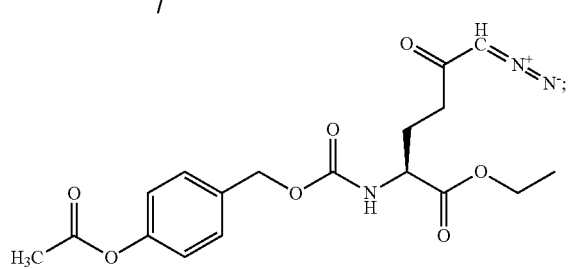
and
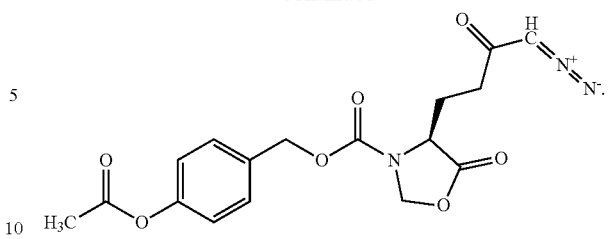
Embodiment XIX. The prodrug of Embodiment XI, wherein $R_2$ is —C(=O)—O—(CR_3R_4)_m—O—C(=O)—$R_{10}$;
wherein:
(i) m is 1:
  $R_3$ is H; and
  $R_4$ is methyl, iPr, or aryl;
(ii) m is 1;
  $R_3$ and $R_4$ are each H; or
(iii) m is 1;
  $R_3$ and $R_4$ are each methyl.
Embodiment XX. The prodrug of Embodiment XIX, wherein the compound of formula (I) is selected from the group consisting of:
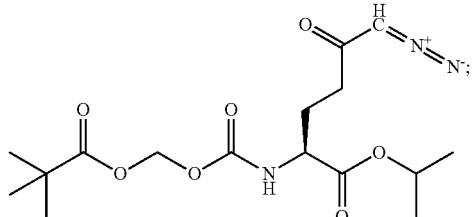
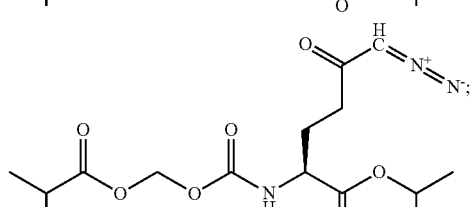
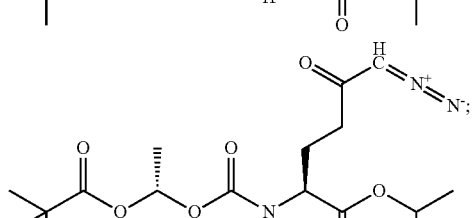
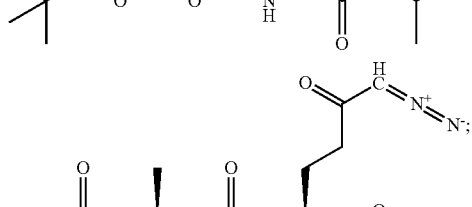

-continued
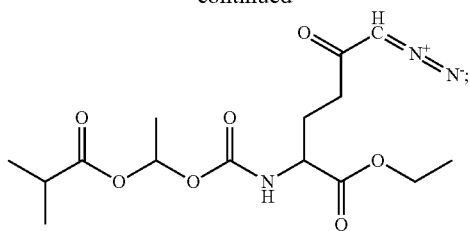
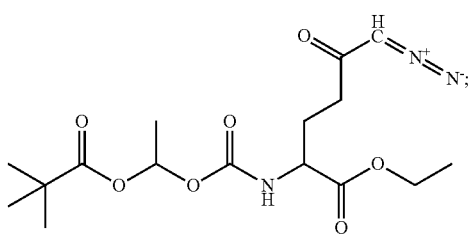
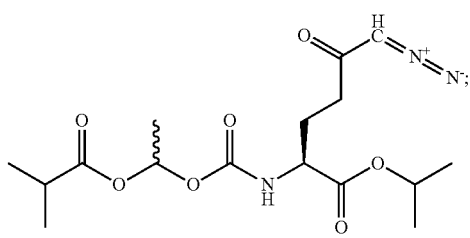
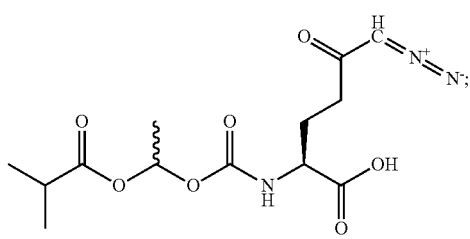
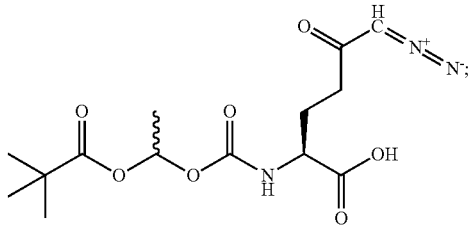
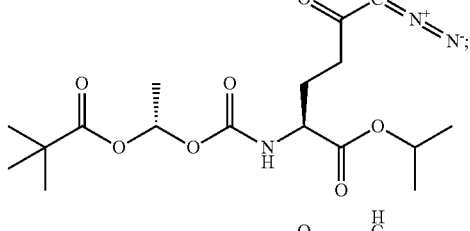
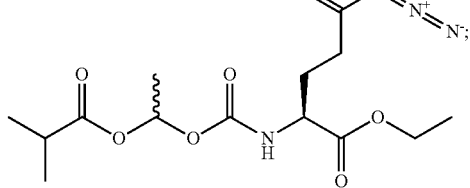
-continued
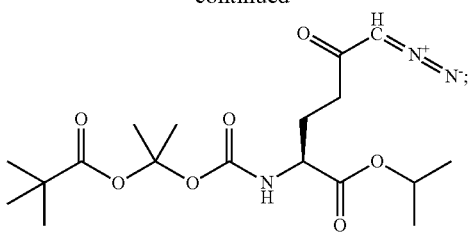
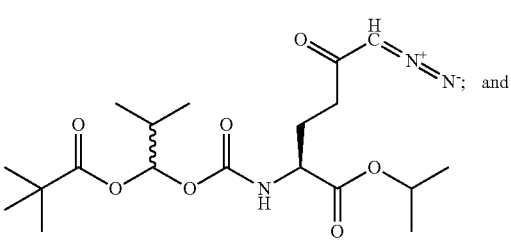
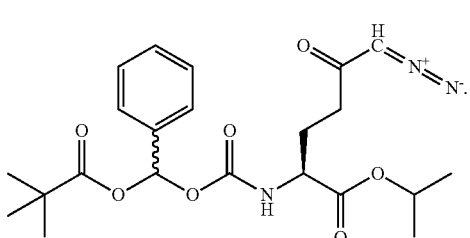
Embodiment XXI. The prodrug of Embodiment XI, wherein the compound of formula I is of formula:
wherein $R_1$ is as defined above in Embodiment I.
Embodiment XXII. The prodrug of Embodiment XXI, wherein the compound of formula (I) is selected from the group consisting of:
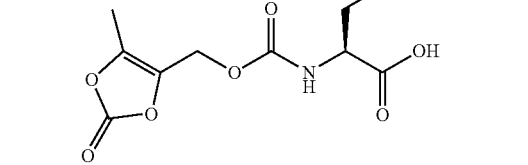

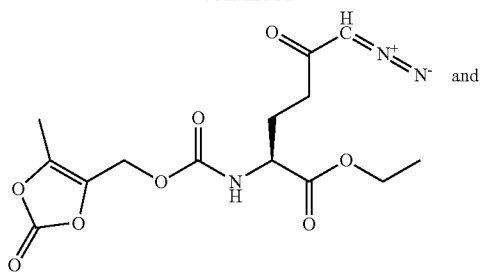

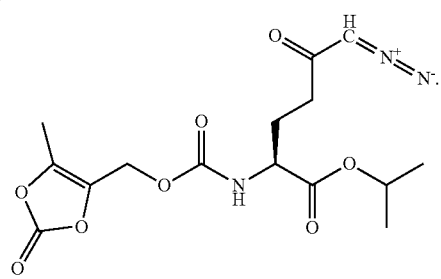

Embodiment XXIII. The prodrug of Embodiment XI, wherein $R_2$ is —C(=O)—Y—(CR$_3$R$_4$)$_m$—NR$_5$R$_6$; wherein Y is a bond;

each m is 1;

each $R_s$ is H;

each $R_6$ is independently H or —C(=O)—(CR$_3$R$_4$)$_m$—NR$_5$R$_6$.

Embodiment XXIV. The prodrug of Embodiment XXIII, wherein the compound of formula (I) is selected from the group consisting of:

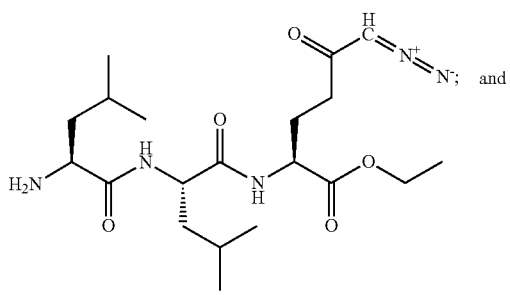

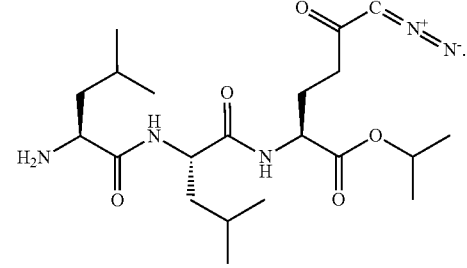

Embodiment XXV. The prodrug of Embodiment XI, wherein $R_2$ is —C(=O)—Ar, or —C(=O)—Y—(CR$_3$R$_4$)$_m$—Ar—O—C(=O)—Ar.

Embodiment XXVI. The prodrug of Embodiment XXV, wherein the compound of formula (I) is selected from the group consisting of:

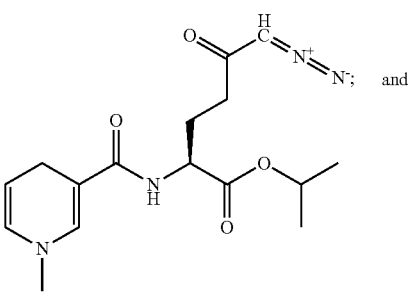

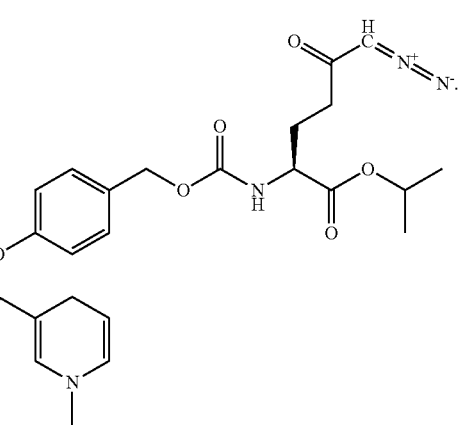

Embodiment XXVII. The prodrug of Embodiment XI, wherein $R_2$ is —C(=O)—Y—(CR$_3$R$_4$)$_m$—Ar—NR$_5$R$_6$; wherein:

Y is O;

each m is independently 0, 1, or 3;

each $R_3$ is independently H, $C_1$-$C_6$ alkyl, or —(CR$_3$R$_4$)$_m$—NR$_5$R$_6$;

each $R_4$ is H;

each $R_5$ is independently H, —C(=O)—(CR$_3$R$_4$)$_m$, —C(=O)—NR$_5$R$_6$, or —C(=O)—(CR$_3$R$_4$)$_m$—NR$_5$R$_6$;

each $R_6$ is H.

Embodiment XXVIII. The prodrug of Embodiment XXVII, wherein the compound of formula (I) is selected from the group consisting of:

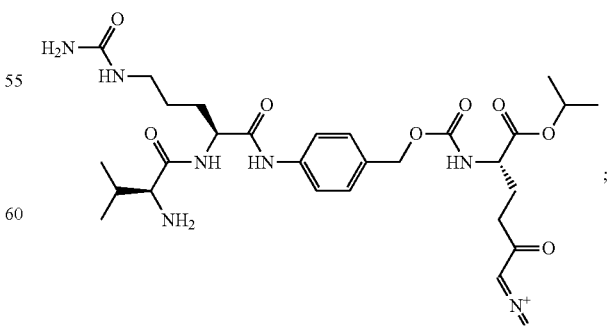

and

-continued

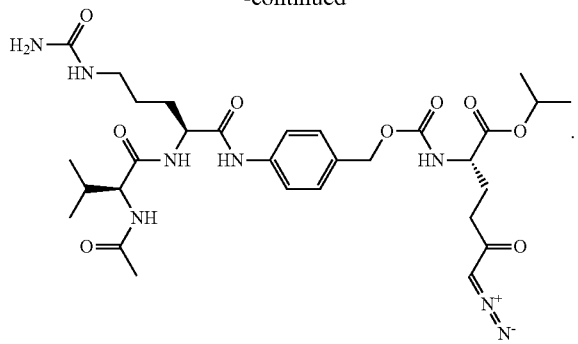

Embodiment XXIX. The prodrug of Embodiment XI, wherein R$_2$ is —C(=O)—Y—(CR$_3$R$_4$)$_m$—NR$_5$R$_6$, wherein:

Y is a bond;
each m is independently 1, 2 or 3;
each R$_3$ is independently H, C$_1$-C$_6$ alkyl, or —(CR$_3$R$_4$)$_m$—NR$_5$R$_6$;
each R$_4$ is H;
each R$_5$ is independently H, —C(=O)—(CR$_3$R$_4$)$_m$, —C(=O)—(NR$_5$R$_6$), or —C(=O)—(CR$_3$R$_4$)$_m$—NR$_5$R$_6$;
each R$_6$ is H.

Embodiment XXX. The prodrug of Embodiment XXIX, wherein the compound of formula (I) is selected from the group consisting of:

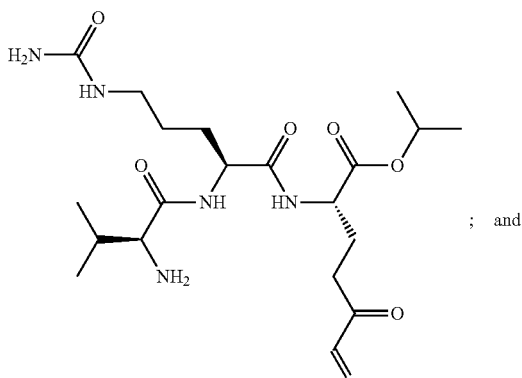

; and

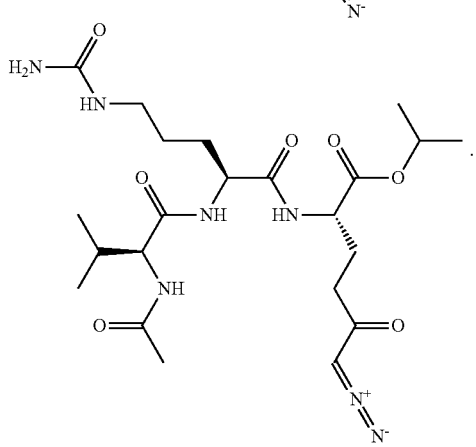

Embodiment XXXI. The prodrug of Embodiment XI, wherein R$_2$ is H and R$_1$ is selected from the group consisting of alkyl and substituted alkyl.

Embodiment XXXII. The prodrug of Embodiment XXXI, wherein the compound of formula (I) is selected from the group consisting of:

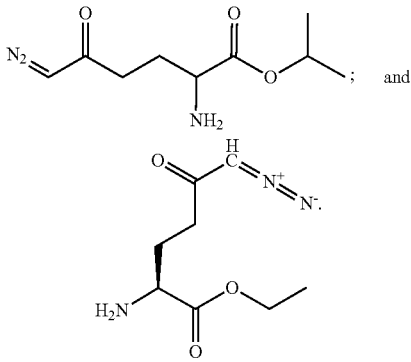

Embodiment XXXIII. A pharmaceutical composition comprising a compound of formula (I), and a pharmaceutically acceptable carrier, diluent, or excipient.

II. Pharmaceutical Compositions and Administration

In another aspect, the present disclosure provides a pharmaceutical composition including one prodrug compound of formula (I), alone or in combination with one or more additional therapeutic agents in admixture with a pharmaceutically acceptable excipient. Accordingly, in some embodiments, the presently disclosed subject matter provides a pharmaceutical composition comprising a compound of formula (I), and a pharmaceutically acceptable carrier, diluent, or excipient. One of skill in the art will recognize that the pharmaceutical compositions include the pharmaceutically acceptable salts of the compounds described above.

Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids, such as arginate and the like, and salts of organic acids like glucuronic or galactunoric acids and the like (see, for example, Berge et al, "Pharmaceutical Salts," Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

In particular embodiments, the salt is a tri(hydrocarbyl) ammonium or tetra(hydrocarbyl)ammonium salt. In yet more particular embodiments, the salt is selected from the group consisting of a tri($C_1$-$C_8$-alkyl)ammonium, tetra($C_1$-$C_8$-alkyl)ammonium, triphenylammonium, tri(hydroxy-$C_1$-$C_8$-alkyl)ammonium, and tetra(hydroxy-$C_1$-$C_8$-alkyl)ammonium salt. In even more particular embodiments, the salt is selected from the group consisting of a trimethylammonium, triethylammonium, tri(hydroxyethyl)ammonium, tripropylammonium, and tri(hydroxypropyl)ammonium salt.

In therapeutic and/or diagnostic applications, the compounds of the disclosure can be formulated for a variety of modes of administration, including oral (sublingual, buccal), peroral, sublingual, systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid (e.g., solutions, suspensions, or emulsions) or solid dosage forms (capsules or tablets) and administered systemically or locally. The agents may be delivered, for example, in a timed-, controlled, or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery. In some embodiments, the pharmaceutical composition is administered orally. In some embodiments, the pharmaceutical composition is administered intravenously. In some embodiments, the pharmaceutical composition is administered intramuscularly. In some embodiments, the pharmaceutical composition is administered intrathecally. In some embodiments, the pharmaceutical composition is administered subcutaneously.

For injection, the agents of the disclosure may be formulated and diluted in aqueous solutions, such as in physiologically compatible buffers, such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1(0) mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers, such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof, such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler, such as lactose, binders, such as starches, and/or lubricants such, as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

III. Methods for Treating a Disease or Disorder

The presently disclosed compounds are, which are orally bioavailable, less toxic prodrugs of glutamine analogs that are glutamine antagonists, allow a clinically acceptable dosing paradigm for diseases or conditions wherein excess and/or aberrant glutamine activity is implicated. As used herein, the term "glutamine antagonist" refers to a glutamine analog that interferes with a glutamine metabolic pathway, e.g., the inhibition or blocking of a metabolic pathway downstream of glutamine in which glutamine acts as a precursor of one or more non-glutamine compounds. Examples of such metabolic pathways are well known (see, e.g., Hensley et al., "Glutamine and cancer: cell biology, physiology, and clinical opportunities" *J Clin Invest.* 2013; 123(9):3678-3684; DeBerardinis et al., "Q's next: the diverse functions of glutamine in metabolism, cell biology and cancer" *Oncogene.* 2009; 29(3):313-324; and Medina et al., "Relevance of glutamine metabolism to tumor cell growth" *Mol Cell Biochem,* 1992; 113(1):1-15). In some contexts, the term glutamine antagonist also includes glutamine analogs that inhibit glutamine uptake by cells, thereby reducing its biological activity. Diseases or conditions wherein excess and/or aberrant glutamine activity is implicated include, but are not limited to, infection, cancer, autoimmune diseases, and neurodegenerative or neurological diseases and other central nervous system disorders.

In general, the presently disclosed methods result in a decrease in the severity of a disease or condition in a subject. The term "decrease" is meant to inhibit, suppress, attenuate, diminish, arrest, or stabilize a symptom of a disease or condition.

As used herein, the terms "treat," "treating," "treatment," and the like refer to reducing or ameliorating a disease or condition, and/or symptoms associated therewith. It will be appreciated that, although not precluded, treating a disease or condition does not require that the disorder, condition or symptoms associated therewith be completely eliminated.

Accordingly, in some embodiments, the presently disclosed subject matter provide a method for treating a disease or a condition, the method comprising administering to a subject in need of treatment thereof, a compound of formula (I), or a pharmaceutical composition of any thereof, in an amount effective for treating the disease or condition.

The presently disclosed subject matter contemplates using a prodrug of formula (I), or a pharmaceutical composition comprising the prodrug of formula (I), optionally together with at least one antimicrobial agent (e.g., antibiotic, antiviral, and the like), to treat an infection.

As used herein, "infection" refers to the invasion of a host organism's bodily tissues by disease-causing organisms, their multiplication, and the reaction of host tissues to these organisms and the toxins they produce. Infectious disease, such as infection by any bacteria or virus, is contemplated for treatment using a compound of formula (I), or a pharmaceutical composition of any thereof.

In some embodiments, the infection comprises a bacterial infection. Antibacterial effects of DON have been demonstrated in *E. coli* (see Coggin et al., "6-Diazo-5-Oxo-L-Norleucine Inhibition of *Escherichia coli*," *Journal of Bacteriology.* 1965; 86). In some embodiments, the compound of formula (I), or pharmaceutical composition of any thereof, inhibits bacterial growth and/or survival.

In some embodiments, the infection comprises a viral infection. The antiviral effects of glutamine analogs, such as DON, have been demonstrated (see, e.g., Cinatl et al., "Antiviral effects of 6-diazo-5-oxo-L-norleucine on replication of herpes simplex virus type 1" *Antiviral Research.* 1997; 33:165-175; Nishio et al., "Antiviral effect of 6-diazo-5-oxo-L-norleucine, antagonist of γ-glutamyl transpeptidase, on replication of human parainfluenza virus type 2," *Journal of General Virology.* 1990; 71:61-67). Examples of viral infections contemplated for treatment using a compound of formula (I), or a pharmaceutical composition of any thereof include, without limitation, herpes simplex virus type 1 (HSV-1), herpes simplex virus type 2 (HSV-2), human cytomegalovirus (HCMV), human parainfluenza virus type 2 (HPIV-2), Maloney leukemia virus (MLV), mumps, paramyxovirus, poliovirus, reovirus type 3, respiratory syncytial virus (RSV), Sendai virus, and vesicular stomatitis virus (VSV).

In some embodiments, the compound of formula (I), or pharmaceutical composition of any thereof, inhibits viral replication. In some embodiments, the compound of formula (I), or pharmaceutical composition of any thereof, inhibits replication of herpes simplex virus type 1 (HSV-1). In some embodiments, the compound of formula (I), or pharmaceutical composition of any thereof, inhibits replication of herpes simplex virus type 2 (HSV-2). In some embodiments, the compound of formula (I), or pharmaceutical composition of any thereof, inhibits replication of human cytomegalovirus (HCMV). In some embodiments, the compound of formula (I), or pharmaceutical composition of any thereof, inhibits replication of human parainfluenza virus type 2 (HPIV-2). In some embodiments, the compound of formula (I), or pharmaceutical composition of any thereof, inhibits replication of Maloney leukemia virus (MLV). In some embodiments, the compound of formula (I), or pharmaceutical composition of any thereof, inhibits replication of mumps. In some embodiments, the compound of formula (I), or pharmaceutical composition of any thereof, inhibits replication of paramyxovirus. In some embodiments, the compound of formula (I), or pharmaceutical composition of any thereof, inhibits replication of poliovirus. In some embodiments, the compound of formula (I), or pharmaceutical composition of any thereof, inhibits replication of reovirus type 3. In some embodiments, the compound of formula (I), or pharmaceutical composition of any thereof, inhibits replication of respiratory syncytial virus (RSV). In some embodiments, the compound of formula (I), or pharmaceutical composition of any thereof, inhibits replication of Sendai virus. In some embodiments, the compound of formula (I), or pharmaceutical composition of any thereof, inhibits replication of vesicular stomatitis virus (VSV).

In some embodiments, the viral infection is influenza. As used herein, "influenza" refers to influenza A, B, or C, parainfluenza viruses, and any other influenza-like virus (see, e.g., U.S. Publication No. 2006/0276438, incorporated by reference herein in its entirety, which discloses using DON, and azaserine for treatment of influenza).

In an aspect, the presently disclosed subject matter involves the use of a compound of formula (I), or a pharmaceutical composition thereof, optionally together with an antiviral agent, for the manufacture of a medicament for treating a viral infection and/or inhibiting replication.

As used herein, "antiviral agent" includes a compound that inhibits the replication of viruses in cells, tissues, or organisms. Examples of antiviral agents contemplated for use in combination with a prodrug of formula (I), or a pharmaceutical composition comprising a prodrug of formula (I) include, but are not limited to, Acyclovir (2-amino-1,9-dihydro-9-[(2-hydroxyethoxy)methyl]-6H-purin-6-one), Valacyclovir (L-valine, 2-[(2-amino-1,6-dihydro-6-oxo-9H-purin-9-yl)methoxy]ethyl ester, Pencyclovir (9-[4-hydroxy-3-(hydroxymethylbutyl)]guanine), Famcyclovir (2-[2-(amino-9H-purin-9-yl)]ethyl-1,3-propanediol diacetate), Ribavirin (1-beta-D-ribofuanosyl-1-H-1,2,4-triazol-3-carboxamide), Lamivudine ((2R,cis)-4-amino-1-(2-hydroxymethyl-1,3-oxathiolan-5-yl)-(1H)-pyrimidine-2-one), Amantadine (1-amantanamine hydrochloride), and Rimantadine (α-methyltricyclo (3.3.1.1/3.7 decane-1-methylamine hydrochloride).

The presently disclosed subject matter contemplates using a prodrug of formula (I), or a pharmaceutical composition comprising the prodrug of formula (I), optionally together with at least one chemotherapeutic agent, at least one radiotherapeutic agent, and/or at least one immunotherapeutic agent to treat cancer. In some embodiments, such treatment includes treatment with any combination of radiotherapy, immunotherapy, photodynamic therapy, proton therapy, and/or surgery.

A "chemotherapeutic agent" is used to connote a compound or composition that is administered in the treatment of cancer. Chemotherapeutic agents contemplated for use in combination with a prodrug of formula (I), or a pharmaceutical composition comprising a prodrug of formula (I) include, but are not limited to, alkylating agents, such as thiotepa and cyclophosphamide; alkyl sulfonates, such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards, such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas, such as carmustine, chlorozotocin, fotemustine, lomustine, nimustine, ranimustine; antibiotics, such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs; such as fludarabine, 6-mercaptopurine, thiamiprine, thioguanine; pyrimidine analogs, such as ancitabine, azacitidine, 6-azauridine, carmofur, cytosine arabinoside, dideoxyuridine, doxifluridine, enocitabine, floxuridine, 5-FU; androgens, such as calusterone, dromostanolone propionate, epitiostanol, mepitiostane, testolactone; anti-adrenals, such as aminoglutethimide, mitotane, trilostane; folic acid replenishers, such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g., paclitaxel and docetaxel; chlorambucil; gemcitabine; 6-thioguanine; mercaptopurine; platinum analogs, such as cisplatin and carboplatin; vinblastine; platinum; etoposide; ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine; retinoic acid; esperamicins; capecitabine; and pharmaceutically acceptable salts, acids or derivatives of any of the above. Chemotherapeutic agents also include anti-hormonal agents that act to regulate or inhibit hormone action on tumors, such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, and goserelin; and pharmaceutically acceptable salts, acids or derivatives of any of the above.

In some embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide, and irinotecan, as well as pharmaceutically acceptable salts, acids, or derivatives of any of these.

In some embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, raltitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain alternative embodiments, the antimitotic agent comprises a vinca alkaloid, such as vincristine, binblastine, vinorelbine, or vindesine, or pharmaceutically acceptable salts, acids, or derivatives thereof.

As used herein, the term "immunotherapeutic agent" refers to a molecule that can aid in the treatment of a disease by inducing, enhancing, or suppressing an immune response in a cell, tissue, organ or subject. Examples of immunotherapeutic agents contemplated for use in combination with a prodrug of formula (I), or a pharmaceutical composition comprising a prodrug of formula (I) include, but are not limited to, immune checkpoint molecules (e.g., antibodies to immune checkpoint proteins), interleukins (e.g., IL-2, IL-7, IL-12, IL-15), cytokines (e.g., interferons, G-CSF, imiquimod), chemokines (e.g., CCL3, CCL26, CXCL7), vaccines (e.g., peptide vaccines, dendritic cell (DC) vaccines, EGFRvIII vaccines, mesothilin vaccine, G-VAX, listeria vaccines), and adoptive T cell therapy including chimeric antigen receptor T cells (CAR T cells).

As used herein, "radiotherapeutic agent" means an agent which may be used in radiotherapy that acts through damaging cells (e.g., malignant cells) as a target through radiation irradiation. An exemplary radiotherapeutic agent contemplated for use in combination with a prodrug of formula (I), or a pharmaceutical composition comprising a prodrug of formula (I) is the titanium peroxide contained in the substrate particle which generates a hydroxyl radial through radiation irradiation, and the hydroxyl radial exerts an action of attacking a target, as described in U.S. Publication No. 2013/0017266, which is incorporated by reference herein in its entirety.

As used herein, a "cancer" in a patient refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells. A "tumor," as used herein, refers to all neoplastic cell growth and proliferation, whether malignant or benign, and all precancerous and cancerous cells and tissues. A "solid tumor," as used herein, is an abnormal mass of tissue that generally does not contain cysts or liquid areas. A solid tumor may be in the brain, colon, breasts, prostate, liver, kidneys, lungs, esophagus, head and neck, ovaries, cervix, stomach, colon, rectum, bladder, uterus, testes, and pancreas, as non-limiting examples. In some embodiments, the solid tumor regresses or its growth is slowed or arrested after the solid tumor is treated with the presently disclosed methods. In other embodiments, the solid tumor is malignant. In some embodiments, the cancer comprises Stage 0 cancer. In some embodiments, the cancer comprises Stage I cancer. In some embodiments, the cancer comprises Stage II cancer. In some embodiments, the cancer comprises Stage III cancer. In some embodiments, the cancer comprises Stage IV cancer. In some embodiments, the cancer is refractory and/or metastatic. For example, the cancer may be refractory to treatment with radiotherapy, chemotherapy or monotreatment with immunotherapy. Cancer as used herein includes newly diagnosed or recurrent cancers, including without limitation, acute lymphoblastic leukemia, acute myelogenous leukemia, advanced soft tissue sarcoma, brain cancer, metastatic or aggressive breast cancer, breast carcinoma, bronchogenic carcinoma, choriocarcinoma, chronic myelocytic leukemia, colon carcinoma, colorectal carcinoma, Ewing's sarcoma, gastrointestinal tract carcinoma, glioma, glioblastoma multiforme, head and neck squamous cell carcinoma, hepatocellular carcinoma, Hodgkin's disease, intracranial ependymoblastoma, large bowel cancer, leukemia, liver cancer, lung carcinoma. Lewis lung carcinoma, lymphoma, malignant fibrous histiocytoma, a mammary tumor, melanoma, mesothelioma, neuroblastoma, osteosarcoma, ovarian cancer, pancreatic cancer, a pontine tumor, premenopausal breast cancer, prostate cancer, rhabdomyosarcoma, reticulum cell sarcoma, sarcoma, small cell lung cancer, a solid tumor, stomach cancer, testicular cancer, and uterine carcinoma.

In some embodiments, the cancer is acute leukemia. In some embodiments, the cancer is acute lymphoblastic leukemia. In some embodiments, the cancer is acute myelogenous leukemia. In some embodiments, the cancer is advanced soft tissue sarcoma. In some embodiments, the cancer is a brain cancer. In some embodiments, the cancer is breast cancer (e.g., metastatic or aggressive breast cancer). In some embodiments, the cancer is breast carcinoma. In some embodiments, the cancer is bronchogenic carcinoma. In some embodiments, the cancer is choriocarcinoma. In some embodiments, the cancer is chronic myelocytic leukemia. In some embodiments, the cancer is a colon carcinoma (e.g., adenocarcinoma). In some embodiments, the cancer is colorectal cancer (e.g., colorectal carcinoma). In some embodiments, the cancer is Ewing's sarcoma. In some embodiments, the cancer is gastrointestinal tract carcinoma. In some embodiments, the cancer is a glioma. In some embodiments, the cancer is glioblastoma multifome. In some embodiments, the cancer is head and neck squamous cell carcinoma. In some embodiments, the cancer is hepatocellular carcinoma. In some embodiments, the cancer is Hodgkin's disease. In some embodiments, the cancer is intracranial ependymoblastoma. In some embodiments, the cancer is large bowel cancer. In some embodiments, the cancer is leukemia. In some embodiments, the cancer is liver cancer. In some embodiments, the cancer is lung cancer (e.g., lung carcinoma). In some embodiments, the cancer is Lewis lung carcinoma. In some embodiments, the cancer is lymphoma. In some embodiments, the cancer is malignant fibrous histiocytoma. In some embodiments, the cancer comprises a mammary tumor. In some embodiments, the cancer is melanoma. In some embodiments, the cancer is mesothelioma. In some embodiments, the cancer is neuroblastoma. In some embodiments, the cancer is osteosarcoma. In some embodiments, the cancer is ovarian cancer. In some embodiments, the cancer is pancreatic cancer. In some embodiments, the cancer comprises a pontine tumor. In some embodiments, the cancer is premenopausal breast cancer. In some embodiments, the cancer is prostate cancer. In some embodiments, the cancer is rhabdomyosarcoma. In some embodiments, the cancer is reticulum cell sarcoma. In some embodiments, the cancer is sarcoma. In some embodiments, the cancer is small cell lung cancer. In some embodiments, the cancer comprises a solid tumor. In some embodiments, the cancer is stomach cancer. In some embodiments, the cancer is testicular cancer. In some embodiments, the cancer is uterine carcinoma.

In some embodiments, the cancer comprises a glutamine-dependent cancer in which glutamine is an important fuel source for cellular energy in the cancer (e.g., hematopoietic tumors, hepatomas, Ehrlich carcinoma (see Huber et al., "Uptake of glutamine antimetabolites 6-diazo-5-oxo-L-norleucine (DON) in sensitive and resistant tumor cell lines," *Int, J Cancer.* 1988; 41:752-755)).

In some embodiments, the cancer is a Myc-dependent cancer. As used herein, "Myc-dependent cancer" refers to a cancer exhibiting activation, overexpression and/or amplification of c-Myc. In some contexts, a "Myc-dependent cancer" is a cancer in which c-Myc plays a role in increased glutamine metabolism in the cancer cells. Examples of Myc-dependent cancers include, without limitation, lymphoma, neuroblastoma, and small cell lung cancer.

In some embodiments, the cancer is an mTORC1-dependent cancer. As used herein, "mTORC1-dependent cancer" refers to a cancer in which mTORC1 is activated in a glutamine-dependent manner, i.e., that is mTORC1 plays a role in increased glutamine metabolism in the cancer cells.

The presently disclosed subject matter contemplates using a prodrug of formula (I), or a pharmaceutical composition comprising the prodrug of formula (I), optionally together with at least one immunosuppressant and/or anti-inflammatory agent, to treat an autoimmune disease, immune disorder, or inflammatory disorder.

As used herein, "immunosuppressant agent" means an agent which may be used in immunotherapy to reduce or prevent an immune response in a cell, organ, tissue, or subject. Examples of immunosuppressant agents contemplated for use in combination with a prodrug of formula (I), or a pharmaceutical composition comprising a prodrug of formula (I) include corticosteriods, calcineurin inhibitors, antiproliferative agents, SIP receptor agonists, kinase inhibitors, monoclonal antilymphocyte antibodies and polyclonal antilymphocyte antibodies. Non-limiting examples of corticosteroids include Prednisone (Deltasone® and Orasone®) and Methylprednisolone (SoluMedrol®). Non-limiting examples of calcineurin inhibitors include Cyclosporine (Cyclosporin A, SangCya, Sandimmune®, Neoral®, Gengraf®), ISA, Tx247, ABT-281, ASM 981 and Tacrolimus (Prograf®, FK506). Non-limiting examples of antiproliferative agents include Mycophenolate Mofetil (CellCept®), Azathioprene (Imuran®), and Sirolimus (Rapamune®). Non-limiting examples of SIP receptor agonists include FTY 720 or analogues thereof. Non-limiting examples of kinase inhibitors include mTOR kinase inhibitors, which are compounds, proteins or antibodies that target, decrease or inhibit the activity and/or function of members of the serine/threonine mTOR family. These include, without limitation, CCI-779, ABT578, SAR543, rapamycin and derivatives or analogs thereof, including 40-O-(2-hydroxyethyl)-rapamycin, rapalogs, including AP23573, AP23464, AP23675 and AP23841 from Ariad, Everolimus (CERTICAN, RAD001), biolimus 7, biolimus 9 and sirolimus (RAPAMUNE). Kinase inhibitors also include protein kinase C inhibitors, which include the compounds described the PCT publications WO 2005/097108 and WO 2005/068455, which are herein incorporated by reference in their entireties. Non-limiting examples of monoclonal antilymphocyte antibodies include Muromonab-CD3 (Orthoclone OKT3®), Interleukin-2 Receptor Antagonist (Basiliximab, Simulect®), and Daclizumab (Zenapax®). Non-limiting examples of polyclonal antilymphocyte antibodies include Antithymocyte globulin-equine (Atgam®)) and Antithymocyte globulin-rabbit (RATG, Thymoglobulin®). Other immunosuppressants include, without limitation, SERP-1, a serine protease inhibitor produced by malignant rabbit fibroma virus (MRV) and myxoma virus (MYX), described in US Patent Publication No. 2004/0029801, which is incorporated herein by reference.

As used herein, "anti-inflammatory agent" refers to an agent that may be used to prevent or reduce an inflammatory response or inflammation in a cell, tissue, organ, or subject. Exemplary anti-inflammatory agents contemplated for use in combination with a prodrug of formula (I), or a pharmaceutical composition comprising a prodrug of formula (I) include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. The anti-inflammatory agent may also be a biological inhibitor of proinflammatory signaling molecules including antibodies to such biological inflammatory signaling molecules.

Autoimmunity is the failure of an organism to recognize its own constituent parts (down to the sub-molecular levels) as "self," which results in an immune response against its own cells and tissues. Any disease that results from such an aberrant immune response is termed an autoimmune disease. An unwanted immune response may be, for example, immune responses associated with an autoimmune disorder, allergies, or inflammatory disorders. The term "immune disorders" are diseases involving the immune system that can include but not be limited to allergies, autoimmune diseases, immune complex diseases, immunodeficiency diseases and cancers of the immune system. In some embodiments, the autoimmune disease, immune disorder, or inflammatory disorder is multiple sclerosis.

The presently disclosed subject matter contemplates using a prodrug of formula (I), or a pharmaceutical composition comprising the prodrug of formula (I), optionally together with at least one neuroprotective agent and/or at least one neurotrophic factor, and/or at least one neuroregenerative agent, to treat a neurodegenerative or neurological disorder or disease.

A "neurodegenerative disorder" is a disease, disorder, or condition that is characterized by the progressive loss of the structure or function of neurons (e.g., degeneration or dysfunction of neurons or other neural cells). Glutaminase-catalyzed hydrolysis of glutamine to glutamate is a predominant source of brain glutamate. Normal central nervous system (CNS) synaptic transmission uses glutamate as the major excitatory amino acid neurotransmitter. Excessive glutamatergic signaling, known as excitotoxicity, is believed to cause CNS damage in various neurodegenerative diseases, such as stroke, amyotrophic lateral sclerosis (ALS), Huntington's disease, Alzheimer's disease, and HIV-associated dementia. Accordingly, without wishing to be bound by theory, it is believed that the presently disclosed prodrugs can be used to treat such neurodegenerative diseases, for example, by inhibiting glutaminase to ameliorate the CNS damage resulting from excitotoxicity due to excessive glutamatergic signaling.

In particular embodiments, the neurodegenerative disorder is multiple sclerosis (MS). DON has been shown to be effective in ameliorating experimental autoimmune enchaphalomyelitis (EAE), an animal model of multiple sclerosis (MS) (see, e.g., Shijie, et al., "Blockade of glutamate release from microglia attenuates experimental autoimmune encephalomyelitis in mice." *Tohoku J. Exp. Med.* 2009; 217:87-92). In particular embodiments, the neurodegenerative disorder is HIV-associated dementia (HAD). In particular embodiments, the neurodegenerative disorder is ischemia (e.g., transient ischemic brain injury). In particular embodiments, the neurodegenerative disorder is stroke. In particular embodiments, the neurodegenerative disorder is amyotrophic lateral sclerosis (ALS). In particular embodiments, the neurodegenerative disorder is Huntington's disease. In particular embodiments, the neurodegenerative disorder is Alzheimer's disease.

In some embodiments, the presently disclosed subject matter provides methods for inhibiting the excess and/or aberrant glutamine activity found in a subject with a disease or condition. As used herein, the term "inhibit" means to decrease or diminish the excess and/or aberrant glutamine activity found in a subject. The term "inhibit" also may mean to decrease, suppress, attenuate, diminish, arrest, or stabilize the development or progression of a disease or condition. Inhibition may occur, for e.g., by at least 10%, 20%, 30%, 40%, 50%, 60%, 70%, 80%, 90%, 95%, 98%, 99%, or even 100% compared to an untreated control subject or a subject without the disease or disorder. As used herein, the term "excess glutamine activity" means an increase in glutamine activity in a subject with a disease or condition as compared to the glutamine activity in a subject without a similar disease or condition, such as an increase of approximately 100%, 100%, 200%, 300%, 400%, 500%, 600%, 700%, 800%, 900%, 1000%, or more. As used herein, the term "aberrant glutamine activity" means a change in the biological activity of glutamine in a subject with a disease or condition as compared to the glutamine activity in a subject without a similar disease or condition, such utilization of glutamine in the growth and/or proliferation of malignant, neoplastic, or other pathologic cellular processes.

In some embodiments, the disease or condition involves excess and/or aberrant glutamine activity. In such aspects, the method further comprises inhibiting the excess and/or aberrant glutamine activity when the compound of formula (I), or the pharmaceutical composition of any thereof, is administered.

In another aspect, the presently discloses subject matter involves the use of a compound of formula (I), or a pharmaceutical composition of any thereof, for treating a disease or condition. In some embodiments, the compound of formula (I), or the pharmaceutical composition of any thereof is used to treat a disease or condition selected from the group consisting of an infection, cancer, an autoimmune disease, an inflammatory disease, and a neurodegenerative or neurological disease. In some embodiments, the compound of formula (I), or the pharmaceutical composition of any thereof is used to treat a disease or condition selected from the group consisting of multiple sclerosis, convulsions, epilepsy, and viral encephalitis. In some embodiments, the compound of formula (I), or the pharmaceutical composition of any thereof is used to treat a disease or condition that involves excess and/or aberrant glutamine activity. In such aspects, the use involves inhibiting the excess and/or aberrant glutamine activity when the compound of formula (I), or the pharmaceutical composition of any thereof, is used to treat the disease or condition.

IV. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

Further, more generally, a "carbyl" refers to a carbon atom or a moiety comprising one or more carbon atoms acting as a bivalent radical.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{25}$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl," by themselves or in combination with other terms, represent, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH—); ethylene (—CH$_2$—CH$_2$—); propylene (—(CH$_2$)$_3$—); cyclohexylene (—C$_6$—H$_{10}$—); —CH═CH—CH═CH—; —CH═CH—CH$_2$—; —CH$_2$CH$_2$CH$_2$CH$_2$—, —CH$_2$CH═CHCH$_2$—, —CH$_2$CsCCH$_2$—, —CH$_2$CH$_2$CH(CH$_2$CH$_2$CH$_3$)CH$_2$—. —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. Aryls include phenyl ($C_6$), naphthyl ($C_{10}$), and biphenyl ($C_{12}$).

The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

In further embodiments, the term "heteroaryl" refers to a $C_5$-$C_{20}$ aromatic ring wherein at least one carbon atom is replaced by a heteroatom selected from O, S, N, optionally substituted by at least one substituent selected from the group consisting of $C_1$-$C_6$ alkyl, hydroxy, $C_1$-$C_4$ alkoxy, mercapto, $C_1$-$C_4$ alkylthio, amino, —NH($C_1$-$C_6$ alkyl), —N($C_1$-$C_6$ alkyl)$_2$, —O($C_6$-$C_{12}$ aryl), —N($C_6$-$C_{12}$ aryl)$_2$, —NH($C_6$-$C_{12}$ aryl), —S($C_6$-$C_{12}$ aryl), halogen, —$CF_3$, —$SO_3H$, —COOH, —COO($C_1$-$C_8$ alkyl), —$SO_2NH_2$, —$SO_2NH$($C_1$-$C_6$ alkyl or $C_6$-$C_{12}$ aryl), —CN, —$NO_3$, —C(O)($C_1$-$C_8$ alkyl), —C(O)($C_6$-$C_{12}$ aryl), —N($C_1$-$C_6$ alkyl or H)C(O)($C_1$-$C_6$ alkyl or H), —C(O)N($C_1$-$C_6$ alkyl or H)$_2$.

Exemplary heteroaryls include, but are not limited to, pyridyl, pyrimidinyl, pyrazinyl, furanyl, thienyl, pyrazolyl, oxazolyl, thiazolyl, isothiazolyl, isoxazolyl, pyrrolyl, imidazolyl, indolyl, indolinolyl, and imidazopyridazinyl.

In further embodiments, the term "aryl" also can refer to $C_6$-$C_{14}$ aryl, optionally substituted by at least one substituent selected from the group consisting of $C_1$-$C_6$ alkyl, hydroxy, $C_1$-$C_4$ alkoxy, mercapto, $C_1$-$C_4$ alkylthio, amino, —NH($C_1$-$C_6$ alkyl), —N($C_1$-$C_6$ alkyl)$_2$, —O($C_6$-$C_{12}$ aryl), —N($C_6$-$C_{12}$ aryl)$_2$, —NH($C_6$-$C_{12}$ aryl), —S($C_6$-$C_{12}$ aryl), halogen, —$CF_3$, —$SO_3H$, —COOH, —COO($C_1$-$C_8$ alkyl), —$SO_2NH_2$, —$SO_2NH$($C_1$-$C_6$ alkyl or $C_6$-$C_{12}$ aryl), —CN, —$NO_3$, —C(O)($C_1$-$C_8$ alkyl), —C(O)($C_6$-$C_{12}$ aryl), —N($C_1$-$C_6$ alkyl or H)C(O)($C_1$-$C_6$ alkyl or H), —C(O)N($C_1$-$C_6$ alkyl or H)$_2$.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g., "3 to 7 membered"), the term "member" refers to a carbon or heteroatom. Further, a structure represented generally by the formula:

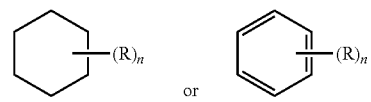

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

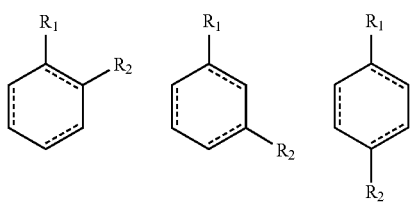

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⁓⁓⁓⁓ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl," "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"', —OC(O)R', —C(O)R', —CO₂R', —C(O)NR'R", —OC'(O)NR'R", —NR"C(O)R', —NR'—C(O)NR"R"', —NR"C(O)OR', —NR—C(NR'R')=NR"', —S(O)R', —S(O)₂R', —S(O)₂NR"R', —NRSO₂R', —CN and —NO₂ in a number ranging from zero to (2m'+1), where m' is the total number of carbon atoms in such groups. R', R", R"' and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R"' and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for alkyl groups above, exemplary substituents for aryl and heteroaryl groups (as well as their divalent derivatives) are varied and are selected from, for example: halogen, —OR', —NR'R", —SR", —NR"C(O)R', —NR'—C(O)NR"R", —NR"C(O)OR', —NR—C(NR'R"R"')=NR"", —NR—C(NR'R")=NR"'—S(O)R', —S(O)₂R', —S(O)₂NR'R", —NRSO₂R', —CN and —NO₂, —R', —N₃, —CH(Ph)₂, fluoro(C₁-C₄)alkoxo, and fluoro(C₁-C₄)alkyl, in a number ranging from zero to the total number of open valences on aromatic ring system; and where R', R", R"' and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R"' and R"" groups when more than one of these groups is present.

Two of the substituents on adjacent atoms of aryl or heteroaryl ring may optionally form a ring of the formula -T-C(O)—(CRR')_q—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH₂)_r—B—, wherein A and B are independently —CRR'—, —O—, —NR—, —S—, —S(O)—, —S(O)₂—, —S(O)₂NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')_s—X'—(C"R"')_d—, where s and d are independently integers of from 0 to 3, and X' is —O—, —NR'—, —S—, —S(O)—, —S(O)₂—, or —S(O)₂NR'—. The substituents R, R', R" and R"' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as a 2-(furan-2-yl)acetyl)- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{12}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., $C_6H_5$—$CH_2$—O—. An aralkyloxyl group can optionally be substituted.

"Alkoxycarbonyl" refers to an alkyl-O—C(=O)—group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)—group. An exemplary aralkoxycarbonyl group is benzyloxycarbonyl.

"Carbamoyl" refers to an amide group of the formula —C(=O)NH₂. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R''', wherein R', R', and R''' are each independently selected from the group consisting of alkyl groups. Additionally, R', R", and/or R''' taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms, such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —S(O$_2$)R.

The term "sulfoxide" refers to a compound having a sulfinyl group —S(O)R.

The term ureido refers to a urea group of the formula —NH—CO—NH$_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds, the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures, succinates, benzoates and salts with amino acids, such as glutamic acid. These salts may be prepared by methods known to those skilled in art. Also included are base addition salts, such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids, such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Methods

General Procedures: The commercially available HPLC grade methanol, catalysts and reagent grade materials were used as received. TLC was performed on Silica gel 60 F254-coated aluminum sheets (Merck) and spots were detected by the solution of $Ce(SO_4)_2 \cdot 4H_2O$ (1%) and $H_3P(Mo_3O_{10})_4$ (2%) in sulfuric acid (10%). Flash chromatography was performed on Silica gel 60 (0.040-0.063 mm, Fluka) or on Biotage® KP-C18-HS or KP-Sil® SNAP cartridges using the Isolera One HPFC system (Biotage, Inc.). All chemicals were purchased from Sigma-Aldrich and were used without further purification. The $^1H$ NMR spectra were measured at 400.1 MHz, 500.1 MHz or 600.1 MHz, $^{13}C$ NMR spectra at 100.8 MHz, 125.7 MHz or 150.9 MHz. For standardization of $^1H$ NMR spectra the internal signal of TMS ($\delta$ 0.0, $CDCl_3$) or residual signals of solvents (δ 7.26 for CDCl$_3$, δ 2.05 for CD$_3$COCD$_3$ and δ 3.31 for CD$_3$OD) were used. In the case of $^{13}$C spectra the residual signals of solvents (δ 77.00 for CDCl$_3$, δ 29.84 and δ 206.26 for CD$_3$COCD$_3$ and δ 49.00 for CD$_3$OD) were used. The chemical shifts are given in δ-scale, the coupling constants J are given in Hz. The ESI mass spectra were recorded using ZQ micromass mass spectrometer (Waters) equipped with an ESCi multimode ion source and controlled by MassLynx software. Alternatively, the low resolution ESI mass spectra were recorded using a quadrupole orthogonal acceleration time-of-flight tandem mass spectrometer (Q-Tof micro, Waters) and high resolution ESI mass spectra using a hybrid FT mass spectrometer combining a linear ion trap MS and the Orbitrap mass analyzer (LTQ Orbitrap XL, Thermo Fisher Scientific). The conditions were optimized for suitable ionization in the ESI Orbitrap source (sheat gas flow rate 35 a.u., aux gas flow rate 10 a.u. of nitrogen, source voltage 4.3 kV, capillary voltage 40 V, capillary temperature 275° C., tube lens voltage 155 V). The samples were dissolved in methanol and applied by direct injection. Optical rotations were measured in CHCl$_3$ or DMF using an Autopol IV instrument (Rudolph Research Analytical). The IR spectra were measured in CHCl$_3$ or KBr.

Mice Efficacy Studies. All mouse efficacy studies were conducted according to protocol #MO13M69 approved by the Animal Care and Use Committee at Johns Hopkins University. Female athymic (RH-Foxn1nu mice) mice between 25 and 30 g were obtained (Harlan Sprague Dawley Inc. Indianapolis. Indiana), and maintained on a 12 hour light-dark cycle with ad libitum access to food and water. U87 human glioma cells were injected s.c. ($5 \times 10^6$ cells in 100 ml of PBS) in four separate locations on the flanks of each mouse. When tumors grew to a mean volume of around 200 mm$^3$, mice were randomized into either vehicle (HEPES-buffered saline, i.p.) or DON (1; 0.8 mg/kg, i.p.). In one cohort, mice were administered a single dose of the appropriate solution two hours after which glutamine levels were quantified in the tumor as described previously (Le et al., 2012). In brief, tumors were harvested, snap frozen, and homogenized in liquid N, then subjected to metabolite extraction using methanol and DI water. Quantification was performed using Agilent 6520 Quadrupole-Time-of-Flight (Q-TOF) mass spectrometer with Agilent 1290 HPLC and using Agilent Mass Hunter and Agilent Qualitative and Quantitative Analysis Software packages. Glutamine content was averaged by group for each individual tumor (n=3-4/group), depicted as relative intensity, and analyzed by one-tailed t test. In a second cohort, efficacy experiments were conducted. Mice were injected once daily for six days; tumor volumes were measured using digital calipers and calculated according to the formula: [volume=(largest tumor dimension)×(smallest tumor dimension)$^2$×0.52] at 2, 4, and 6 days after the onset of treatment. Each individual tumor (n=8-10/group) was normalized to its pretreatment volume, averaged and analyzed by repeated measures two-way analysis of variance (ANOVA). If significant, a Bonferroni post hoc test was subsequently applied. Significance was defined as $p<0.05$.

In Vitro Stability Studies: The stock solution for most prodrugs was prepared as a 10 mM solution in DMSO to carry out the in vitro studies.

The chemical stability of prodrugs was evaluated using simulated gastric fluid (SGF; pH 1.2) and phosphate buffered saline (PBS; pH 7.4). Briefly, prodrugs were spiked (10 µM) in respective solutions and incubated at 37° C. for 1 h. At predetermined time points (0, 30 and 60 min), aliquots of 100 µL were removed and diluted with 100 µL of water. Prodrug disappearance was monitored using the developed liquid chromatography and tandem mass spectrometry (LC/MS/MS) method described below.

For metabolic stability, plasma (dog, human, monkey, mouse and pig and human) was used. For stability, prodrugs (10 µM) were spiked in each matrix and incubated in an orbital shaker at 37° C. At predetermined times (0, 30 and 60 min), 100 µL aliquots of the mixture in triplicate were removed and the reaction quenched by addition of three times the volume of ice cold acetonitrile spiked with the internal standard (losartan 0.5 µM). The samples were vortexed for 30 s and centrifuged 12000 g for 10 min. 50 µL supernatant diluted with 50 µL water was transferred to a 250 µL polypropylene vial sealed with a Teflon cap. Prodrug disappearance was monitored over time using a liquid chromatography and tandem mass spectrometry (LC/MS/MS) method as described below.

For LC/MS/MS, prodrugs were separated with Thermo Scientific Accela UPLC system coupled to Accela open autosampler on an Agilent C18 (100×2.1 mm id) UPLC column. The autosampler was temperature controlled and operating at 10° C. The mobile phase used for the chromatographic separation was composed of acetonitrile/water containing 0.1% formic acid and was run at a flow rate of 0.5 mL/minute for 4.5 minutes using gradient elution. The column effluent was monitored using TSQ Vantage triple-quadrupole mass-spectrometric detector, equipped with an electrospray probe set in the positive ionization mode. Samples were introduced into the ionization source through a heated nebulized probe (350° C.).

For quantification of compound remaining, disappearance of prodrugs was measured from ratio of peak areas of analyte to IS. Percentage remaining was calculated in the following manner.

$$\frac{\text{Avg. Response} * @ 60 \text{ min}}{\text{Avg. Response} @ 0 \text{ min}} \times 100$$

where response=[(Area of analyte)/(Area of internal standard)]

*Average response is average of two samples at each time point.

Pharmacokinetic Studies in Mice. All pharmacokinetic studies in mice were conducted according to protocol (#MO13M113) approved by the Animal Care and Use Committee at Johns Hopkins University. C57BL/6 mice between 25 and 30 g were obtained from Harlan, and maintained on a 12 hour light-dark cycle with ad libitum access to food and water. To evaluate the brain and plasma pharmacokinetics of DON and its prodrug 5c, 8-12 week old C57BL/6 were administered DON (1; 0.8 mg/kg, p.o. in phosphate-buffered saline) and its prodrug 5c (at 0.8 mg/kg equivalent DON (1), p.o. in phosphate-buffered saline with 5% EtOH and 5% Tween-80). The mice were sacrificed by pentobarbital injection at 10, 30 and 90 minutes post drug administration, and blood was collected via cardiac puncture and placed into iced EDTA coated BD microtainers. Blood samples were spun at 2,000 g for 15 minutes, and plasma was removed and stored at −80° C. Brain tissues were harvested following blood collection and immediately snap frozen in liquid nitrogen and stored at −80° C. until LC/MS analysis.

Pharmacokinetic Studies in Non-human primates. All monkey studies were conducted according to protocol (#PR15M298) approved by the Animal Care and Use Committee at Johns Hopkins University. Two female pigtail monkeys (approximately 3.5 kg, non-drug naive) were adjacently housed in stainless steel cages on a social interaction rack (contains 4 cages, each 32.5" wide×28" deep×32" high) maintaining temperature of 64-84° F., humidity of 30-70% with alternating 14-10 hour light/dark cycle as per the USDA Animal Welfare Act (9 CFR. Parts 1, 2, and 3). Food was provided daily in amounts appropriate for the size and age of the animals and RO purified water provided ad libitum through an in-cage lixit valve. Food enrichment was provided Monday through Friday. Prior to drug administration, macaques were sedated with ketamine given as an intramuscular injection prior to test article administration. Sedation was maintained through blood and cerebrospinal fluid (CSF) sample collections with ketamine at a starting rate of 15 mg/kg with additional doses of 20-30 mg during the first hour. At subsequent time points ketamine was given at 10-15 mg/kg. DON (50 mM HEPES buffered saline) and 5c (Diastereoisomer 1), (50 mM HEPES buffered saline containing 5% ethanol and 5% tween) were administered (1.6 mg/kg equivalent) to the animals at a dosing volume of 1 mL/kg intravenously. CSF sample (target of 50 μL) was obtained by percutaneous puncture of the cisterna magna at 30 min post dose. Blood samples (1 mL) were collected at 15, 30, 1, 2 4 and 6 h post dose by percutaneous puncture of a peripheral vein. Samples were processed for plasma (centrifuged at a temperature of 4° C., at 3,000×g, for 10 minutes). All samples were maintained chilled on ice throughout processing. Samples were collected in microcentrifuge tubes, flash frozen, and placed in a freezer set to maintain −80° C. until LC/MS analysis.

Bioanalysis of DON. A highly sensitive method for analysis of DON in biological matrices (Alt, et al., 2015) has been previously published. However due to chemical lability of DON and its prodrugs, a milder derivatization method employing dabsyl chloride was developed and validated. Briefly, DON was extracted from samples (50 mg) with 250 μL methanol containing Glutamate-d5 (10 μM ISTD) by vortexing in low retention tubes. Samples were centrifuged at 16,000×g for 5 minutes to precipitate proteins. Supernatants (200 μL) were moved to new tube and dried at 45° C. under vacuum for 1 hour. To each tube, 50 μL of 0.2 M sodium bicarbonate buffer (pH 9.0) and 100 μL of 10 mM dabsyl chloride in acetone was added. After vortexing, samples were incubated at 60° C. for 15 minutes to derivatize. Samples (2 μL) were injected and separated on an Agilent 1290 equipped with a an Agilent Eclipse plus C18 RRHD 2.1 X100 mm column over a 2.5 minute gradient from 20-95% acetonitrile+0.1% formic acid and quantified on an Agilent 6520 QTOF mass spectrometer. Calibration curves over the range of 0.005-17.1 μg/mL in plasma and CSF for DON were constructed from the peak area ratio of the analyte to the internal standard using linear regression with a weighting factor of 1/(nominal concentration). Correlation coefficient of greater than 0.99 was obtained in all analytical runs. The mean predicted relative standard deviation for back calculated concentrations of the standards and QC's for all analytes were within the range of 85 to 115%, except for the lowest concentration which was within the range of 80 to 120% with an overall accuracy and precision of 6.7% and 6.6%, respectively.

Pharmacokinetic Analysis. Mean concentration-time data were used for pharmacokinetic analysis. Non-compartmental-analysis module in WinNonlin® (version 5.3) was used to assess pharmacokinetic parameters. Peak plasma concentrations ($C_{max}$) and time to $C_{max}$ ($T_{max}$) were the observed values. Area under the curve (AUC) was calculated by log-linear trapezoidal rule to the end of sample collection ($AUC_{last}$).

Procedure for Pharmacokinetic analysis for DON release from its prodrugs: DON is extracted from samples (50 μL) with 250 μL methanol containing Glutamate-d5 (10 μM ISTD) by vortexing in low retention tubes. Samples are centrifuged at 16,000×g for 5 minutes to precipitate proteins. Supernatants (200 μL) are moved to new tube and dried at 45° C. under vacuum (approximately 1 hour). To each tube, 50 μL of 0.2 M sodium bicarbonate buffer (pH 9.0) and 100 μL dabsyl chloride stock is added. After vortexing, samples are incubated at 60° C. for 15 minutes to derivatize. Samples (2-10 μL) are injected and separated on an Agilent 1290 equipped with a SB-AQ column over a 4 minute gradient from 20-95% acetonitrile+0.1% formic acid and quantified on an Agilent 6520 QTOF mass spectrometer.

Example 2

Prodrug Strategy—Masking Carboxylate Functionality

In one embodiment. DON prodrugs were designed by masking only the carboxylate functionalities using alkyl esters of DON with unprotected α-amino groups. Some of the alkyl esters of DON with an unprotected α-amino functionality, however, were found to undergo cyclization forming a 5-membered cyclic Schiff's base. The cyclization observed was pH dependent and rapid at pH 5-7. At a lower pH, which would normally prevent or reverse the cyclization, the diazo functionality became unstable. As a result, the cyclization was virtually irreversible rendering some of the N-α-free alkyl esters undesirable as DON prodrugs (FIG. 1A).

Example 3

Prodrug Strategy—Masking Amino Functionality

In another embodiment, DON prodrugs were designed by masking only the amino functionalities using N-protected derivatives of Don with an unprotected carboxy functionality. The N-protected derivatives of DON with an unprotected carboxy functionality (FIG. 1B and FIG. 1C) also were not as stable. More particularly, the acidic carboxy functionality caused gradual slow decomposition of the diazo-group. In certain salt forms, the carboxylate anion destabilizes the N-α-protecting group. Even further, as is shown in FIG. 1D, FIG. 1E, FIG. 1F, FIG. 1G and FIG. 1H, many prodrugs tested with a free carboxylate (with the exception of 26) showed negligible exposure compared to DON when given orally, further suggesting the benefits of derivatizing both carboxylate and amine functionalities for oral availability.

Example 4

Synthesis

Schemes for synthesis of representative prodrug compounds are shown below (Scheme 1, Scheme 2, Scheme 3, Scheme 4, Scheme 5, Scheme 6, Scheme 7, and Scheme 8).

Scheme 1.

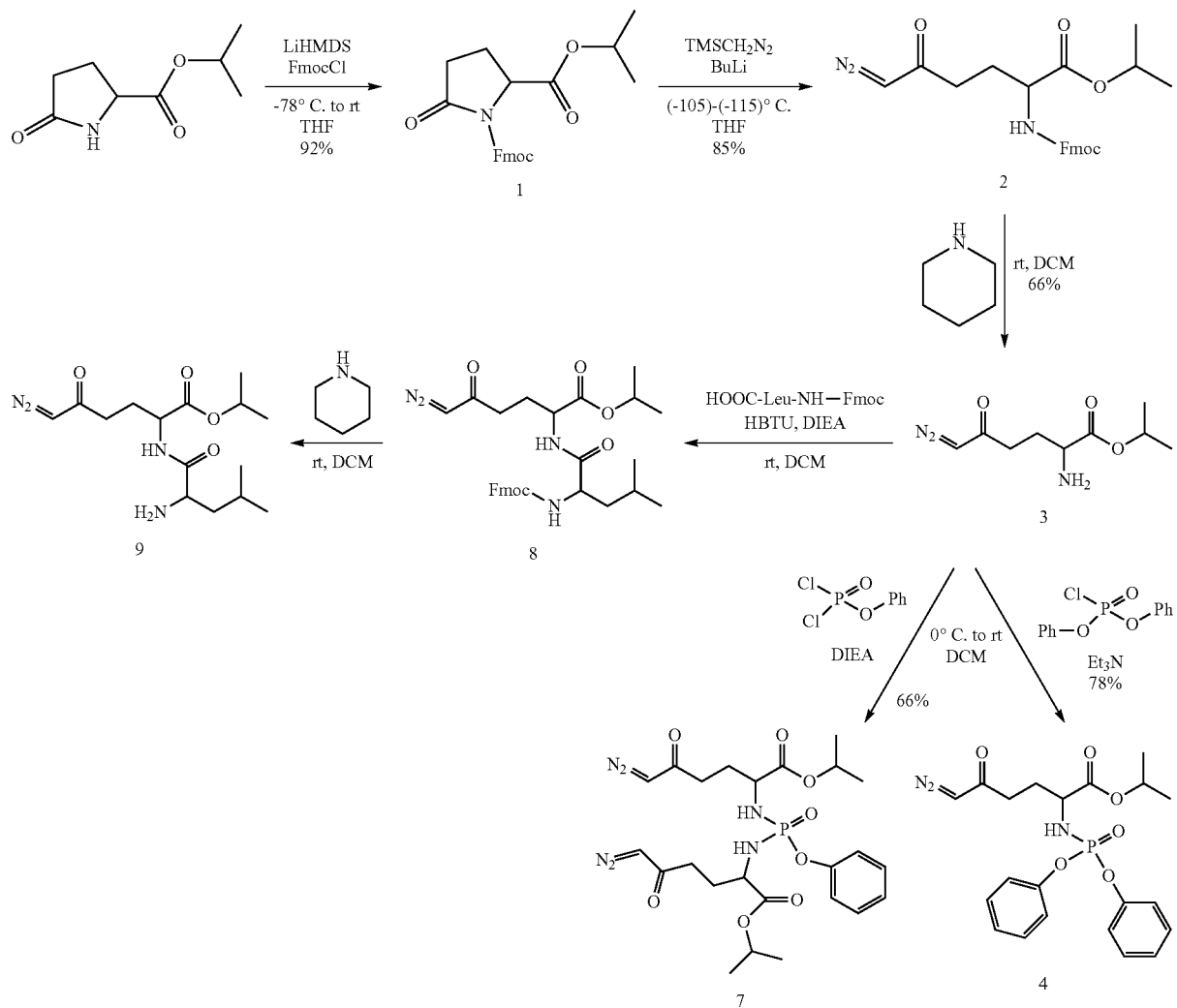

Synthesis of Isopropyl 6-diaza-2-((diphenoxyphosphoryl)amino)-5-oxohexanoate (4)

1-methylethyl 5-oxoprolinate JAM0256

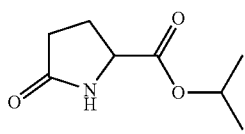

JAM0256 was prepared from known literature. $^1$H NMR and $^{13}$C NMR spectra were in agreement with the published data.

1-(9H-fluoren-9-ylmethyl) 2-(1-methylethyl) 5-oxopyrrolidine-1,2-dicarboxylate (1)

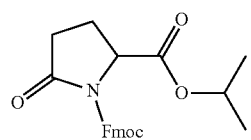

Referring to scheme 1, the previous compound JAM0256 (US2008/107623 A1) (2.94 g, 17.16 mmol) was dissolved in absolute THF (90 mL) under argon and cooled to −78° C. A solution of LiHMDS (1M in hexanes, 16.3 mL, 16.302 mmol, 0.95 equiv.) was added dropwise and the solution was stirred at the same temperature for 15 min. The resultant yellow mixture was transferred via cannula to a solution of Fmoc chloride (22.2 g, 85.8 mmol, 5 equiv.) in absolute THF (90 mL) at −78° C. The reaction mixture was stirred at −78° C. for 2 h. After this period, the reaction was quenched with saturated NH$_4$Cl (100 mL). Then it was extracted with ethyl acetate (3×50 mL), the combined organic layers were washed with water (40 mL), brine (40 mL) and dried over anhydrous MgSO$_4$. The organic solvent was evaporated in vacuo. The residue was chromatographed on silica gel (hexane-ethyl acetate 2:1) to afford the desired product 1 (6.2 g, 92%) as a colorless solid. $^1$H NMR (400 MHz, CDCl$_3$): 1.23 (3H, d, J=6.2), 1.26 (3H, d, J=6.3), 2.06-2.13 (1H, m), 2.34-2.45 (1H, m), 2.53-2.61 (1H, m), 2.67-7.76 (1H, m), 4.31 (1H, t, J=7.5), 4.40-4.44 (1H, m), 4.53-4.57 (1H, m), 4.65 (1H, dd, J=9.4, 2.6), 5.07 (1H, hept, J=6.3), 7.31-7.35 (2H, m), 7.39-7.43 (2H, m), 7.71-7.78 (4H, m). $^{13}$C NMR (101 MHz, CDCl$_3$): 21.69, 21.78, 22.01, 31.31, 46.64, 58.99, 69.20, 69.78, 120.06, 120.08, 125.43, 125.57, 127.32 (2C), 127.98 (2C), 141.31, 141.33, 143.39, 143.43, 151.56, 170.58, 172.92. Optical rotation: $[\alpha]^{22}_D$ −24.1° (c 0.332, CHCl$_3$). IR (CHCl$_3$): 3068 w, 3029 m, 2985 m, 2939 w, 2883 vw, 1797 s, 1758 s, sh, 1739 vs, 1724 vs, sh, 1609 vw, 1580 vw, 1479 w, 1463 m, 1452 s, 1421 w, 1386 s, 1377 m, 1305 vs, 1194 m, 1105 s, 1045 m, 1033 m, 621 w, 425 w cm$^{-1}$. ESI MS: 416 ([M+Na]$^+$). HR ESI MS: calcd for C$_{23}$H$_{23}$O$_5$NNa 416.14684; found 416.14694.

Isopropyl 2-((((9H-fluoren-9-yl)methoxy)carbonyl)amino)-6-diazo-5-oxohexanoate (2)

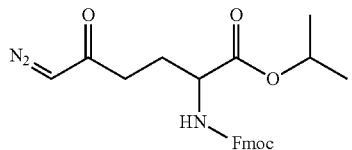

Referring to scheme 1, trimethylsilyl diazomethane solution (2M in diethyl ether, 6 mL, 11.93 mmol, 1.2 equiv.) was dissolved in absolute THF (55 mL) under argon and cooled to −98° C. A solution of n-butyllithium (2.5 M in hexanes, 4.9 mL, 12.23 mmol, 1.23 equiv.) was added dropwise and the solution was stirred at −98° C. for 30 min. The resultant mixture was transferred via cannula to a solution of previous compound 1 (3.91 g, 9.94 mmol, 1 equiv.) in absolute THF (100 mL) at −116° C. The reaction mixture was slowly warmed to −78° C., and then quenched with saturated NH4Cl. Then it was extracted with ethyl acetate (3×50 mL), the combined organic layers were washed with water (40 mL), brine (40 mL) and dried over anhydrous MgSO$_4$. The organic solvent was evaporated in vacuo. The residue was chromatographed on silica gel (chloroform-acetone 20:1) to afford the desired product 2 (3.68 g, 85%) as a yellowish solid. $^1$H NMR (400 MHz, CDCl$_3$) 1.25-1.28 (6H, m), 1.95-2.04 (1H, m), 2.17-2.26 (1H, m), 2.31-2.52 (2H, m), 4.22 (1H, t, J=7.1), 4.29-4.43 (3H, m), 5.06 (1H, hept, J=6.1), 5.27 (1H, s), 5.59 (1H, d, J=8.2), 7.30-7.34 (2H, m), 7.38-7.42 (2H, m), 7.59-7.62 (2H, m), 7.75-7.77 (2H, m). $^{13}$C NMR (101 MHz, CDCl$_3$): 21.81, 21.84, 27.69, 36.56, 47.21, 53.67, 67.10, 69.62, 120.08, 120.09, 125.18, 125.21, 127.16 (2C), 127.81 (2C), 141.35, 141.37, 143.75, 143.96, 156.16, 171.50, 193.67. Optical rotation: $[\alpha]^{22}_D$ +15.1° (c 0.674, CHCl$_3$). IR (CHCl$_3$): 3428 m, 3116 w, 3068 w, 2985 m, 2940 w, 2882 w, 2110 vs, 1731 vs, sh, 1719 vs, 1641 s, 1608 w, sh, 1580 vw, 1509 s, 1478 m, 1466 m, 1451 s, 1418 w, sh, 1386 s, sh, 1377 s, 1349 s, 1232 s, 1105 s, 1052 s, 1033 m, 622 w, 539 m, 488 m, 426 w cm$^{-1}$. ESI MS: 458 ([M+Na]$^+$). HR ESI MS: calcd for C$_{24}$H$_{25}$O$_5$NaN 458.16864; found 458.16873.

Isopropyl 2-amino-6-diazo-5-oxohexanoate (3)

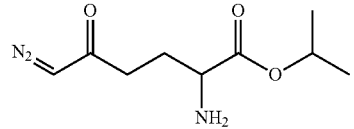

Referring to scheme 1, the previous compound 2 (900 mg, 2.07 mmol), was dissolved in dichloromethane (10 mL). Piperidine (514 μL 5.17 mmol, 2.5 equiv.) was added and the reaction mixture was stirred at room temperature for 4 h. The organic solvent was evaporated in vacuo. The residue was chromatographed on silica gel (chloroform-methanol 30:1) to afford the desired product (290 mg, 66%) as a yellow oil. $^1$H NMR (400 MHz, CDCl$_3$): 1.21 (3H, d, J=1.8), 1.23 (3H, d, J=1.8), 1.52 (2H, bs), 1.74-1.85 (1H, m), 2.02-2.10 (1H, m), 2.36-2.53 (2H, bm), 3.37 (1H, dd, J=8.4, 5.0), 5.00 (1H, hept, J=6.3), 5.27 (1H, s). $^{13}$C NMR (101 MHz, CDCl$_3$): 21.87, 21.89, 29.65, 36.99, 53.94, 68.64, 175.21, 194.25. Optical rotation: $[\alpha]^{22}_D$ +6.5° (c 0.444, CHCl$_3$). IR (CHCl$_3$): 3390 w, 3323 vw, 3116 w, 2984 s, 2939 m, 2877 w, 2109 vs, 1725 vs, 1640 s, 1467 m, 1454 m, 1439 w, sh, 1388 s, sh, 1376 vs, 1349 s, 1199 s, 1106 vs cm$^{-1}$. ESI MS: 236 ([M+Na]$^+$); HR ESI MS: calcd for C$_9$H$_{15}$O$_3$N$_3$Na 236.1006; found 236.1007.

Isopropyl 6-diazo-2-((diphenoxyphosphoryl)amino)-5-oxohexanoate (4)

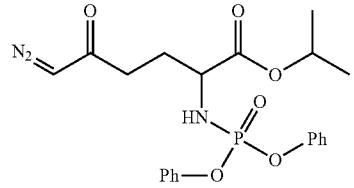

Referring to scheme 1, isopropyl DON 3 (80 mg, 0.38 mmol) was dissolved in absolute dichloromethane (4 mL) and triethylamine (210 μL, 1.5 mmol, 4 equiv.) was added. This solution was cooled to 0° C., and diphenyl chlorophosphate (156 μL, 0.75 mmol, 2 equiv.) was added dropwise. The reaction mixture was stirred at 0° C. for 30 min and then the cooling bath was removed. The reaction mixture was then stirred at room temperature for 2 h. The organic solvent was evaporated in vacuo. The residue was chromatographed on silica gel (chloroform-acetone 30:1) to afford the desired product (131 mg, 78%) as a yellow solid. $^1$H NMR (400 MHz, CDCl$_3$): 1.19 (3H, d, J=1.0), 1.21 (3H, d, J=1.0), 1.84-1.93 (1H, m), 2.07-2.16 (1H, m), 2.19-2.41 (2H, m), 3.79-3.84 (1H, m), 4.97 (1H, hept, J=6.2), 5.07 (1H, s). $^{13}$C NMR (101 MHz, CDCl$_3$): 21.75, 21.81, 29.34, 35.88, 54.29, 69.80, 80.90, 120.32 (2C, d, $J_{C,P}$=5.0), 120.39 (2C, d, $J_{C,P}$=4.9), 125.23 (2C, d, $J_{C,P}$=1.0), 125.28 (2C, d, $J_{C,P}$=1.0), 130.00 (2C), 150.68 (d, $J_{C,P}$=5.8), 150.75 (d, $J_{C,P}$=6.2), 171.93 (d, $J_{C,P}$=5.9), 193.51. $^{31}$P NMR (101 MHz, CDCl$_3$): 0.32 Optical rotation: $[\alpha]^{22}_D$ +15.1° (c 0.337, CHCl$_3$). IR (CHCl$_3$): 3383 w, 3115 w, 3101 vw, 3063 vw, 2985 m, 2938 w, 2878 vw, 2110 vs, 1731 s, 1642 s, 1600 m, sh, 1591 m, 1490 s, 1467 w, 1456 m, 1448 vw, sh, 1426 m, 1385 s, sh, 1377 s, 1350 m, 1191 vs, 1163 s, 1071 w, 1026 m, 941 vs, 904 m, 821 w, 690 m, 617 w, 487 m cm⁻¹. ESI MS: 468 ([M+Na]⁺). HR ESI MS: calcd for $C_{21}H_{24}O_6N_3NaP$ 468.12949; found 468.12952.

Synthesis of ethyl 2-((((4-acetoxybenzyl)oxy)carbonyl)amino)-6-diazo-5-oxohexanoate (6)

1-[4-(acetyloxy)benzyl] 2-ethyl 5-oxopyrrolidine-1,2-dicarboxylate (5)

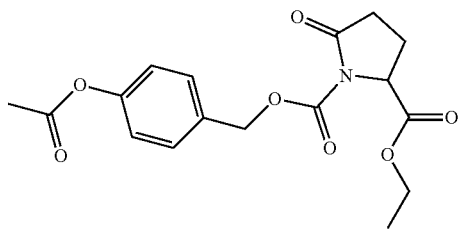 [SMILES: CCOC(=O)C1CCC(=O)N1C(=O)OCc1ccc(OC(C)=O)cc1]

To a solution of phosgene (15% wt in toluene, 10 mL, 14 mmol, 2.5 equiv.) cooled to 0° C. was added a solution of 4-Acetoxybenzyl alcohol (934 mg, 5.6 mmol) in toluene (6.7 mL). The reaction mixture was stirred at the same temperature overnight. The volatiles were removed in vacuo and the product 4-(Acetoxy)benzyl Chloroformate was dissolved in THF (5 mL) and used without any purification. Ethyl pyroglutamate (800 mg, 5.1 mmol) was dissolved in absolute THF (13 mL) under argon and cooled to −78° C. A solution of LiHMDS (1M in hexanes, 6.12 mL, 6.12 mmol, 1.2 equiv.) was added dropwise and the solution was stirred at the same temperature for 15 min. The resultant yellow mixture was transferred via cannula to a solution of 4-(Acetoxy)benzyl chloroformate (5.6 mmol, 1 equiv) at −78° C. The reaction mixture was stirred at −78° C. for 2 h. After this period, the reaction was quenched with saturated NH₄Cl (100 mL). Then it was extracted with ethyl acetate (3×50 mL), the combined organic layers were washed with water (40 mL), brine (40 mL) and dried over anhydrous MgSO₄. The organic solvent was evaporated in vacuo. The residue was chromatographed on silica gel (hexane-ethyl acetate 1:1) to afford the desired product 5 (1.16 g, 65%) as a colorless solid. ¹H NMR (400 MHz, CDCl₃): 1.16 (3H, t, J=7.2), 1.99-2.06 (1H, m), 2.25 (3H, s), 2.28-2.36 (1H, m), 2.42-2.50 (1H, m), 2.55-2.64 (1H, m), 4.11 (1H, qd, J=7.1, 2.6), 4.62 (1H, dd, J=9.4, 2.7), 5.16 (1H, d, J=12.4), 4.25 (1H, d, J=12.4), 7.02-7.05 (2H, m), 7.35-7.39 (2H, m). ¹³C NMR (101 MHz, CDCl₃): 14.02, 21.08, 21.79, 30.99, 58.74, 61.82, 67.58, 121.75, 129.46, 132.62, 150.70, 150.83, 169.28, 170.97, 172.93. Optical rotation: $[\alpha]^{22}_D$ −30.7° (c 0.298, CHCl3). IR (CHCl3): 2968 w, 2942 vw, 2876 vw, 1797 s, 1753 vs, 1717 s, sh, 1609 w, 1597 vw, 1510 m, 1476 vw, 1463 w, 1450 w, 1447 w, 1421 w, 1402 w, sh, 1380 m, 1372 m, 1303 s, 1288 s, 1259 m, 1198 vs, 1166 s, 1107 vw, 1045 m, 1019 m, 1012 m, sh, 913 w, 846 w, 596 w, cm⁻¹. ESI MS: 372 ([M+Na]⁺). HR ESI MS: calcd for $C_{17}H_{19}O_7NNa$ 372.10537, found 372.10541.

Ethyl 2-((((4-acetoxybenzyl)oxy)carbonyl)amino)-6-diazo-5-oxohexanoate (6)

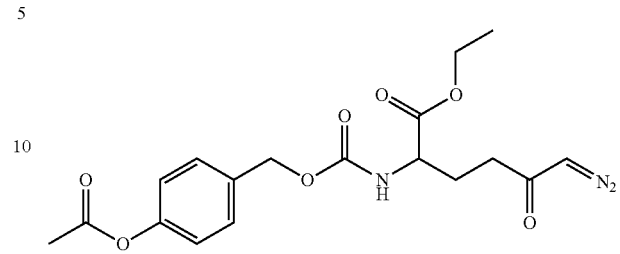

Trimethylsilyl diazomethane solution (2M in diethyl ether, 1.7 mL, 3.43 mmol, 1.2 equiv.) was dissolved in absolute THF (17 mL) under argon and cooled to −98° C. A solution of n-butyllithium (2.5 M in hexanes, 1.4 mL, 3.52 mmol, 1.23 equiv.) was added dropwise and the solution was stirred at −98° C. for 30 min. The resultant mixture was transferred via cannula to a solution of previous compound 5 (1.0 g, 2.86 mmol, 1 equiv.) in absolute THF (27 mL) at −116° C. The reaction mixture was slowly warmed to −78° C. and then quenched with saturated NH₄Cl. Then it was extracted with ethyl acetate (3×50 mL), the combined organic layers were washed with water (40 mL), brine (40 mL) and dried over anhydrous MgSO₄. The organic solvent was evaporated in vacuo. The residue was chromatographed on silica gel (chloroform-acetone 20:1) to afford the desired product 6 (460 mg, 41%) as a yellowish solid. ¹H NMR (400 MHz, CDCl₃): 1.25 (3H, t, J=7.1), 1.92-2.03 (1H, m), 2.13-2.23 (1H, m), 2.28 (3H, s), 2.32-2.43 (1H, m), 4.18 (1H, q, J=7.1), 4.29-4.34 (1H, m), 5.04 (1H, d, J=12.4), 5.10 (1H, d, J=12.1) 5.22 (1H, s), 7.31 (1H, d, J=8.2), 7.04-7.07 (2H, m), 7.34-7.37 (2H, m). ¹³C NMR (101 MHz, CDCl₃): 14.22, 21.19, 27.53, 36.45, 53.62, 61.78, 66.38, 121.78, 129.52, 134.01, 150.59, 156.01, 169.51, 171.90, 193.60. Optical rotation: $[\alpha]^{22}_D$ +15.5° (c 0.129, CHCl₃). IR (CHCl₃): 3428 w, 3116 w, 2966 w, 2110 s, 1721 vs, 1742 s, sh, 1641 m, 1609 w, sh, 1595 vw, sh, 1509 s, 1418 vw, 1381 s, sh, 1371 s, 1344 m, 1197 vs, 1166 m, 1106 vw, 1053 m, br, 1019 m, 1012 m, sh, 913 w, 848 w, 595 w, 492 w cm⁻¹. ESI MS: 414 ([M+Na]⁺). HR ESI MS: calcd for $C_{18}H_{21}O_7N_3Na$ 414.12717; found 414.12713.

Synthesis of 1-methylethyl 2,6-bis[4-(1λ⁵-diazynylidene)-3-oxobutyl]-9-methyl-7-oxo-4-phenoxy-8-oxa-3,5-diaza-4-phosphadecan-1-oate 4-oxide (7)

1-methylethyl 2,6-bis[4-(1λ⁵-diazynylidene)-3-oxobutyl]-9-methyl-7-oxo-4-phenoxy-8-oxa-3,5-diaza-4-phosphadecan-1-oate 4-oxide (7)

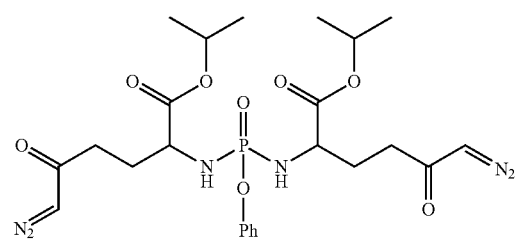

Referring to scheme 1, isopropyl DON 3 (100 mg, 0.38 mmol) was dissolved in absolute dichloromethane (3 mL) and diisopropylethyl amine (327 µL, 1.88 mmol, 4 equiv.) was added. This solution was cooled to 0° C., and phenyl dichlorophosphate (31.6 µL, 0.21 mmol, 0.45 equiv.) was added dropwise. The reaction mixture was stirred at 0° C. for 30 min and then the cooling bath was removed. The reaction mixture was then stirred at room temperature for 2 h. The organic solvent was evaporated in vacuo. The residue was chromatographed on silica gel (ethyl acetate-methanol 40:1) to afford the desired product (78 mg, 66%) as a yellow oil. $^1$H NMR (400 MHz, CDCl$_3$): 1.21-1.24 (12H, m), 1.81-1.93 (2H, m), 2.09-2.19 (2H, m), 2.24-2.52 (4H, m), 3.61-3.70 (2H, m), 3.90-3.98 (2H, m), 4.99 (1H, hept, J=6.3) 4.99 (1H, hept, J=6.2), 5.24 (1H, s), 5.33 (1H, s), 7.10-7.14 (1H, m), 7.17-7.20 (2H, m), 7.28-7.31 (2H, m). $^{13}$C NMR (101 MHz, CDCl$_3$): 21.81 (4C), 29.26, 29.43, 36.21 (2C), 53.78 (d, $J_{C,P}$=1.7), 53.97, 69.54, 69.66, 120.43 (d, $J_{C,P}$=4.8), 124.76, 129.76 (2C), 151.03 (2C, d, $J_{C,P}$=6.8), 172.47 (d, $J_{C,P}$=5.5), 172.64 (d, $J_{C,P}$=5.2), 194.07 (2C). $^{31}$P NMR (101 MHz, CDCl$_3$): 11.08. Optical rotation: $[\alpha]^{22}_D$+6.4° (c 0.313, CHCl3). IR (CHCl$_3$): 3099 w, 3303 w, 2104 vs, 1732 s, 1639 s, 1592 w, 1492 m, 1385 sh, m, 1376 s, 1240 sh, m, 1211 s, 1183 sh, m, 1167 m, 1144 m, 1132 sh, m, 1106 s, 1072 w, 1025 w, 1006 m, 923 m, 832 sh, w, 771 w, m, 692 w cm$^{-1}$.

ESI MS: 587 ([M+Na]$^+$). HR ESI MS: calcd for C$_{24}$H$_{33}$N$_6$O$_8$PNa 587.19897; found 587.19899.

Synthesis of isopropyl 2-(2-amino-4-methylpentanamido)-6-diazo-5-oxohexanoate (9)

Isopropyl 2-(2-((((9H-fluoren-9-yl)methoxy)carbonyl)amino)-4-methylpentanamido)-6-diazo-5-oxohexanoate (8)

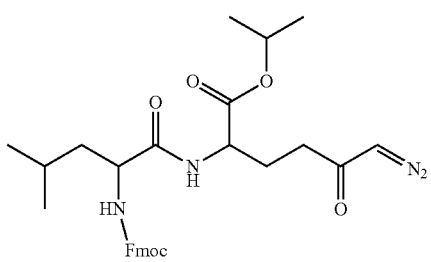

Referring to scheme 1, Fmoc-NH-(L)-Leu-COOH (874 mg, 2.47 mmol, 1.1 eq.) and HBTU (1023 mg, 2.70 mmol, 1.2 eq.) were suspended in dry DCM (15 mL). DIEA (872 mg, 1.18 mL, 6.75 mmol, 3 eq.) and then the solution of NH$_2$-DON-COOiPr (448 mg, 2.25 mmol, 1 eq.) in dry DCM (5 mL) were added by syringe. The reaction mixture was stirred for 2 h at room temperature under an inert atmosphere. DCM (20 mL) was added and the organic phase was washed with sat. NaHCO$_3$ (40 mL), 1M HCl (40 mL), water (2×40 mL) and sat. NaCl (40 mL), dried over MgSO$_4$. DCM was evaporated. The crude product was purified by column chromatography (DCM/EtOAc 4:1, R$_f$ 0.27) and light yellow solid (949 mg) was obtained in a 79% yield. $^1$H NMR (400 MHz, CDCl$_3$): 0.91-0.96 (6H, m), 1.23-1.25 (6H, m), 1.51-1.73 (3H, m), 1.93-2.02 (1H, m), 2.14-2.24 (1H, m), 2.26-2.44 (2H, m), 4.16-4.24 (1H, m), 4.33-4.37 (1H, m), 4.39-4.44 (1H, m), 4.47-4.52 (1H, m), 4.96-5.08 (1H, m), 5.18 (1H, s), 5.36 (1H, d, J=8.2), 6.84 (1H, d, J=7.8), 7.30 (2H, tt, J=7.4, 1.2), 7.37-7.42 (2H, m), 7.58 (2H, d, J=7.4), 7.75 (2H, d, J=7.5). $^{13}$C NMR (101 MHz, CDCl$_3$): 21.70, 21.72, 22.04, 22.92, 24.66, 27.04, 36.37, 41.75, 47.14, 52.05, 53.56, 67.08, 69.47, 119.98, 120.01, 125.06, 125.13, 127.10, 127.11, 127.74, 127.75, 141.28 (2C), 143.76, 143.81, 156.14, 170.95, 172.29, 193.80. Optical rotation: $[\alpha]^{22}_D$-6.10 (c 0.472, CHCl$_3$). IR (CHCl$_3$): 3304 m, sh, 3067 w, 3018 w, 2105 s, 1730 s, 1704 s, 1659 vs, 1639 sh, m, 1612 sh, w, 1580 sh, w, 1539 s, 1478 m, 1451 m, 1467 m, 1386 sh, s, 1375 s, 1244 s, 1172 sh, m, 1145 m, 1106 s, 834 sh, w, 759 m, 740 s, 621 m, 427 cm$^{-1}$. EST MS: 571 ([M+Na]$^+$). HR ESI MS: calcd for C$_{24}$H$_{33}$O$_4$N$_4$Na 571.25271; found 571.25271.

Isopropyl 2-(2-amino-4-methylpentanamido)-6-diazo-5-oxohexanoate (9)

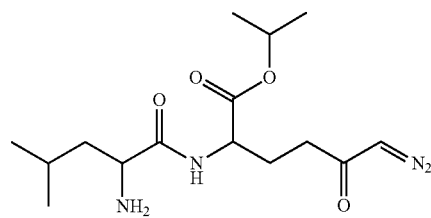

The same method of preparation as for previous compound 3 was used. Referring to scheme 1, compound 8 (90 mg, 0.164 mmol), dichloromethane (1 mL), piperidine (41 µL 0.41 mmol, 2.5 equiv.). Chromatography on silica gel (chloroform-methanol 20:1). Product (31 mg, 66%) as a yellow solid. $^1$H NMR (400 MHz, CDCl$_3$): 0.94 (3H, d, J=6.3), 0.98 (3H, d, J=6.4), 1.25 (3H, d, J=2.8), 1.26 (3H, d, J=2.8), 1.35-1.42 (1H, m), 1.76-1.79 (2H, m), 1.95-2.04 (1H, m), 2.17-2.25 (1H, m), 2.33-2.49 (2H, m), 3.48 (1H, dd, J=9.7, 4.1), 4.52 (1H, td, J=8.5, 4.7), 5.04 (1H, hept, J=6.3), 5.35 (1H, s), 7.87 (1H, d, J=8.3). $^{13}$C NMR (101 MHz, CDCl$_3$): 27.59, 28.19, 33.40, 66.39, 80.90, 124.87, 128.33, 128.35, 128.66, 136.10, 140.58, 166.01, 172.75. Optical rotation: $[\alpha]^{22}_D$+0° (c 0.33, CH$_2$Cl$_2$). IR (CHCl$_3$): 3412 w, 3343 w, 2110 vs, 1731 s, 1663 s, 1643 sh, s, 1603 sh, w, 1510 s, 1413 w, 1386 sh, s, 1376 sh, s, 1370 sh, s, 1349 m, 1145 m, 1105 s cm$^{-1}$. ESI MS: 327 ([M+H]$^+$). HR ESI MS: calcd for C$_{15}$H$_{27}$O$_4$N$_4$Na 327.20268; found 327.20280.

Synthesis of 1-methylethyl L-leucyl-L-leucyl-6-(11$^5$-diazynylidene)-5-oxo-L-norleucinate (11)

1-Methylethyl N-[(9H-fluoren-9-ylmethoxy)carbonyl]-L-leucyl-L-leucyl-6-(11$^5$-diazynylidene)-5-oxo-L-norleucinate (10)

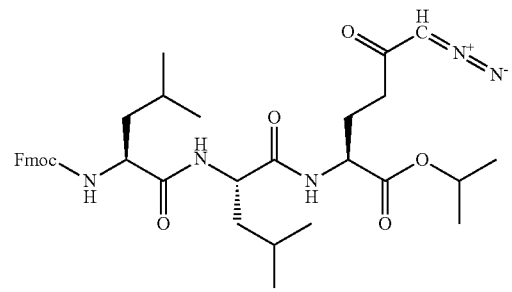

Fmoc-NH-(L)-Leu-COOH (224 mg, 0.634 mmol, 1.1 equiv.) and 2-benzotriazol-1-yl-tetramethyluronium tetrafluoroborate (TBTU) (222 mg, 0.69 mmol, 1.2 equiv.) were suspended in absolute dichloromethane (5 mL) and diisopropylethyl amine (301 μL, 1.73 mmol, 3 equiv.) was added. The reaction mixture was stirred at room temperature for 30 min, and then the solution of 9 (188 mg, 0.58 mmol) in dry dichloromethane (3 mL) were added by syringe. The reaction mixture was stirred for 2 h at room temperature under inert atmosphere. The organic solvent was evaporated in vacuo. The residue was chromatographed on silica gel (hexane:ethyl acetate, 1:1) to afford the desired product 10 (188 mg, 49%) as a yellowish amorphous solid. $^1$H NMR (400 MHz, CDCl$_3$): 0.86-0.98 (12H, m), 1.24 (3H, d, J=5.0), 1.25 (3H, d, J=5.0), 1.47-1.56 (2H, m), 1.57-1.72 (4H, m), 1.91-2.04 (1H, m), 2.14-2.24 (1H, m), 2.26-2.48 (2H, m), 4.14-4.22 (1H, m), 4.21 (1H, t, J=6.8), 4.36-4.49 (4H, m), 5.03 (1H, hept, J=6.3), 5.14 (1H, d, J=7.5), 5.32 (1H, s), 6.41 (1H, d, J=7.7), 6.83 (1H, d, J=6.8), 7.32 (2H, tt, J=7.4, 1.3), 7.41 (2H, tt, J=7.5, 1.5), 7.58 (2H, d, J=7.5), 7.77 (2H, tt, J=7.6, 1.1). $^{13}$C NMR (101 MHz, CDCl$_3$): 21.82, 21.84, 21.96, 22.22, 22.91, 23.14, 24.83 (2C), 27.22, 36.46, 41.29, 41.39, 47.26, 51.94, 52.12, 53.74, 55.00, 67.22, 69.54, 120.12, 120.14, 125.11, 125.15, 127.22 (2C), 127.88, 127.89, 141.42 (2C), 143.77, 143.89, 156.42, 171.03, 171.81, 172.39, 193.97. Optical rotation: $[\alpha]^{22}_D$ −25.2° (c 0.385, CHCl$_3$). IR (CHCl3): 3426 m, 3332 w, sh, 3116 w, 3068 w, 2961 s, 2873 m, 2110 s, 1726 vs, 1672 vs, 1640 sh, m, 1610 sh, w, 1579 sh, w, 1541 m, 1506 vs, 1479 m, 1468 m, 1387 s, 1371 sh, s, 1377 s, 1349 m, 1286 m, 1234 s, 1171 sh, m, 1146 m, 1105 s, 1046 m, 1023 sh, w, 824 w, 585 w, 488 w, sh, 426 w cm$^{-1}$. ESI MS: 684 ([M+Na]$^+$). HR ESI MS: calcd for C$_{36}$H$_{47}$O$_7$N$_5$Na 684.33677; found 684.33607.

1-Methylethyl L-leucyl-L-leucyl-6-(1l$^5$-diazynylidene)-5-oxo-L-norleucinate (11)

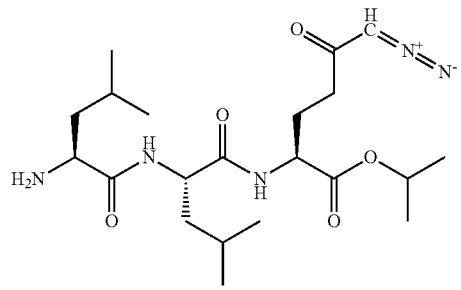

Compound 10 (180 mg, 0.272 mmol), was dissolved in dichloromethane (4 mL). Piperidine (67 μL 0.68 mmol, 2.5 equiv.) was added and the reaction mixture was stirred at room temperature for 4 h. The organic solvent was evaporated in vacuo. The residue was chromatographed on silica gel (chloroform:methanol, 30:1) to afford the desired product 11 (80 mg, 67%) as a yellow amorphous solid. $^1$H NMR (400 MHz, CDCl$_3$): ): 0.88-0.98 (12H, m), 1.24 (3H, d, J=5.2), 1.26 (3H, d, J=5.3), 1.37-1.47 (1H, m), 1.50-1.79 (5H, m), 1.91-2.07 (1H, m), 2.08-2.28 (3H, m), 2.31-2.50 (2H, m), 3.52 (1H, dd J=9.5, 3.8), 4.39 (1H, td, J=8.7, 5.3), 4.46 (1H, td, J=8.0, 4.6), 5.03 (1H, hept, J=6.2), 5.37 (1H, s), 7.02 (1H, d, J=7.4), 7.77 (1H, d, J=8.1). $^{13}$C NMR (101 MHz, CDCl$_3$): 21.46, 21.83, 21.86, 22.05, 23.09, 23.53, 24.95, 25.01, 27.13, 36.52, 40.89, 43.94, 51.55, 52.16, 53.61, 55.01, 69.49, 171.09, 172.36, 175.91, 194.21. Optical rotation: $[\alpha]^{22}_D$ −31.7° (c 0.439, CHCl$_3$). IR (CHCl3): 3415 w, 3343 w, br, 3117 w, 2984 m, 2961 s, 2936 m, 2873 m, 2855 w, 2110 vs, 1731 s, 1665 vs, br, 1653 vs, br, 1630 s, sh, 1509 s, 1468 m, 1454 w, 1450 w, 1440 w, 1386 s, 1377 s, 1370 s, 1349 m, 1201 m, 1183 w, 1146 m, 1105 s cm$^{-1}$. ESI MS: 440 ([M+H]$^+$). HR ESI MS: calcd for C$_{21}$H$_{38}$O$_5$N$_5$ 440.28675; found 440.28674.

Scheme 2

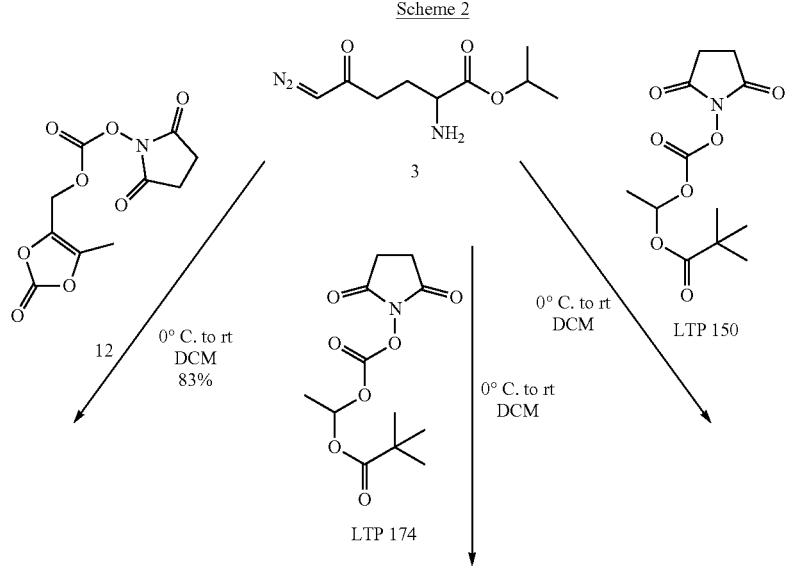

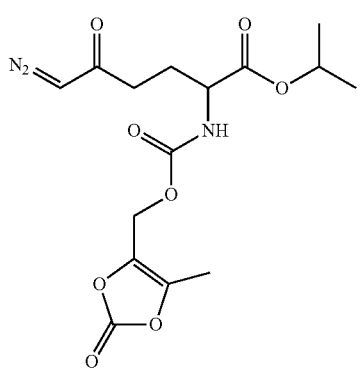

13

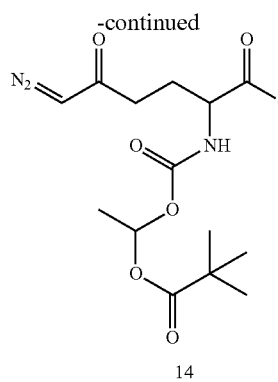

14

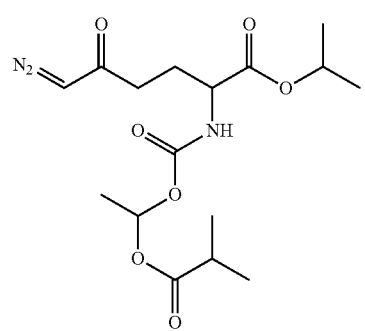

JAM0335

Synthesis of 1-methylethyl 6-(1λ⁵-diaznylidene)-N-{[(5-methyl-2-oxo-1,3-dioxol-4-yl)methoxy]carbonyl}-5-oxo-L-norleucinate (13)

2,5-Dioxopyrrolidin-1-yl-((5-methyl-2-oxo-1,3-dioxol-4-yl)methyl carbonate (12)

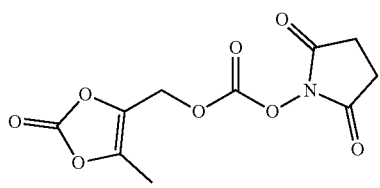 [SMILES: Cc1oc(=O)oc1COC(=O)ON1C(=O)CCC1=O]

4-(Hydroxymethyl)-5-methyl-1,3-dioxol-2-one (1.00 g, 7.89 mmol, 1 eq.) was dissolved in dry $Et_2O$ (30 ml) and the solution was cooled to 0° C. At this temperature pyridine (608 mg, 619 μL, 7.69 mmol, 1 eq.) was added and finally the solution of S-ethyl carbonochloridothionate (1.04 g, 874 μL, 8.38 mmol, 1.09 eq.) in dry $Et_2O$ (8 mL) was added by dropwise. The mixture was stirred for 1 h at 0° C., and overnight at rt (18 h). $Et_2O$ was removed by vacuo and DCM (70 mL) was added. The reaction mixture was washed with sat. NaHCO3 (40 mL) and with water (3×40 mL), dried with MgSO4 and DCM was removed by rotavap. The crude product was purified by column chromatography (hexane/EtOAc 5:1, $R_f$ 0.24). A light yellow liquid (1.29 g) was obtained in 77% yield. S-Ethyl O-((5-methyl-2-oxo-1,3-dioxol-4-yl)methyl) carbonothioate (800 mg, 3.67 mmol, 1 eq.) and N-hydroxysuccinimide (844 mg, 7.33 mmol, 2 eq.) were suspended in dry DCM (8 mL). The solution was cooled to 0° C., and peracetic acid (836 mg (100%), 2.32 g (36%), 11.00 mmol, 3 eq., 36% solution in acetic acid) was added by dropwise in 10 minutes. The final mixture was stirred for 30 minutes at 0° C., and 2 h at rt. DCM (20 mL) was added and the organic phase was washed with water (2×35 mL) and sat. NaCl (35 mL). DCM was evaporated and the product 12 was obtained as a colorless solid compound (750 mg) in 76% yield. ¹H NMR (400 MHz, CDCl₃): 2.20 (3H, s), 2.86 (4H, s), 5.05 (2H, s). ¹³C NMR (101 MHz, CDCl₃): 9.67, 25.58, 59.89, 131.61, 142.20, 151.65, 168.39. IR (CHCl3): 1842 m, 1824 s, 1819 s, 1792 s, 1749 vs, 1431 w, 1386 w, 1309 m, 1195 s, 935 w, 900 w, 811 vw cm⁻¹. ESI MS: 294 ([M+Na]⁺). HR ESI MS: calcd for $C_{10}H_9O_8NNa$ 294.02204; found 294.02213.

1-Methylethyl 6-(1λ⁵-diazynylidene)-N-{[(5-methyl-2-oxo-1,3-dioxol-4-yl)methoxy]carbonyl}-5-oxo-L-norleucinate (13)

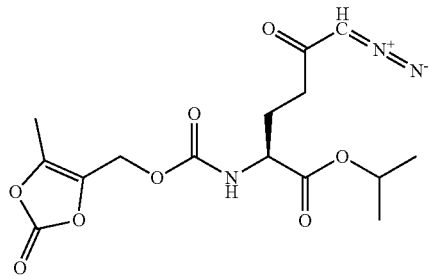 [SMILES: Cc1oc(=O)oc1COC(=O)N[C@@H](CCC(=O)C=[N+]=[N-])C(=O)OC(C)C]

Referring to scheme 2, compound 12 (70 mg, 0.258 mmol, 1.1 equiv) was dissolved in absolute dichloromethane (2 mL). This solution was cooled to 0° C., and a solution of 3 (50 mg, 0.235 mmol) in dichloromethane (1 mL) was added dropwise. Reaction mixture was stirred 15 min at 0° C. cooling bath was removed. The reaction mixture was then stirred at room temperature for 1 h. The organic solvent was evaporated in vacuo. The residue was chromatographed on silica gel (chloroform:acetone, 10:1) to afford the desired product 13 (72 mg, 83%) as a yellow oil. ¹H NMR (400 MHz, CDCl₃): 1.24 (3H, d, J=3.4), 1.26 (3H, d, J=5.6), 1.94-2.04 (1H, m), 2.13-2.24 (1H, m), 2.16 (3H, s), 2.32-2.49 (2H, m), 4.23-4.28 (1H, m), 4.77-4.87 (2H, m), 5.04 (1H, hept, J=6.3), 5.28 (3H, s), 5.66 (1H, d, J=7.9). ¹³C NMR (101 MHz, CDCl₃): 9.51, 21.82, 21.85, 27.32, 36.33, 53.86, 54.57, 69.79, 133.93, 140.07, 152.31, 155.25, 171.12, 193.50. Optical rotation: $[\alpha]^{22}_D$+15.10 (c 0.417, CHCl3). IR (CHCl3): 3424 w, 3012 w, 2984 w, 2935 w, 2111 s, 1836 sh, s, 1821 vs, 1736 sh, vs, 1725 vs, 1641 m, 1603 sh, w, 1509 s, 1391 sh, m, 1383 s, 1366 sh, m, 1105 s cm⁻¹. ESI MS: 392 ([M+Na]⁺). HR ESI MS: calcd for $C_{15}H_{19}O_8N_3Na$ 392.10644; found 392.10650.

Synthesis of 1-methylethyl 6-(1λ⁵-diazynylidene)-N-({1-[(2,2-dimethylpropanoyl)oxy]ethoxy} carbonyl)-5-oxo-L-norleucinate (14a) and (14b)

1-((((2,5-Dioxopyrrolidin-1-yl)oxy)carbonyl)oxy) ethyl pivalate (LTP 174)

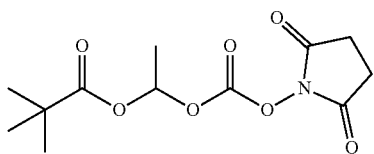 [SMILES: CC(OC(=O)ON1C(=O)CCC1=O)OC(=O)C(C)(C)C]

LTP 174 was prepared according to the literature procedure (WO 2008033572 A1).

1-Methylethyl 6-(1λ⁵-diazynylidene)-N-({1-[(2,2-dimethylpropanoyl)oxy]ethoxy} carbonyl)-5-oxo-L-norleucinate (14a) and (14b)

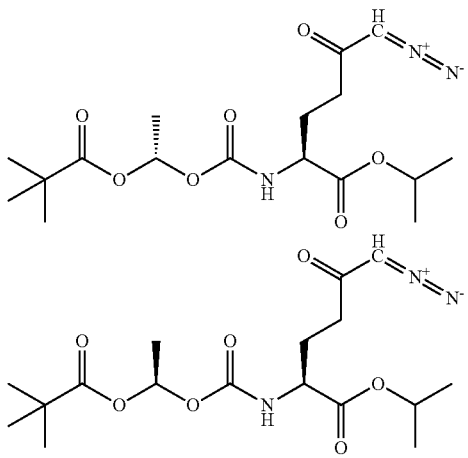

Referring to scheme 2, compound 14a and 14b were prepared from 3 (200 mg, 0.938 mmol) as described for the preparation of 13 using dichloromethane (8 mL) and 1-((((2,5-dioxopyrrolidin-1-yl)oxy)carbonyl)oxy)ethyl pivalate (297 mg, 1.032 mmol, 1.1 equiv.) to give isopropyl (2S)-6-diazo-5-oxo-2-(((1-(pivaloyloxy)ethoxy)carbonyl)amino) hexanoate 14 (as a mixture of diastereoisomers), followed by chromatography on silica gel (chloroform:acetone, 20:1) yielding two diastereoisomers: diastereoisomer #1 arbitrarily designated 14a (90 mg, $R_f$=0.25) and diastereoisomer #2 arbitrarily designated 14b (50 mg, $R_f$=0.2) as a yellow oils (39%). ¹H NMR (400 MHz, CDCl₃): 1.18 (9H, s), 1.25 (3H, d, J=3.0), 1.26 (3H, d, J=3.1), 1.46 (3H, d, J=5.4), 1.94-2.04 (1H, m), 2.15-2.24 (1H, m), 2.31-2.49 (2H, m), 4.24-4.30 (1H, m), 5.04 (1H, hept, J=6.2), 5.28 (1H, s), 5.50 (1H, d, J=7.9), 6.77 (1H, q, J=5.4). ¹³C NMR (101 MHz, CDCl₃): 19.78, 21.83, 21.85, 27.00 (3C), 27.79, 36.56, 38.79, 53.58, 69.76, 89.70, 153.90, 171.16, 176.61, 193.59. IR (CHCl3): 3427 w, 3116 w, 2984 m, 2960 sh, m, 2937 w, 2875 w, 2857 sh, w, 2110 s, 1745 sh, vs, 1730 sh, vs, 1641 m, 1508 s, 1480 m, 1467 sh, w, 1461 w, 1455 sh, w, 1392 sh, s, 1383 sh, s, 1377 s, 1371 sh, s, 1365 sh, s, 1350 m, 1027 m cm⁻¹. Optical rotation (14a): $[α]^{22}_D$+22.0° (c 0.191, CHCl3). Optical rotation (14b): $[α]^{22}_D$+7.6° (c 0.158, CHCl3). ESI MS (14a): 408 ([M+Na]⁺). ESI MS (14b): 408 ([M+Na]⁺). HR ESI MS (14a): calcd for $C_{17}H_{27}O_7N_3Na$ 408.17412; found 408.17425. HR ESI MS (14b): calcd for $C_{17}H_{27}O_7N_3Na$ 408.17412; found 408.17421. Diastereomer 14b was used in the biological studies described herein. The absolute stereochemistry of 14b has not been determined.

Synthesis of Isopropyl 6-diazo-2-(((1-((3-methylbutanoyl)oxy)ethoxy)carbonyl)amino)-5-oxohexanoate (JAM0335)

1-((((2,5-Dioxopyrrolidin-1-yl)oxy)carbonyl)oxy) ethyl isobutyrate (LTP 150)

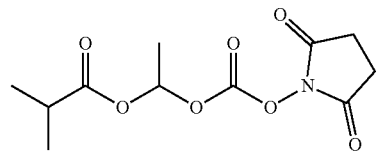 [SMILES: CC(OC(=O)ON1C(=O)CCC1=O)OC(=O)C(C)C]

LTP 150 was prepared according the literature procedure (Magill et al., 1957.

Isopropyl 6-diazo-2-(((1-((3-methylbutanoyl)oxy)ethoxy)carbonyl)amino)-5-oxohexanoate (JAM0335)

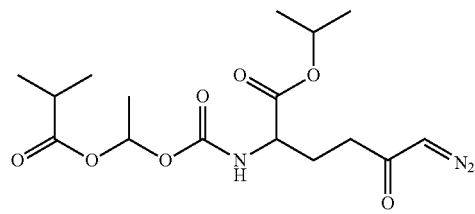

The same method of preparation as for previous compound 13 was used. Referring to scheme 2, LTP150 (74 mg, 0.258 mmol, 1.1 equiv.), dichloromethane (2 mL). Compound 3 (50 mg, 0.235 mmol), dichloromethane (1 mL), Chromatography on silica gel (chloroform-acetone 20:1). Product (31 mg, 66%) was isolated as a yellow oil. ¹H NMR (400 MHz, CDCl₃): 1.48 (9H, s), 2.54-2.64 (4H, m), 5.11 (2H, s), 5.48 (1H, m), 6.07 (1H, d, J=1.2), 7.30-7.40 (5H, m). ¹³C NMR (101 MHz, CDCl₃): 27.59, 28.19, 33.40, 66.39, 80.90, 124.87, 128.33, 128.35, 128.66, 136.10, 140.58, 166.01, 172.75. ESI MS: 313 ([M+Na]⁺). HR ESI MS: calcd for $C_{17}H_{22}O_4Na$ 313.14103; found 313.14103.

Synthesis of 1-methylethyl 6-(1λ⁵-diazynylidene)-N-({1-[(2-methylpropanoyl)oxy]ethoxy}carbonyl)-5-oxo-L-norleucinate (15)

1-Methylethyl 6-(1λ⁵-diazynylidene)-N-({1-[(2-methylpropanoyl)oxy]ethoxy}carbonyl)-5-oxo-L-norleucinate (15)

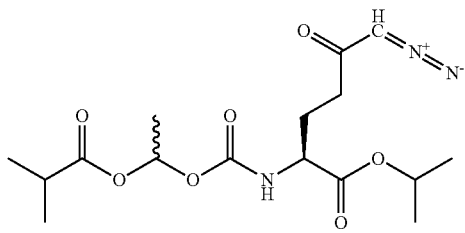 [SMILES: CC(C)OC(=O)[C@H](CCC(=O)C=[N+]=[N-])NC(=O)OC(C)OC(=O)C(C)C]

Compound 15 was prepared from 3 (300 mg, 1.4 mmol) as described for the preparation of 13 using 1-[[[(2,5-Dioxopyrrolidin-1-yl)oxy]carbonyl]oxy]ethyl 2-methylpropanoate (prepared by WO 2005066122, 423 mg, 1.55 mmol, 1.1 equiv.) and dichloromethane (4 mL), followed by chromatography on silica gel (chloroform:acetone, 20:1). A yellow oil (426 mg, 82%). $^1$H NMR (400 MHz, CDCl$_3$): 1.13-1.17 (6H, m), 1.24-1.26 (6H, m), 1.46 (3H, d, J=5.4), 1.89-2.03 (1H, m), 2.15-2.26 (1H, m), 2.31-2.58 (3H, m), 4.25-4.31 (1H, m), 5.03 (1H, hept, J=6.3), 5.29 and 5.34 (1H, 2×s), 5.48 and 5.52 (1H, 2×d, J=8.2 and 7.9), 6.75-6.81 (1H, m). $^{13}$C NMR (101 MHz, CDCl$_3$): 18.78 (2C), 19.83, 21.81, 21.84, 27.81, 33.98, 36.40, 53.47, 54.92, 69.75, 89.53, 153.87, 171.12, 175.19, 193.60. IR (CHCl3): 3427 w, 3116 w, 2983 m, 2940 w, 2879 w, 2110 s, 1746 vs, 1733 vs, 1641 m, 1509 s, 1449 m, 1387 s, 1349 s, 1341 m, 1321 m, 1030 s cm$^{-1}$. ESI MS: 394 ([M+Na]$^+$). HR ESI MS: calcd for C$_{16}$H$_{25}$O$_7$N$_3$Na 394.15847; found 394.15859.

Scheme 3

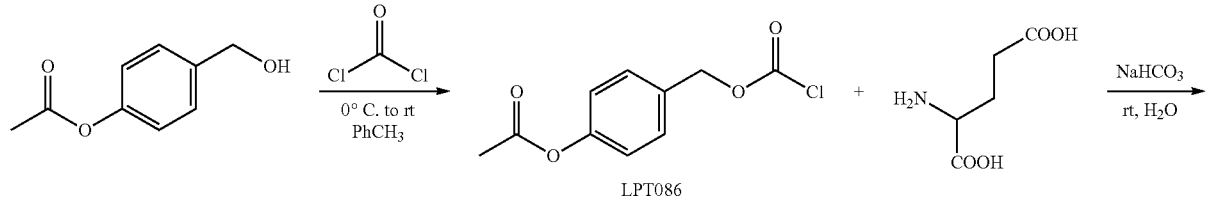

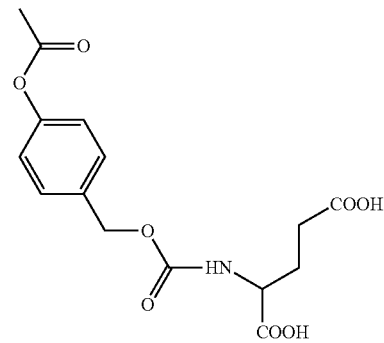

LTP087 paraformaldehyde
PTSA | reflux, PhCH$_3$

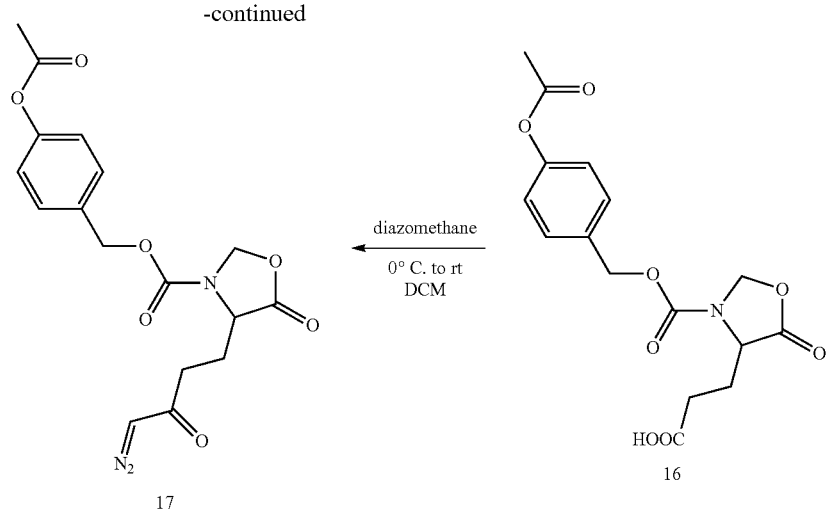

Synthesis of 4-acetoxybenzyl 4-(4-diazo-3-oxobutyl)-5-oxooxazolidine-3-carboxylate (17)

3-(3-(((4-acetoxybenzyl)oxy)carbonyl)-5-oxooxazolidin-4-yl)propanoic acid 16)

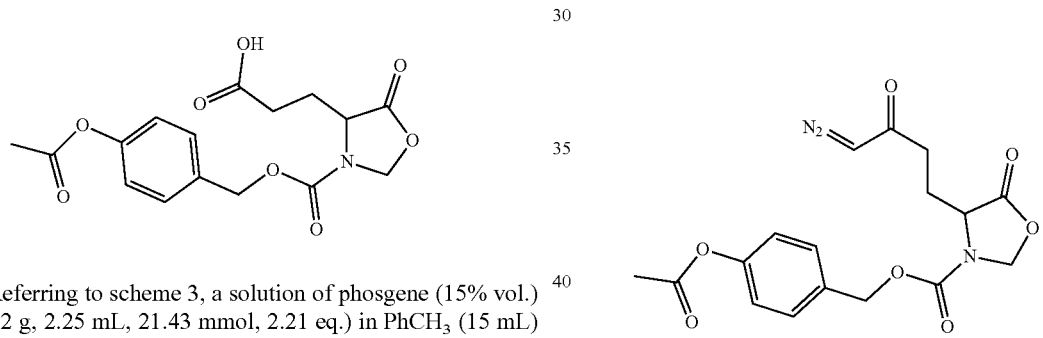

Referring to scheme 3, a solution of phosgene (15% vol.) (2.12 g, 2.25 mL, 21.43 mmol, 2.21 eq.) in PhCH₃ (15 mL) was cooled to 0° C. 4-(Hydroxymethyl)phenyl acetate (1.61 g, 9.70 mmol, 1 eq.) in PhCH₃ (15 mL) was added dropwise over 15 min. The reaction mixture was stirred for 1 h at 0° C., and then at room temperature overnight (20 h). Solvent was evaporated and the crude product 4-chlorocarbonyl)oxy]methyl}phenyl acetate (LTP 086) was used for the next step without purification. L-glutamic acid (951 mg, 6.46 mmol, 1 eq.) was suspended in water (8 mL) and NaHCO₃ (1.37 g, 16.30 mmol, 2.52 eq.) was added in few portions. After 15 min of stirring, crude LTP 086 (2.2 g, 9.70 mmol, 1 eq.) was added by syringe over 2 minutes at room temperature. The mixture was stirred at room temperature overnight (20 h). 1 M HCl was added until the mixture was at a pH of 1 and the water phase was then extracted with EtOAc (10×15 mL). Combined organic fractions were washed with sat. NaCl (150 mL), dried over MgSO₄ and the solvent was evaporated. The crude product N-[[[4-(acetyloxy)phenyl]methoxy]carbonyl]-L-gluamamic acid (LTP 087) (2.2 g, 6.48 mmol, 1 eq.) was used in the next step without purification. LTP 087 (2.2 g, 6.48 mmol, 1 eq.) was dissolved in PhCH₃ (45 mL). Paraformaldehyde (389 mg, 12.97 mmol, 2 eq.) and p-Toluenesulfonic acid (PTSA) (123 mg, 0.648 mmol, 0.1 eq.) were added and the mixture was refluxed for 1 h. Toluene was evaporated and the crude product was purified by column chromatography (CHCl₃/MeOH 20:1). The desired product 16 was obtained as a colorless viscous oil (280 mg) in a 12% yield over three steps.

4-acetoxybenzyl 4-(4-diazo-3-oxobutyl)-5-oxooxazolidine-3-carboxylate (17)

The compound LTP088 (257 mg, 0.732 mmol) was dissolved in absolute THF (3 mL), cooled to −15° C., and triethylamine (153 µL, 1.097 mmol, 1.5 equiv.) was added dropwise. Then ethylchloroformate was added and the reaction mixture was stirred at −15° C. for 1.5 h. Then a solution of diazomethane was added and the reaction mixture was stirred for another 30 min at −15° C., and then the cooling bath was removed. The reaction mixture was then stirred at room temperature for 2 h. The organic solvent was evaporated in vacuo. The residue was chromatographed on silica gel (hexane-ethyl acetate 1:1) to afford the desired product (220 mg, 66%) as a yellow amorphous solid. $^1$H NMR (400 MHz, CDCl₃): 2.14 (2H, m), 2.29 (3H, s), 2.32-2.56 (2H, m), 4.34 (1H, t, J=6.2), 5.11-5.25 (4H, m), 5.51 (1H, s), 7.07-7.10 (2H, m), 7.37-7.40 (2H, m). $^{13}$C NMR (101 MHz, CDCl₃): 21.19, 25.80, 35.36, 54.12, 67.49, 77.89, 122.06 (2C), 129.96 (2C), 130.02, 150.97, 152.98, 169.49, 171.81, 192.64. IR (CHCl₃): 3116 w, 2964 vw, 2922 w, 2111 s, 1802 s, 1768 m, sh, 1756 s, 1716 vs, 1642 m, 1610 w, 1597 vw, sh, 1510 m, 1423 m, 1410 s, 1383 m, 1371 s, 1355 s, 1197 vs, 1167 s, 1128 m, 1106 w, 1019 m, 1013 w, 914 m, 850 w, 596 w, 492 w, cm⁻¹. ESI MS: 398 ([M+Na]⁺). HR ESI MS: calcd for $C_{17}H_{17}O_7N_3Na$ 398.09587; found 398.09596.

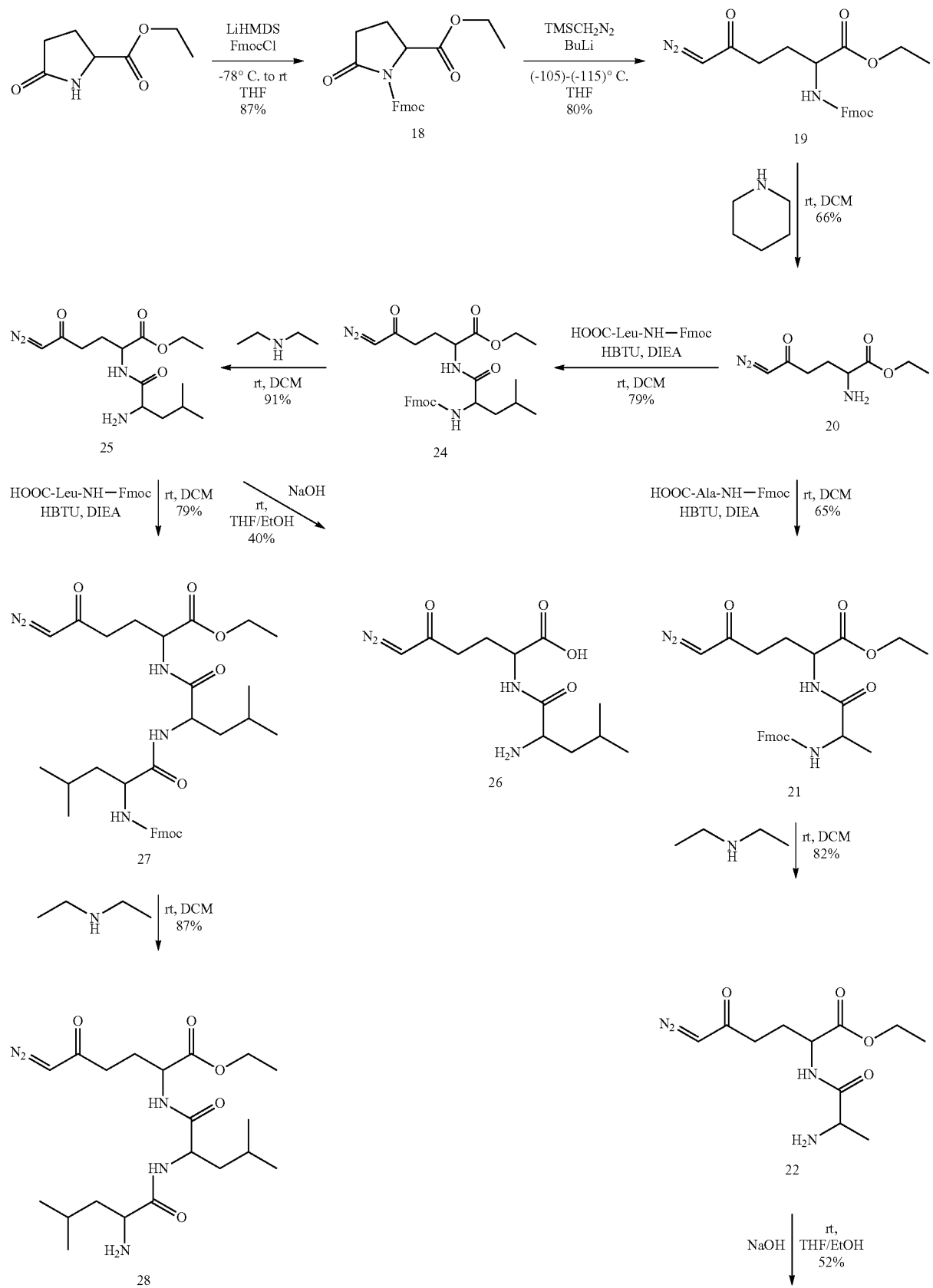

-continued

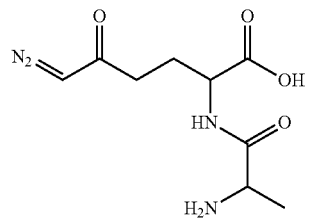

23

Synthesis of ethyl 2-(2-aminopropanamido)-6-diazo-5-oxohexanoate (22)

1-(9H-fluoren-9-ylmethyl)-2-ethyl-5-oxopyrrolidine-1,2-dicarboxylate (18)

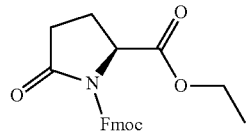

Referring to scheme 4, 5-Oxo-L-proline ethyl ester (4.00 g, 25.45 mmol, 1 eq.) was dissolved in absolute THF (120 mL) under inert and cooled to −78'° C. A solution of LiHMDS (1M in THF, 24.2 mL, 24.18 mmol, 0.95 eq.) was added dropwise and the solution was stirred at the same temperature for 20 min. The resultant yellow mixture was transferred via cannula to a solution of Fmoc chloride (32.9 g, 127.3 mmol, 5 eq.) in absolute THF (90 mL) at −78° C. The reaction mixture was stirred at −78° C. for 2 h and at rt overnight (18 h). After this period the reaction was quenched with saturated $NH_4Cl$ (34 mL) and water (18 mL). Water phase was extracted with EtOAc (60 mL) and combined organic parts were washed with brine (2×100 mL) and dried over anhydrous $MgSO_4$. The organic solvent was evaporated under vacuo. The residue was chromatographed on silica gel (hexane:EtOAc 3:1 to 1:1) and finally on reverse LC (MeOH:$H_2O$, 2:1 to 100% MeOH) to afford the desired product 18 (8.40 g, 87%) as a colourless solid. $^1H$ NMR (400 MHz, $CDCl_3$): 1.26 (3H, d, J=7.1), 2.12 (1H, ddt, J=13.4, 9.4, 2.9), 2.40 (1H, ddt, J=13.4, 10.8, 9.3), 2.57 (1H, ddd, J=17.5, 9.2, 3.1), 2.72 (1H, ddd, J=17.5, 10.7, 9.4), 4.20 (2H, q, J=7.1), 4.30 (1H, t, J=7.3), 4.44 (1H, dd, J=10.5, 7.4), 4.57 (1H, dd, J=10.6, 7.3), 4.65 (1H, dd, J=9.4, 2.5), 7.33 (2H, tt, J=7.4, 1.1), 7.41 (2H, tdd, J=6.9, 1.3, 0.6), 7.71 (1H, dd, J=7.5, 1.0), 7.75 (1H, dd, J=7.5, 1.0), 7.77 (2H, dd, J=7.8, 1.0). $^{13}C$ NMR (101 MHz, $CDCl_3$): 14.14, 21.96, 31.21, 46.62, 58.76, 61.92, 69.03, 119.99, 120.01, 125.30, 125.44, 127.26 (2C), 127.91 (2C), 141.27, 141.29, 143.35, 143.40, 151.44, 170.80, 172.99. Optical rotation: $[\alpha]^{22}_D$ −17.2° (c 0.285, CHCl3). IR (CHCl3): 3068 m, 2985 m, 2941 w, 2898 w, 2875 w, 1797 vs, 1745 vs, br, 1723 vs, 1609 w, 1580 vw, 1478 m, 1463 m, 1452 s, 1400 m, sh, 1385 s, 1197 vs, 1116 vw, sh, 1104 m, 1097 w, sh, 1033 s, 621 m, 426 w, $cm^{-1}$. ESI MS: 402 ([M+Na]$^+$). HR ESI MS: calcd for $C_{22}H_{21}O_5NNa$ 402.1312; found 402.1313.

Ethyl 2-((((9H-fluoren-9-yl)methoxy)carbonyl)amino)-6-diazo-5-oxohexanoate (19)

Trimethylsilyl diazomethane solution (2M in diethyl ether, 7.9 mL, 15.81 mmol, 1.2 eq.) was dissolved in absolute THF (70 mL) under argon and cooled to −98° C. A solution of n-butyllithium (2.5 M in hexanes, 6.5 mL, 16.21 mmol, 1.23 eq.) was added dropwise and the solution was stirred at −98° C. for 30 min. The resultant mixture was transferred via cannula to a solution of 18 (5.00 g, 13.18 mmol, 1 eq.) in absolute THF (120 mL) at −116° C. The reaction mixture was stirred for 30 min at this temperature and then slowly warmed to −78° C., and quenched with saturated $NH_4Cl$ (150 mL). Water phase was extracted with ethyl acetate (3×50 mL), the combined organic layers were washed with brine (200 mL) and dried over anhydrous $MgSO_4$. The organic solvent was evaporated in vacuo. The residue was chromatographed on silica gel ($CHCl_3$:acetone, 20:) to afford the desired product 19 (4.42 g, 80%) as a yellowish solid. $^1H$ NMR (400 MHz, $CDCl_3$): 1.29 (3H, t, J=7.1), 1.93-2.10 (1H, m), 2.17-2.29 (1H, m), 2.33-2.53 (2H, m), 4.22 (3H, t, J=7.1), 4.32-4.43 (3H, m), 5.27 (1H, bs), 5.56 (1H, d, J=8.1), 7.32 (2H, tt, J=7.4, 1.3), 7.41 (2H, t, J=7.5), 7.60 (2H, t, J=6.6), 7.77 (2H, dd, J=7.6, 1.0). $^{13}C$ NMR (101 MHz, $CDCl_3$): 14.30, 27.63, 36.56, 47.26, 53.63, 54.96, 61.89, 67.17, 120.11, 120.14, 125.22, 125.24, 127.20 (2C), 127.86 (2C), 141.40, 141.43, 143.78, 143.99, 156.18, 172.03, 193.65. Optical rotation: $[\alpha]^{22}_D$ +10.6° (c 0.265, CHCl3). IR (CHCl3): 3428 w, 3116 w, 3068 w, 2985 w, 2942 w, 2907 vw, 2110 s, 1740 s, sh, 1721 vs, 1642 m, 1510 s, 1478 w, 1465 w, 1451 m, 1381 s, 1105 w, 1052 m, 1033 m, 622 w, 426 w $cm^{-1}$. ESI MS: 444 ([M+Na]$^+$). HR ESI MS: calcd for $C_{23}H_{23}O_5N_3Na$ 444.15299; found 444.15292.

Ethyl 2-amino-6-diazo-5-oxohexanoate (20)

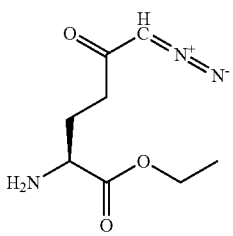

Compound 20 was prepared from 19 (100 mg, 0.237 mmol) as described for the preparation of 3 using dichloromethane (10 mL) and piperidine (58 μL 0.59 mmol, 2.5 equiv), followed by chromatography on silica gel (chloroform:methanol, 30:1). A yellow oil (31 mg, 66%). $^1$H NMR (400 MHz, CDCl$_3$): 1.27 (3H, t, J=7.1), 1.55 (2H, bs), 1.78-1.88 (0H, m), 2.06-2.17 (1H, m), 2.40-2.54 (2H, bm), 3.44 (1H, dd, J=8.3, 5.1), 4.17 (2H, q, J=7.1), 5.27 (1H, s). $^{13}$C NMR (101 MHz, CDCl$_3$): 14.24, 29.56, 36.86, 53.77, 54.56, 61.05, 175.58, 194.15. Optical rotation: $[\alpha]^{22}{}_D$+° (c 0.33, CH$_2$Cl$_2$). IR (CHCl3): 3410 w, vbr, 3327, vw, vbr, 2986 m, 2941 w, 2910 w, 2874 w, 2110 s, 1739 vs, 1641 m, 1605 sh, 1586 m, 1552 w, 1513 w, br, 1476 w, 1463 m, 1446 m, 1395 m, sh, 1377 s, 1200 s, 1115 m, 1096 in cm$^{-1}$. ESI MS: 182 ([M–H$_2$O+H]$^+$). HR ESI MS: calcd for C$_{12}$H$_{12}$N$_3$O$_2$ 182.0930; found 182.0931.

Ethyl 2-(2-((((9H-Fluoren-9-yl)methoxy)carbonyl)amino)propanamido)-6-diazo-5-oxohexanoate (21)

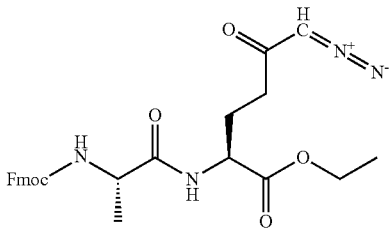

Fmoc-NH-(L)-Ala-COOH (483 mg, 1.55 mmol, 1.1 eq.) and HBTU (642 mg, 1.69 mmol, 1.2 eq.) were suspended in dry DCM (10 mL). DIEA (547 mg, 737 μL, 4.32 mmol, 3 eq.) and then the solution of 20 (281 mg, 1.41 mmol, 1 eq.) in dry DCM (3 mL) were added by syringe. The reaction mixture was stirred for 2 h at rt under inert atmosphere. DCM (15 mL) was added and the organic phase was washed with sat. NaHCO$_3$ (25 mL), 1M HCl (25 mL), water (2×25 mL) and sat. NaCl (25 mL), dried oved MgSO$_4$. DCM was evaporated. The crude product was purified by column chromatography (DCM:EtOAc, 1:1, R$_f$ 0.40) to give 21 as a light yellow solid (452 mg, 65%). $^1$H NMR (400 MHz, CDCl$_3$): 1.28 (3H, t, J=7.5), 1.42 (3H, d, J=7.1), 1.98-2.08 (1H, m), 2.16-2.28 (1H, m), 2.30-2.48 (2H, m), 4.15-4.30 (4H, m), 4.39 (2H, d, J=7.3), 4.53 (1H, td, J=8.0, 4.5), 5.21 (1H, s), 5.38 (1H, d, J=7.4), 6.81 (1H, d, J=7.8), 7.32 (2H, t, J=7.5), 7.41 (2H, t, J=7.5), 7.60 (2H, d, J=7.5), 7.77 (2H, d, J=7.5). $^{13}$C NMR (101 MHz, CDCl$_3$): 14.25, 18.86, 27.00, 36.48, 38.74, 47.22, 50.65, 55.11, 61.84, 67.24, 120.11, 120.13, 125.20, 125.24, 127.22 (2C), 127.87 (2C), 141.40 (2C), 143.92 (2C), 156.01, 171.58, 172.47, 193.99. Optical rotation: $[\alpha]^{22}{}_D$+0.4° (c 0.225, CHCl3). IR (CHCl3): 3424 m, 3330 w, br, 3116 vw, 3068 vw, 2986 m, 2941 w, 2908 w, 2875 vw, 2110 s, 1731 vs, 1720 vs, sh, 1682 vs, 1639 m, 1585 vw, 1503 vs, 1478 m, 1451 s, 1377 s, 1233 s, 1116 m, 1105 m, sh, 1095 w, 1032 m, 622 w, 424 w, cm$^{-1}$. ESI MS: 515 ([M+Na]$^+$). HR ESI MS: calcd for C$_{26}$H$_{28}$O$_6$N$_4$Na 515.19011; found 515.19044.

Ethyl 2-(2-aminopropanamido)-6-diazo-5-oxohexanoate (22)

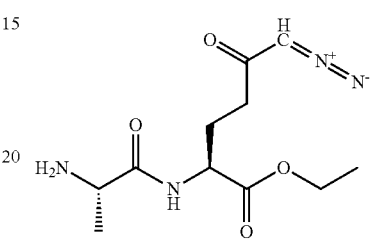

Compound 21 (225 mg, 0.457 mmol, 1 eq.) was dissolved in dry DCM (4 mL). Diethylamine (167 mg, 236 μL, 2.28 mmol, 5 eq.) was added by syringe. The reaction mixture was stirred for 6 h at rt under inert atmosphere. DCM was evaporated. The crude product was purified by column chromatography (CHCl$_3$:MeOH, 15:1, R$_f$ 0.07) to give 22 as a light yellow solid (101 mg, 82%). $^1$H NMR (400 MHz, CDCl$_3$): 1.22 (3H, t, J=7.1), 1.28 (3H, d, J=7.0), 1.89-1.94 (2H, m), 1.94-2.01 (1H, m), 2.10-2.21 (1H, m), 2.27-2.43 (2H, m), 3.47 (1H, q, J=7.0), 4.13 (2H, q, J=7.1), 4.47 (1H, td, J=8.4, 4.9), 5.32 (1H, s), 7.81 (1H, d, J=8.4). $^{13}$C NMR (101 MHz, CDCl$_3$): 14.28, 18.56, 27.44, 36.80, 51.63, 55.05, 58.55, 61.74, 171.90, 175.25, 193.93. Optical rotation: $[\alpha]^{22}{}_D$−31.1° (c 0.260, CHCl3+DMF). IR (CHCl3): 3393 w, 3336 vw, br, 3211 vw, br, 3116 vw, 2958 m, 2927 s, 2871 m, 2856 m, 2110 s, 1736 m, 1684 vs, 1639 m, 1517 w, 1379 s, 1115 vw, sh, 1097 w, cm$^{-1}$. ESI MS: 271 ([M+H]$^+$). HR ESI MS: calcd for C$_{11}$H$_{19}$O$_4$N$_4$ 271.14008; found 271.14024.

Synthesis of 2-(2-aminopropanamido)-6-diazo-5-oxohexanoic acid (23)

2-(2-Aminopropanamido)-6-diazo-5-oxohexanoic acid (23)

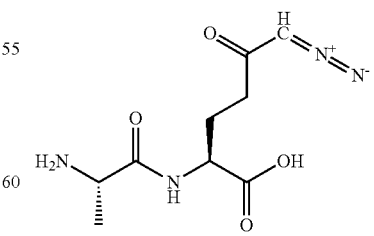

Referring to scheme 4, compound 22 (225 mg, 0.457 mmol, 1 eq.) was suspended in EtOH (3 mL) and THF (3 mL). 1M solution of NaOH (16 mg, 397 μL, 0.95 eq.) was added and the mixture was stirred for 15 minutes. The reaction was quenched with 1 M formic acid (397 µL, 0.95 eq.) and after 10 minutes of stirring the mixture was evaporated to dryness. The crude product was purified by preparative HPLC with Et₃N/CH₃COOH buffer. The desired product 23 was obtained as a light orange solid (50 mg) in 52% yield. ¹H NMR (400 MHz, CDCl₃): 1.45 (3H, d, J=7.0), 2.06-2.22 (2H, m), 2.45-2.56 (2H, m), 4.01-4.13 (2H, m), 5.86 (1H, brs).

Synthesis of ethyl 2-(2-amino-4-methylpentanamido)-6-diazo-5-oxohexanoate (25)

Ethyl 2-(2-((((9H-fluoren-9-yl)methoxy)carbonyl) amino)-4-methylpentanamido)-6-diazo-5-oxohexanoate (24)

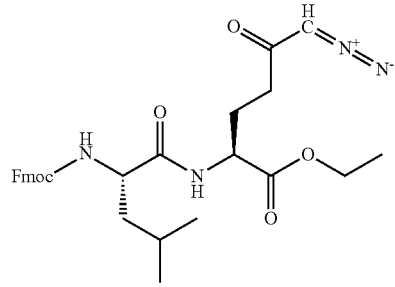

Referring to scheme 4, Fmoc-NH-(L)-Leu-COOH (874 mg, 2.47 mmol, 1.1 eq.) and HBTU (1023 mg, 2.70 mmol, 1.2 eq.) were suspended in dry DCM (15 mL). DIEA (872 mg, 1.18 mL, 6.75 mmol, 3 eq.) and then the solution of 20 (448 mg, 2.25 mmol, 1 eq.) in dry DCM (5 mL) were added by syringe. The reaction mixture was stirred for 2 h at rt under inert atmosphere. DCM (20 mL) was added and the organic phase was washed with sat. NaHCO₃ (40 mL), 1M HCl (40 mL), water (2×40 mL) and sat. NaCl (40 mL), dried oved MgSO₄. DCM was evaporated. The crude product was purified by column chromatography (DCM:EtOAc, 4:1, R_f 0.27) to give 24 as a light yellow solid (949 mg, 79%). ¹H NMR (400 MHz, CDCl₃): 0.95 (6H, d, J=5.9), 1.26 (3H, t, J=7.5), 1.50-1.59 (1H, m), 1.62-1.75 (2H, m), 1.95-2.05 (1H, m), 2.17-2.27 (1H, m), 2.29-2.45 (2H, m), 4.14-4.25 (4H, m), 4.34-4.45 (2H, m), 4.49-4.58 (1H, m), 5.19 (1H, s), 5.27 (1H, d, J=8.4), 6.80 (1H, d, J=7.6), 7.31 (2H, t, J=7.4), 7.40 (2H, t, J=7.8), 7.59 (2H, d, J=7.5), 7.76 (2H, d, J=7.6). ¹³C NMR (101 MHz, CDCl₃): 14.12, 22.03, 22.92, 24.66, 26.96, 36.33, 41.65, 47.14, 51.94, 53.56, 55.00, 61.73, 67.09, 120.00, 120.03, 125.05, 125.13, 127.12 (2C), 127.76, 127.77, 141.29, 143.64, 143.75, 143.79, 156.15, 171.46, 172.26, 193.81. Optical rotation: $[\alpha]^{22}_D$ -9.7° (c 0.109, DMF). IR (CHCl3): 3304 m, sh, 3067 w, 3018 w, 2105 s, 1730 s, 1704 s, 1659 vs, 1639 sh, m, 1612 sh, w, 1580 sh, w, 1539 s, 1478 m, 1451 m, 1467 m, 1386 sh, s, 1375 s, 1244 s, 1172 sh, m, 1145 m, 1106 s, 834 sh, w, 759 m, 740 s, 621 m, 427 cm⁻¹. ESI MS: 557 ([M+Na]⁺). HR ESI MS: calcd for $C_{29}H_{34}O_6N_4Na$ 557.23706; found 557.23707.

Ethyl 2-(2-amino-4-methylpentanamido)-6-diazo-5-oxohexanoate (25)

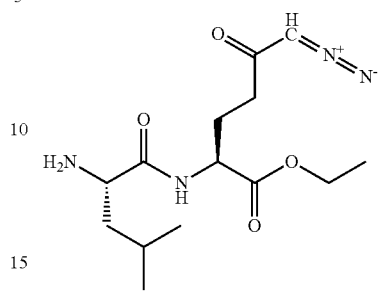

Referring to scheme 4, compound 24 (945 mg, 1.77 mmol, 1 eq.) was dissolved in dry DCM (9 mL). Diethylamine (646 mg, 914 µL, 8.84 mmol, 5 eq.) was added by syringe. The reaction mixture was stirred for 4 h at rt under inert atmosphere. DCM was evaporated. The crude product was purified by column chromatography (CHCl₃:MeOH, 15:1, R_f 0.38) to give 25 as a colorless solid (500 mg, 91%). ¹H NMR (400 MHz, CDCl₃): 0.94 (6H, dd, J=14.0, 6.3), 1.27 (3H, t, J=7.1), 1.28-1.37 (1H, m), 1.45 (2H, s), 1.57-1.83 (2H, m), 1.92-2.08 (1H, m), 2.16-2.26 (1H, m), 2.26-2.49 (2H, m), 3.39 (1H, dd, J=10.0, 3.9), 4.19 (2H, dq, J=7.1, 1.4), 4.54 (1H, dt, J=8.5, 4.8), 5.30 (1H, s), 7.85 (1H, d, J=8.3). ¹³C NMR (101 MHz, CDCl₃): 14.25, 21.40, 23.54, 24.97, 27.71, 36.82, 44.29, 51.48, 53.60, 54.86, 61.65, 171.99, 175.99, 193.67. Optical rotation: $[\alpha]^{12}_D$ -54.8° (c 0.323, CHCl3). IR (CHCl3): 3412 w, 3343 w, 2110 vs, 1731 s, 1663 s, 1643 sh, s, 1603 sh, w, 1510 s, 1413 w, 1386 sh, s, 1376 sh, s, 1370 sh, s, 1349 m, 1145 m, 1105 s cm⁻¹. ESI MS: 335 ([M+Na]⁺). HR ESI MS: calcd for $C_{14}H_{25}O_4N_4$ 313.18703; found 313.18712.

Synthesis of 2-(2-amino-4-methylpentanamido)-6-diazo-5-oxohexanoic acid triethylammonium salt (26)

2-(2-Amino-4-methylpentanamido)-6-diazo-5-oxohexanoic acid triethylammonium salt (26)

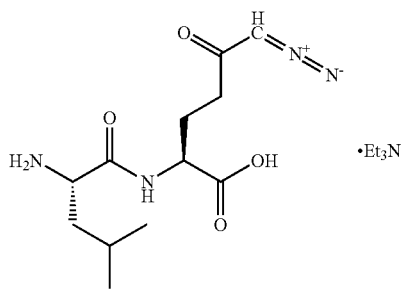 [SMILES: "·Et3N" ; CC(C)C[C@H](N)C(=O)N[C@@H](CCC(=O)C=[N+]=[N-])C(=O)O]

Compound 25 (134 mg, 0.429 mmol, 1 eq.) was suspended in EtOH (3 mL) and THF (3 mL). 1M solution of NaOH (16 mg, 408 µL, 0.95 eq.) was added and the mixture was stirred for 15 minutes. The reaction was quenched with 1 M formic acid (408 µL, 0.95 eq.) and after 10 minutes of stirring the mixture was evaporated to dryness. The crude product was purified by preparative HPLC with Et₃N/

CH$_3$COOH buffer. The desired product 26 was obtained as a light orange solid (46 mg) in 40% yield. $^1$H NMR (400 MHz, CDCl$_3$): 1.10 (6H, d, J=6.4), 1.50-1.61 (1H, m), 1.63-1.83 (2H, m), 1.96-2.06 (1H, m), 2.11-2.23 (1H, m), 2.33-2.48 (1H, m), 3.67 (1H, dd, J=8.6, 5.6), 4.27 (1H, dd, J=7.0, 5.1), 5.51 (1H, brs).

Synthesis of ethyl 2-(2-(2-amino-4-methylpentanamido)-4-methylpentanamido)-6-diazo-5-oxohexanoate (28)

Ethyl 11-(4-diazo-3-oxobutyl)-1-(9H-fluoren-9-yl)-5,8-diisobutyl-3,6,9-trioxo-2-oxa-4,7,10-triazadodecan-12-oate (27)

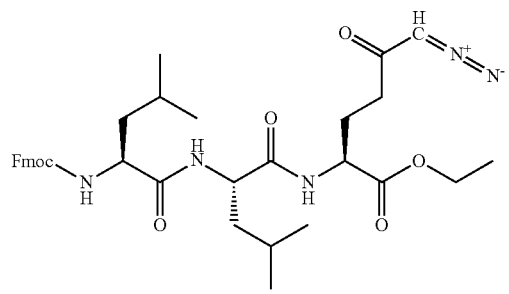

Referring to scheme 4, Fmoc-NH-(L)-Leu-COOH (125 mg, 0.352 mmol, 1.1 eq.) and HBTU (146 mg, 0.384 mmol, 1.2 eq.) were suspended in dry DCM (3 mL). DIEA (124 mg, 167 µL, 0.960 mmol, 3 eq.) and then the solution of 25 (100 mg, 0.320 mmol, 1 eq.) in dry DCM (3 mL) were added by syringe. The reaction mixture was stirred for 3 h at rt under inert atmosphere. DCM (10 mL) was added and the organic phase was washed with sat. NaHCO$_3$ (20 mL), 1M HCl (20 mL), water (2×20 mL) and sat. NaCl (20 mL), dried oved MgSO$_4$. DCM was evaporated. The crude product was purified by column chromatography (DCM:EtOAc, 2:1, R$_f$ 0.35) to give 27 as a colorless solid (145 mg, 79%). $^1$H NMR (400 MHz, CDCl$_3$): 0.92 (6H, d, J=6.5), 0.95 (6H, d, J=6.1), 1.28 (3H, t, J=7.1), 1.49-1.59 (2H, m), 1.60-1.74 (4H, m), 1.95-2.06 (1H, m), 2.18-2.28 (1H, m), 2.30-2.50 (2H, m), 4.17-4.27 (4H, m), 4.32-4.64 (4H, m), 5.29 (1H, d, J=8.0), 5.35 (1H, s), 6.54 (1H, d, J=8.0), 7.00 (1H, d, J=7.7), 7.31 (2H, t, J=7.5, 2.6), 7.40 (2H, td, J=7.3, 2.2), 7.57 (2H, d, J=7.5), 7.76 (2H, d, J=7.5). $^{13}$C NMR (101 MHz, CDCl$_3$): 14.26, 21.96, 22.17, 22.94, 23.15, 24.85, 27.12, 29.84, 36.48, 38.28, 41.17, 41.33, 47.27, 51.94, 52.03, 61.79, 67.22, 120.14, 120.16, 125.10, 125.14, 127.23 (2C), 127.90, 127.91, 141.43, 143.75, 143.89, 156.43, 171.54, 171.81, 172.39, 194.00. Optical rotation: [α]$^{22}_D$–34.5° (c 0.109, DMF). IR (CHCl3): 3426 m, 3317 w, br, 3116 w, 3068 w, 2961 s, 2873 m, 2109 s, 1795 w, 1731 vs, 1719 vs, 1667 vs, br, 1635 s, sh, 1508 vs, 1478 m, 1468 m, 1451 s, 1385 s, 1375 s, 1371 s, 1233 s, 1045 m, 1033 m, 622 w, 426 w, cm$^{-1}$. ESI MS: 670 ([M+Na]$^+$). HR ESI MS: calcd for C$_{25}$H$_{45}$O$_7$N$_5$Na 670.32112; found 670.32122.

Ethyl 2-(2-(2-amino-4-methylpentanamido)-4-methylpentanamido)-6-diazo-5-oxohexanoate (28)

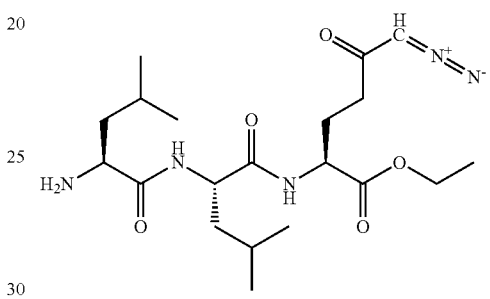

Compound 27 (136 mg, 0.210 mmol, 1 eq.) was dissolved in dry DCM (3 mL). Diethylamine (77 mg, 109 µL, 1.05 mmol, 5 eq.) was added by syringe. The reaction mixture was stirred for 8 h at rt under inert atmosphere. DCM was evaporated. The crude product was purified by column chromatography (CHCl$_3$/MeOH 20:1, R$_f$ 0.30) to give 28 as a light yellow oil (77 mg, 87%). $^1$H NMR (400 MHz, CDCl$_3$): 0.92 (6H, t, J=6.0), 0.95 (6H, t, J=5.9), 1.26 (3H, t, J=7.1), 1.34-1.41 (1H, m), 1.52-1.61 (1H, m), 1.60-1.79 (4H, m), 1.95-2.03 (1H, m), 2.15-2.25 (1H, m), 2.30-2.52 (2H, m), 3.48 (1H, dd, J=9.5, 4.1), 3.96 (2H, s), 4.18 (2H, q, J=7.1), 4.41 (1H, td, J=8.8, 5.4), 4.49 (1H, td, J=8.0, 4.6), 5.36 (1H, s), 7.08-7.17 (1H, m), 7.74 (1H, d, J=8.2). $^{13}$C NMR (101 MHz, CDCl$_3$); 14.25, 21.51, 22.02, 23.06, 23.45, 24.91, 24.97, 27.03, 36.49, 40.77, 43.77, 51.63, 52.04, 53.54, 55.13, 61.76, 171.60, 172.44, 175.74, 194.29. Optical rotation: [α]$^{22}_D$–25.8° (c 0.124, DMF). IR (KBr): 3413 s, vbr, 3314 s, vbr, 3072 m, br, 2105 s, 1739 s, 1655 vs, br, 1539 s, br, 1468 s, 1386 s, 1370 s, 1208 s, br, 1029 s, cm$^{-1}$. ESI MS: 426 ([M+H]$^+$). HR ESI MS: calcd for C$_{20}$H$_{36}$O$_5$N$_5$ 426.27110; found 426.27124.

Scheme 5

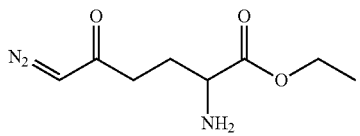

NaOH | rt, THF

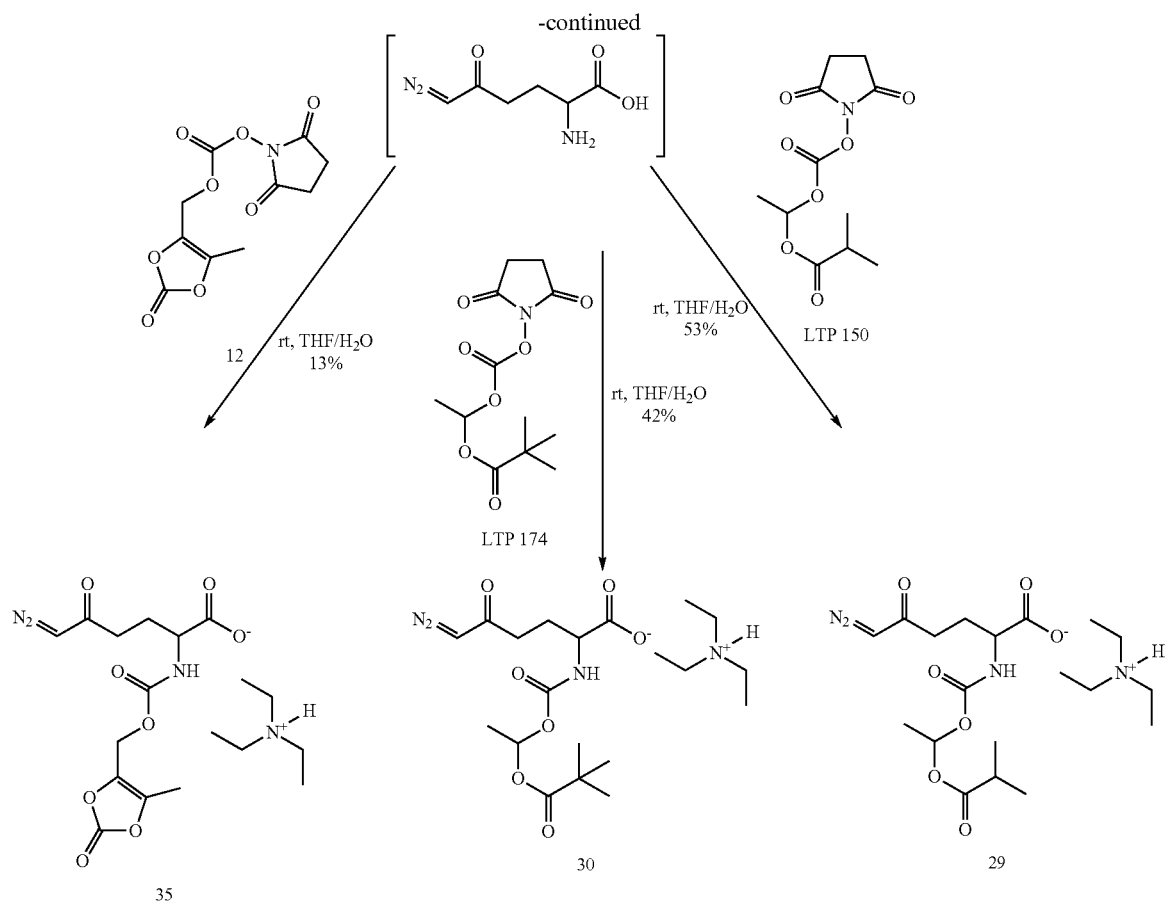

Synthesis of 6-diazo-2-(((1-(isobutyryloxy)ethoxy)carbonyl)amino)-5-oxohexanoic acid triethylammonium salt (29)

6-Diazo-2-(((1-(isobutyryloxy)ethoxy)carbonyl)amino)-5-oxohexanoic acid triethylammonium salt (29)

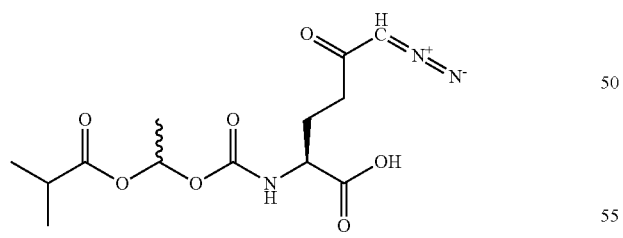

Referring to scheme 5, compound 20 (121 mg, 0.607 mmol, 1 eq.) was dissolved in THF (5 mL). 1M solution of NaOH (24 mg, 607 μL, 1 eq.) was added and the mixture was stirred for 1 h. Water (2 mL) and 1-[[[(2,5-Dioxopyrrolidin-1-yl)oxy]carbonyl]oxy]ethyl 2-methylpropanoate (LTP 150) (183 mg, 0.668 mmol, 1.1 eq.) in THF (3 mL) were added. The solution was stirred for next 2 h at rt. The reaction was quenched with 1 M formic acid (607 μL, 1 eq.) and after 5 minutes of stirring the mixture was evaporated to dryness. The crude product was purified by preparative HPLC with Et$_3$N/CH$_3$COOH buffer to give 29 as a light orange solid (106 mg, 53%). $^1$H NMR (400 MHz, CDCl$_3$): 1.11 (6H, d, J=6.4), 1.35-1.46 (3H, m), 1.84-2.32 (2H, m), 2.36-2.75 (2H, m), 4.15-4.48 (1H, m), 4.60-4.97 (1H, m), 5.70-6.12 (1H, m), 6.67-6.82 (1H, m), 8.40 (1H, bs).

Synthesis of 6-diazo-2-(((1-(pivaloyloxy)ethoxy)carbonyl)amino)-5-oxohexanoic acid triethylammonium salt (30)

6-Diazo-2-(((1-(pivaloyloxy)ethoxy)carbonyl)amino)-5-oxohexanoic acid triethylammonium salt (30)

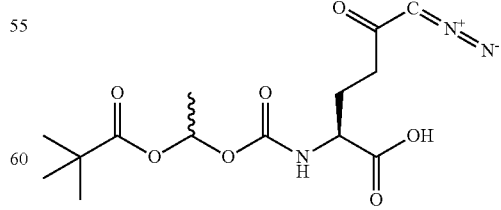

Referring to scheme 5, compound 20 (89 mg, 0.446 mmol, 1 eq.) was dissolved in THF (3 mL). 1M solution of NaOH (18 mg, 446 μL, 1 eq.) was added and the mixture was stirred for 1 h. Water (1 mL) and 1-((((2,5-Dioxopyrrolidin-1-yl)oxy)carbonyl)oxy)ethyl pivalate (LTP174) (141 mg, 0.490 mmol, 1.1 eq.) in THF (1.5 mL) were added. The solution was stirred for next 2 h at rt. The reaction was quenched with 1 M formic acid (446 µL, 1 eq.) and after 5 minutes of stirring the mixture was evaporated to dryness. The crude product was purified by preparative HPLC with Et$_3$N/CH$_3$COOH buffer to give 30 as a light orange solid (64 mg) in 42% yield. $^1$H NMR (400 MHz, CDCl$_3$): 1.18 (9H, s), 1.36-1.59 (3H, m), 1.94-2.36 (2H, m), 2.40-2.77 (2H, m), 4.18-4.48 (1H, m), 4.53-4.97 (1H, m), 5.45-6.07 (1H, m), 6.68-6.84 (1H, m), 8.87 (1H, bs).

Synthesis of ethyl 6-diazo-2-(((1-(isobutyryloxy)ethoxy)carbonyl)amino)-5-oxohexanoate (31)

Ethyl 6-diazo-2-(((1-(isobutyryloxy)ethoxy)carbonyl)amino)-5-oxohexanoate (31)

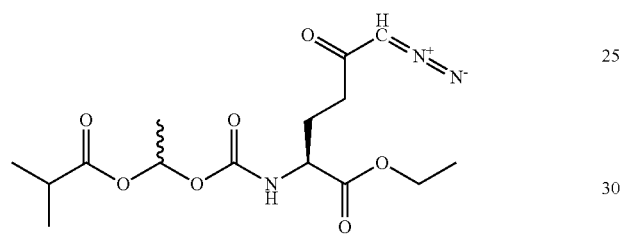

1-[[[(2,5-Dioxopyrrolidin-1-yl)oxy]carbonyl]oxy]ethyl 2-methylpropanoate (226 mg, 0.828 mmol, 1.1 eq) was suspended in dry DCM (6 mL). The reaction mixture was cooled to 0° C., and compound 20 (150 mg, 0.753 mmol, 1 eq.) in dry DCM (3 mL) was added by drop wise. The mixture was stirred for 15 minutes at 0° C., and then 1 h at rt. The crude product was purified by column chromatography (EtOAc/hexane 1:10 to 1:2) and the desired compound 31 was obtained in 56% yield (150 mg) as a yellow oil (mixture of two stereoisomers 1:1). $^1$H NMR (400 MHz, CDCl$_3$, Stereoisomer 1): 1.14 (6H, d, J=6.7), 1.27 (3H, t, J=7.1), 1.46 (3H, d, J=5.4), 1.88-2.09 (1H, m), 2.16-2.29 (1H, m), 2.34-2.47 (2H, m), 2.51 (1H, sep, J=7.1), 4.19 (2H, q, J=7.1), 4.27-4.36 (1H, m), 5.29 (1H, brs), 5.49 (1H, d, J=8.3), 6.78 (1H, q, J=7.7). $^{13}$C NMR (101 MHz, CDCl$_3$, Stereoisomer 1): 14.26, 18.78, 18.80, 19.84, 27.73, 33.99, 36.35, 53.39, 54.92, 61.92, 89.54, 153.87, 171.62, 175.18, 193.54. $^1$H NMR (400 MHz, CDCl$_3$, Stereoisomer 2): 1.16 (6H, d, J=6.7), 1.27 (3H, t, J=7.1), 1.46 (3H, d, J=5.4), 1.88-2.09 (1H, m), 2.16-2.29 (1H, m), 2.34-2.47 (2H, m), 2.51 (1H, sep, J=7.1), 4.20 (2H, q, J=7.1), 4.27-4.36 (1H, m), 5.29 (1H, brs), 5.53 (1H, d, J=8.1), 6.80 (1H, q, J=7.7). $^{13}$C NMR (101 MHz, CDCl$_3$, Stereoisomer 2): 14.26, 18.80, 18.85, 19.87, 27.84, 33.99, 36.47, 53.50, 54.97, 61.92, 89.72, 153.95, 171.79, 175.30, 193.77. Optical rotation: $[\alpha]^{22}{}_D$+19.8° (c 0.177, CHCl3). IR (CHCl3): 3428 w, 3116 w, 2981 m, 2940 w, 2877 w, 2856 w, 2110 vs, 1741 vs, br, 1641 m, 1510 s, 1469 m, 1388 s, 1377 s, 1232 m, 1199 m, cm$^{-1}$. ESI MS: 380 ([M+Na]$^+$). HR ESI MS: calcd for C$_{15}$H$_{24}$O$_7$N$_3$ 358.16088; found 358.16118.

Scheme 6

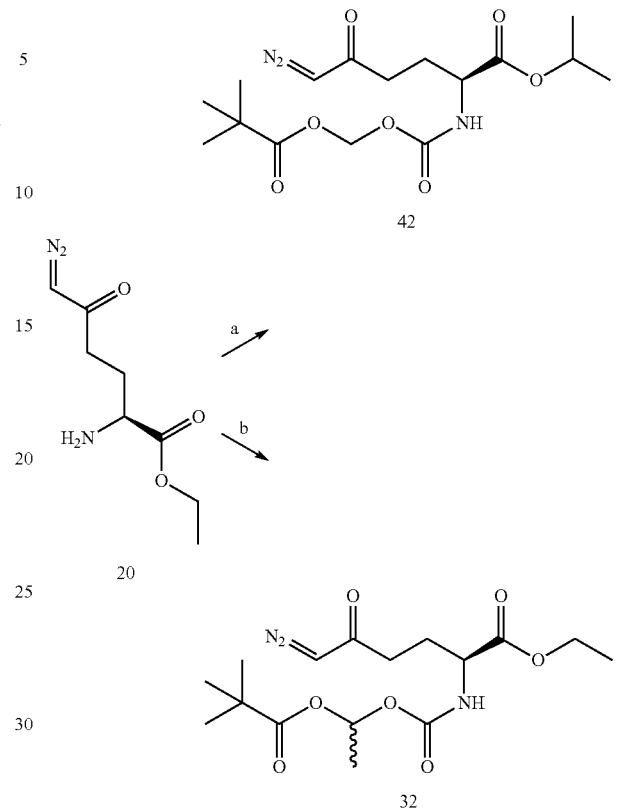

Reagents and conditions: (a) POM-NHS, DCM, 40% (b) Me-POM-NHS, DCM, 68%

Synthesis of ethyl 6-diazo-2-(((1-(pivaloyloxy)ethoxy)carbonyl)amino)-5-oxohexanoate (32)

Ethyl 6-diazo-2-(((1-(pivaloyloxy)ethoxy)carbonyl)amino)-5-oxohexanoate (32)

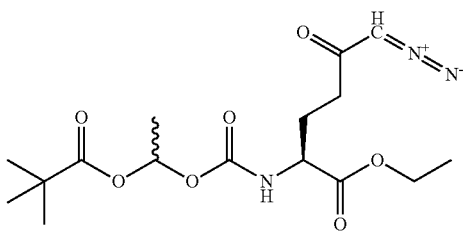 [SMILES: CCOC(=O)[C@H](CCC(=O)C=[N+]=[N-])NC(=O)OC(C)OC(=O)C(C)(C)C]

Referring to scheme 6, 1-((((2,5-Dioxopyrrolidin-1-yl)oxy)carbonyl)oxy)ethyl pivalate (238 mg, 0.828 mmol, 1.1 eq) was suspended in dry DCM (6 mL). The reaction mixture was cooled to 0° C., and compound 20 (150 mg, 0.753 mmol, 1 eq.) in dry DCM (3 mL) was added by drop wise. The mixture was stirred for 15 minutes at 0° C., and then 1 h at rt. The crude product was purified by column chromatography (EtOAc/hexane 1:10 to 1:2) and the desired compound 32 was obtained in 68% yield (190 mg) as a yellow oil (mixture of two stereoisomers 1:1). $^1$H NMR (400 MHz, CDCl$_3$, Stereoisomer 1): 1.16 (9H, s), 1.26 (3H, t, J=7.1), 1.43 (3H, s), 1.88-2.05 (1H, m), 2.14-2.26 (1H, m), 2.30-2.50 (2H, m), 4.18 (2H, q, J=7.1), 4.24-4.34 (1H, m), 5.31 (1H, brs), 5.51 (1H, d, J=7.7), 6.74 (1H, q, J=7.3). $^{13}$C NMR (101 MHz, CDCl$_3$, Stereoisomer 1): 14.23, 19.72, 26.95, 27.57, 36.31, 38.74, 53.33, 54.89, 61.85, 89.66, 153.87, 171.61, 176.56, 193.56. $^1$H NMR (400 MHz, CDCl$_3$, Stereoisomer 2): 1.18 (9H, s), 1.26 (3H, t, J=7.1), 1.45 (3H, s), 1.88-2.05 (1H, m), 2.14-2.26 (1H, m), 2.30-2.50 (2H, m), 4.18 (2H, q, J=7.1), 4.24-4.34 (1H, m), 5.33 (1H, brs), 5.55 (1H, d, J=7.9), 6.76 (1H, q, J=7.3). $^{13}$C NMR (101 MHz, CDCl$_3$, Stereoisomer 2): 14.24, 19.74, 26.97, 27.80, 36.46, 38.75, 53.48, 54.89, 61.87, 89.81, 153.95, 171.77, 176.68, 193.75. Optical rotation: $[\alpha]^{22}_D$+16.2° (c 0.259, CHCl3). IR (CHCl3): 3428 m, 3358 w, 3116 w, 2982 s, 2874 m, 2110 s, 1740 vs, 1640 s, 1510 s, 1480 m, 1393 s (sh), 1377 s, 1349 s, 1284 s, 1232 s, 1025 s, cm$^{-1}$. ESI MS: 394 ([M+Na]$^+$). HR ESI MS: calcd for C$_{16}$H$_{25}$O$_7$N$_3$Na 394.15847; found 394.15886.

Synthesis of ethyl 2-(2-amino-3-(1H-indol-3-yl) propanamido)-6-diazo-5-oxohexanoate (34)

Ethyl 2-(2-((((9H-fluoren-9-yl)methoxy)carbonyl) amino)-3-(1H-indol-3-yl) propanamido)-6-diazo-5-oxohexanoate (33)

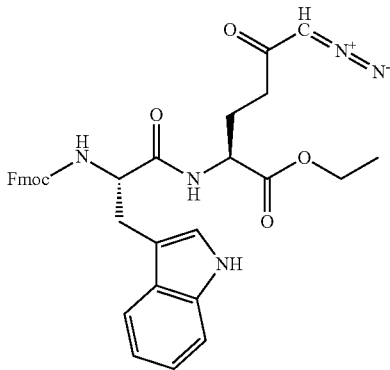

Referring to scheme 7, Fmoc-NH-(L)-Trp-COOH (353 mg, 0.828 mmol, 1.1 eq.) and HBTU (343 mg, 0.904 mmol, 1.2 eq.) were suspended in dry DCM (5 mL). DIEA (292 mg, 394 µL, 2.26 mmol, 3 eq.) and then the solution of 20 (150 mg, 0.753 mmol, 1 eq.) in dry DCM (3 mL) were added by syringe. The reaction mixture was stirred for 2 h at rt under inert atmosphere. DCM (20 mL) was added and the organic phase was washed with sat. NaHCO$_3$ (20 mL), 1M HCl (20 mL), water (30 mL) and sat. NaCl (30 mL), dried over MgSO$_4$. DCM was evaporated. The crude product was purified by LC (DCM/EtOAc 2:1, R$_f$ 0.21) to give 33 as a light yellow solid (303 mg) in 66% yield. $^1$H NMR (400 MHz, CDCl$_3$): 1.22 (3H, t, J=7.2), 1.82-1.93 (1H, m), 2.00-2.26 (3H, m), 3.18 (1H, dd, J=14.5, 7.1), 3.38 (1H, dd, J=14.0, 5.3), 4.09 (2H, q, J=8.2), 4.20 (1H, t, J=7.1), 4.32-4.48 (3H, m), 4.50-4.59 (1H, m), 5.05 (1H, bs), 5.51 (1H, d, J=7.9), 6.61 (1H, d, J=7.5), 7.07 (1H, bs), 7.13 (1H, t, J=7.4), 7.20 (1H, t, J=7.2), 7.30 (2H, t, J=7.5), 7.35 (1H, d, J=8.0), 7.40 (2H, t, J=7.5), 7.57 (2H, t, J=6.6), 7.67 (1H, d, J=7.9), 7.76 (2H, d, J=7.6), 8.28 (1H, bs). $^{13}$C NMR (101 MHz, CDCl$_3$): 14.20, 27.09, 28.51, 36.20, 47.25, 52.13, 54.86, 55.76, 61.77, 67.25, 110.29, 111.39, 118.88, 120.00, 120.10, 120.11, 122.41, 123.66, 125.25, 125.29, 126.92, 127.22 (2C), 127.62, 127.86 (2C), 136.38, 141.40, 143.87, 143.96, 156.09, 171.28, 171.48, 193.84. Optical rotation: $[\alpha]^{22}_D$-28.6° (c 0.178, DMF). IR (KBr): 3424 s, 3308 m, sh, 2978 w, 2106 m, 1728 s, 1697 m, sh, 1654 m, 1519 m, 1478 w, 1450 m, 1382 m, sh, 1376 m, 1343 m, 1289 m, 1224 m, 1104 m-w, 1081 m-w, 1040 m, 1032 m, 877 w, 855 w, 760 m, 742 m, 621 m, 427 w, cm$^{-1}$. ESI MS: 630 ([M+Na]$^+$). HR ESI MS: calcd for C$_{34}$H$_{33}$O$_6$N$_5$Na 630.23230; found 630.23236.

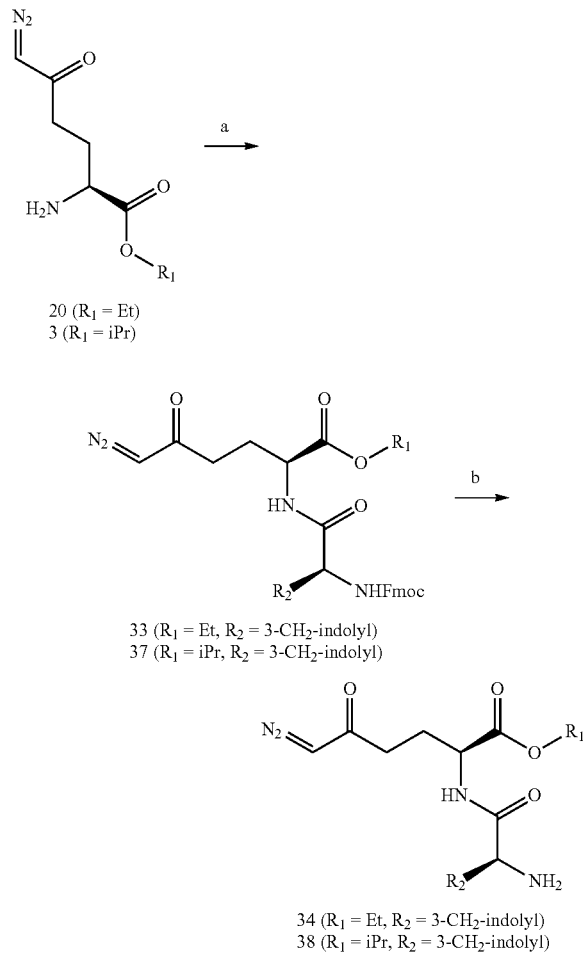

Scheme 7

20 (R$_1$ = Et)
3 (R$_1$ = iPr)

33 (R$_1$ = Et, R$_2$ = 3-CH$_2$-indolyl)
37 (R$_1$ = iPr, R$_2$ = 3-CH$_2$-indolyl)

34 (R$_1$ = Et, R$_2$ = 3-CH$_2$-indolyl)
38 (R$_1$ = iPr, R$_2$ = 3-CH$_2$-indolyl)

Reagents and conditions: (a) Fmoc-NH-(L)-Trp-COOH, HBTU, DIEA, DCM for 33 (66%) and 37 (46%); (b) piperidine, DCM, rt, 50% for 34; 53% for 38.

Ethyl 2-(2-amino-3-(1H-indol-3-yl)propanamido)-6-diazo-5-oxohexanoate (34)

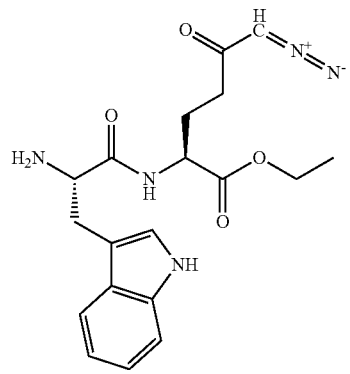 [SMILES: CCOC(=O)[C@H](CCC(=O)C=[N+]=[N-])NC(=O)[C@@H](N)Cc1c[nH]c2ccccc12]

Referring to scheme 7, compound 33 (303 mg, 0.499 mmol, 1 eq.) was dissolved in dry DCM (5 mL). Piperidine (212 mg, 244 μL, 2.49 mmol, 5 eq.) was added by syringe. The reaction mixture was stirred for 4.5 h at rt under inert atmosphere. DCM was evaporated. The crude product was purified by column LC (CHCl$_3$/MeOH 20:1 to 10:1, R$_f$ 0.29) and a colorless solid 34 (96 mg) was obtained in 50% yield. $^1$H NMR (400 MHz. CDCl$_3$): 1.27 (3H, t, J=7.0), 1.57 (2H, bs), 1.91-2.01 (11, m), 2.06-2.27 (3H, m), 3.05 (1H, dd, J=14.4, 8.1), 3.30 (1H, dd, J=14.4, 4.0), 3.75 (1H, dd, J=8.1, 4.2), 4.18 (1H, qd, J=7.1, 2.0), 4.55 (1H, td, J=8.3, 4.1), 5.11 (1H, bs), 7.09 (1H, d, J=2.4), 7.12 (1H, ddd, J=8.1, 7.0, 1.1), 7.20 (1H, ddd, J=8.1, 7.0, 1.2), 7.37 (1H, dt, J=8.2, 1.0), 7.68 (1H, dd, J=7.9, 1.1), 7.88 (1H, d, J=8.3), 8.31 (1H, bs). $^{13}$C NMR (101 MHz, CDCl$_3$): 14.29, 27.60, 30.82, 36.58, 51.56, 54.77, 55.50, 61.71, 111.36, 111.49, 119.23, 119.79, 122.39, 123.45, 127.69, 136.52, 171.92, 175.02, 193.81. Optical rotation: [α]$^{22}_D$ −57.6° (c 0.210, DMF). IR (CHCl3): 3479 m, 3355 w, 3215 vw, 3116 w, 2982 m, 2930 m, 2872 w, 2855 w, 2110 vs, 1737 s, 1687 s, 1641 m, 1511 m, 1373 m, 1353 m, 1336 m, sh, 1191 m, 1115 w, 1092 m, 1009 w, cm$^{-1}$. ESI MS: 408 ([M+Na]$^+$). HR ESI MS: calcd for C$_{19}$H$_{23}$O$_4$N$_5$Na 408.16423; found 408.16435.

Synthesis of 6-diazo-2-(((((5-methyl-2-oxo-1,3-dioxol-4-yl)methoxy)carbonyl)amino)-5-oxohexanoic acid triethylammonium salt (35)

6-Diazo-2-(((((5-methyl-2-oxo-1,3-dioxol-4-yl)methoxy)carbonyl)amino)-5-oxohexanoic acid triethylammonium salt (35)

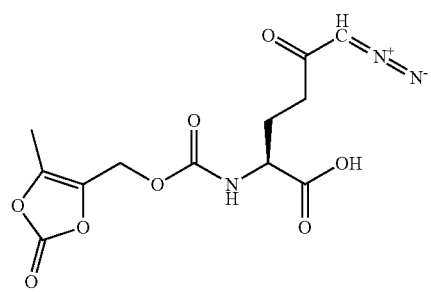 [SMILES: Cc1oc(=O)oc1COC(=O)N[C@@H](CCC(=O)C=[N+]=[N-])C(=O)O]

Referring to scheme 5, compound 20 (238 mg, 1.19 mmol, 1 eq.) was dissolved in THF (10 mL). 1M solution of NaOH (48 mg, 1.18 mL, 1 eq.) was added and the mixture was stirred for 1 h. Water (4 mL) and 12 (389 mg, 1.43 mmol, 1.2 eq.) in THF (10 mL) were added. The solution was stirred for next 2 h at rt. The reaction was quenched with 1 M formic acid (1.15 mL, 0.95 eq.) and after 5 minutes of stirring the mixture was evaporated to dryness. The crude product was purified by preparative HPLC with Et$_3$N/CH$_3$COOH buffer. The desired product 35 was obtained as a light orange solid (50 mg) in 13% yield. $^1$H NMR (400 MHz, CDCl$_3$): 1.96-2.28 (2H, m), 2.15 (3H, s), 2.37-2.70 (2H, m), 4.40-4.76 (1H, m), 4.98 (2H, s).

Scheme 8

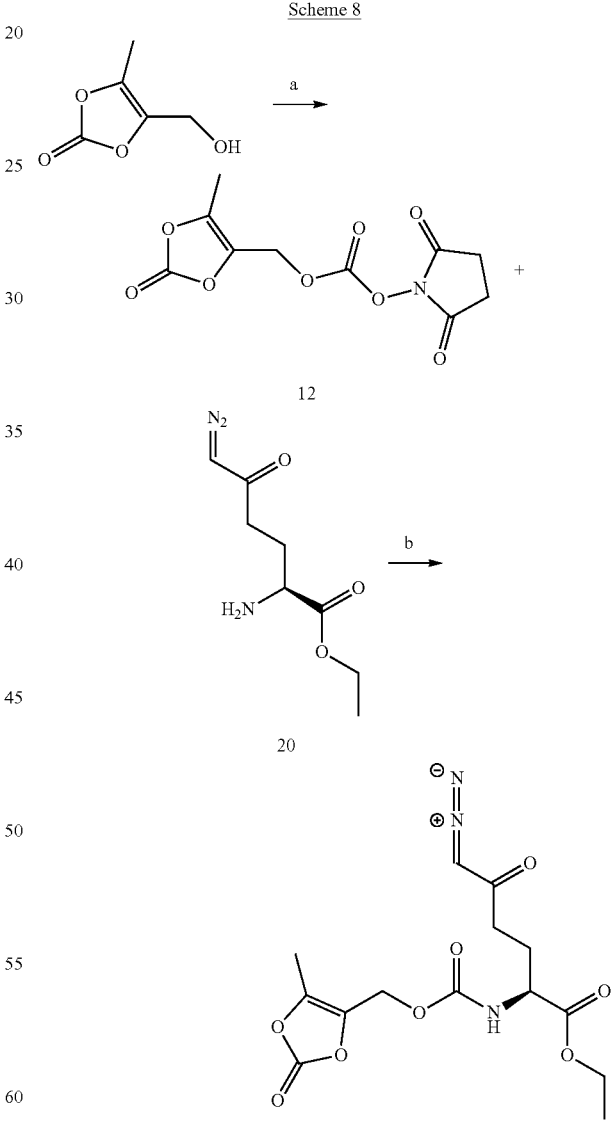

Reagents and conditions: (a) S-ethyl carbonochloridothionate, pyridine, Et$_2$O; NHS, peracetic acid, DCM 58%; (b) DCM, 0° C.-rt, 65%

Synthesis of ethyl 6-diazo-2-((((5-methyl-2-oxo-1,3-dioxol-4-yl)methoxy)carbonyl) amino)-5-oxohexanoate (36)

Ethyl 6-diazo-2-((((5-methyl-2-oxo-1,3-dioxol-4-yl)methoxy)carbonyl)amino)-5-oxohexanoate (36)

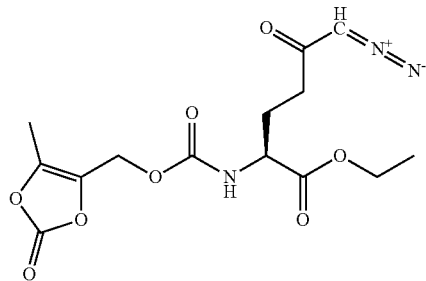 [SMILES: CCOC(=O)[C@H](CCC(=O)C=[N+]=[N-])NC(=O)OCc1oc(=O)oc1C]

Referring to scheme 8, compound 12 (180 mg, 0.663 mmol, 1.1 eq) was suspended in dry DCM (5 mL). The reaction mixture was cooled to 0° C., and compound 20 (120 mg, 0.602 mmol, 1 eq.) in dry DCM (3 mL) was added by drop wise. The mixture was stirred for 15 minutes at 0° C., and then 1 h at rt. The crude product was purified by column chromatography (EtOAc:hexane, 1:1) and the desired compound 36 was obtained in 65% yield (139 mg) as an yellow oil. $^1$H NMR (400 MHz, CDCl$_3$): 1.27 (3H, t, J=7.1), 1.95-2.06 (1H, m), 2.10-2.27 (1H, m), 2.16 (3H, s), 2.31-2.50 (2H, m), 4.19 (2H, q, J=7.1), 4.29 (1H, td, J=8.1, 4.8), 4.82 (2H, dd, J=13.9), 5.29 (1H, brs), 5.72 (1H, d, J=7.7). $^{13}$C NMR (101 MHz, CDCl$_3$): 9.48, 14.24, 27.18, 36.32, 53.76, 54.58, 55.00, 61.92, 133.90, 140.08, 152.30, 155.26, 171.63, 193.52. Optical rotation: [α]$^{22}_D$+12.2° (c 0.229, CHCl3). IR (CHCl3): 3425 m, 3345 w, vbr, 3116 w, 2111 vs, 1838 s, sh, 1820 vs, 1736 vs, 1722 vs, sh, 1640 s, 1511 s, 1229 s, 1200 s, 1114 m, 1097 m, 1045 s, cm$^{-1}$. ESI MS: 378 ([M+Na]$^+$). HR ESI MS: calcd for C$_{14}$H$_{17}$O$_8$N$_3$Na 378.09079; found 378.09102.

Synthesis of isopropyl 2-(2-amino-3-(1H-indol-3-yl)propanamido)-6-diazo-5-oxohexanoate (38)

Isopropyl 2-(2-((((9H-fluoren-9-yl)methoxy)carbonyl)amino)-3-(1H-indol-3-yl)propanamido)-6-diazo-5-oxohexanoate (37)

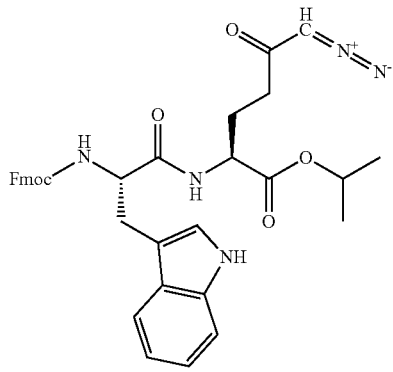

Referring to scheme 7, Fmoc-NH-(L)-Trp-COOH (880 mg, 2.06 mmol, 1.1 eq.) and HBTU (854 mg, 2.25 mmol, 1.2 eq.) were suspended in dry DMF (14 mL). DIEA (727 mg, 980 µL, 5.63 mmol, 3 eq.) and then the solution of 3 (400 mg, 1.88 mmol, 1 eq.) in dry DMF (5 mL) were added by syringe. The reaction mixture was stirred for 4 h at rt under inert atmosphere. DMF was evaporated, DCM (100 mL) was added and the organic phase was washed with sat. NaHCO$_3$ (100 mL), water (100 mL), IM HCl (100 mL), water (100 mL) and sat. NaCl (100 mL), dried over MgSO$_4$. DCM was evaporated. The crude product was purified by column chromatography (DCM:EtOAc, 5:1, R$_f$ 0.15) to give 37 as a light yellow solid (540 mg) in 46% yield. $^1$H NMR (400 MHz, CDCl$_3$): 1.19 (3H, d, J=6.3), 1.23 (3H, t, J=6.3), 1.81-1.92 (1H, m), 2.01-2.28 (3H, m), 3.18 (1H, dd, J=14.5, 7.1), 3.39 (1H, dd, J=14.2, 5.2), 4.20 (1H, t, J=7.1), 4.30-4.48 (3H, m), 4.54 (1H, q, J=6.9), 4.88-4.99 (1H, m), 5.07 (1H, bs), 5.50 (1H, d, J=7.9), 6.59 (1H, d, J=7.4), 7.07 (1H, bs), 7.14 (1H, t, J=7.0), 7.20 (1H, t, J=7.2), 7.30 (2H, tdd, J=7.5, 2.5, 1.1), 7.36 (1H, d, J=8.0), 7.40 (2H, t, J=7.5), 7.56 (2H, t, J=6.6), 7.67 (1H, d, J=7.9), 7.77 (2H, d, J=7.6), 8.23 (1H, bs). $^{13}$C NMR (101 MHz, CDCl$_1$): 21.78, 21.83, 27.20, 28.47, 36.20, 47.23, 52.19, 54.91, 55.75, 67.23, 69.22, 110.28, 111.40, 118.88, 120.03, 120.10, 120.12 (2C), 122.45, 123.66, 125.25, 125.30, 127.23 (2C), 127.61, 127.86 (2C), 136.35, 141.40 (2C), 143.85, 143.96, 156.09, 170.80, 171.42, 193.92. Optical rotation: [α]$^{22}_D$-32.0° (c 0.193, DMF). IR (KBr): 3424 s, 3300 m, 3130 vw, 2980 w, 2932 s, 2110 m, 1722 s, 1695 s, 1654 s, 1625 m, 1547 m, sh, 1532 m, 1520 m, sh, 1478 w, 1385 m, 1375 m, 1353 m, 1343 m, 1288 m, 1236 m, 1182 w, 11145 m, 1105 m, 1031 m–w, 1010 w, 852 w, 798 w, 758 m, 741 m, 621 w, 427 w–m, cm$^{-1}$. ESI MS: 644 ([M+Na]$^+$). HR ESI MS: calcd for C$_{35}$H$_{35}$O$_6$N$_5$Na 644.24795; found 644.24811.

Isopropyl 2-(2-amino-3-(1H-indol-3-yl)propanamido)-6-diazo-5-oxohexanoate (38)

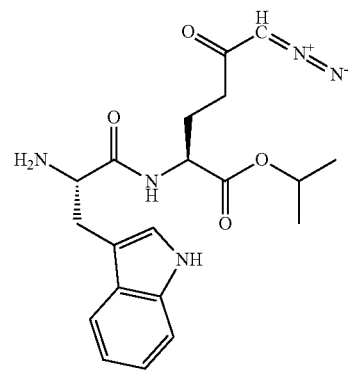 [SMILES: CC(C)OC(=O)[C@H](CCC(=O)C=[N+]=[N-])NC(=O)[C@@H](N)Cc1c[nH]c2ccccc12]

Referring to scheme 7, compound 37 (500 mg, 0.804 mmol, 1 eq.) was dissolved in dry DCM (15 mL). Piperidine (342 mg, 393 µL, 4.02 mmol, 5 eq.) was added by syringe. The reaction mixture was stirred for 4 h at rt under inert atmosphere. DCM was evaporated. The crude product was purified by column LC (CHCl$_3$/MeOH 30:1, R$_f$ 0.14) to give 38 as a yellow amorphous solid (170 mg) in 53% yield. $^1$H NMR (400 MHz, CDCl$_3$): 1.24 (3H, d, J=6.0), 1.25 (3H, d, J=6.0), 1.50 (2H, bs), 1.88-2.00 (1H, m), 2.04-2.27 (3H, m), 3.04 (1H, dd, J=14.4, 8.2), 3.30 (1H, ddd, J=14.2, 4.2, 0.9), 3.74 (1H, dd, J=8.1, 4.2), 4.51 (1H, td, J=8.3, 4.0), 5.02 (1H, hept, J=6.0), 5.11 (1H, bs), 7.08 (1H, d, J=2.3), 7.11 (1H, ddd, J=8.0, 7.1, 1.0), 7.19 (1H, ddd, J=8.1, 7.1, 1.1), 7.36 (1H, d, J=8.1), 7.67 (1H, d, J=7.9), 7.88 (1H, d, J=8.2), 8.45 (1H, bs). $^{13}$C NMR (101 MHz, CDCl$_3$): 21.83, 27.65, 30.81, 36.55, 51.64, 54.80, 55.51, 69.49, 111.37 (2C), 119.17, 119.72, 122.31, 123.48, 127.67, 136.53, 171.42, 175.09, 193.92. Optical rotation: $[\alpha]^{22}_D$ –1.2° (c 0.012, CHCl3). IR (CHCl3): 3311 m, vbr, 2980 w, 2924 w, 2874 w, vs, 2853 w, 2104 vs, 1731 s, 1650 s, br, 1618 m, sh, 1512 m, 1388 m, sh, 1375 s, 1253 m, 1232 m, 1183 m, 1145 m, 1105 s, 1010 w, 972 vw, 933 vw, 744 m, cm$^{-1}$. ESI MS: 422 ([M+Na]$^+$). HR ESI MS: calcd for $C_{20}H_{25}O_4N_5Na$ 422.17988; found 422.17992.

Synthesis of isopropyl 6-diazo-2-(((2-methyl-1-(pivaloyloxy)propoxy)carbonyl)amino)-5-oxo-hexanoate (40)

1-((((2,5-Dioxopyrrolidin-1-yl)oxy)carbonyl)oxy)-2-methylpropyl pivalate (39)

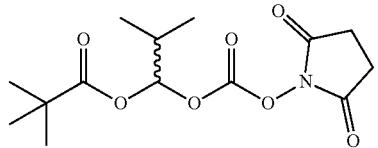 [SMILES: CC(C)C(OC(=O)ON1C(=O)CCC1=O)OC(=O)C(C)(C)C]

1-Chloro-2-methylpropyl carbonochloridate (2.00 g, 1.71 mL, 11.69 mmol, 1 eq.) was dissolved in dry Et$_2$O (20 mL). The reaction mixture was cooled to 0° C., and the mix of Et$_3$N (1.18 g, 1.63 mL, 11.69 mmol, 1 eq.) and EtSH (727 mg, 866 μL, 11.69 mmol, 1 eq.) dissolved in dry Et$_2$O (10 mL) was added by dropwise method during 10 minutes. The reaction mixture was stirred overnight (23 h) at rt, precipitate was filtered over pad of celite and solvent was removed under reduced pressure. The crude product O-(1-chloro-2-methylpropyl) S-ethyl carbonothioate (colorless liquid, 2.20 g, 96%) was used for further step without purification. O-(1-Chloro-2-methylpropyl) S-ethyl carbonothioate (1.20 g, 6.10 mmol, 1 eq.) was dissolved in pivalic acid (3.74 g, 4.20 mL, 36.61 mmol, 6 eq.) and freshly prepared salt of pivalic acid (1.87 g, 2.10 mL, 18.31 mmol, 3 eq.) and DIEA (2.37 g, 3.19 mL, 18.31 mmol, 3 eq.) was added in few portions. The reaction mixture was heated to 60° C. for 70 h. EtOAc (100 mL) was added and the organic phase was extracted with water (50 mL), sat. NaHCO$_3$ (3-50 mL), sat. NaCl (50 mL), dried over MgSO4 and solvent was evaporated. The crude product 1-(((ethylthio)carbonyl)oxy)-2-methylpropyl pivalate (light yellow liquid, 1.32 g, 83%) was used for further step without purification. 1-(((Ethylthio)carbonyl)oxy)-2-methylpropyl pivalate (1.28 g, 4.88 mmol, 1 eq.) was dissolved in dry DCM (13 mL), N-hydroxysuccinimide (1.12 g, 9.76 mmol, 2 eq.) was added and the suspension was cooled to 0° C. Peracetic acid (1.11 g (100%), 3.09 g (36%), 14.64 mmol, 3 eq., 36% solution in acetic acid) was added by dropwise in 10 minutes. The final mixture was stirred for 60 minutes at 0° C., and 2 h at rt. DCM (40 mL) was added and the organic phase was washed with water (20 mL) and sat. NaCl (20 mL) and dried over MgSO$_4$. DCM was evaporated and the product was purified by LC (hexane/EtOAc 5:3, R$_f$ 0.26). The product 39 was obtained as a light yellow oil (863 mg) in 56% yield (over 3 steps). $^1$H NMR (400 MHz, CDCl$_3$): 1.00 (6H, d, J=6.9), 1.21 (9H, s), 2.08-2.19 (1H, m), 2.81 (4H, s), 6.55 (1H, d, J=5.0). $^{13}$C NMR (101 MHz, CDCl$_3$): 16.06, 16.38, 25.55, 26.89, 31.84, 39.05, 98.19, 150.37, 168.48, 176.14. Optical rotation: $[\alpha]^{22}_D$ –3.0° (c 0.230, CHCl3). IR (CHCl3): 2978 m, 2938 w, 2878 w, 1821 s, 1795 s, 1748 vs, br, 1481 m, 1463 w, 1432 m, 1396 w, 1373 m, 1366 m, sh, 1279 m, 1199 s, 1046 m, 998 m, sh, 987 m, 932 s cm$^{-1}$. ESI MS: 338 ([M+Na]$^+$). HR ESI MS: calcd for $C_{14}H_{21}O_7NNa$ 338.12102; found 338.12115.

Isopropyl 6-diazo-2-(((2-methyl-1-(pivaloyloxy)propoxy)carbonyl)amino)-5-oxohexanoate (40)

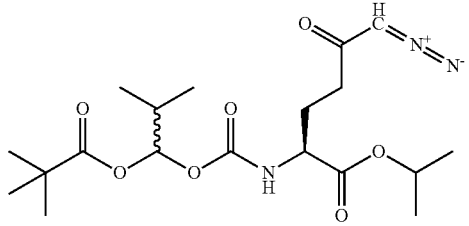 [SMILES: CC(C)OC(=O)[C@H](CCC(=O)C=[N+]=[N-])NC(=O)OC(OC(=O)C(C)(C)C)C(C)C]

Compound 39 (399 mg, 1.27 mmol, 0.9 eq) was suspended in dry DCM (7 mL). The reaction mixture was cooled to 0° C., and compound 3 (300 mg, 1.41 mmol, 1 eq.) in dry DCM (3 mL) was added by drop wise. The mixture was stirred for 15 minutes at 0° C. and then 2 h at rt. The crude product was purified by column chromatography (EtOAc/hexane 1:2, R$_f$ 0.29 and 0.31) and the desired compound 40 was obtained in 54% yield (285 mg) as a yellow oil (mixture of two stereoisomers 1:1). $^1$H NMR (400 MHz, CDCl$_3$, stereoisomer 1): 0.94 (6H, d, J=6.8), 1.16 (9H, s), 1.23 (6H, t, J=6.3), 1.83-2.50 (4H, m), 4.22-4.31 (1H, m), 5.02 (1H, hept, J=6.8), 5.29 (1H, bs), 5.48 (1H, d J=8.3), 6.52 (1H, d, J=4.9). $^{13}$C NMR (101 MHz, CDCl$_3$, stereoisomer 1): 16.40, 16.54, 27.00, 28.05, 31.87, 36.29, 38.96, 53.38, 54.82, 69.64, 94.21, 154.28, 171.31, 176.56, 193.87. $^1$H NMR (400 MHz, CDCl$_3$, stereoisomer 2): 0.93 (6H, d, J=6.8), 1.18 (9H, s), 1.22 (6H, t, J=6.3), 1.83-2.50 (4H, m), 4.22-4.31 (1H, m), 5.00 (1H, sept, J=6.8), 5.37 (1H, bs), 5.45 (1H, d, J=8.3), 6.48 (1H, d, J=4.9). $^{13}$C NMR (101 MHz, CDCl$_3$, stereoisomer 2): 16.37, 16.54, 26.98, 27.74, 31.91, 36.55, 38.92, 53.54, 54.82, 69.66, 93.87, 154.22, 171.17, 176.81, 193.58. Optical rotation: $[\alpha]^{22}_D$ +11.5° (c 0.261, CHCl3). IR (CHCl3): 3428 m, 3116 w, 2982 s, 2936 m, 2878 m, 2110 vs, 1741 vs, br, 1731 vs, sh, 1641 s, 1508 s, 1480 m, 1463 m, 1400 m, sh, 1385 s, sh, 1377 s, 1365 s, sh, 1281 s, 1231 s, 1183 m, 1146 s, 1105 s, 990 s, 941 m cm$^{-1}$. ESI MS: 436 ([M+Na]$^+$). HR ESI MS: calcd for $C_{19}H_{31}O_7N_3Na$ 436.20542; found 436.20553.

Synthesis of isopropyl 6-diazo-5-oxo-2-(((((pivaloyloxy)methoxy)carbonyl)amino) hexanoate (42)

(((((2,5-Dioxopyrrolidin-1-yl)oxy)carbonyl)oxy) methyl pivalate (41)

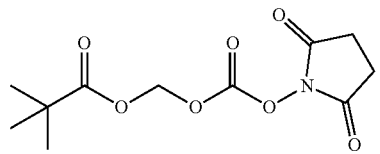 [SMILES: CC(C)(C)C(=O)OCOC(=O)ON1C(=O)CCC1=O]

Chloromethyl carbonochloridate (2.00 g, 1.38 mL, 15.51 mmol, 1 eq.) was dissolved in dry Et$_2$O (20 mL). The reaction mixture was cooled to 0° C., and the mix of Et$_3$N (1.57 g, 2.16 mL, 15.51 mmol, 1 eq.) and EtSH (964 mg, 1.15 mL, 15.51 mmol, 1 eq.) dissolved in dry Et$_2$O (5 mL) was added by dropwise method during 5 minutes. The reaction mixture was stirred overnight (25 h) at rt, precipitate was filtered over pad of celite and solvent was removed under reduced pressure. The crude product O-(chloromethyl) S-ethyl carbonothioate (colorless liquid) was used for further step without purification. O-(Chloromethyl) S-ethyl carbonothioate (2.40 g, 15.51 mmol, 1 eq.) was dissolved in pivalic acid (9.51 g, 93.14 mmol, 6 eq.) and freshly prepared salt of pivalic acid (4.76 g, 46.57 mmol, 3 eq.) and DIEA (6.02 g, 8.1 mL, 46.57 mmol, 3 eq.) was added in few portions. The reaction mixture was heated to 60° C. for 22 h. EtOAc (100 mL) was added and the organic phase was extracted with water (100 mL), sat. NaHCO$_3$ (3×100 mL), sat. NaCl (100 mL), dried over MgSO$_4$ and solvent was evaporated. The crude product (((ethylthio)carbonyl)oxy) methyl pivalate (light yellow liquid, 3.30 g, 97%) was used for further step without purification. (((Ethylthio)carbonyl) oxy)methyl pivalate (3.20 g, 14.53 mmol, 1 eq.) was dissolved in dry DCM (40 mL), N-hydroxysuccinimide (3.34 g, 29.05 mmol, 2 eq.) was added and the suspension was cooled to 0° C. Peracetic acid (3.31 g (100%), 9.21 g (36%), 43.58 mmol, 3 eq., 36% solution in acetic acid) was added by dropwise in 15 minutes. The final mixture was stirred for 60 minutes at 0° C., and 2 h at rt. DCM (50 mL) was added and the organic phase was washed with water (30 mL) and sat. NaCl (30 mL) and dried over MgSO4. DCM was evaporated and the product was purified by LC (hexane: EtOAc, 2:1, R$_f$ 0.27). The product 41 was obtained as a colorless solid (2.54 g) in 64% yield (over 3 steps). $^1$H NMR (400 MHz, CDCl$_3$): 1.24 (9H, s), 2.84 (4H, s), 5.86 (2H, s). $^{13}$C NMR (101 MHz, CDCl$_3$): 25.56 (2C), 26.86 (3C), 38.96, 83.67, 150.90, 168.34 (2C), 176.54. IR (CHCl3): 2979 m, 2939 w, 2876 w, 1823 s, 1796 vs, 1649 vs, 1481 m, 1463 m, 1456 w, 1431 m, 1398 w, 1371 m, 1367 m, 1280 m, 1199 vs, 1110 vs, 1047 m, 998 s, 986 s, 942 m, sh, 924 s, 853 w, cm$^{-1}$. ESI MS: 296 ([M+Na]$^+$). HR ESI MS: calcd for C$_{11}$H$_{15}$O$_7$NNa 296.07407; found 296.07410.

Isopropyl 6-diazo-5-oxo-2-((((pivaloyloxy)methoxy) carbonyl)amino) hexanoate (42)

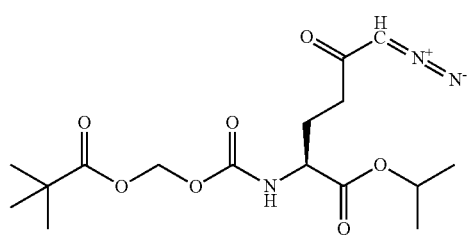 [SMILES: CC(C)OC(=O)[C@H](CCC(=O)C=[N+]=[N-])NC(=O)OCOC(=O)C(C)(C)C]

Referring to scheme 6, compound 41 (320 mg, 1.17 mmol, 1.0 eq) was suspended in dry DCM (6 mL). The reaction mixture was cooled to 0° C., and NH$_2$-DON-COOEt (250 mg, 1.17 mmol, 1 eq.) in dry DCM (3 mL) was added by drop wise. The mixture was stirred for 15 minutes at 0° C., and then 2 h at rt. The crude product was purified by column chromatography (EtOAc:hexane, 1:2, R$_f$ 0.21) and the desired compound 42 was obtained in 40% yield (175 mg) as a yellow oil. $^1$H NMR (400 MHz, CDCl$_3$): 1.19 (9H, s), 1.23 (3H, d, J=6.2), 1.24 (3H, d, J=6.2), 1.90-2.05 (1H, m), 2.14-2.25 (1H, m), 2.31-2.51 (2H, m), 4.28 (1H, td, J=8.2, 4.7), 5.03 (1H, hept, J=6.2), 5.27 (1H, bs), 5.65 (1H, d, J=8.1), 5.69 (1H, d, 0.1=5.7), 5.73 (1H, d, J=5.7). $^{13}$C NMR (101 MHz, CDCl$_3$): 21.79, 21.81, 26.97, 36.34, 38.86, 53.63, 54.90, 69.75, 80.33, 154.40, 171.01, 177.51, 193.43. Optical rotation: [α]$^{22}_D$+13.0° (c 0.184, CHCl3). IR (CHCl3): 3424 m, 3354 w, br, 3116 w, 2984 s, 2937 m, 2875 s, 2110 vs, 1747 vs, 1730 vs, sh, 1642 s, 1512 s, 1481 m, 1466 m, 1453 m, 1377 s, 1282 s, 1182 m, 1145 s, 1105 s, 994 s, 942 m, cm$^{-1}$. ESI MS: 394 ([M+Na]$^+$). HR ESI MS: calcd for C$_{16}$H$_{25}$O$_7$N$_3$Na 394.15847: found 394.15855.

Synthesis of isopropyl 6-diazo-5-oxo-2-((((2-(pivaloyloxy)propan-2-yl)oxy)carbonyl) amino) hexanoate (44)

2-(((4-Nitrophenyloxy)carbonyl)oxy)propan-2-yl pivalate (43)

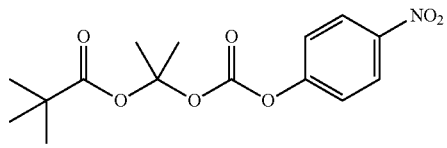 [SMILES: CC(C)(OC(=O)Oc1ccc([N+](=O)[O-])cc1)OC(=O)C(C)(C)C]

2-Chloropropan-2-yl (4-nitrophenyl) carbonate (prepared by a method reported in US 2006/229361 A1, 300 mg, 1.16 mmol, 1 eq.) was dissolved in dry DCM (15 mL). Mercury pivalate (559 mg, 1.39 mmol, 1.2 eq.) was added an d reaction mixture was stirred overnight (19 h) at rt under inert. The solid precipitate (HgCl$_2$) was removed by filtration, DCM (15 mL) was added and RM was extracted with sat. NaHCO$_3$ (15 mL), sat brine (15 mL), dried over MgSO$_4$ and solvent was evaporated. Product 43 was obtained as a light yellow oil (301 mg) in 80% yield. $^1$H NMR (400 MHz, CDCl$_3$): 1.20 (9H, s), 1.91 (6H, s), 7.34-7.40 (2H, m), 8.24-8.30 (2H, m). $^{13}$C NMR (101 MHz, CDCl$_3$): 25.28 (2C), 27.02 (3C), 39.59, 107.71, 121.98 (2C), 125.40 (2C), 145.50, 149.07, 155.41, 175.97. IR (CHCl3): 3031 w, 2976 w, 2875 w, 1777 m, 1736 m, 1618 w, 1595 w, 1528 m–s, 1493 m, 1481 w, 1439 w, 1396 w, 1376 w, 1349 m, 1322 w, 1264 m, 1191 m, 1112 vs, 1094 s, sh, 1030 w, 980 w, 859 m, 682 vw, 491 vw cm$^{-1}$. ESI MS: 348 ([M+Na]$^+$). HR ESI MS: calcd for C$_{15}$H$_{19}$O$_7$NNa 348.10537; found 348.10543.

Isopropyl 6-diazo-5-oxo-2-((((2-(pivaloyloxy)propan-2-yl)oxy)carbonyl) amino) hexanoate (44)

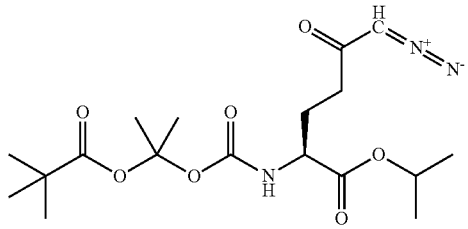 [SMILES: CC(C)OC(=O)[C@H](CCC(=O)C=[N+]=[N-])NC(=O)OC(C)(C)OC(=O)C(C)(C)C]

Compound 43 (48 mg, 0.148 mmol, 1 eq.) was dissolved in dry DMF (2 mL) and reaction mixture was cooled to 0° C. Compound 3 (79 mg, 0.369 mmol, 2.5 eq.) dissolved in dry DMF (1 mL) was added by syringe. Reaction mixture was stirred at 0° C. under inert overnight for 3 h. DMF was evaporated and the crude mixture was purified by LC (hexane:EtOAc, 2:1). Product 44 was obtained as a light yellow oil (49 mg) in 83% yield. $^1$H NMR (400 MHz, CDCl$_3$): 1.19 (9H, s), 1.23 (3H, d, J=6.3), 1.24 (3H, d, J=6.3), 1.80 (3H, s), 1.83 (3H, s), 1.90-2.01 (1H, m), 2.14-2.27 (1H, m), 2.29-2.51 (2H, m), 4.24 (1H, dt, J=8.3, 4.7), 5.05 (1H, hept, J=6.3), 5.31 (1H, bs), 5.44 (1H, d, J=8.2). $^{13}$C NMR (101 MHz, CDCl$_3$): 21.80, 21.82, 25.76, 25.91, 27.07 (3C), 27.79, 36.46, 39.48, 53.26, 54.87, 69.59, 105.44, 153.16, 171.31, 176.21, 193.63. Optical rotation: $[\alpha]^{22}_D$+12.8° (c 0.133, CHCl3). IR (CHCl3): 3430 w, 3116 w, 2984 m, 2936 m, 2874 m, 2110 s, 1732 vs, br, 1641 m, 1502 s, 1481 m, 1466 m, 1462 m, 1455 m, 1452 m, 1397 m, sh, 1384 s, 1374 s, 1365 s, sh, 1198 s, 1184 s, 1147 m, sh, 1128 s, 1112 s, 1105 s, 1045 m, 942 w cm$^{-1}$.

Synthesis of isopropyl 6-diazo-5-oxo-2-(((phenyl (pivaloyloxy)methoxy)carbonyl)amino) hexanoate (47)

Chloro(phenyl)methyl (4-nitrophenyl) carbonate (45)

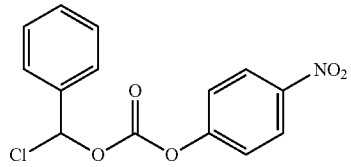 [SMILES: O=C(Oc1ccc([N+](=O)[O-])cc1)OC(Cl)c1ccccc1]

Chloro(phenyl)methyl carbonochloridate (prepared by US20110319422, 900 mg, 4.39 mmol, 1 eq.) was dissolved in dry DCM (20 mL). 4-Nitrophenol (611 mg, 4.39 mmol, 1 eq.) was added and the mixture was cooled to 0° C. Pyridine (347 mg, 355 μL, 4.39 mmol, 1 eq.) dissolved in dry DCM (5 mL) was added by dropwise method during 5 minutes. Reaction mixture was stirred for 2 h at rt. DCM was evaporated and the crude product was purified by LC (DCM:hexane, 1:1). The product 45 was obtained as a colorless solid (520 mg) in 39% yield. $^1$H NMR (400 MHz, CDCl$_3$): 7.33 (1H, s), 7.41-7.50 (5H, m), 7.58-7.63 (2H, m), 8.28-8.34 (2H, m). $^{13}$C NMR (101 MHz, CDCl$_3$): 87.37, 121.83 (2C), 125.59 (2C), 126.41 (2C), 129.07 (2C), 130.56, 136.35, 145.91, 150.50, 155.07. Optical rotation: $[\alpha]^{22}_D$-0.9° (c 0.318, CHCl3). IR (CHCl3): 3119 w, 3088 w, 3071 vw, 3032 w, 1788 vs, 1772 s, sh, 1619 m, 1595 m, 1530 vs, 1492 s, 1456 m, 1349 vs, 1317 m, 1296 m, 1232 vs, sh, 1178 m, sh, 1165 m, 1111 m, 1105 w, sh, 1078 m, 1054 s, 1029 m, 1014 m, 1002 w, 978 s, 920 w, 872 s, 854 s, 830 vw, 708 s, 695 m, sh, 680 w, 626 vw, 618 vw, 530 vw, 495 w, 403 w cm$^{-1}$. ESI MS: 329 ([M+Na]$^+$). HR ESI MS: calcd for C$_{14}$H$_{10}$O$_5$NClNa 330.01397; found 330.01367.

(((4-Nitrophenyloxy)carbonyl)oxy)(phenyl)methyl pivalate (46)

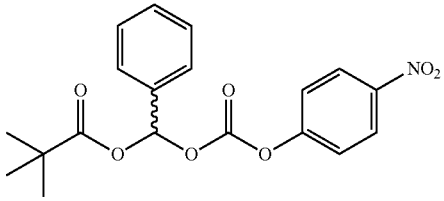 [SMILES: CC(C)(C)C(=O)OC(OC(=O)Oc1ccc([N+](=O)[O-])cc1)c1ccccc1]

Compound 45 (100 mg, 0.325 mmol, 1 eq.) and mercury pivalate (157 mg, 0.390 mmol, 1.2 eq.) were dissolved in dry DCM (6 mL). Reaction mixture was stirred at rt under inert overnight (16 h). DCM (10 mL) was added and reaction mixture was washed with sat. NaHCO$_3$ (10 mL) and brine (10 mL), organic phase was dried over MgSO$_4$ and DCM was evaporated. The product 46 (115 mg) was obtained in 95% yield and was used for further step without any purification. $^1$H NMR (400 MHz, CDCl$_3$): 1.28 (9H, s), 7.38-7.43 (2H, m), 7.44-7.50 (3H, m), 7.57-7.60 (1H, m), 7.61 (1H, s), 8.23-8.33 (2H, m). $^{13}$C NMR (101 MHz, CDCl$_3$): 27.02 (3C), 39.11, 93.80, 121.86 (2C), 125.47 (2C), 126.84 (2C), 128.97 (2C), 130.48, 134.39, 145.69, 150.73, 155.32, 176.44. Optical rotation: $[\alpha]^{22}_D$-6.0° (c 0.201, CHCl3). IR (CHCl3): 3118 w, 3087 w, 3072 w, 3031 w, 2980 m, 2875 w, 1775 vs, 1747 s, 1618 m, 1595 m, 1529 vs, 1493 s, 1480 m, 1459 m, 1399 m, 1365 m, 1349 vs, 1279 vs, 1248 vs, 1165 s, 1123 vs, 1112 s, sh, 1030 s, 1014 m, 1003 m, 970 s, br, 943 s, 918 m, 865 s, 860 s, 832 w, 697 s, 682 w, 633 w, 619 vw, 530 vw, 495 w, 403 vw cm$^{-1}$. ESI MS: 396 ([M+Na]$^+$). HR ESI MS: calcd for C$_{19}$H$_{19}$O$_7$NNa 396.10537; found 396.10546.

Isopropyl 6-diazo-5-oxo-2-(((phenyl(pivaloyloxy) methoxy)carbonyl)amino) hexanoate (47)

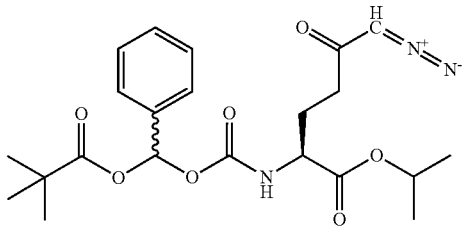 [SMILES: CC(C)OC(=O)[C@H](CCC(=O)C=[N+]=[N-])NC(=O)OC(OC(=O)C(C)(C)C)c1ccccc1]

Compound 46 (115 mg, 0.308 mmol, 1 eq.) was dissolved in dry DCM (3 mL). DON iPr ester (72 mg, 0.339 mmol, 1.1 eq.) dissolved in dry DCM (2 mL) was added by syringe. Reaction mixture was stirred at rt under inert overnight (24 h) under inert. Further DONiPr ester (72 mg, 0.339 mmol, 1.1 eq.) dissolved in dry DCM (2 mL) was added and stirring was continued for next 24 h. DCM was evaporated and the crude mixture was purified by preparative HPLC (AcN/H$_2$O, HCOOH). Product 47 was obtained as a light brown oil (66 mg) in 48% yield. $^1$H NMR (400 MHz, CDCl$_3$): 1.17-1.31 (15H, m), 1.90-2.06 (1H, m), 2.12-2.31 (1H, m), 2.31-2.54 (2H, m), 4.27-4.36 (1H, m), 5.03 (1H, hept, J=6.3), 5.29 (1H, bs), 5.59 (1H, d, J=8.1), 7.36-7.42 (3H, m), 7.46-7.51 (2H, m), 7.61 (s, 1H). $^{13}$C NMR (101 MHz, CDCl$_3$): 21.82 (2C), 26.99 (3C), 27.70, 36.35, 38.99, 53.55, 54.90, 69.79, 90.93, 126.57 (2C), 128.66 (2C), 129.64, 135.95, 153.82, 171.10, 176.33, 193.51. Optical rotation: $[\alpha]^{22}_D$+12.5° (c 0.246, CHCl3). IR (CHCl3): 3425 w, 3116 w, 3098 vw, 3070 vw, 3029 m, 2984 m, 2875 w, 2110 s, 1735 vs, br, 1641 s, 1590 w, 1507 s, 1480 m, 1457 m, 1398 m, 1377 s, 1367 s, sh, 1366 s, sh, 1280 s, 1182 m, 1146 s, sh, 1133 s, 1105 s, 1085 m, 1057 s, 1027 s, 1003 m, 942 m, 918 w, 697 m, 619 vw cm$^{-1}$. ESI MS: 470 ([M+Na]$^+$).

Synthesis of isopropyl 6-diazo-2-((((isobutyryloxy)methoxy)carbonyl)amino)-5-oxohexanoate (49)

(((2,5-Dioxopyrrolidin-1-yl)oxy)carbonyl)oxy)methyl isobutyrate (48)

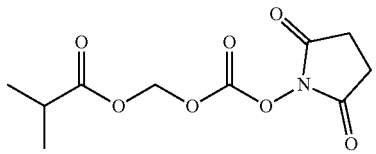 [SMILES: CC(C)C(=O)OCOC(=O)ON1C(=O)CCC1=O]

Chloromethyl carbonochloridate (1.00 g, 690 µL, 7.76 mmol, 1 eq.) was dissolved in dry Et$_2$O (10 mL). The reaction mixture was cooled to 0° C., and a mixture of Et$_3$N (785 mg, 1081 µL, 7.76 mmol, 1 eq.) and EtSH (482 mg, 574 µL, 7.76 mmol, 1 eq.) dissolved in dry Et$_2$O (3 mL) was added by dropwise method over 5 minutes. The reaction mixture was stirred overnight (18 h) at rt, precipitate was filtered over pad of celite and solvent was removed under reduced pressure. The crude product -(chloromethyl) S-ethyl carbonothioate (colorless liquid) was used for further step without purification. O-(Chloromethyl) S-ethyl carbonothioate (1.10 g, 7.11 mmol, 1 eq.) was dissolved in isobutyric acid (1.88 g, 1.94 mL, 21.35 mmol, 3 eq.) and freshly prepared salt of isobutyric acid (1.88 g, 1.94 mL, 21.35 mmol, 3 eq.) and DIEA (2.76 g, 3.81 mL, 21.35 mmol, 3 eq.) was added in few portions. The reaction mixture was heated to 60° C. for 20 h. EtOAc (50 mL) was added and the organic phase was extracted with water (50 mL), sat. NaHCO$_3$ (3×50 mL), sat. NaCl (50 mL), dried over MgSO$_4$ and solvent was evaporated. The crude product ((((ethylthio)carbonyl)oxy)methyl isobutyrate (light yellow liquid, 1.14 g, 72%) was used for further step without purification. (((Ethylthio)carbonyl)oxy)methyl isobutyrate (1.12 g, 5.04 mmol, 1 eq.) was dissolved in dry DCM (15 mL), N-hydroxysuccinimide (1.16 g, 10.08 mmol, 2 eq.) was added and the suspension was cooled to 0° C. Peracetic acid (1.15 g (100%), 3.19 g (36%), 15.12 mmol, 3 eq., 36% solution in acetic acid) was added by dropwise in 10 minutes. The final mixture was stirred for 60 minutes at 0° C., and 2 h at rt. DCM (20 mL) was added and the organic phase was washed with water (15 mL) and sat. NaCl (15 mL) and dried over MgSO$_4$. DCM was evaporated and the product was purified by LC (hexane:EtOAc, 2:1, R$_f$ 0.24). The product 48 was obtained as a colorless oil (842 mg) in 64% yield (over 3 steps). $^1$H NMR (400 MHz, CDCl$_3$): 1.19 (6H, d, J=7.0), 2.63 (1H, hept, J=7.0), 2.83 (4H, s), 5.85 (2H, s). $^{13}$C NMR (101 MHz, CDCl$_3$): 18.60, 25.54, 33.77, 83.50, 150.92, 168.39, 175.08. IR (CHCl3): 2981 m, 2945 w, 2880 w, 1823 s, 1795 vs, 1748 vs, br, 1720 m, sh, 1471 m, 1431 m, 1389 w, 1370 m, 1231 vs, 1199 vs, 1113 s, 1045 m, 925 s, cm$^{-1}$. ESI MS: 282 ([M+Na]$^+$). HR ESI MS: calcd for C$_{10}$H$_{13}$O$_7$NNa 282.05842: found 282.05848.

Isopropyl 6-diazo-2-((((isobutyryloxy)methoxy)carbonyl)amino)-5-oxohexanoate (49)

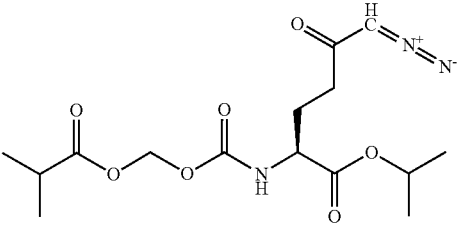 [SMILES: CC(C)OC(=O)[C@H](CCC(=O)C=[N+]=[N-])NC(=O)OCOC(=O)C(C)C]

Compound 48 (268 mg, 1.03 mmol, 1.1 equiv) was dissolved in absolute dichloromethane (8 mL). This solution was cooled to 0° C., and a solution of the compound 3 (200 mg, 0.94 mmol), in dichloromethane (1 mL) was added dropwise. The reaction mixture was stirred for 15 min at 0° C. in a cooling bath. The reaction mixture was then stirred at room temperature for 1 h. The organic solvent was evaporated in vacuo. The residue was chromatographed on silica gel (chloroform:acetone, 10:1) to effort the desired product 49 (180 mg, 54%) as a yellow amorphous solid. $^1$H NMR (400 MHz, CDCl$_3$): 1.17-1.19 (6H, m), 1.25-1.27 (6H, m), 1.94-2.04 (1H, m), 2.18-2.26 (1H, m), 2.32-2.49 (2H, m), 2.59 (1H, hept, J=6.9), 4.31 (1H, td, J=8.1, 4.7), 5.05 (1H, hept, J=6.3), 5.28 (1H, s), 5.62 (1H, d, J=8.0), 5.71 (1H, d, J=5.8), 5.75 (1H, d, J=5.8). $^{13}$C NMR (101 MHz, CDCl$_3$): 18.82 (2C), 21.84, 21.86, 27.67, 33.91, 36.37, 53.66, 54.99, 69.84, 80.14, 154.45, 171.03, 176.19. IR (CHCl3):3424 w, 2111 s, vs, 1750 sh, vs, 1732 vs, 1641 m, s, 1512 s, 1387 sh, s, 1377 s, 1370 sh, s cm$^{-1}$. Optical rotation: $[\alpha]^{22}_D$+5.4° (c 0.202, CH$_2$Cl2). ESI MS: 380 ([M+Na]$^+$). HR ESI MS: calcd for C$_{15}$H$_{23}$O$_7$N$_3$Na 380.14282; found 380.14286.

Synthesis of isopropyl 2-((((4-(2-(2-amino-3-methylbutanamido)-5-ureidopentanamido) benzyl)oxy)carbonyl)amino)-6-diazo-5-oxohexanoate (51)

Isopropyl 2-(((((4-(2-(2-((((9H-fluoren-9-yl)methoxy)carbonyl)amino)-3-methylbutanamido)-5-ureidopentanamido)benzyl)oxy)carbonyl)amino)-6-diazo-5-oxohexanoate (50)

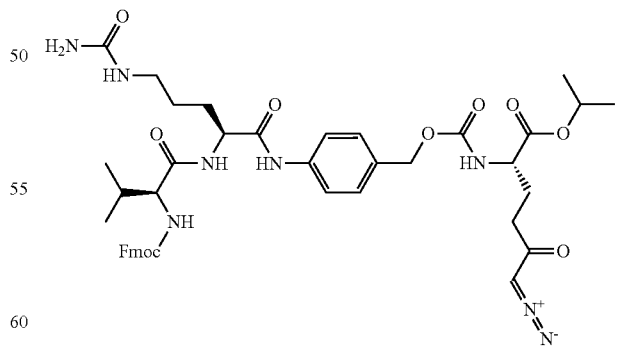

9-Fluorenylmethyloxycarbonyl-valyl-citrullyl-(4-aminobenzyl)-(4-nitrophenyl) carbonate (191 mg, 0.249 mmol, 1.2 equiv.), was dissolved in dry DMF (2.0 mL) and a solution of compound 3 (44 mg, 0.208 mmol) in dry DMF (1.0 mL) was added dropwise. To this reaction mixture was added diisopropylethyl amine (130 µL, 0.747 mmol, 3 equiv.) dropwise. The reaction mixture was stirred at room temperature overnight. The organic solvent was evaporated in vacuo. The residue was chromatographed on silica gel (chloroform:methanol, 15:1) to yield the desired product 50 (110 mg, 53%) as a white amorphous solid. $^1$H NMR (400 MHz, DMSO): 0.85 (3H, d, J=6.8), 0.88 (3H, d, J=6.9), 1.16 (3H, d, J=6.6), 1.18 (3H, d, J=6.6), 1.31-1.49 (2H, m), 1.54-1.81 (3H, m), 1.89-2.03 (2H, m), 2.35-2.44 (2H, m), 2.89-3.05 (2H, m), 3.91-3.98 (2H, m), 4.20-4.34 (3H, m), 4.39-4.44 (1H, m), 4.86-5.00 (3H, m), 5.40 (2H, s), 5.97 (1H, t, J=5.9), 6.05 (1H, s), 7.28 (2H, d, J=8.7), 7.32 (2H, td, J=7.5, 1.2), 7.39-7.44 (3H, m), 7.59 (2H, d, J=8.3), 7.66 (1H, d, J=7.7), 7.74 (2H, t, J=7.8), 7.89 (2H, d, J=7.6), 8.12 (1H, d, J=7.5), 10.06 (1H, s). $^{13}$C NMR (101 MHz, DMSO): 18.28, 19.23, 21.45, 21.52, 25.78, 26.80, 29.48, 30.46, 36.32, 38.58, 46.69, 53.10, 53.42, 60.08, 65.29, 65.69, 68.04, 118.91 (2C), 120.10 (2C), 125.37 (2C), 127.07 (2C), 127.65 (2C), 128.61 (2C), 131.65, 138.64, 140.71 (2C), 143.77, 143.90, 156.13 (2C), 158.90, 170.60, 171.28, 171.55, 194.03. IR (KBr): 3400 s, br, sh, 3327 s, br, 3066 w, 2964 m, 2937 m, 2106 s, 1705 vs, br, 1651 vs, 1609 s, 1533 vs, 1517 vs, sh, 1479 m, 1466 m, 1450 s, 1415 m, 1386 s, sh, 1376 s, 1334 s, 1320 s, sh, 1248 s, 1183 m, 1145 m, 1106 s, 1047 m, 1020 m, sh, 826 w, 777 w, sh, 621 w, 427 w cm$^{-1}$. Optical rotation: $[\alpha]^{22}_D$ –15.6° (c 0.631, DMSO). ESI MS: 863 ([M+Na]$^+$). HR ESI MS: calcd for $C_{43}H_{52}N_8O_{10}Na$ 863.36986; found 863.36997.

Isopropyl 2-((((4-(2-(2-amino-3-methylbutanamido)-5-ureidopentanamido) benzyl)oxy)carbonyl)amino)-6-diazo-5-oxohexanoate (51)

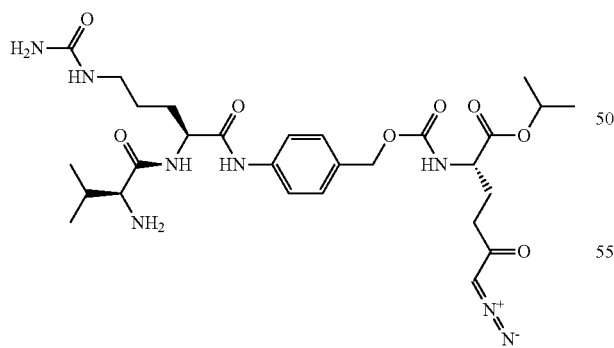

Compound 50 (110 mg, 0.131 mmol) was dissolved in dry DMF (0.5 mL). Piperidine (32 µL 0.327 mmol, 2.5 equiv.) was added and the reaction mixture was stirred at room temperature for 4 h. The organic solvent was evaporated in vacuo. The residue was chromatographed on silica gel (chloroform:methanol, 2:1) to afford the desired product 51 (70 mg, 87%) as a white amorphous solid.

Synthesis of isopropyl 2-((((4-(2-(2-acetamido-3-methylbutanamido)-5-ureidopentanamido) benzyl)oxy)carbonyl)amino)-6-diazo-5-oxohexanoate (52)

Isopropyl 2-((((4-(2-(2-acetamido-3-methylbutanamido)-5-ureidopentanamido) benzyl)oxy)carbonyl)amino)-6-diazo-5-oxohexanoate (52)

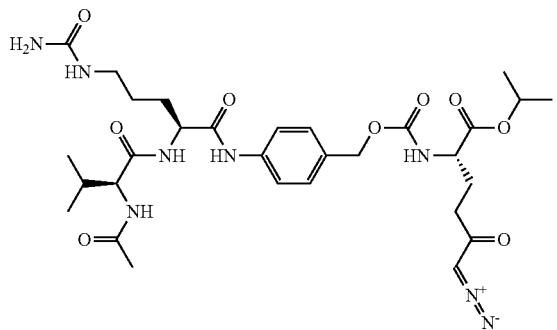 [SMILES: CC(=O)N[C@H](C(=O)N[C@@H](CCCNC(N)=O)C(=O)Nc1ccc(COC(=O)N[C@@H](CCC(=O)C=[N+]=[N-])C(=O)OC(C)C)cc1)C(C)C]

Compound 51 (100 mg, 0.162 mmol), was dissolved in dry DMF (2 mL) and to this solution was added diisopropylethyl amine (144 µL, 0.842 mmol, 5.1 equiv.) was added dropwise followed by acetanhydride (76.5 µL, 0.81 mmol, 5.0 equiv.). The reaction mixture was stirred at room temperature for 2 h. The organic solvent was evaporated in vacuo. The residue was chromatographed on silica gel (chloroform:methanol, 7:1) to afford the desired product 52 (97 mg, 91%) as a yellow amorphous solid.

Synthesis of Isopropyl 2-(2-(2-amino-3-methylbutanamido)-5-ureidopentanamido)-6-diazo-5-oxohexanoate (56)

Isopropyl 2-(2-((((9H-fluoren-9-yl)methoxy)carbonyl)amino)-5-ureidopentanamido)-6-diazo-5-oxohexanoate (53)

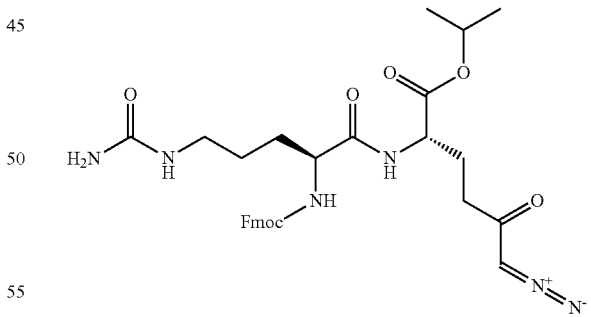

Fmoc-Cit-COOH (2.05 g, 5.16 mmol, 1.1 equiv.) and TBTU (1.81 g, 5.63 mmol, 1.2 equiv.) were solved in absolute DMF (40 mL) and diisopropylethyl amine (2.51 mL, 14.07 mmol, 3 equiv.) was added. The reaction mixture was stirred at room temperature for 30 min, and then the solution of 3 (1.0 g, 4.69 mmol) in absolute DMF (20 mL) were added by syringe. The reaction mixture was stirred for 2 h at room temperature under inert atmosphere. The organic solvent was evaporated in vacuo. The residue was chromatographed on silica gel (chloroform:methanol, 15:1) to afford the desired product 53 (1.84 g, 66%) as a yellow amorphous solid. $^1$H NMR (4(0) MHz, DMSO): 1.16 (3H, d, J=4.6), 1.17 (3H, d, J=4.4), 1.37-1.57 (3H, m), 1.61-1.70 (1H, m), 1.76-1.86 (1H, m), 1.94-2.03 (1H, m), 2.33-2.46 (2H, m), 2.94-3.03 (2H, m), 4.03-4.08 (1H, m), 4.15-4.31 (4H, m), 4.88 (1H, hept, J=6.3), 5.42 (2H, s), 5.96 (1H, t, J=5.8), 6.01 (1H, s), 7.31-7.34 (2H, m), 7.39-7.43 (2H, m), 7.53 (1H, d, J=8.1), 7.73-7.74 (2H, m), 7.88 (2H, d, J=7.5), 8.28 (1H, d, J=7.5). $^{13}$C NMR (101 MHz, DMSO): 21.45, 21.49, 25.91, 26.72, 29.39, 36.22, 38.77, 46.68, 51.48, 54.06, 65.67, 68.02, 120.10 (2C), 125.36 (2C), 127.09 (2C), 127.65 (2C), 140.72 (2C), 143.80, 143.91, 155.96, 158.87, 171.05, 172.29, 194.04. IR (KBr): 3435 vs, br, 3348 vs, br, sh, 3068 m, 2979 m, 2936 m, 2871 w, 2105 s, 1723 s, 1678 vs, br, 1610 s, sh, 1540 s, br, 1478 s, 1466 m, sh, 1450 m, 1386 s, sh, 1376 s, 1252 s, 1220 m, sh, 1184 m, sh, 1146 m, 1105 s, 1052 m, 1032 m, 760 m, 741 m, 621 m, 427 s cm$^{-1}$. ESI MS: 615 ([M+Na]$^+$). HR ESI MS: calcd for $CH_{30}H_{36}O_7N_6Na$ 615.25377; found 615.25383.

Isopropyl 2-(2-amino-5-ureidopentanamido)-6-diazo-5-oxohexanoate (54)

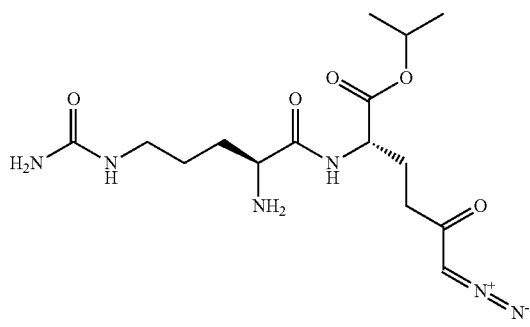 [SMILES: CC(C)OC(=O)[C@H](CCC(=O)C=[N+]=[N-])NC(=O)[C@@H](N)CCCNC(N)=O]

Compound 53 (1.84 g, 3.11 mmol), was dissolved in dry DMF (24 mL). Piperidine (767 μL 7.76 mmol, 2.5 equiv.) was added and the reaction mixture was stirred at room temperature for 4 h. The organic solvent was evaporated in vacuo. The residue was chromatographed on silica gel (chloroform:methanol, 2:1) to afford the desired product 54 (874 mg, 76%) as a white amorphous solid. $^1$H NMR (400 MHz, DMSO): 1.17 (3H, d, J=4.4), 1.18 (3H, d, J=4.3), 1.27-1.47 (3H, m), 1.48-1.58 (1H, m), 1.76-1.85 (1H, m), 1.93-2.01 (1H, m), 2.31-2.43 (2H, m), 2.93 (2H, q, J=6.4), 3.14 (1H, dd, J=7.3, 5.3), 4.88 (1H, hept, J=6.3), 5.36 (2H, s), 5.90 (1H, t, J=5.7), 6.07 (1H, s), 8.13 (1H, d, J=7.7). $^{13}$C NMR (101 MHz, DMSO): 21.45, 21.50, 26.08, 26.48, 32.69, 36.25, 51.22, 54.21, 68.03, 158.72, 171.18, 175.56, 194.05. IR (CHCl3): 3509 w, 3414 w, sh, 3446 w, 3357 m, br, sh, 3116 w, 2939 w, 2110 s, 1731 s, 1664 vs, br, 1598 m, 1467 w, 1450 m, 1387 m, sh, 1377 s, 1349 m, 1183 w, 1145 m cm$^{-1}$. Optical rotation: $[\alpha]^{22}_D$–3.2° (c 0.218, $CH_2Cl_2$). ESI MS: 371 ([M+H]$^+$). HR ESI MS: calcd for $C_{31}H_{40}O_{15}N_3Na$ 393.18569; found 393.18575.

Isopropyl 11-(4-diazo-3-oxobutyl)-1-(9H-fluoren-9-yl)-5-isopropyl-3,6,9-trioxo-8-(3-ureidopropyl)-2-oxa-4,7,10-triazadodecan-12-oate (55)

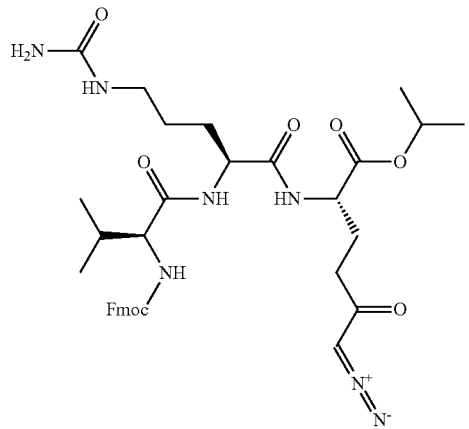

Fmoc-Val-COOH (484 mg, 1.43 mmol, 1.1 equiv.) and TBTU (499 mg, 1.55 mmol, 1.2 equiv.) were solved in absolute DMF (10 mL) and diisopropylethyl amine (677 μL, 3.89 mmol, 3 equiv.) was added. The reaction mixture was stirred at room temperature for 30 min, and then the solution of compound 54 (480 mg, 1.30 mmol) in absolute DMF (5 mL) were added by syringe. The reaction mixture was stirred for 3 h at room temperature under inert atmosphere. The organic solvent was evaporated in vacuo. The residue was chromatographed on silica gel (chloroform:methanol, 15:1) to afford the desired product 55 (750 mg, 84%) as a white amorphous solid. $^1$H NMR (400 MHz, DMSO): 0.84 (3H, d, J=6.7), 0.86 (3H, d, J=6.8), 1.16 (3H, d, J=4.5), 1.17 (3H, d, J=4.5), 1.32-1.54 (3H, m), 1.60-1.68 (1H, m), 1.73-1.82 (1H, m), 1.91-2.04 (2H, m), 2.30-2.46 (2H, m), 2.90-3.02 (2H, m), 3.90 (1H, dd, J=9.1, 7.0), 4.13-4.18 (1H, m), 4.20-4.34 (4H, m), 4.87 (1H, hept, J=6.2), 5.41 (2H, s), 5.94 (1H, t, J=5.8), 6.04 (1H, s), 7.30-7.34 (2H, m), 7.39-7.45 (3H, m), 7.72-7.76 (2H, m), 7.89 (2H, d, J=7.5), 8.01 (1H, d, J=7.6), 8.31 (1H, d, J=7.4). $^{13}$C NMR (101 MHz, DMSO): 18.26, 19.26, 21.48, 21.52, 25.99, 26.57, 29.54, 30.51, 36.09, 38.79, 46.71, 51.37, 52.15, 60.05, 65.68, 68.04, 120.15 (2C), 125.41 (2C), 127.12 (2C), 127.68 (2C), 140.72, 140.75, 143.79, 143.93, 156.12, 158.84, 171.03, 171.11, 171.76, 194.15. IR (KBr): 3415 m, vbr, sh, 3360 m, br, 3283 m, 3068 w, 2964 w, 2937 w, 2873 w, 2106 m, 1727 m, 1686 s, 1655 vs, sh, 1645 vs, 1540 s, br, 1478 w, 1465 m, 1451 m, 1386 m, sh, 1376 m, 1293 m, 1249 m, 1226 m, 1183 w, sh, 1146 m, 1106 m, 1033 w, 1009 vw, 760 w, 741 w, 621 vw, 427 vw cm$^{-1}$. Optical rotation: $[\alpha]^{22}_D$–19.3° (c 0.114, DMSO). ESI MS: 714 ([M+Na]$^+$). HR ESI MS: calcd for $C_{35}H_{45}N_7O_8Na$ 714.32218; found 714.32218.

Isopropyl 2-(2-(2-amino-3-methylbutanamido)-5-ureidopentanamido)-6-diazo-5-oxohexanoate (56)

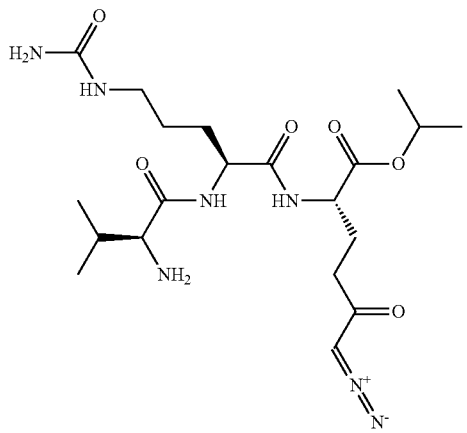 [SMILES: CC(C)OC(=O)[C@H](CCC(=O)C=[N+]=[N-])NC(=O)[C@H](CCCNC(N)=O)NC(=O)[C@@H](N)C(C)C]

Compound 55 (200 mg, 0.289 mmol), was dissolved in dry DMF (3 mL). Piperidine (71 µL 0.723 mmol, 2.5 equiv.) was added and the reaction mixture was stirred at room temperature for 4 h. The organic solvent was evaporated in vacuo. The residue was chromatographed on silica gel (chloroform:methanol, 2:1) to afford the desired product 56 (110 mg, 81%) as a white amorphous solid. $^1$H NMR (400 MHz, DMSO): 0.77 (3H, d, J=6.8), 0.87 (3H, d, J=6.9), 1.16 (3H, d, J=5.3), 1.18 (3H, d, J=5.2), 1.30-1.52 (3H, m), 1.57-1.68 (1H, m), 1.73-1.83 (1H, m), 1.86-2.01 (2H, m), 2.34-2.44 (2H, m), 2.89-3.00 (2H, m), 4.06-4.18 (2H, m), 4.29-4.37 (1H, m), 4.88 (1H, hept, J=6.3), 5.37 (2H, s), 5.91 (1H, t, J=5.8), 6.05 (1H, s), 8.04 (1H, d, J=7.8), 8.34 (1H, d, J=7.4). $^{13}$C NMR (101 MHz, DMSO): 17.49, 18.76, 21.46, 21.50, 25.86, 26.44, 29.61, 30.44, 36.08, 38.64, 51.45, 51.93, 57.96, 68.04, 158.99, 169.93, 170.95, 171.58, 194.03. IR (KBr): 3500 w, br, sh, 3338 m, vbr, 3116 w, 2984 s 2965 s, 2936 m, 2874 m, 2109 s, 1731 s, 1653 vs, br, sh, 1552 s, br, 1517 s, 1466 m, 1452 m, 1387 s, sh, 1376 s, 1234 s, 1183 m, 1145 s, 1106 s cm$^{-1}$. Optical rotation: $[\alpha]^{22}_D$–13.0° (c 0.270, DMSO). ESI MS: 470 ([M+H]$^+$). HR ESI MS: calcd for $C_{20}H_{36}O_6N_7$ 470.27216; found 470.27208.

Synthesis of isopropyl 2-(2-(2-acetamido-3-methylbutanamido)-5-ureidopentanamido)-6-diazo-5-oxohexanoate (57)

Isopropyl 2-(2-(2-acetamido-3-methylbutanamido)-5-ureidopentanamido)-6-diazo-5-oxohexanoate (57)

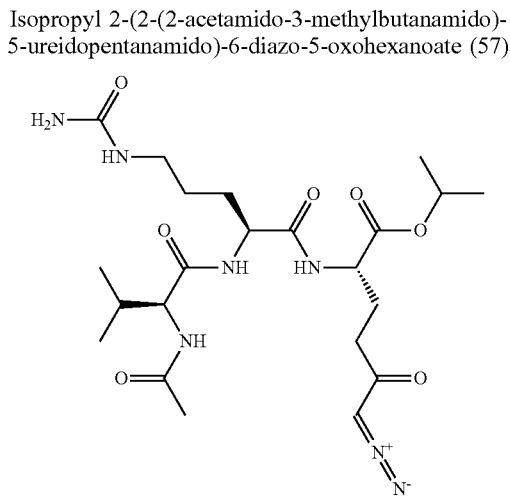

Compound 56 (50 mg, 0.107 mmol), was dissolved in dry DMF (1 mL) and to this solution was added diisopropylethyl amine (95 µL, 0.543 mmol, 5.1 equiv.) was added dropwise followed by acetanhydride (50 µL, 0.532 mmol, 5.0 equiv.). The reaction mixture was stirred at room temperature for 2 h. The organic solvent was evaporated in vacuo. The residue was chromatographed on silica gel (chloroform:methanol, 7:1) to afford the desired product 57 (50 mg, 92%) as a yellow amorphous solid. $^1$H NMR (400 MHz, CDCl$_3$): 0.82 (3H, d, J=6.9), 0.84 (3H, d, J=7.1), 1.16 (3H, d, J=4.8), 1.17 (3H, d, J=4.9), 1.31-1.53 (3H, m), 1.60-1.68 (1H, m), 1.73-1.82 (1H, m), 1.86 (3H, s), 1.89-2.00 (2H, m), 2.31-2.44 (2H, m), 2.93-2.97 (2H, m), 4.12-4.17 (2H, m), 4.21-4.26 (1H, m), 4.87 (1H, hept, J=6.3), 5.39 (2H, s), 5.92 (1H, t, J=5.8), 6.02 (1H, s), 7.86 (1H, d, J=8.7), 7.97 (1H, d, J=7.6), 8.20 (1H, d, J=7.5). $^{13}$C NMR (101 MHz, CDCl$_3$): 18.20, 19.21, 21.45, 21.49, 22.51, 25.95, 26.56, 29.36, 30.40, 36.10, 38.77, 51.33, 52.11, 57.67, 68.01, 158.80, 169.37, 170.97, 171.05, 171.70, 194.05. Optical rotation: $[\alpha]^{22}_D$–22.60 (c 0.257, DMSO). ESI MS: 534 ([M+Na]$^+$). HR ESI MS: calcd for $C_{22}H_{37}O_7N_7Na$ 534.26467; found 513.26456.

Synthesis of (S)-6-diazo-5-oxo-2-(((((4-(((2S,3R,4S,5S,6R)-3,4,5-trihydroxy-6-(hydroxymethyl)tetrahydro-2H-pyran-2-yl)oxy)benzyl)oxy)carbonyl)amino) hexanoate (59)

2-(acetoxymethyl)-6-(4-(((((6-diazo-1-ethoxy-1,5-dioxohexan-2-yl)carbamoyl) oxy)methyl)phenoxy) tetrahydro-2H-pyran-3,4,5-triyl triacetate (58)

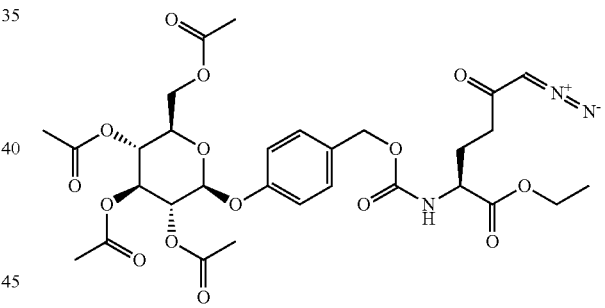

4-[[[(4-Nitrophenoxy)carbonyl]oxy]methyl]phenyl-β-D-glucopyranoside, 2,3,4,6-tetraacetate (prepared using a method analogous to the one reported in Angew. Chem. Int. Ed. 2006, 45, 5345-5348, 800 mg, 1.3 mmol), was dissolved in dry DMF (6 mL) and a solution of the compound 20 (330 mg, 1.66 mmol, 1.3 equiv.), in dry DMF (3 mL) was added dropwise. To this reaction mixture was diisopropylethyl amine (0.91 mL, 5.2 mmol, 4 equiv.) was added dropwise. The reaction mixture was stirred at room temperature overnight. The organic solvent was evaporated in vacuo. The residue was chromatographed on silica gel (chloroform:acetone, 7:1) to effort the desired product 58 (596 mg, 68%) as a yellow amorphous solid. $^1$H NMR (400 MHz, CDCl$_3$): 1.25 (3H, m), 1.93-2.04 (1H, m), 2.02 (3H, s), 2.03 (3H, s), 2.04 (3H, s), 2.06 (3H, s), 2.15-2.23 (1H, m), 2.28-2.51 (2H, m), 3.85 (1H, ddd, J=10.0, 5.3, 2.5), 4.13-4.20 (3H, m), 4.25-4.34 (2H, m), 5.03-5.07 (3H, m), 5.13-5.17 (1H, m), 5.21-5.31 (3H, m), 5.49 (1H, d, J=7.9), 6.94-6.97 (2H, m), 7.27-7.31 (2H, m). $^{13}$C NMR (101 MHz, CDCl$_3$): 14.24, 20.71, 20.72, 20.80, 21.82, 27.59, 36.50, 53.61, 54.87, 61.80, 62.01, 66.56, 68.34, 71.23, 72.16, 72.78, 99.13, 117.05 (2C), 129.95 (2C), 131.38, 156.06, 156.86, 169.39, 169.50, 170.32, 170.66, 171.91, 193.55. IR (CHCl3): 3429 w, 2110 s, 1757 vs, 1744 sh, vs, 1720 sh, s, 1641 m, 1613 m, 1592 w, 1512 s, 1377 m, 1368 s, 1178 m, 1070 sh, s, 651 w cm$^{-1}$. Optical rotation: $[\alpha]^{22}_D$ -3.3° (c 0.631, CH$_2$Cl$_2$). ESI MS: 680 ([M+H]$^+$). HR ESI MS: calcd for C$_{30}$H$_{38}$O$_{15}$N$_3$ 680.22974; found 680.22998.

Ethyl (S)-6-diazo-5-oxo-2-((((4-(((2S,3R,4S,5S,6R)-3,4,5-trihydroxy-6-(hydroxymethyl)tetrahydro-2H-pyran-2-yl)oxy)benzyl)oxy)carbonyl)amino)hexanoate (59)

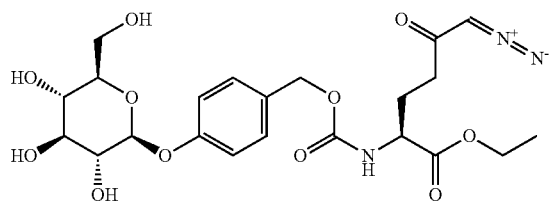 [SMILES: CCOC(=O)[C@H](CCC(=O)C=[N+]=[N-])NC(=O)OCc1ccc(O[C@@H]2O[C@H](CO)[C@@H](O)[C@H](O)[C@H]2O)cc1]

Compound 58 (833 mg, 1.3 mmol), was dissolved in methanol (20 mL) and a hydrazine hydrate solution 50-60% in water (417 µL, 7.36 mmol, 6.0 equiv.) was added dropwise. The reaction mixture was stirred at room temperature overnight. The organic solvent was evaporated in vacuo. The residue was chromatographed on silica gel (chloroform-methanol 7:1) to effort the desired product 59 (240 mg, 37%) as yellow amorphous solid. $^1$H NMR (400 MHz. DMSO): 1.18 (3H, t, J=7.1), 1.72-1.81 (1H, m), 1.91-2.00 (1H, m), 2.34-2.45 (2H, m), 3.12-3.19 (1H, m), 3.20-3.28 (2H, m), 3.29-3.34 (1H, m), 3.42-3.48 (1H, m), 3.66-3.71 (1H, m), 3.97-4.03 (1H, m), 4.05-4.12 (2H, m), 4.54 (1H, t, J=5.8), 4.86 (1H, d, J=7.3) 4.96 (2H, s), 5.01 (1H, d, J=5.3), 5.08 (1H, d, J=4.6), 5.30 (1H, d, J=4.8), 6.05 (1H, s), 7.01 (2H, d, J=8.6), 7.28 (2H, d, J=8.6), 7.67 (1H, d, J=7.8). $^{13}$C NMR (101 MHz, DMSO): 14.07, 25.82, 36.30, 53.27, 60.59, 60.70, 65.30, 69.72, 73.23, 76.63, 77.04, 100.28, 116.11 (2C), 129.49 (2C), 130.09, 156.16, 157.14, 172.06, 201.32. IR (KBr): 3413 m, 2979 w, 2935 w, 2108 m, 1718 m, 1649 m, 1614 m, 1592 w, 1513 m, 1392 m, sh, 1383 m, 1346 m, 1233 s, 1179 m, sh, 1074 s, 1046 s, sh, 1018 m, 948 w, sh, 832 w, 511 w cm$^{-1}$. Optical rotation: $[\alpha]^{22}_D$ -18.9° (c 0.254, DMSO). ESI MS: 534 ([M+Na]$^+$). HR ESI MS: calcd for C$_{22}$H$_{29}$O$_{11}$N$_3$Na 534.16943; found 534.16951.

Synthesis of isopropyl 2-(2-acetamido-3-(1H-indol-3-yl)propanamido)-6-diazo-5-oxohexanoate (60)

Isopropyl 2-(2-acetamido-3-(1H-indol-3-yl)propanamido)-6-diazo-5-oxohexanoate (60)

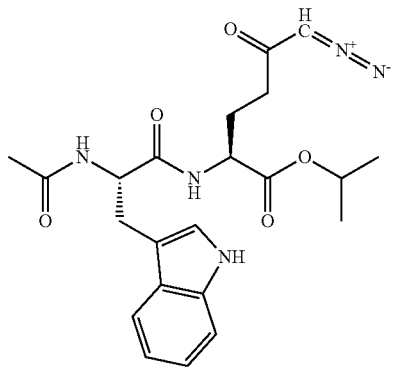 [SMILES: CC(=O)N[C@@H](Cc1c[nH]c2ccccc12)C(=O)N[C@@H](CCC(=O)C=[N+]=[N-])C(=O)OC(C)C]

Compound 38 (425 mg, 1.06 mmol, 1 eq.) was dissolved in dry DMF (8 mL). Pyridine (168 mg, 171 µL, 2.13 mmol, 2 eq.), followed by acetanhydride (130 mg, 121 µL, 1.28 mmol, 1.2 eq.) were added by syringe. The reaction mixture was stirred for 2 h at rt under inert atmosphere. DMF was evaporated. The crude product was purified by column LC (CHCl$_3$:MeOH, 20:1) to give 423 mg of product 60 as a yellow amorphous solid (90% yield). $^1$H NMR (400 MHz, CDCl$_3$): 1.20 (3H, d, J=6.3), 1.24 (3H, d, J=6.3), 1.81-1.94 (1H, m), 1.98 (3H, s), 2.04-2.33 (3H, m), 3.17 (1H, dd, J=14.6, 7.2), 3.33 (1H, dd, J=14.7, 5.4), 4.37 (1H, td, J=7.7, 4.4), 4.75 (1H, td, J=7.4, 5.4), 4.95 (1H, hept, J=6.3), 5.16 (1H, bs), 6.22 (d, J=7.6), 6.64 (1H, d, J=7.3), 7.09-7.14 (2H, m), 7.18 (1H, ddd, J=8.2, 7.0, 1.3), 7.32-7.38 (1H, m), 7.66 (1H, dd, J=7.9, 1.1), 8.31 (1H, bs). $^{13}$C NMR (101 MHz, CDCl$_3$): 21.77, 21.82, 23.38, 26.97, 28.29, 36.25, 52.28, 54.07, 54.95, 69.54, 110.38, 111.42, 118.78, 119.79, 122.27, 123.57, 127.74, 136.35, 170.25, 170.85, 171.58, 194.04. Optical rotation: $[\alpha]^{22}_D$ -11.6° (c 0.284, CHCl3). IR (CHCl3): 3478 m, 3417 m, 3329 w, vbr, 3117 w, 2986 m, 2934 w, 2874 vw, 2855 w, 2110 s, 1732 s, 1660 vs, br, 1635 s, sh, 1600 w, sh, 1554 m, br, sh, 1505 s, br, 1467 w, 1457 m, 1385 s, sh, 1377 w, vbr, 1350 m, 1183 m, 1146 m, 1105 s, 1093 m, sh, 1012 w. ESI MS: 464 ([M+Na]$^+$). HR ESI MS: calcd for C$_{22}$H$_{27}$O$_5$N$_5$Na 464.19044; found 464.19050.

Scheme 9

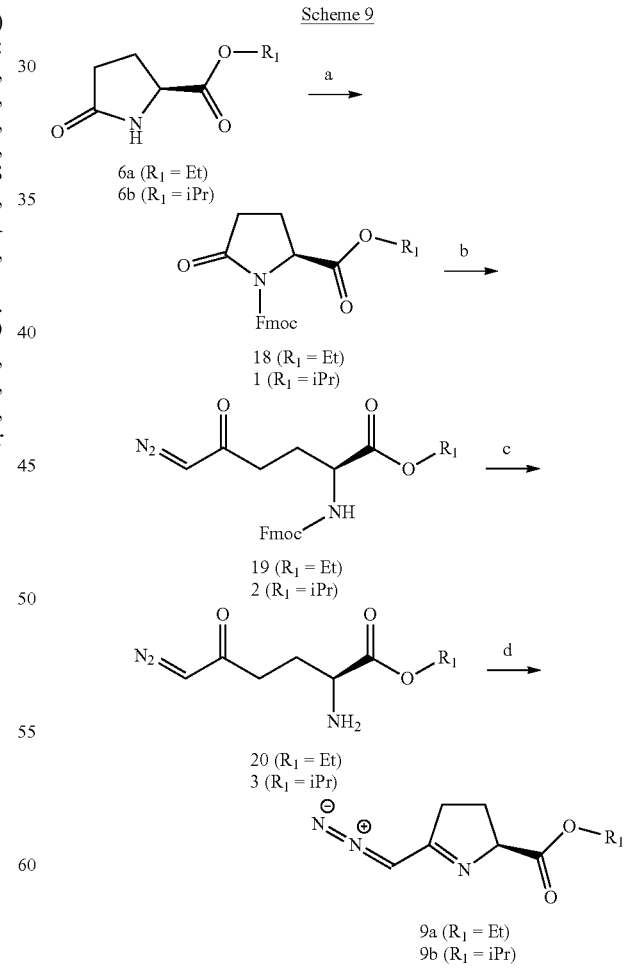

Reagents and conditions: (a) LiHMDS, FMOC-Cl, THF, -78° C., 87% for 7a, 92% for 7b; (b) n-BuLi, TMS diazomethane, THF, −116 to −78° C., 80% for 8a, 85% for 8b; (c) Piperidine, DCM, rt, 66% for 2a and 66% for 2b; (d) CH₃CN, 60° C., 50% for 9a; CDCl₃, rt, overnight, 41% for 9b.

Ethyl 5-(diazomethyl)-3,4-dihydro-2H-pyrrole-2-carboxylate (9a)

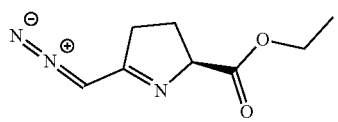

Referring to scheme 9, compound 20 (117 mg, 0.588 mmol, 1 eq.) was dissolved in CH₃CN (1 mL). The reaction mixture was heated for 2 h at 60° C. under inert atmosphere. The CH₃CN was evaporated and the crude product was purified by HPLC (CH₃CN/H₂O, HCOOH) affording a light orange oil (53 mg) in 50% yield. $^1$H NMR (CDCl₃): 1.27 (3H, t, J=7.1), 2.83-2.93 (1H, m), 2.93-3.07 (2H, m), 3.09-3.20 (1H, m), 4.24 (2H, dq, J=7.1, 2.4), 5.17 (1H, dd, J=9.2, 3.5), 7.43 (1H, s); $^{13}$C NMR (101 MHz, CDCl₃): 14.11, 19.98, 34.19, 59.06, 62.53, 126.82, 142.77, 168.70; IR (CHCl₃): 2942 w, 2910 w, 2875 vw, 2103 vw, 1747 vs, 1475 w, 1676 m, 1605 vw, 1552 w, 1462 w, 1446 w, 1396 w, 1377 m, 1202 vs, 1177 m, 1116 w, 1095 m, cm$^{-1}$; ESI MS: 182 ([M+H]⁺), HR ESI MS: calcd for C₈H₁₂O₂N₃ 182.0930; found 182.0931.

Isopropyl 5-(diazomethyl)-3,4-dihydro-2H-pyrrole-2-carboxylate (9b)

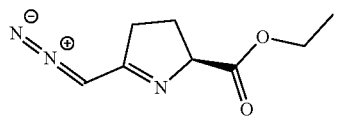

Referring to scheme 9, compound 3 (100 mg, 0.469 mmol, 1 eq.) was dissolved in CDCl₃ (2 mL). The reaction mixture was stirred at rt overnight. The CDCl₃ was evaporated and the crude product was purified by HPLC (CH₃CN/H₂O, HCOOH) and a light orange oil (41 mg) was obtained in 45% yield. $^1$H NMR (CDCl₃): 1.25 (3H, d, J=6.1), 1.27 (3H, d, J=6.1), 2.81-2.95 (2H, m), 2.96-3.06 (1H, m), 3.08-3.18 (1H, m), 5.09 (1H, hept, J=6.1), 5.13 (1H, dd, J=9.1, 3.4), 7.43 (1H, s); $^{13}$C NMR (101 MHz, CDCl₃): 20.00, 21.69 (2C), 21.75, 34.24, 59.20, 70.48, 126.84, 142.71, 168.25; Optical rotation: [α]$^{22}_D$ −31.8° (c 0.110, CHCl₃); IR (CHCl₃): 2104 w, 1741 vs, 1675 w, 1644 w, 1551 w, 1465 m, 1388 m, sh, 1376 m, 1209 s, 1182 m, 1147 m, 1106 s, cm$^{-1}$; ESI MS: 196 ([M+H]⁺); HR ESI MS: calcd for C₉H₁₄O₂N₃ 196.10805; found 196.10808.

Example 5

Evaluation of DON Prodrugs

Overview. The presently disclosed subject matter demonstrates profound efficacy of DON in murine model of GBM, although overt toxicities were observed. In attempt to increase DON's therapeutic index, several DON prodrugs were systematically synthesized. The initial strategy involved masking DON's carboxylic acid with simple alkyl esters, such as ethyl ester 20 and isopropyl ester 3 (FIG. 20). However, 3 and 20 exhibited chemical instability cyclizing to form a unique diazo-imine. Given this instability, both the primary amine and the carboxylate of DON were next masked with prodrug moieties. Three types of amine promoieties were used, including (oxodioxolenyl)methyl carbamate esters (13 and 36), dipeptides (9 and 25), and pivaloyl-oxy-methyl (POM)-based esters (14, 32 and 42). The dual promoiety-containing prodrugs resulted in sufficient chemical stability permitting further evaluation in in vitro metabolic stability assays. While all of the prodrugs exhibited rapid metabolism in mouse plasma, some provided excellent plasma stability in monkeys and humans. When evaluated in vivo, the most stable DON prodrug (5c, methyl-POM-DON-isopropyl-ester) achieved 10-fold enhanced brain:plasma ratio versus DON in monkeys, thus providing a possible clinical path to DON utilization in GBM patients.

Chemistry. Scheme 9 outlines the synthesis and characterization of the ester based prodrugs 20 and 3 of DON and their subsequent cyclization to novel diazo-imines 9a-b. The pyroglutamate esters 6a-b (D'Andrea, et al., 2008) were FMOC-protected to afford compounds 18 and 1. Formation of the diazoketones 19 and 2 was accomplished using TMS diazomethane in good yield. Rapid deprotection with piperidine afforded the ester based prodrugs 20 and 3. Unexpectedly slow cyclization was observed even under mild conditions (e.g. stirring in chloroform at room temperature) affording the novel diazo-imines 9a and 9b. It is believed that this is the first example of this functional group being described in the chemical literature. Attempts to avoid the cyclization of 20 and 3 by salt formation to protonate the amine resulted in instability of the diazo group. Furthermore, unlike most imines, the 5-member cyclic diazo-imines 9a-b were found to be stable, even at acidic pH, and did not convert back to DON esters (results not shown).

TABLE 3

| Novel Diazo-imines | |
|---|---|
| 9a | 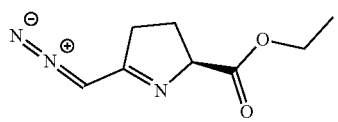 |
| 9b | 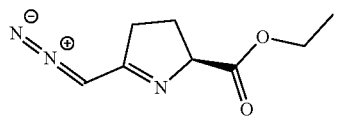 |

Given their sufficient chemical stability, compounds 20 and 3 were utilized as synthetic intermediates for preparation of dual promoiety prodrugs (Schemes 8 and 2). The (oxodioxolenyl) methyl carbamate adducts 36 and 13 were synthesized as outlined in Schemes 8 and 2. The 4-(hydroxymethyl)-5-methyl-1,3-dioxol-2-one was reacted with S-ethyl carbonochloridothionate. (Keicher, et al., 2009) followed by N-hydroxysuccinimide to provide 12. Reaction of 20 and 3 with 12 afforded the (oxodioxolenyl) methyl carbamate esters 36 and 13 in excellent yields.

Schemes 1, 4, and 7 outline the synthesis of DON dipeptide esters. DON esters 20 and 3 were coupled with Fmoc-L-leucine or Fmoc-L-tryptophan using HBTU in high yield to form the protected dipeptides 33 and 37 (scheme 7). Deprotection with diethyl amine or piperidine afforded the desired leucine-DON 25 (scheme 4) and 9 (scheme 1) and tryptophan-DON prodrugs 34 and 38 (scheme 7).

As shown in Scheme 6, the POM derivative 42 was synthesized from 20 using the POM-N-hydroxysuccinamate ester (Gallop, et al., 2008) in 40% yield. Introduction of methyl group in the POM ester led to the formation of methyl-POM derivatives 32 (scheme 6) and 14 (scheme 2), with an added chiral center. Both 32 and 14 were synthesized from 20 and 3 using 1-((((2,5-dioxopyrrolidin-1-yl)oxy)carbonyl)oxy)ethyl pivalate (Gallop, et al., 2008), 32 was obtained as a mixture of two diastereomers (1:1 ratio) in 68% yield. 14 was also obtained diastereomeric mixture (1:1) ratio, but was further purified into its corresponding diastereomers 14a and 14b, of which diastereomer 14b was used for subsequent biological testing as described below. The acetal methyl stereochemistry of 14a and 14b was assigned arbitrarily.

Results and Discussion.

DON showed robust inhibition of glutamine metabolism and antitumor efficacy in a murine GBM model. Despite several lines of evidence indicating the potential therapeutic efficacy of targeting glutamine metabolism in GBM, the effect of DON on GBM tumor growth has not yet been reported in vivo. Using the U87 flank xenograft mouse model of GBM, (Eshleman, et al., 2002) it has been first confirmed that systemic administration of DON (0.8 mg/kg, i.p) inhibited glutamine metabolism as reflected by an accumulation of endogenous glutamine in the tumor (FIG. 21A; $p<0.05$) similar to other model systems. (Willis, et al., 1977; Windmueller, et al., 1974) Then its antitumor efficacy was evaluated, and observed that DON not only halted tumor growth, but also effectively induced tumor regression. Specifically, vehicle-treated mice displayed significant tumor growth over the course of the experiment, while DON-treated mice (0.8 mg/kg, i.p, q.d.) exhibited >50% reduction in tumor volume (FIG. 21B; main effect of time $[F(3,48)=6.049, p=0.0014]$; treatment $[F(1.16)=33.42, p<0.0001]$; interaction $[F(3,48)=21.70, p<0.0001]$). Although DON exhibited excellent anti-tumor efficacy, all mice receiving DON displayed significant signs of toxicity including weight loss (12±4.1%), hunching, ptosis, and lethargy. These findings are consistent with other reports of DON's efficacy and toxicity both in vitro and in vivo. (Fogal, et al., 2015; Cervantes-Madrid, et al., 2015: Potter, et al., 2015)

Some simple DON alkyl ester prodrugs found to be unstable. Masking both DON's carboxylate and amine functionalities enhanced the stability of certain prodrugs. A prodrug strategy is often employed to enhance tissue penetration and change the pharmacokinetic parameters of effective drugs. Indeed, prodrug strategies are common in drug development as 5-7% of the approved worldwide drugs are prodrugs (Rautio, et al., 2008). The initial prodrug strategy for DON involved masking the carboxylic acid with simple alkyl esters such as ethyl 20 and isopropyl 3. The synthesis of these two derivatives was straightforward affording compounds 20 and 3 in good yield. It is surprising that these simple DON alkyl esters had not previously been reported in the chemical literature, given that DON chemistry and utility has been described by numerous groups for over 60 years (Magill, et al., 1957; Dion, et al., 1956; Magill, et al., 1956; Coffey, et al., 1956). One potential reason is that it has been discovered that 20 and 3 were unstable, slowing cyclizing to form unique diazo-imines 9a and 9b. These two unique derivatives were found to be chemically stable even at acidic pH, precluding their use as DON prodrugs.

Given the instability of certain simple ester prodrugs, both the primary amine and the carboxylate of DON were masked with prodrug moieties. This dual promoiety strategy was rationalized to eliminate the potential for cyclization and potentially further improve the lipophilicity. Three amine promoieties including (oxodioxolenyl)methyl carbamate esters were used (FIG. 20, compounds 36, 13), dipeptides (25 and 38), and pivaloyl-oxy-methyl (POM)-based esters (42, 32, 14b). These promoeities were chosen because they target distinct metabolic enzymes including paraoxonase, aminopeptidases, and carboxylesterases, respectively. To impart further metabolic stability of the POM derivative (Table 3, 42), corresponding methyl-POM analogs were prepared (32, 14b). All dual promoiety-containing prodrugs exhibited sufficient chemical stability to permit further evaluation.

All DON prodrugs were rapidly metabolized in mouse plasma, however 32 and 14b found to be stable in human and monkey plasma. Table 3 outlines the plasma stability of DON prodrugs 36, 13, 25, 9, 34, 38, 42, 32 and 14b. All prodrugs were completely metabolized in mouse plasma within the 60 min incubation time. However in monkey and human plasma, the prodrugs 32 and 14b, with methyl-POM on the amine and ethyl or isopropyl ester on the carboxylate respectively, demonstrated moderate/high stability with 60-75% of the prodrug remaining in monkey plasma, and 80-90% remaining in human plasma within the 60 min incubation time. Given 14b had the best stability profile in human plasma, it was selected for further evaluation in pharmacokinetic studies and compared to DON for its ability to penetrate the brain and liberate DON.

TABLE 4

| Compound # | PLASMA STABILITY | | |
|---|---|---|---|
| | Mouse | Monkey | Human |
| 36 | 0 | 0 | 0 |
| 13 | 0 | 0 | 0 |
| 25 | 0 | 1 | 1 |
| 9 | 0 | 1 | 1 |
| 34 | 0 | 4 | 12 |
| 38 | 0 | 10 | 30 |
| 42 | 0 | 0 | 9 |
| 32 | 0 | 75 | 88 |
| 14b | 0 | 61 | 91 |

Lead prodrug 14 enhanced brain delivery of DON in monkeys but not in mice.

As expected from a DON prodrug which is completely metabolized in mouse plasma, it has been found that oral administration of DON (1) (0.8 mg/kg) and 14b (0.8 mg/kg equivalent) exhibited similar DON plasma (FIG. 22A) and brain (FIG. 22B) concentration profiles when dosed in mice. The $AUC_{0-t}$ of DON following administration of DON and 14b in plasma were 1.25 nmol*h/mL and 1.22 nmol*h/mL respectively, suggesting rapid and complete liberation of DON from 14b in vivo. Similarly in the mouse brain, the $AUC_{0-t}$ of DON following DON or 14b administration was 0.57 nmol*h/g and 0.69 nmol*h/g, respectively, with the brain/plasma approximately 0.46 from DON vs 0.56 from prodrug 14b. These pharmacokinetic results corroborated the in vitro metabolism studies suggesting 14b was completely converted to DON in mouse plasma.

Following the mouse studies, the pharmacokinetics of DON and 14b were evaluated in monkeys, as monkeys better mimicked the human plasma stability profile. In pigtail macaques, i.v. administration of DON and 14b (1.6 mg/kg DON equivalent) demonstrated significantly different DON plasma profiles FIG. 23A). DON administration provided high plasma exposures with $AUC_{0-t}$ of 42.7 nmol*h/mL. In contrast, 14b administration delivered about 7 fold lower plasma exposure of DON with $AUC_{0-t}$ of 5.71 nmol*h/mL. The opposite observation was seen in the CSF where enhanced DON levels were observed after 14 administration. In the CSF at 30 min post dose, DON administration resulted in 0.33 nmol/g DON while 14b delivered 1.43 nmol/g DON. When comparing plasma to CSF ratio at 30 min, 14b demonstrated 10-fold enhancement of DON CSF delivery versus DON (FIG. 23B).

The glutamine antagonist 6-diazo-5-oxo-L-norleucine (DON, 1) has shown robust anti-cancer efficacy in preclinical and clinical studies, but its development was halted due to marked systemic toxicities. Herein it has been demonstrated that DON inhibits glutamine metabolism and provides antitumor efficacy in a murine model of glioblastoma, although toxicity was observed. To enhance DON's therapeutic index, a prodrug strategy was used to increase its brain delivery and limit systemic exposure. Unexpectedly, simple alkyl ester-based prodrugs were ineffective due to chemical instability cyclizing to form a unique diazo-imine. However, masking both DON's amine and carboxylate functionalities imparted sufficient chemical stability for biological testing. While these dual moiety prodrugs exhibited rapid metabolism in mouse plasma, several provided excellent stability in monkey and human plasma. The most stable compound (14b, methyl-POM-DON-isopropyl-ester) is highly stable in plasma from monkey, human, pigs and dog but is rapidly metabolized in mice. When evaluated in monkeys at an equimolardoses, 14b delivered lower levels of DON to plasma but higher levels in CSF it achieved 10-fold enhanced brain:plasma ratio versus DON. This strategy may provide a path to DON utilization in GBM patients.

Example 6

Compound 14b Enhanced CSF Delivery of DON in Monkey

Method

Compound: Compound 14b was dissolved in 50 mM HEPES buffered saline containing 5% ethanol and 5% tween on the date of administration.

Monkey: Monkey studies were conducted according to protocol (#PR15M298) approved by the Animal Care and Use Committee at Johns Hopkins University. Two female pigtail monkeys (approximately 3.5 kg, non-drug naive) were adjacently housed in stainless steel cages on a social interaction rack (contains 4 cages, each 325" wide×28" deep×32" high) maintaining temperature of 64-84° F., humidity of 30-70% with alternating 14-10 hour light/dark cycle as per the USDA Animal Welfare Act (9 CFR, Parts 1, 2, and 3). Food was provided daily in amounts appropriate for the size and age of the animals and RO purified water provided ad libitum through an in-cage lixit valve. Food enrichment was provided Monday through Friday.

Treatment: Prior to drug administration, macaques were sedated with ketamine given as an intramuscular injection prior to test article administration. Sedation was maintained through blood and cerebrospinal fluid (CSF) sample collections with ketamine at a starting rate of 15 mg/kg with additional doses of 20-30 mg during the first hour. At subsequent time points ketamine was given at 10-15 mg/kg. DON (50 mM HEPES buffered saline) and compound 14b (50 mM HEPES buffered saline containing 5% ethanol and 5% tween) were administered (1.6 and 3.6 mg/kg equivalent dose of DON) to the animals at a dosing volume of 1 mL/kg intravenously. CSF sample (target of 50 µL) was obtained by percutaneous puncture of the cisterna magna at 30 min post dose. Blood samples (1 mL) were collected at 15 min, 30 min, 1 h, 2 h, 4 h, and 6 h post dose by percutaneous puncture of a peripheral vein. Samples were processed for plasma (centrifuged at a temperature of 4° C., at 3,000 g, for 10 minutes). All samples were maintained chilled on ice throughout processing. Samples were collected in microcentrifuge tubes, flash frozen, and placed in a freezer set to maintain −80° C. until LC/MS analysis.

Data Analysis: DON was extracted from samples (50 mg) with 250 µL methanol containing glutamate-$d_5$ (10 µM ISTD) by vortexing in low retention tubes. Samples were centrifuged at 16,000 g for 5 minutes to precipitate proteins. Supernatants (200 µL) were moved to new tubes and dried at 45° C. under vacuum for 1 hour. To each tube, 50 µL of 0.2 M sodium bicarbonate buffer (pH 9.0) and 100 µL of 10 mM dabsyl chloride in acetone was added. After vortexing, samples were incubated at 60° C. for 15 minutes to derivatize. Samples (2 µL) were injected and separated on an Agilent 1290 equipped with an Agilent Eclipse plus C18 RRHD 2.1×100 mm column over a 2.5 minute gradient from 20-95% acetonitrile+0.1% formic acid and quantified on an Agilent 6520 QTOF mass spectrometer. Calibration curves over the range of 0.005-17.1 µg/mL in plasma and CSF for DON were constructed from the peak area ratio of the analyte to the internal standard using linear regression with a weighting factor of 1/(nominal concentration). Correlation coefficient of greater than 0.99 was obtained in all analytical runs. The mean predicted relative standard deviation for back calculated concentrations of the standards and QC's for all analytes were within the range of 85 to 115%, except for the lowest concentration which was within the range of 80 to 120% with an overall accuracy and precision of 6.7% and 6.6% respectively.

Results

The pharmacokinetics of DON and compound 14b in monkeys were evaluated. In pigtail macaques, i.v. administration of DON (1.6 mg/kg) and compound 14b (3.6 mg/kg; 1.6 mg/kg DON equivalent) demonstrated significantly different DON plasma profiles (FIG. 58A). DON administration provided high plasma exposures with AUC0-t of 42.7 nmol*h/mL. In contrast, compound 14b administration delivered ~7 fold lower plasma exposure of DON with AUC0-t of 5.71 nmol*h/mL. The opposite observation was seen in the CSF where enhanced DON levels were observed after compound 14b administration. In the CSF at 30 min post dose, DON administration resulted in 0.33 nmol/g DON while compound 14b delivered 1.43 nmol/g DON. When comparing plasma to CSF ratio at 30 min, compound 14b demonstrated unexpected 10-fold enhancement of DON CSF delivery versus DON (FIG. 58B).

Example 7

Compounds 14b and 47 Enhanced CSF Delivery of DON in Swine

Method

Compound: Compound 47 was dissolved in a sterile saline containing 5% ethanol and 5% Tween 80 on the date of administration.

Swine: Swine studies were conducted under a protocol approved by the Johns Hopkins Animal Care and Use Committee. Adult, female Göttingen×Yucutan miniature swine (Massachusetts General Hospital, MA) were housed in Johns Hopkins University facilities accredited by the Association for Assessment and Accreditation of Laboratory Animal Care International in compliance with the Animal Welfare Act, Animal Welfare Regulations, and the Public Health Service Policy on the Humane Care and Use of Laboratory Animals. Animals were maintained on a 14-h light and 10-h dark schedule, provided ad libitum water and a commercial miniswine diet (Teklad, Madison, WI) with environmental enrichment (fruit/vegetables) twice daily.

DON and Compounds 14b and 47 Treatment: Animals were individually housed while on study in order to monitor behavior and clinical health following drug administration. Whole blood for drug pharmacokinetic evaluation was collected from a dual lumen central venous catheter (CVC) implanted in the external jugular vein prior to study initiation. Animals were anesthetized with a combination of ketamine hydrochloride (20-30 mg/kg, i.m.) and xylazine (2 mg/kg, i.m.), intubated, and maintained under isoflurane (1-2%) inhalant anesthesia A temporary peripheral saphenous vein catheter was placed in the hind limb to allow for anatomical separation of drug infusion and whole blood sampling via CVC. DON and compounds 14b and 47 were dissolved in a sterile saline solution containing 5% ethanol and 5% Tween 80 prior to i.v. infusion via saphenous vein catheter over 1 hour (1 ml/min) for a final dose of 1.6 mg/kg or molar equivalent administered at 1 ml/kg (n=1/dose). Blood samples (1 mL) were taken from CVC at predose, 5, 15, 30, 45, and 60 min. Plasma was separated by low speed centrifugation at 3000 g for 10 min at 4° C. CSF was obtained from the cisterna magna using a 3.5 in×22 gauge spinal needle (Becton Dickinson Health Care, Franklin Lakes, New Jersey. USA) at 60 min post-dose. All samples were flash frozen upon harvest and stored at −80 C until bioanalysis.

Data analysis: Quantitation of DON in plasma, CSF, and brain homogenate by LC-MS/MS was performed. Briefly. DON was extracted from plasma, CSF, and brain samples with methanol containing glutamate-$d_5$ (10 µM ISTD) by vortexing followed by centrifugation 16000 g for 5 min. Supernatants were aliquoted and dried at 45° C. for under vacuum for 1 h. Sodium bicarbonate buffer (0.2M, pH 9.0) and dabsyl chloride (10 mM) in acetone were added to each tube, mixed, and incubated for 15 min at 60° C. to derivatize. Samples were then injected and separated on an Agilent 1290 equipped with an Agilent Eclipse plus C18 RRHD 2.1×100 mm column over a 2.5 min gradient from 20 to 95% acetonitrile+0.1% formic acid and quantified on an Agilent 6520 QTOF mass spectrometer. Peak area ratio of the analyte to the internal standard was plotted against a 14 standard curve to yield DON concentrations for each sample.

Result

The pharmacokinetic of DON, compound 14b and compound 47 were evaluated in swine. IV administration of compounds 14b and 47 (1.6 mg/kg DON equivalent dose) resulted in 3-5-fold lower DON plasma exposures relative to an equimolar dose of DON (FIG. 59A). Plasma $AUC_{0-t}$ for DON and compounds 14b and 47 were 29.9, 8.00 and 5.70 nmol h/mL, respectively. The opposite trend occurred in CSF, where compounds 14b and 47 delivered substantially higher amounts of DON to the CSF (FIG. 59B), resulting in unexpected increased CSF-to-plasma ratios (FIG. 59C).

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Ahluwalia, G. S.; Grem, J. L.; Hao, Z.; Cooney, D. A. Metabolism and action of amino acid analog anti-cancer agents. *Pharmacol Ther* 1990, 46, 243-271.

Alt, J.; Potter, M. C.; Rojas, C.; Slusher, B. S. Bioanalysis of 6-diazo-5-oxo-1-norleucine in plasma and brain by ultra-performance liquid chromatography mass spectrometry. *Anal Biochem* 2015, 474, 28-34.

Barclay, R. K.; Phillipps, M. A. Effects of 6-diazo-5-oxol-norleucine and other tumor inhibitors on the biosynthesis of nicotinamide adenine dinucleotide in mice. *Cancer Res* 1966, 26, 282-286.

Cervantes-Madrid, D.; Romero, Y.; Duenas-Gonzalez, A. Reviving Lonidamine and 6-Diazo-5-oxo-L-norleucine to Be Used in Combination for Metabolic Cancer Therapy. *Biomed Res Int* 2015, 2015, 690492.

Coffey. G. L.; Ehrlich, J.; Fisher, M. W.; Hillegas, A. B.; Kohberger, D. L.; Machamer, H. E.; Rightsel, W. A.; Roegner, F. R. 6-Diazo-5-oxo-L-norleucine, a new tumor-inhibitory substance. I. Biologic studies. *Antibiot Chemother (Northfield)* 1956, 6, 487-497.

D'Andrea, S.; Zheng, Z.; Scola, P. Inhibitors of Hepatitis C Virus. In Google Patents; 2008.

Dion, H. W.; Fusari, S. A.; Jakubowski, Z. L.; Zora, J. G.; Bartz, Q. R. 6-Diazo-5-oxo-L-norleucine. A New Tumor-inhibitory Substance. II.1 Isolation and Characterization. *J. Am. Chem. Soc.* 1956, 78, 3075-3077.

Dranoff, G.; Elion, G. B.; Friedman, H. S.; Bigner, D. D. Combination chemotherapy in vitro exploiting glutamine metabolism of human glioma and medulloblastoma. *Cancer Res* 1985, 45, 4082-4086.

Dranoff, G.; Elion, G. B.; Friedman, H. S.; Campbell, G. L.; Bigner, D. D. Influence of glutamine on the growth of human glioma and medulloblastoma in culture. *Cancer Res* 1985, 45, 4077-4081.

Eagan, R. T.; Frytak, S.; Nichols, W. C.; Creagan, E. T.; Ingle, J. N. Phase II study on DON in patients with previously treated advanced lung cancer. *Cancer Treat Rep* 1982, 66, 1665-1666.

Earhart, R. H.; Amato, D. J.; Chang, A. Y.; Borden, E. C.; Shiraki, M.; Dowd, M. E.; Comis, R. L.; Davis, T. E.; Smith, T. J. Phase II trial of 6-diazo-5-oxo-L-norleucine versus aclacinomycin-A in advanced sarcomas and mesotheliomas. *Invest New Drugs* 1990, 8, 113-119.

Earhart, R. H.; Koeller, J. M.; Davis, H. L. Phase I trial of 6-diazo-5-oxo-L-norleucine (DON) administered by 5-day courses. *Cancer Treat Rep* 1982, 66, 1215-1217.

Erickson, J. W.; Cerione, R. A. Glutaminase: a hot spot for regulation of cancer cell metabolism? *Oncotarget* 2010, 1, 734-740.

Eshleman, J. S.; Carlson, B. L.; Mladek, A. C.; Kastner, B. D.; Shide, K. L.; Sarkaria, J. N. Inhibition of the mammalian target of rapamycin sensitizes U87 xenografts to fractionated radiation therapy. *Cancer Res* 2002, 62, 7291-7297.

Fogal, V.; Babic, I.; Chao, Y.; Pastorino, S.; Mukthavaram, R.; Jiang, P.; Cho, Y. J.; Pingle, S. C.; Crawford, J. R.; Piccioni, D. E.; Kesari, S. Mitochondrial p32 is upregulated in Myc expressing brain cancers and mediates glutamine addiction. *Oncotarget* 2015, 6, 1157-1170.

Gallop, M. A.; Xu, F.; Phan, T.; Dilip, U.; Peng, G. Acyloxyalkyl carbamate prodrugs, methods of synthesis and use. In Google Patents: 2008.

Grayzel, A. I.; Seegmiller, J. E.; Love, E. Suppression of uric acid synthesis in the gouty human by the use of 6-diazo-5-oxo-L-norleucine. *J Clin Invest* 1960, 39, 447-454.

Gross, M. I.; Demo, S. D.; Dennison, J. B.; Chen, L.; Chernov-Rogan, T.; Goyal, B.; Janes, J. R; Laidig, G. J.; Lewis, E. R.; Li, J.; MacKinnon, A. L.; Parlati, F.; Rodriguez, M. L. M.; Shwonek, P. J.; Sjogren, E. B.; Stanton, T. F.; Wang, T.; Yang, J.; Zhao, F. Y.; Bennett, M. K. Antitumor Activity of the Glutaminase Inhibitor CB-839 in Triple-Negative Breast Cancer. *Mol Cancer Ther* 2014.

Harding, J. J. T., M. L.; Munster, P. N.; Le, M. H.; Molineaux, C.; Bennett, M. K.; Mittra, E.; Burris, H. A.; Clark, A. S.; Dunphy, M.; Meric-Bernstam, F.; Patel, M. R.; DeMichele, A.; Infante, J. R. Safety and tolerability of increasing doses of CB-839, a first-in-class, orally administered small molecule inhibitor of glutaminase, in solid tumors. *J Clin Oncol* 2015.

Hensley, C. T.; Wasti, A. T.; DeBerardinis, R. J. Glutamine and cancer: cell biology, physiology, and clinical opportunities. *J Clin Invest* 2013, 123, 3678-3684.

Hofer, A.; Steverding, D.; Chabes, A.; Brun, R.; Thelander, L. Trypanosoma brucei CTP synthetase: a target for the treatment of African sleeping sickness. *Proc Natl Acad Sci USA* 2001, 98, 6412-6416.

Hu, X.; Stern, H. M.; Ge, L.; O'Brien, C.; Haydu, L.; Honchell, C. D.; Haverty, P. M.; Peters, B. A.; Wu, T. D.; Amler, L. C.; Chant, J.; Stokoe, D.; Lackner, M. R.; Cavet, G. Genetic alterations and oncogenic pathways associated with breast cancer subtypes. *Mol Cancer Res* 2009, 7, 511-522.

Keicher, J. D.; Roberts, C. D.; Rajwanshi, V. K.; Griffith, R C.; Zheng, X.; Liehr, S. J. R.; Prhavc, M.; Kim, C. U.; Ray, A. S. Amino tricyclic-nucleoside compounds, compositions, and methods of use. In Google Patents: 2009.

Konopleva, M. Y.; Flinn, I. W.; Wang, E.; DiNardo, C. D.; Bennett, M.; Molineaux, C.; Le, M.; Maris, M.; Frankfurt, O. In Phase I study: Safety and tolerability of increasing doses of cb-839, an orally-administered small molecule inhibitor of glutaminase, in acute leukemia. Haematologica, 2015; Ferrata Storti Foundation Via Giuseppe Belli 4, 27100 Pavia, Italy: 2015; pp 378-379.

Le, A.; Lane, A. N.; Hamaker, M.; Bose, S.; Gouw, A.; Barbi, J.; Tsukamoto, T.; Rojas, C. J.; Slusher, B. S.; Zhang, H.; Zimmerman, L. J.; Liebler, D. C.; Slebos, R. J.; Lorkiewicz, P. K.; Higashi, R. M.; Fan, T. W.; Dang, C. V. Glucose-independent glutamine metabolism via TCA cycling for proliferation and survival in B cells. *Cell Metab* 2012, 15, 110-121.

Lee, Y. Z.; Yang, C. W.; Chang, H. Y.; Hsu, H. Y.; Chen, I. S.; Chang, H. S.; Lee, C. H.; Lee, J. C.; Kumar. C. R.; Qiu, Y. Q.; Chao, Y. S.; Lee, S. J. Discovery of selective inhibitors of Glutaminase-2, which inhibit mTORC1, activate autophagy and inhibit proliferation in cancer cells. *Oncotarget* 2014, 5, 6087-6101.

Lynch, G.; Kemeny, N.; Casper, E. Phase II evaluation of DON (6-diazo-5-oxo-L-norleucine) in patients with advanced colorectal carcinoma. *Am J Clin Oncol* 1982, 5, 541-543. Magill, G. B.; Myers, W. P. Alterations in calcium metabolism in cancer patients treated with 6-diazo-5-oxo-L-norleucine. *Proc Soc Exp Biol Med* 1956, 93, 314-318.

Magill, G. B.; Myers, W. P.; Reilly, H. C.; Putnam, R. C.; Magill. J. W.; Sykes, M. P.; Escher, G. C.; Karnofsky, D. A.; Burchenal, J. H. Pharmacological and initial therapeutic observations on 6-diazo-5-oxo-1-norleucine (DON) in human neoplastic disease. *Cancer* 1957, 10, 1138-1150.

McDermott, L. A.; Iyer, P.; Vernetti, L.; Rimer, S.; Sun, J.; Boby, M.; Yang, T.; Fioravanti, M., O'Neill, J.; Wang, L.; Drakes, D.; Katt, W.; Huang, Q.; Cerione, R. Design and evaluation of novel glutaminase inhibitors. *Bioorg Med Chem* 2016, 24, 1819-1839.

Ostrom, Q. T.; Gittleman, H.; Fulop, J., Liu, M.; Blanda, R.; Kromer, C.; Wolinsky, Y.; Kruchko, C.; Bamholtz-Sloan, J. S. CBTRUS Statistical Report: Primary Brain and Central Nervous System Tumors Diagnosed in the United States in 2008-2012. *Neuro Oncol* 2015, 17 Suppl 4, iv1-iv62.

Potter, M. C.; Baxter, V. K.; Mathey, R. W.; Alt, J.; Rojas, C.; Griffin, D. E.; Slusher, B. S. Neurological sequelae induced by alphavirus infection of the CNS are attenuated by treatment with the glutamine antagonist 6-diazo-5-oxo-1-norleucine. *J Neurovirol* 2015, 21, 159-173.

Rahman, A.; Smith, F. P.; Luc, P. T.; Woolley, P. V. Phase I study and clinical pharmacology of 6-diazo-5-oxo-L-norleucine (DON). *Invest New Drugs* 1985, 3, 369-374.

Rautio, J.; Kumpulainen, H.; Heimbach, T.; Oliyai, R.; Oh, D.; Jarvinen, T.; Savolainen, J. Prodrugs: design and clinical applications. *Nat Rev Drug Discov* 2008, 7, 255-270.

Ru, P.; Williams, T. M.; Chakravarti, A.; Guo, D. Tumor metabolism of malignant gliomas. *Cancers (Basel)* 2013, 5, 1469-1484.

Schulze, A.; Harris, A. L. How cancer metabolism is tuned for proliferation and vulnerable to disruption. *Nature* 2012, 491, 364-373.

Shukla, K.; Ferraris, D. V.; Thomas, A. G.; Stathis, M.; Duvall, B.; Delahanty, G.; Alt, J.; Rais, R.; Rojas, C.; Gao, P., Xiang, Y.; Dang, C. V.; Slusher, B. S.; Tsukamoto, T. Design, synthesis, and pharmacological evaluation of bis-2-(5-phenylacetamido-1,2,4-thiadiazol-2-yl)ethyl sulfide 3 (BPTES) analogs as glutaminase inhibitors. *J Med Chem* 2012, 35, 10551-10563.

Sklaroff, R. B.; Casper, E. S.; Magill, G. B.; Young, C. W. Phase I study of 6-diazo-5-oxo-L-norleucine (DON). *Cancer Treat Rep* 1980, 64, 1247-1251.

Stupp, R.; Hegi, M. E.; Mason, W. P.; van den Bent, M. J.; Taphoorn, M. J.; Janzer, R. C.; Ludwin, S. K.; Allgeier, A.; Fisher, B.; Belanger, K.; Hau, P.; Brandes, A. A.; Gijtenbeek, J.; Marosi, C.; Vecht, C. J.; Mokhtari, K.; Wesseling, P.; Villa, S.; Eisenhauer, E.; Gorlia, T.; Weller, M.; Lacombe, D.; Caimcross, J. G.; Mirimanoff, R. O. Effects of radiotherapy with concomitant and adjuvant temozolomide versus radiotherapy alone on survival in glioblastoma in a randomised phase III study: 5-year analysis of the EORTC-NCIC trial. *Lancet Oncol* 2009, 10, 459-466.

Stupp, R.; Mason, W. P.; van den Bent, M. J.; Weller, M.; Fisher, B.; Taphoom, M. J.; Belanger, K.; Brandes, A. A.;

Marosi, C.; Bogdahn, U.; Curschmann, J.; Janzer, R. C.; Ludwin, S. K.; Gorlia, T.; Allgeier, A.; Lacombe, D.; Cairncross, J. G.; Eisenhauer, E.; Mirimanoff, R. O. Radiotherapy plus concomitant and adjuvant temozolomide for glioblastoma. *N Engl J Med* 2005, 352, 987-996.

Sullivan, M. P.; Beatty, E. C., Jr.; Hyman, C. B.; Murphy, M. L.; Pierce, M. I.; Severo, N. C. A comparison of the effectiveness of standard dose 6-mercaptopurine, combination 6-mercaptopurine and DON, and high-loading 6-mercaptopurine therapies in treatment of the acute leukemias of childhood: results of a coperative study. *Cancer Chemother Rep* 1962, 18, 83-95.

Sullivan, M. P.; Nelson, J. A.; Feldman, S.; Van Nguyen, B. Pharmacokinetic and phase I study of intravenous DON (6-diazo-5-oxo-L-norleucine) in children. *Cancer Chemother Pharmacol* 1988, 21, 78-84.

Tanaka, K., Sasayama, T.; Irino, Y.; Takata, K.; Nagashima, H.; Satoh, N.; Kyotani, K.; Mizowaki, T.; Imahori, T.; Ejima, Y.; Masui, K.; Gini, B.; Yang, H.; Hosoda, K.; Sasaki, R.; Mischel, P. S.; Kohmura, E. Compensatory glutamine metabolism promotes glioblastoma resistance to mTOR inhibitor treatment, *J Clin Invest* 2015, 125, 1591-1602.

Thangavelu, K.; Chong, Q. Y.; Low, B. C.; Sivaraman, J. Structural basis for the active site inhibition mechanism of human kidney-type glutaminase (KGA). *Sci Rep* 2014, 4, 3827.

Upadhyay, R. K. Drug delivery systems, CNS protection, and the blood brain barrier. *Biomed Res Int* 2014, 2014, 869269.

Weller, M.; van den Bent, M.; Hopkins, K.; Tonn, J. C.; Stupp, R.; Falini, A.; Cohen-Jonathan-Moyal, E.; Frappaz, D.; Henriksson, R.; Balana, C.; Chinot, O.; Ram, Z.; Reifenberger, G.; Soffietti, R.; Wick, W. EANO guideline for the diagnosis and treatment of anaplastic gliomas and glioblastoma. *Lancet Oncol* 2014, 15, e395-403.

Willis, R. C.; Seegmiller, J. E. The inhibition by 6-diazo-5-oxo-1-norleucine of glutamine catabolism of the cultured human lymphoblast, *J Cell Physiol* 1977, 93, 375-382.

Windmueller, H. G.; Spaeth, A. E. Uptake and metabolism of plasma glutamine by the small intestine. *J Biol Chem* 1974, 249, 5070-5079.

Wise, D. R.; Thompson, C. B. Glutamine addiction: a new therapeutic target in cancer. *Trends Biochem Sci* 2010, 35, 427-433.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound having formula (I):

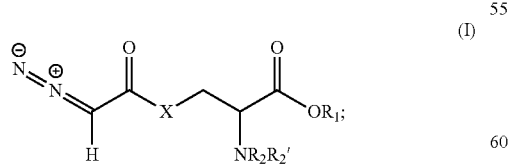

or a pharmaceutically acceptable salt thereof, wherein:
X is —(CH$_2$)$_n$—, wherein n is 1;
R$_1$ is selected from the group consisting of H, C$_{1-6}$ alkyl, and substituted C$_{1-6}$ alkyl;
R$_2$ is —C(=O)—O—(CR$_3$R$_4$)$_m$—O—C(=O)—R$_{10}$;

R$_2$' is selected from the group consisting of H, C$_1$-C$_6$ alkyl, and substituted C$_1$-C$_6$ alkyl;
each R$_3$ and R$_4$ are independently H, C$_1$-C$_6$ alkyl, substituted C$_1$-C$_6$ alkyl, aryl,

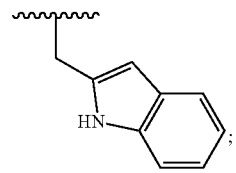

substituted aryl or
m is 1; and
R$_{10}$ is selected from the group consisting of alkyl, substituted alkyl, cycloalkyl, substituted cycloalkyl, monosaccharide, acylated monosaccharide, aryl, substituted aryl, heteroaryl, and substituted heteroaryl.

2. The compound of claim 1, wherein R$_1$ is selected from the group consisting of methyl, ethyl, and isopropyl.

3. The compound of claim 1 having formula (III):

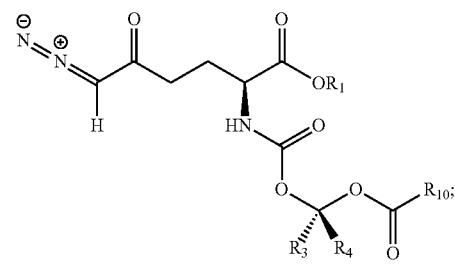

or a pharmaceutically acceptable salt thereof, wherein:
R$_1$ is selected from the group consisting of H and C$_{1-6}$ alkyl;
R$_3$ and R$_4$ are independently selected from the group consisting of H, C$_1$-C$_6$ alkyl, substituted C$_1$-C$_6$ alkyl, aryl, and substituted aryl; and
R$_{10}$ is C$_{1-6}$ alkyl.

4. The compound of claim 1, wherein the compound of formula (I) is selected from the group consisting of:

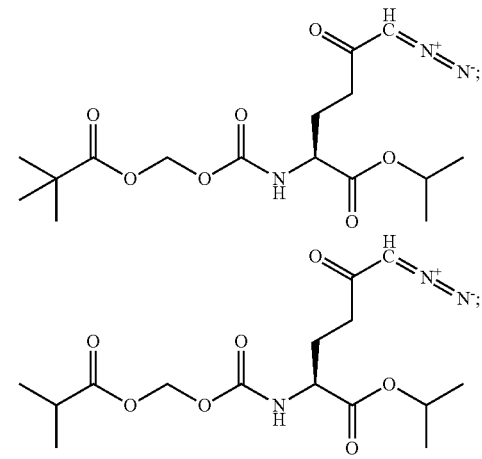

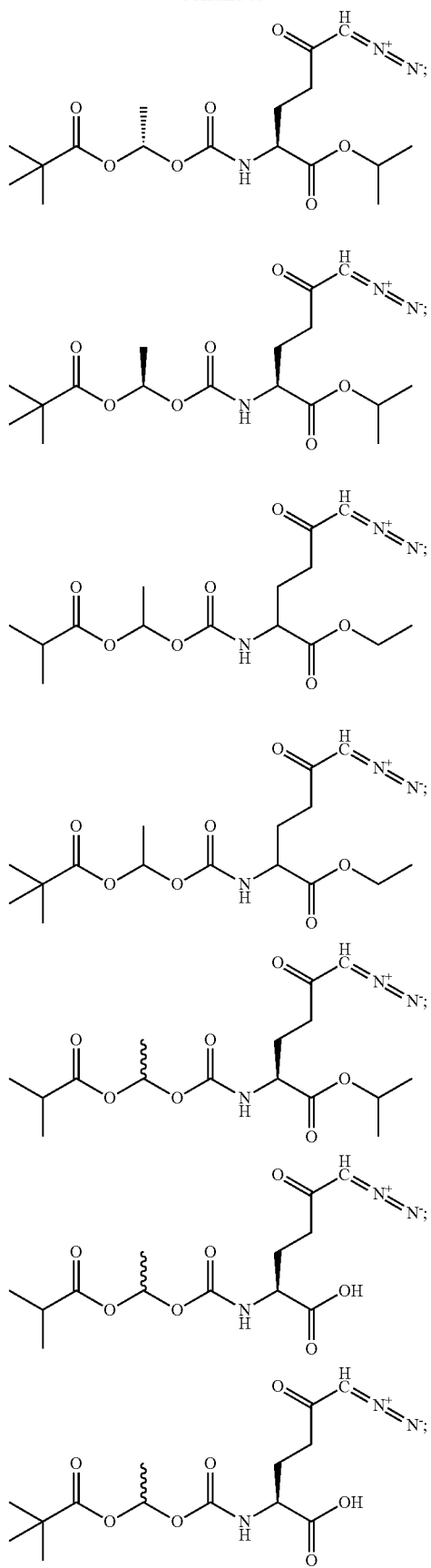

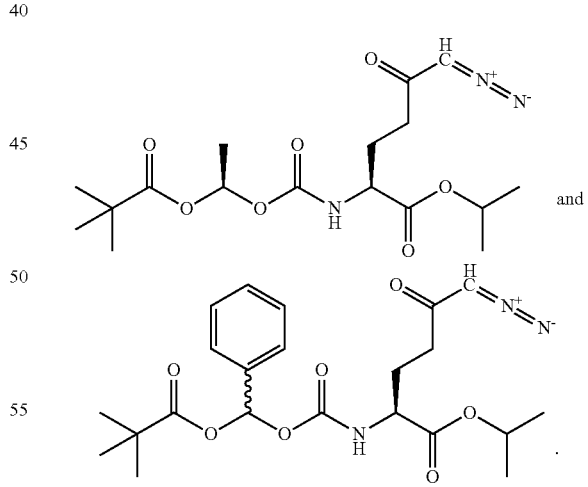

5. The compound of claim 4 selected from the group consisting of:

6. A pharmaceutical composition comprising the compound of claim 1 and a pharmaceutically acceptable carrier, diluent, or excipient.

7. A method of treating cancer in a subject, the method comprising administering to the subject in need thereof a compound of claim 1, or a pharmaceutically acceptable salt thereof, wherein the cancer is hepatocellular cancer, brain cancer, lung cancer, breast cancer, head and neck cancer, pancreatic cancer, prostate cancer, melanoma, colorectal cancer, acute lymphoblastic leukemia, acute myelogenous leukemia, or chronic myelocytic leukemia.

8. The method of claim 7, wherein the cancer is colorectal cancer.

9. The method of claim 7, wherein the cancer is breast cancer.

10. The method of claim 7, wherein the cancer is brain cancer.

11. The method of claim 7, wherein the cancer is pancreatic cancer.

12. The method of claim 7, wherein the cancer is prostate cancer.

13. The compound of claim 1, wherein
$R_3$ is H; and
$R_4$ is methyl, iPr, or aryl.

14. The compound of claim 1, wherein
$R_3$ and $R_4$ are each H.

15. The compound of claim 1, wherein
$R_3$ and $R_4$ are each methyl.

16. The compound of claim 3, wherein $R_{10}$ is selected from the group consisting of isopropyl and tert-butyl.

\* \* \* \* \*